United States Patent
Damude et al.

(10) Patent No.: US 7,879,591 B2
(45) Date of Patent: Feb. 1, 2011

(54) **HIGH EICOSAPENTAENOIC ACID PRODUCING STRAINS OF *YARROWIA LIPOLYTICA***

(75) Inventors: Howard Glenn Damude, Hockessin, DE (US); Zhixiong Xue, Chadds Ford, PA (US); Narendra S. Yadav, Wilmington, DE (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/485,141

(22) Filed: Jun. 16, 2009

(65) Prior Publication Data

US 2009/0325265 A1    Dec. 31, 2009

Related U.S. Application Data

(63) Continuation-in-part of application No. 11/265,761, filed on Nov. 2, 2005.

(60) Provisional application No. 60/624,812, filed on Nov. 4, 2004.

(51) Int. Cl.
  C12N 1/16    (2006.01)
  C12N 9/10    (2006.01)
  C12N 15/70   (2006.01)
  C12P 21/06   (2006.01)
  C07H 21/04   (2006.01)

(52) U.S. Cl. .................. 435/254.2; 435/193; 435/69.1; 435/320.1; 536/23.2

(58) Field of Classification Search ........................ None
  See application file for complete search history.

(56) References Cited

U.S. PATENT DOCUMENTS

| | | | |
|---|---|---|---|
| 7,537,920 B2 | 5/2009 | Renz et al. | |
| 2002/0156262 A1* | 10/2002 | Leung et al. | 536/23.2 |
| 2004/0142441 A1* | 7/2004 | Weiss et al. | 435/193 |
| 2006/0174376 A1 | 8/2006 | Renz et al. | |
| 2009/0094707 A1 | 4/2009 | Cirpus et al. | |

FOREIGN PATENT DOCUMENTS

| | | | |
|---|---|---|---|
| WO | 2004076617 A2 | 9/2004 |
| WO | 2004087902 A2 | 10/2004 |
| WO | 2006052870 A2 | 5/2006 |
| WO | 2006069936 A2 | 7/2006 |
| WO | 2008146745 A1 | 12/2008 |
| WO | 2009001315 A2 | 12/2008 |
| WO | 2009014140 A1 | 1/2009 |

OTHER PUBLICATIONS

Whisstock et al. Quaterly Reviews of Biophysics, 2003, "Prediction of protein function from protein sequence and structure", 36(3): 307-340.*
Chica et al. Semi-rational approaches to engineering enzyme activity: combining the benefits of directed evolution and rational design, Curr Opin Biotechnol. Aug. 2005;16(4):378-84. Review.*
Witkowski et al. Conversion of a beta-ketoacyl synthase to a malonyl decarboxylase by replacement of the active-site cysteine with glutamine, Biochemistry. Sep. 7, 1997;38(36):11643-50.*
W.E.M. Lands, Metabolism of Glycerolipides: A Comparison of Lecithin and Triglyceride Synthesis, Journal of Biological Chemistry, vol. 231, pp. 883-888 (1958).
H. Shindou et al., Acyl-Coa: Lysophospholipid Acyltransferases, Journal of Biological Chemistry, vol. 284, No. 1, pp. 1-5 (2009).
H. Shindou et al., Recent Progress on Acyl Coa: Lysophospholipid Acyltransferase Research, Journal of Lipid Research, vol. 50, S46-S51 (2009).
E.P. Kennedy et al., The Function of Cytidine Coenzymes in the Biosynthesis of Phospholipides, Journal of Biological Chemistry, vol. 222, pp. 193-214 (1956).

* cited by examiner

*Primary Examiner*—Robert B Mondesi
*Assistant Examiner*—Iqbal H Chowdhury

(57) ABSTRACT

Lysophosphatidic acid acyltransferase ["LPAAT"] participates in the second step of oil biosynthesis and is expected to play a key role in altering the quantity of long-chain polyunsaturated fatty acids ["LC-PUFAs"] produced in oils of oleaginous organisms. An LPAAT isolated from *Mortierella alpina* ["MaLPAAT1"] that is suitable for use in the manufacture of oils enriched in LC-PUFAs in oleaginous organisms is disclosed. Most desirably, the substrate specificity of the instant MaLPAAT1 will be particularly useful to enable increased $C_{18}$ to $C_{20}$ elongation conversion efficiency and increased $\Delta 4$ desaturation conversion efficiency in recombinant host cells producing LC-PUFAs.

9 Claims, 9 Drawing Sheets

Fig. 2A

Figure 1A:
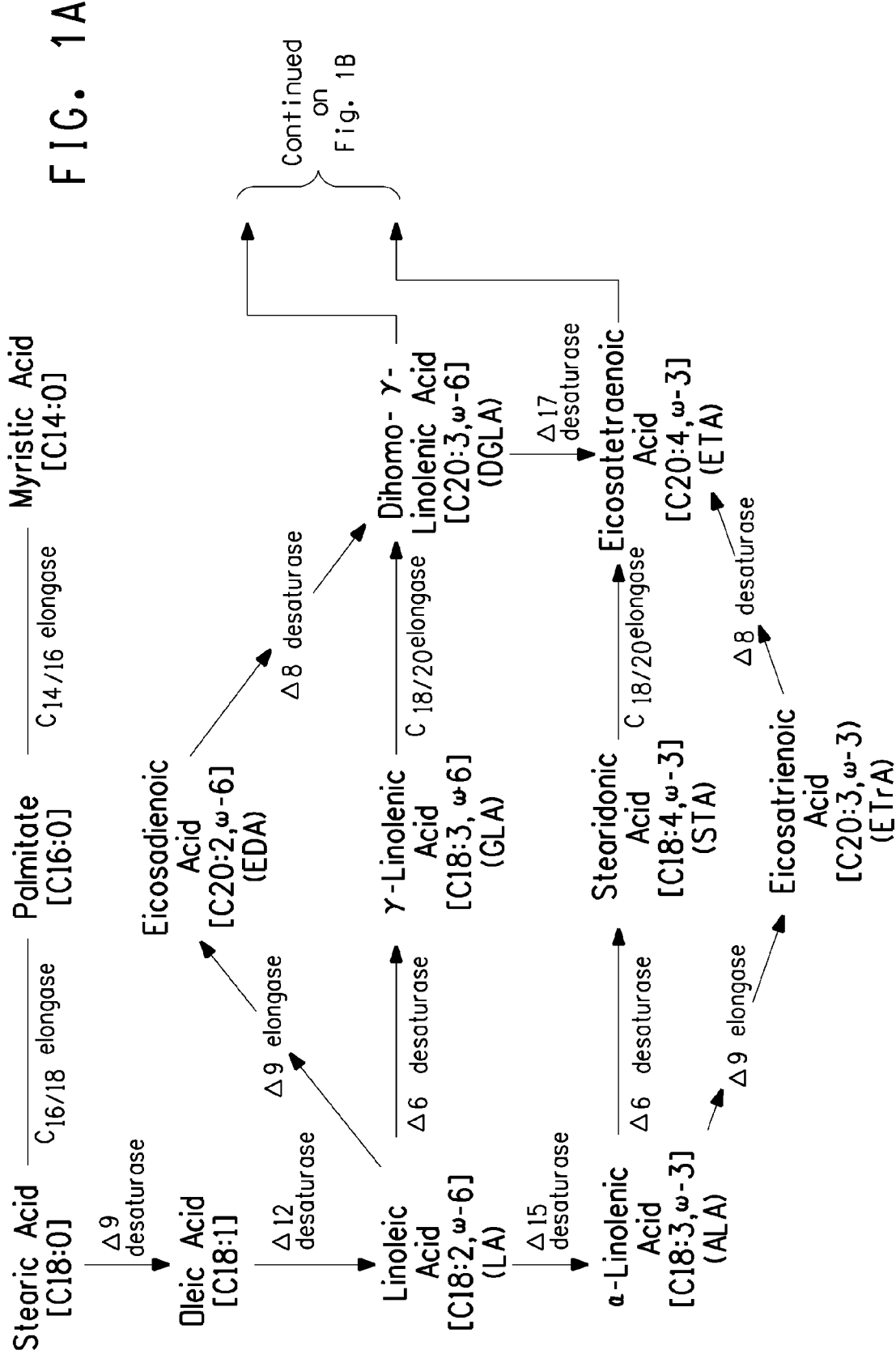

```
                    1                                                   50
SEQ ID NO:31   (1)  MDESTTTTHHSETSSKTSSHPRRLGPEMNPIYKGLRAIVWAFYFNLGAS
SEQ ID NO:33   (1)  ---------------------------------MNPIYKGLRAIVWAFYFNLGAS
SEQ ID NO:37   (1)  ----------------------------------MLGSVTRPTKALLYGSALFSFCS
SEQ ID NO:34   (1)  ------------------------------MSSMSSIEPALSSFPGNLAVILVFYLA
SEQ ID NO:35   (1)  -----------------------------------MSIGSSNPVLLAAIP------FVYLFV
SEQ ID NO:2    (1)  -----------------------------------MSIGSSNPVLLAAIP------FVYLFV 51                                                  100
SEQ ID NO:31   (51) LISITQVLSLPLALIAPGVYQWHISKTQGHFGAFLLRMNQLFAPSDIVLT
SEQ ID NO:33   (23) LISITQVLSLPLALIAPGVYQWHISKTQGHFGAFLLRMNQLFAPSDIVLT
SEQ ID NO:37   (24) LLNVVQVFSILLQPFSKRLFFEVNARVAGSMWKVMQLIMEKKHKAAITFS
SEQ ID NO:34   (28) LPRLLAVLPQKIQFIAKCLIVLTATFLMSVAGCFVAIVCALLQKRYAIN-
SEQ ID NO:35   (22) LPRILAFLPQKAQFLAKCIVVLIATLIMSVAGCLISIVCALLDKRYVIN-
SEQ ID NO:2    (22) LPRVLAFLPQKAQFLAKCIVVLIATLIMSVAGCFISIVCALLDKRYVIN- 101                                                 150
SEQ ID NO:31   (101) GDESVRGIVKVYKGRNLKEAGEPGSGQGEDILLDMPERMVFIANHQIYSD
SEQ ID NO:33   (73)  GDESVRGIVKVYKGRNLKEAGEPGSGQGEDILLDMPERMVFIANHQIYSD
SEQ ID NO:37   (74)  G-----DKIPHHES-------------------------AIVFGNHRSFVD
SEQ ID NO:34   (77)  ------YVVARIFSYIACRPCGVTFNIVGEEHLENTPA--IVVCNHQSSMD
SEQ ID NO:35   (71)  ------YVVSRLFSFLAARPCGVTYKIVGEEHLDKYPA--IVVCNHQSSMD
SEQ ID NO:2    (71)  ------YVVSRLFSFLAARPCGVTYKIVGEEHLDKYPA--IVVCNHQSSMD
```

Fig. 2B

```
                     151                                                  200
SEQ ID NO:31  (151)  WMYLWCFSYFAERHRALKIILRGDLTWIPVFGWGMRFFDFIFLKRNDWAH
SEQ ID NO:33  (123)  WMYLWCFSYFAERHRALKIILRGDLTWIPVFGWGMRFFDFIFLKRNDWAH
SEQ ID NO:37  ( 95)  FYMFHTVAARRGMLNYMKYFAKDSLKYIPFYGWGMWIMGMLFINRN-WQQ
SEQ ID NO:34  (120)  MMVLG-----RVFPMRCVVMAKKELQYFFPLGIFMTLSNAIFIDRKNHKK
SEQ ID NO:35  (114)  MMVLG-----RVFPKHCVVMAKKELLYFPFLGMFMKLSNAIFIDRKNHKK
SEQ ID NO:2   (114)  MMVLG-----RVFPKHCVVMAKKELLYFPFLGMFMKLSNAIFIDRKNHKK 201                                                  250
SEQ ID NO:31  (201)  DRRAIEENLGRVKEKDP-LWLVVFPEGTVVSKETRLRSVAFSKKASLSDH
SEQ ID NO:33  (173)  DRRAIEENLGRVKEKDP-LWLVVFPEGTVVSKETRLRSVAFSKKASLSDH
SEQ ID NO:37  (144)  DQLKINKMFARILDIQAPVWVASFLEGSRLTPSKLAASQKFMLGRGLPLL
SEQ ID NO:34  (165)  AIESTTQAVADMKKHN--SGIWIFPEGTRS-------RLDTADLLPFK
SEQ ID NO:35  (159)  AIESTTQAVADMKKHN--SGIWIFPEGTRS-------RLDKADLLPFK
SEQ ID NO:2   (159)  AIESTTQAVADMKKHN--SGIWIFPEGTRS-------RLDKADLLPFK 251                                                  300
SEQ ID NO:31  (250)  RHVLLPRTSGLFVCINKLRGS-VDYLYDATVGYSNVEYG-EIPQELYPLP
SEQ ID NO:33  (222)  RHVLLPRTSGLFVCINKLRGS-VDYLYDATVGYSNVEYG-EIPQELYPLP
SEQ ID NO:37  (194)  SNVMMPRTKGFIACVNKFRGTHVKCVYDFTFAYYHKTKGFGVPPDLVRVH
SEQ ID NO:34  (204)  KGAFHLAIQSGLPILPIVSAG-YNHIYDSAKRSFPGGE--LEIRVLEPIP
SEQ ID NO:35  (198)  KGAFHLAIQAQLPILPIVSQG-YSHIYDSSKRYFPGGE--LEIRVLEPIP
SEQ ID NO:2   (198)  KGAFHLAIQAQLPIIISQG-YSHIYDSSKRYFPGGE--LEIRVLEPIP
```

Fig. 2C

```
                          301                                                350
SEQ ID NO:31  (298)  GLYINKAQPKEINMHLRRFAIKDIPTSEPEFVEWVRARWVEKDELMEEFY
SEQ ID NO:33  (270)  GLYINKAQPKEINMHLRRFAIKDIPTSEPEFVEWVRARWVEKDELMEEFY
SEQ ID NO:37  (244)  TGQLSPEY--KEHVHVRRYQLDDLPTDEEKLSEWVQKYVEKDAFLEQMK
SEQ ID NO:34  (251)  TTGMTADDVNDLMERTRAVMLKNLKEMDVNSLAVSSKPSLSVDELKSAPA
SEQ ID NO:35  (245)  TKGLTTDDVNDLMDKTRNLMLKHLKDMDSHCSSAVG-------NGSLPL
SEQ ID NO:2   (245)  TTGLTTDDVNDLMDKTRNLMLKHLKEMDSQYSSSTAE-------NGSTHI 351                                                400
SEQ ID NO:31  (348)  TKGRFPSQLTAADIGEKEVKTAGGPTEGQSVRIPLKARGMMDYLMPSVMN
SEQ ID NO:33  (320)  TKGRFPSQLTAADIGEKEVKTAGGPTEGQSVRIPLKARGMMDYLMPSVMN
SEQ ID NO:37  (292)  EN--WTDGIDGGVWSENWM-------------------------------
SEQ ID NO:34  (301)  LKQEAKSTAVVEEGVSYDSVKKRKTVKA----------------------
SEQ ID NO:35  (287)  DADIAKSTATS--IGNTDDAVTKRRTLKE---------------------
SEQ ID NO:2   (288)  DADIAKSTATS--IGNTDDAITKRRTPKE---------------------

401           420
SEQ ID NO:31  (398)  LIALPVLAFAMRYAVQQASG
SEQ ID NO:33  (370)  LIALPVLAFAMRYAVQQASG
SEQ ID NO:37  (309)  --------------------
SEQ ID NO:34  (330)  --------------------
SEQ ID NO:35  (314)  --------------------
SEQ ID NO:2   (315)  --------------------
```

HIGH EICOSAPENTAENOIC ACID PRODUCING STRAINS OF YARROWIA LIPOLYTICA

This application is a Continuation-In-Part of U.S. patent application Ser. No. 11/265,761, filed Nov. 2, 2005, and claims the benefit of U.S. Provisional Application No. 60/624,812, filed Nov. 4, 2004, the disclosures of which are hereby incorporated by reference in their entirety.

FIELD OF THE INVENTION

This invention is in the field of biotechnology. More specifically, this invention pertains to the identification of a nucleic acid fragment isolated from *Mortierella alpina* encoding a lysophosphatidic acid acyltransferase (LPAAT). This enzyme (identified herein as "MaLPAAT1") is useful for altering the $C_{18}$ to $C_{20}$ elongation conversion efficiency and/or Δ4 desaturation conversion efficiency in oleaginous organisms expressing $C_{18/20}$ elongase and/or Δ4 desaturase for synthesis of long-chain polyunsaturated fatty acids ["LC-PUFAs"].

BACKGROUND OF THE INVENTION

Glycerophospholipids, the main component of biological membranes, contain a glycerol core with fatty acids attached as R groups at the sn-1 position and sn-2 position, and a polar head group joined at the sn-3 position via a phosphodiester bond. The specific polar head group (e.g., phosphatidic acid, chlorine, ethanolamine, glycerol, inositol, serine, cardiolipin) determines the name given to a particular glycerophospholipid, thus resulting in phosphatidylcholines ["PC"], phosphatidylethanolamines ["PE"], phosphatidylglycerols ["PG"], phosphatidylinositols ["PI"], phosphatidylserines ["PS"] and cardiolipins ["CL"]. Glycerophospholipids possess tremendous diversity, not only resulting from variable phosphoryl head groups, but also as a result of differing chain lengths and degrees of saturation of their fatty acids. Generally, saturated and monounsaturated fatty acids are esterified at the sn-1 position, while polyunsaturated fatty acids are esterified at the sn-2 position.

Glycerophospholipid biosynthesis is complex. Table 1 below summarizes the steps in the de novo pathway, originally described by Kennedy and Weiss (*J. Biol. Chem.*, 222.193-214 (1956)):

TABLE 1

General Reactions Of de Novo Glycerophospholipid Biosynthesis

| | |
|---|---|
| sn-Glycerol-3-Phosphate → Lysophosphatidic Acid (1-acyl-sn-glycerol 3-phosphate or "LPA") | Glycerol-3-phosphate acyltransferase (GPAT) [E.C. 2.3.1.15] esterifies 1st acyl-CoA to sn-1 position of sn-glycerol 3-phosphate |
| LPA → Phosphatidic Acid (1,2-diacylglycerol phosphate or "PA") | Lysophosphatidic acid acyltransferase (LPAAT) [E.C. 2.3.1.51] esterifies 2nd acyl-CoA to sn-2 position of LPA |
| PA → 1,2-Diacylglycerol ("DAG") Or PA → Cytidine Diphosphate Diacylglycerol ("CDP-DG") | Phosphatidic acid phosphatase [E.C. 3.1.3.4] removes a phosphate from PA; DAG can subsequently be converted to PC, PE or triacylglycerols ["TAG"], wherein TAG synthesis requires either a diacylglycerol acyltransferase (DGAT) [E.C. 2.3.1.20] or a phospholipid: diacylglycerol acyltransferase (PDAT) [E.C.2.3.1.158] CDP-diacylglycerol synthase [EC 2.7.7.41] causes condensation of PA and cytidine triphosphate, with elimination of pyrophosphate; CDP-DG can subsequently be converted to PI, PS, PG or CL |

Following their de novo synthesis, glycerophospholipids can undergo rapid turnover of the fatty acyl composition at the sn-2 position. This "remodeling", or "acyl editing", is important for membrane structure and function, biological response to stress conditions, and manipulation of fatty acid composition and quantity in biotechnological applications. Specifically, the remodeling has been attributed to deacylation of the glycerophospholipid and subsequent reacylation of the resulting lysophospholipid.

In the Lands' cycle (Lands, W. E., *J. Biol. Chem.*, 231:883-888 (1958)), remodeling occurs through the concerted action of a phospholipase, such as phospholipase $A_2$, that releases fatty acids from the sn-2 position of phosphatidylcholine and acyl-CoA:lysophospholipid acyltransferases ["LPLATs"], such as lysophosphatidylcholine acyltransferase ["LPCAT"] that reacylates the lysophosphatidylcholine ["LPC"] at the sn-2 position. Other glycerophospholipids can also be involved in the remodeling with their respective lysophospholipid acyltransferase activity, including LPLAT enzymes having lysophosphatidylethanolamine acyltransferase ["LPEAT"] activity, lysophosphatidylserine acyltransferase ["LPSAT"] activity, lysophosphatidylglycerol acyltransferase ["LPGAT"] activity and lysophosphatidylinositol acyltransferase ["LPIAT"] activity. In all cases, LPLATs are responsible for removing acyl-CoA fatty acids from the cellular acyl-CoA pool and acylating various lysophospholipid substrates at the sn-2 position in the phospholipid pool. Finally, LPLATs also include LPAAT enzymes that are involved in the de novo biosynthesis of PA from LPA.

Several recent reviews by Shindou et al. provide an overview of glycerophospholipid biosynthesis and the role of LPLATs (*J. Biol. Chem.*, 284(1):1-5 (2009); *J. Lipid Res.*, 50:S46-S51 (2009)). Numerous LPLATs have been reported in public and patent literature, based on a variety of conserved motifs.

The effect of LPLATs on polyunsaturated fatty acid ["PUFA"] production has also been contemplated, since fatty acid biosynthesis requires rapid exchange of acyl groups between the acyl-CoA pool and the phospholipid pool. Specifically, desaturations occur mainly at the sn-2 position of phospholipids, while elongation occurs in the acyl-CoA pool. For example, Example 16 of Intl. App. Pub. No. WO 2004/087902 (Renz et al.) describes the isolation of *Mortierella alpina* LPAAT-like proteins (encoded by the proteins of SEQ ID NO:31 and SEQ ID NO:33, having 417 amino acids in length or 389 amino acids in length, respectively) that are identical except for an N-terminal extension of 28 amino acid residues in SEQ ID NO:31. Intl. App. Pub. No. WO 2004/087902 also reports an increase in the efficiency of $C_{18}$ to $C_{20}$ elongation, an increase in Δ6 desaturation, and an increase in long-chain PUFA biosynthesis when one of these *Mortierella alpina* LPAAT-like proteins was expressed in an engineered strain of *Saccharomyces cerevisiae* that was fed exogenous 18:2 and α-linolenic ["ALA"; 18:3] fatty acids, that resulted in a large amount of the fatty acid substrates. Intl. App. Pub. No. WO 2004/087902 teaches that these improvements are due to reversible LPCAT activity in the LPAAT-like proteins and that not all LPAAT-like proteins have the LPCAT activity. Similar results were obtained upon expression of a LPCAT from *Caenorhabditis elegans* (clone T06E8.1) (Example 4 of Intl. App. Pub. No. WO 2004/087902; see also Intl. App. Pub. No. WO 2004/076617).

Numerous other references generally describe benefits of co-expressing LPLATs with PUFA biosynthetic genes, to increase the amount of a desired fatty acid in the oil of a transgenic organism, increase total oil content or selectively increase the content of desired fatty acids (e.g., Intl. App. Pub. Nos. WO 2004/076617, WO 2006/069936, WO 2006/052870, WO 2009/001315, WO 2009/014140).

Considerable efforts have focused on isolating LPLATs from the filamentous fungus, *Mortierella alpina*. In addition to the LPAAT proteins set forth as SEQ ID NO:31 and SEQ ID NO:33 (supra, isolated from Intl. App. Pub. No. WO 2004/087902), a variety of additional LPAAT homologs from *Mortierella alpina* have been described. For example, MaLPAAT3 (329 amino acids in length; SEQ ID NO:34 [SEQ ID NO:2 therein]) and MaLPAAT4 (313 amino acids in length; SEQ ID NO:35 [SEQ ID NO:4 therein]) are described in Intl. App. Pub. No. WO 2008/146745 (Suntory). U.S. Pat. No. 7,189,559 also describes a LPAAT homolog from *Mortierella alpina* of 308 amino acid residues (SEQ ID NO:37 [SEQ ID NO:2 therein]).

Despite the work described above, a novel LPAAT gene from the filamentous fungus *Mortierella alpina* is described herein. This gene is clearly differentiated from those *M. alpina* LPAAT-like sequences provided in the art and its expression has been demonstrated to improve the $C_{18}$ to $C_{20}$ elongation conversion efficiency, Δ4 desaturation conversion efficiency, and production of LC-PUFAs in oleaginous organisms expressing $C_{18/20}$ elongase and Δ4 desaturase for synthesis of long-chain PUFAs.

SUMMARY OF THE INVENTION

In one embodiment the invention concerns an isolated nucleic acid molecule encoding a polypeptide having lysophosphatidic acid acyltransferase activity, selected from the group consisting of:
(a) an isolated nucleic acid molecule encoding the amino acid sequence substantially as set forth in SEQ ID NO:2;
(b) an isolated nucleic acid molecule that hybridizes with
   (a) under the following hybridization conditions: 0.1× SSC, 0.1% SDS, 65° C. and washed with 2×SSC, 0.1% SDS followed by 0.1×SSC, 0.1% SDS; or,
(c) an isolated nucleic acid molecule that is completely complementary to (a) or (b).

In a second embodiment, the invention concerns an isolated nucleic acid molecule comprising at least one nucleotide sequence selected from the group consisting of:
(a) a nucleotide sequence encoding a lysophosphatidic acid acyltransferase enzyme of at least 314 amino acids that has at least 44% identity based on the BLAST method of alignment when compared to a polypeptide having the sequence as set forth in SEQ ID NO:2; and
(b) a nucleotide sequence comprising the complement of (a).

In a third embodiment, the invention concerns a recombinant DNA construct comprising the isolated nucleic acid molecule of the invention operably linked to at least one regulatory sequence.

In a fourth embodiment, the invention concerns a transformed host cell comprising the recombinant DNA construct of the invention. Suitable host cells can be selected from the group consisting of: bacteria, yeast, algae, stramenopiles, oomycetes, euglenoids, fungi and plants. In a preferred embodiment, the yeast is an oleaginous yeast and the oleaginous yeast can be selected from the group consisting of: *Yarrowia*, *Candida*, *Rhodotorula*, *Rhodosporidium*, *Cryptococcus*, *Trichosporon* and *Lipomyces*. More specifically, the host cell is *Yarrowia lipolytica*.

BIOLOGICAL DEPOSITS

The following biological material was made under the terms of the Budapest Treaty on the International Recognition of the Deposit of Microorganisms for the Purposes of Patent Procedure:

| Biological Material | Accession Number | Date of Deposit |
|---|---|---|
| *Yarrowia lipolytica* Y4128 | ATCC PTA-8614 | Aug. 23, 2007 |

As used herein, "ATCC" refers to the American Type Culture Collection International Depository Authority located at ATCC, 10801 University Blvd., Manassas, Va. 20110-2209, U.S.A. The listed deposit will be maintained in the indicated international depository for at least 30 years and will be made available to the public upon the grant of a patent disclosing it. The availability of a deposit does not constitute a license to practice the subject invention in derogation of patent rights granted by government action.

BRIEF DESCRIPTION OF THE DRAWINGS AND SEQUENCE DESCRIPTIONS

The invention can be more fully understood from the following detailed description and the accompanying sequence descriptions, which form a part of this application.

Figure 1B:
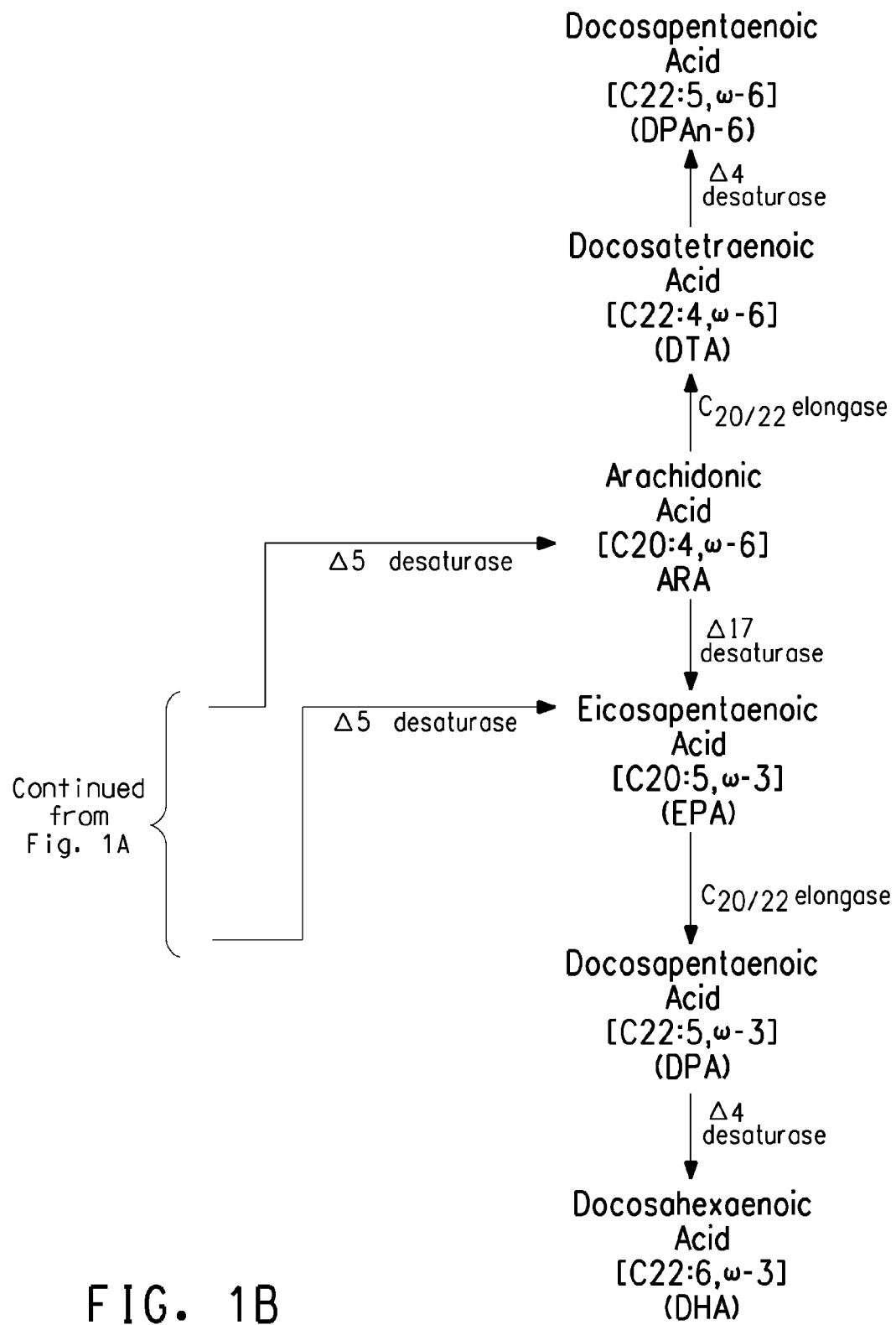

FIG. 1A and FIG. 1B illustrate the ω-3/ω-6 fatty acid biosynthetic pathway, and should be viewed together when considering the description of this pathway below.

FIG. 2A, FIG. 2B and FIG. 2C, when viewed together, provide an alignment of various *Mortierella alpina* LPAATs described herein and in Intl. App. Pub. Nos. WO 2004/087902 and WO 2008/146745 and U.S. Pat. No. 7,189,559.

FIG. 3 provides plasmid maps for the following: (A) pY201, comprising a chimeric YAT1::ScAle1S::Lip1 gene; and, (B) pY208, comprising a chimeric YAT1::MaLPAAT1S::Lip1 gene.

Figure 4:
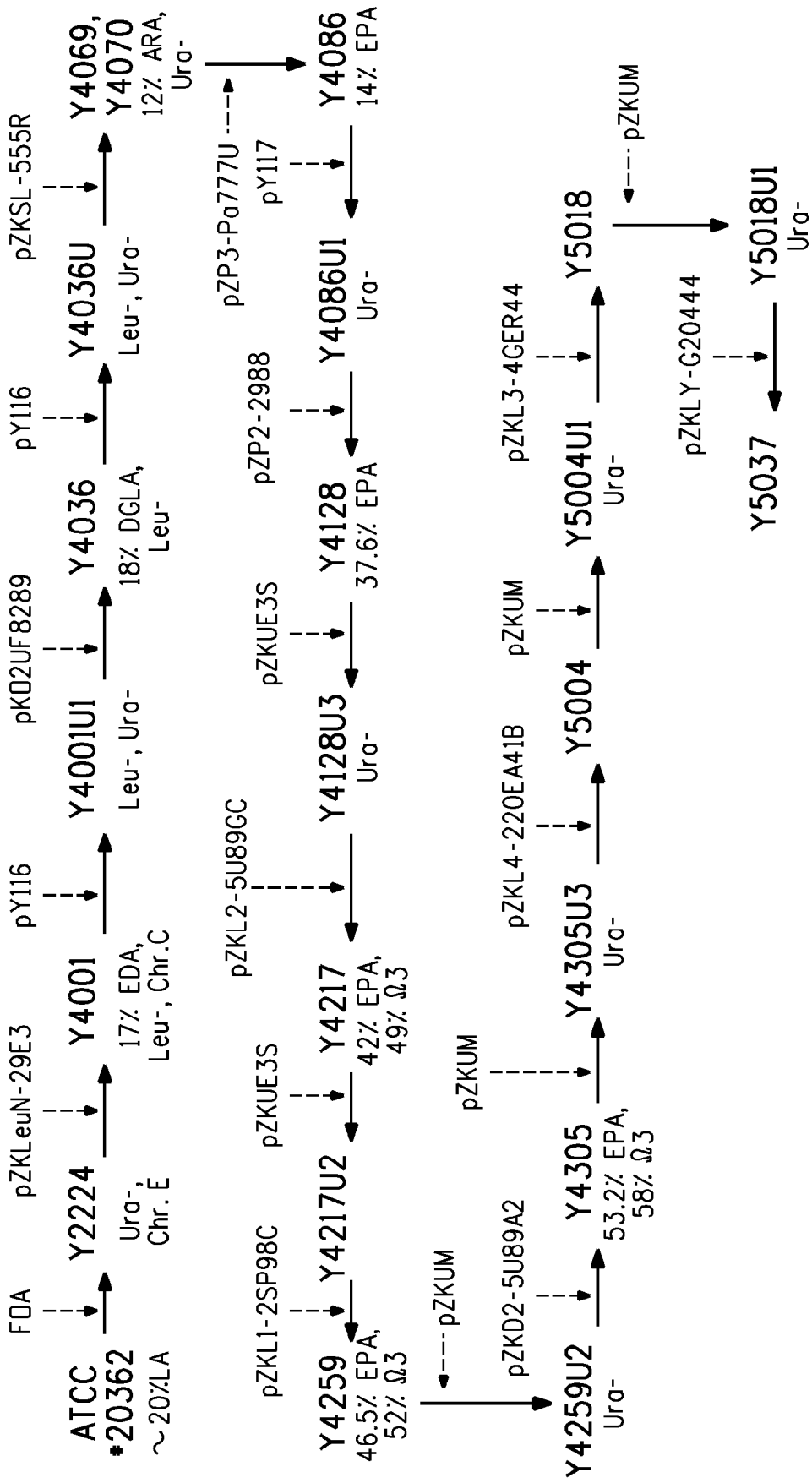

FIG. 4 diagrams the development of *Yarrowia lipolytica* strain Y5037, producing 18.6 EPA % TFAs, 22.8 DPA % TFAs and 9.7 DHA % TFAs.

FIG. 5 provides plasmid maps for the following: (A) pZKL4-220EA41B; and, (B) pZKUM.

FIG. 6 provides plasmid maps for the following: (A) pZKL3-4GER44; and, (B) pZKLY-G20444.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-65 are ORFs encoding genes or proteins (or portions thereof), primers or plasmids, as identified in Table 2.

TABLE 2

Summary Of Nucleic Acid And Protein SEQ ID Numbers

| Description and Abbreviation | Nucleic acid SEQ ID NO. | Protein SEQ ID NO. |
| --- | --- | --- |
| *Mortierella alpina* lysophosphatidic acid acyltransferase CDS ["MaLPAAT1"] | 1 (945 bp) | 2 (314 AA) |
| Synthetic lysophosphatidic acid acyltransferase derived from *Mortierella alpina*, codon-optimized for expression in *Yarrowia lipolytica* ["MaLPAAT1S"] | 3 (955 bp) | 4 (314 AA) |
| *Mortierella alpina* LPAAT1 internal cDNA fragment | 5 (211 bp) | — |
| Primer MaLP1_5-1 | 6 | — |
| Primer MaLP2_5-1 | 7 | — |
| Primer MaLP1_3-2 | 8 | — |
| Primer MaLP2_3-2 | 9 | — |
| T7 oligo | 10 | — |
| M13-28Rev | 11 | — |
| Primer MaLP3R1-1 | 12 | — |
| Primer MaLP3R1-2 | 13 | — |
| CDSIII/3' PCR primer from BD-Clontech Creator Smart ® cDNA library kit | 14 | — |
| *Mortierella alpina* LPAAT1, 3'end | 15 (669 bp) | — |
| Top strand of Genome Walker adaptor | 16 | — |
| Bottom strand of Genome Walker adaptor | 17 | — |
| Primer MaLPAT2-5-1 | 18 | — |
| Primer AP1 | 19 | — |
| Primer MaLPAT2-5-2 | 20 | — |
| Primer AP2 | 21 | — |
| *Mortierella alpina* LPAAT1-5'end, genomic | 22 (1947 bp) | — |
| 5'-CDSIII Primer | 23 | — |
| *Mortierella alpina* LPAAT1-5'end, cDNA | 24 (502 bp) | — |
| *Mortierella alpina* LPAAT1, intron | 25 (189 bp) | — |
| *Mortierella alpina* LPAAT1, composite | 26 (2756 bp) | — |
| Primer MaLP1_5NotI | 27 | — |
| Primer MaLP1_3NotI | 28 | — |
| Plasmid pLF109 | 29 (3981 bp) | — |
| *Mortierella alpina* LPAAT (corresponding to SEQ ID NOs: 16 and 17 within Intl. App. Pub. No. WO 2004/087902) | 30 (1254 bp) | 31 (417 AA) |
| *Mortierella alpina* LPAAT (corresponding to SEQ ID NOs: 18 and 19 within Intl. App. Pub. No. WO 2004/087902) | 32 (1170 bp) | 33 (389 AA) |
| *Mortierella alpina* LPAAT3 (corresponding to SEQ ID NO: 2 within Intl. App. Pub. No. WO 2008/146745) | — | 34 (329 AA) |
| *Mortierella alpina* LPAAT4 (corresponding to SEQ ID NO: 4 within Intl. App. Pub. No. WO 2008/146745) | — | 35 (313 AA) |
| *Mortierella alpina* LPAAT2 homolog (corresponding to SEQ ID NOs: 1 and 2 within U.S. Pat. No. 7,189,559) | 36 (1086 bp) | 37 (308 AA) |
| 1-acyl-sn-glycerol-3-phosphate acyltransferase motif NHxxxxD | — | 38 |
| 1-acyl-sn-glycerol-3-phosphate acyltransferase motif EGTR | — | 39 |

TABLE 2-continued

Summary Of Nucleic Acid And Protein SEQ ID Numbers

| Description and Abbreviation | Nucleic acid SEQ ID NO. | Protein SEQ ID NO. |
|---|---|---|
| *Saccharomyces cerevisiae* Ale1 ("ScAle1") | 40 (1860 bp) | 41 (619 AA) |
| Synthetic Ale1 derived from *Saccharomyces cerevisiae*, codon-optimized for expression in *Yarrowia lipolytica* ("ScAle1S") | 42 (1870 bp) | 43 (619 AA) |
| Plasmid pY201 | 44 (9641 bp) | — |
| *Escherichia coli* LoxP recombination site, recognized by a Cre recombinase enzyme | 45 (34 bp) | — |
| Plasmid pY208 | 46 (8726 bp) | — |
| Plasmid pZKL4-220EA41B | 47 (16,424 bp) | — |
| Synthetic $C_{20}$ elongase derived from *Euglena anabaena*, codon-optimized for expression in *Yarrowia lipolytica* ("EaC20ES") | 48 (900 bp) | 49 (299 AA) |
| Synthetic $C_{20}$ elongase derived from *Euglena gracilis*, codon-optimized for expression in *Yarrowia lipolytica* ("EgC20ES") | 50 (912 bp) | 51 (303 AA) |
| Truncated synthetic Δ4 desaturase derived from *Euglena anabaena*, codon-optimized for expression in *Yarrowia lipolytica* ("EaD4S-1") | 52 (1644 bp) | 53 (547 AA) |
| Truncated synthetic Δ4 desaturase (version B) derived from *Euglena anabaena*, codon-optimized for expression in *Yarrowia lipolytica* ("EaD4SB") | 54 (1644 bp) | 55 (547 AA) |
| Plasmid pZKUM | 56 (4313 bp) | — |
| Plasmid pZKL3-4GER44 | 57 (17,088 bp) | — |
| Synthetic Δ4 desaturase derived from *Eutreptiella cf_gymnastica* CCMP1594, codon-optimized for expression in *Yarrowia lipolytica* ("E1594D4S") | 58 (1548 bp) | 59 (515 AA) |
| Truncated synthetic Δ4 desaturase derived from *Euglena gracilis*, codon-optimized for expression in *Yarrowia lipolytica* ("EgD4S-1") | 60 (1542 bp) | 61 (513 AA) |
| Plasmid pZKLY-G20444 | 62 (15,617 bp) | — |
| Synthetic DHA synthase derived from *Euglena gracilis*, codon-optimized for expression in *Yarrowia lipolytica* ("EgDHAsyn1S") | 63 (2382 bp) | 64 (793 AA) |
| Lewin, T. W. et al. & Yamashita et al. 1-acyl-sn-glycerol-3-phosphate acyltransferase motif GxxFI-[D/R]-R | — | 65 |
| Lewin, T. W. et al. 1-acyl-sn-glycerol-3-phosphate acyltransferase motif [V/I]-[P/X]-[I/V/L]-[I/V]-P-[V/I] | — | 66 |
| Yamashita et al. 1-acyl-sn-glycerol-3-phosphate acyltransferase motif IVPIVM | — | 67 |

DETAILED DESCRIPTION OF THE INVENTION

The disclosure of each reference set forth herein is hereby incorporated by reference in its entirety.

Identified herein is a novel *Mortierella alpina* lysophosphatidic acid acyltransferase ["LPAAT"] enzyme and gene encoding the same that may be used for the manipulation of biochemical pathways for the production of healthful long-chain polyunsaturated fatty acids ["LC-PUFAs"]. Thus, the subject invention finds many applications.

LC-PUFAs, or derivatives thereof, are used as dietary substitutes, or supplements, particularly infant formulas, for patients undergoing intravenous feeding or for preventing or treating malnutrition. Alternatively, the purified LC-PUFAs (or derivatives thereof) may be incorporated into cooking oils, fats or margarines formulated so that in normal use the recipient would receive the desired amount for dietary supplementation. The LC-PUFAs may also be incorporated into infant formulas, nutritional supplements or other food and drink products and may find use as cardiovascular-protective, anti-depression, anti-inflammatory or cholesterol lowering agents. Optionally, the compositions may be used for pharmaceutical use, either human or veterinary.

In this disclosure, a number of terms and abbreviations are used. The following definitions are provided.

"Open reading frame" is abbreviated as "ORF".

"Polymerase chain reaction" is abbreviated as "PCR".

"American Type Culture Collection" is abbreviated as "ATCC".

"Polyunsaturated fatty acid(s)" is abbreviated as "PUFA(s)".

"Acyl-CoA:lysophospholipid acyltransferase" is abbreviated as "LPLAT".

"Lysophosphatidic acid acyltransferase" is abbreviated as "LPAAT".

"Triacylglycerols" are abbreviated as "TAGs".

"Co-enzyme A" is abbreviated as "CoA".

"Total fatty acids" are abbreviated as "TFAs".

"Fatty acid methyl esters" are abbreviated as "FAMEs".

"Dry cell weight" is abbreviated as "DCW".

The term "invention" or "present invention" as used herein is not meant to be limiting to any one specific embodiment of the invention but applies generally to any and all embodiments of the invention as described in the claims and specification.

The term "glycerophospholipids" refers to a broad class of molecules, having a glycerol core with fatty acids at the sn-1 position and sn-2 position, and a polar head group (e.g., phosphate, choline, ethanolamine, glycerol, inositol, serine, cardiolipin) joined at the sn-3 position via a phosphodiester bond. Glycerophospholipids thus include phosphatidylcholines ["PC"], phosphatidylethanolamines ["PE"], phosphatidylglycerols ["PG"], phosphatidylinositols ["PI"], phosphatidylserines ["PS"] and cardiolipins ["CL"].

"Lysophospholipids" are derived from glycerophospholipids, by deacylation of the sn-2 position fatty acid. Lysophospholipids include, e.g., lysophosphatidic acid ["LPA"], lysophosphatidylcholine ["LPC"], lysophosphatidyletanolamine ["LPE"], lysophosphatidylserine ["LPS"], lysophosphatidylglycerol ["LPG"] and lysophosphatidylinositol ["LPI"].

The term "acyltransferase" refers to an enzyme responsible for transferring an acyl group from a donor lipid to an acceptor lipid molecule.

The term "acyl-CoA:lysophospholipid acyltransferase" ["LPLAT"] refers to a broad class of acyltransferases, having the ability to acylate a variety of lysophospholipid substrates at the sn-2 position. More specifically, LPLATs include LPA acyltransferases ["LPAATs"] having the ability to catalyze conversion of LPA to PA, LPC acyltransferases ["LPCATs"] having the ability to catalyze conversion of LPC to PC, LPE acyltransferases ["LPEATs"] having the ability to catalyze conversion of LPE to PE, LPS acyltransferases ["LPSATs"] having the ability to catalyze conversion of LPS to PS, LPG acyltransferases ["LPGATs"] having the ability to catalyze conversion of LPG to PG, and LPI acyltransferases ["LPIATs"] having the ability to catalyze conversion of LPI to PI. Standardization of LPLAT nomenclature has not been formalized, so various other designations have been previously used in the art. Additionally, it is important to note that some LPLATs, such as the *Saccharomyces cerevisiae* Ale1 (ORF YOR175C; SEQ ID NO:40), have broad specificity and thus a single enzyme may be capable of catalyzing several LPLAT reactions, including LPAAT, LPCAT and LPEAT reactions (Tamaki, H. et al., *J. Biol. Chem.*, 282:34288-34298 (2007); Ståhl, U. et al., *FEBS Letters*, 582:305-309 (2008); Chen, Q. et al., *FEBS Letters*, 581:5511-5516 (2007); Benghezal, M. et al., *J. Biol. Chem.*, 282:30845-30855 (2007); Riekhof, et al., *J. Biol. Chem.*, 282:28344-28352 (2007)).

The term "LPAAT" refers to a lysophosphatidic acid acyltransferase enzyme (EC 2.3.1.51). This enzyme is responsible for the transfer of an acyl-CoA group onto 1-acyl-sn-glycerol 3-phosphate ["LPA"] to produce CoA and 1,2-diacyl-sn-glycerol 3-phosphate ["PA"]. The literature also refers to LPAAT as acyl-CoA:1-acyl-sn-glycerol-3-phosphate 2-O-acyltransferase, 1-acyl-sn-glycerol-3-phosphate acyltransferase and/or 1-acylglycerolphosphate acyltransferase (abbreviated as AGAT). LPAATs described herein will possess a 1-acyl-sn-glycerol-3-phosphate acyltransferase family motif selected from the group consisting of: NHxxxxD (SEQ ID NO:38) and EGTR (SEQ ID NO:39).

The term "MaLPAAT1" refers to a LPAAT (SEQ ID NO:2) isolated from *Mortierella alpina*, encoded by the nucleotide sequence set forth as SEQ ID NO:1. In contrast, the term "MaLPAAT1S" refers to a synthetic LPAAT derived from *M. alpina* that is codon-optimized for expression in *Yarrowia lipolytica* (i.e., SEQ ID NOs:3 and 4).

The term "conserved domain" or "motif" means a set of amino acids conserved at specific positions along an aligned sequence of evolutionarily related proteins. While amino acids at other positions can vary between homologous proteins, amino acids that are highly conserved at specific positions likely indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The term "oil" refers to a lipid substance that is liquid at 25° C. and usually polyunsaturated. In oleaginous organisms, oil constitutes a major part of the total lipid. Oil is composed primarily of triacylglycerols ["TAGs"] but may also contain other neutral lipids, phospholipids and free fatty acids. The fatty acid composition in the oil and the fatty acid composition of the total lipid are generally similar; thus, an increase or decrease in the concentration of PUFAs in the total lipid will correspond with an increase or decrease in the concentration of PUFAs in the oil, and vice versa.

"Neutral lipids" refer to those lipids commonly found in cells in lipid bodies as storage fats and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or triacylglycerol, respectively, or collectively, acylglycerols. A hydrolysis reaction must occur to release free fatty acids from acylglycerols.

The term "triacylglycerols" ["TAGs"] refers to neutral lipids composed of three fatty acyl residues esterified to a glycerol molecule. TAGs can contain LC-PUFAs and saturated fatty acids, as well as shorter chain saturated and unsaturated fatty acids.

The term "total fatty acids" ["TFAs"] herein refer to the sum of all cellular fatty acids that can be derivitized to fatty acid methyl esters ["FAMEs"] by the base transesterification method (as known in the art) in a given sample, which may be the biomass or oil, for example. Thus, total fatty acids include fatty acids from neutral lipid fractions (including diacylglycerols, monoacylglycerols and TAGs) and from polar lipid fractions (including the PC and the PE fractions) but not free fatty acids.

The term "total lipid content" of cells is a measure of TFAs as a percent of the dry cell weight ["DCW"]. Thus, total lipid content ["TFAs % DCW"] is equivalent to, e.g., milligrams of total fatty acids per 100 milligrams of DCW.

The concentration of a fatty acid in the total lipid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., % EPA of total lipids is equivalent to EPA % TFAs).

In some cases, it is useful to express the content of a given fatty acid(s) in a cell as its weight percent of the dry cell weight ["% DCW"]. Thus, for example, eicosapentaenoic acid % DCW would be determined according to the following formula: (eicosapentaenoic acid % TFAs)*(TFAs % DCW)]/100.

The terms "lipid profile" and "lipid composition" are interchangeable and refer to the amount of individual fatty acids contained in a particular lipid fraction, such as in the total lipid or the oil, wherein the amount is expressed as a weight percent of TFAs. The sum of each individual fatty acid present in the mixture should be 100.

The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["ω-6" or "n-6"] versus "omega-3 fatty acids" ["ω-3" or "n-3"] are provided in U.S. Pat. No. 7,238,482, which is hereby incorporated herein by reference.

Nomenclature used to describe PUFAs herein is given in Table 3. In the column titled "Shorthand Notation", the omega-reference system is used to indicate the number of carbons, the number of double bonds and the position of the double bond closest to the omega carbon, counting from the omega carbon, which is numbered 1 for this purpose. The remainder of the Table summarizes the common names of ω-3 and ω-6 fatty acids and their precursors, the abbreviations that will be used throughout the specification and the chemical name of each compound.

TABLE 3

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-Linolenic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Sciadonic | SCI | cis-5,11,14-eicosatrienoic | 20:3b ω-6 |
| Juniperonic | JUP | cis-5,11,14,17-eicosatetraenoic | 20:4b ω-3 |
| Eicosa-tetraenoic | ETA | cis-8,11,14,17-eicosatetraenoic | 20:4 ω-3 |
| Eicosa-pentaenoic | EPA | cis-5,8,11,14,17-eicosapentaenoic | 20:5 ω-3 |
| Docosatrienoic | DRA | cis-10,13,16-docosatrienoic | 22:3 ω-6 |
| Docosa-tetraenoic | DTA | cis-7,10,13,16-docosatetraenoic | 22:4 ω-6 |
| Docosa-pentaenoic | DPAn-6 | cis-4,7,10,13,16-docosapentaenoic | 22:5 ω-6 |
| Docosa-pentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

Although the ω-3/ω6 PUFAs listed in Table 3 are the most likely to be accumulated in the oil fractions of oleaginous yeast using the methods described herein, this list should not be construed as limiting or as complete.

The term "long-chain polyunsaturated fatty acid" ["LC-PUFA"] refers to those PUFAs that have chain lengths of $C_{20}$ or greater. Thus, the term LC-PUFA includes at least EDA, DGLA, ARA, ETrA, ETA, EPA, DTA, DPAn-6, DPA and DHA.

The term "PUFA biosynthetic pathway" refers to a metabolic process that converts oleic acid to ω-6 fatty acids such as LA, EDA, GLA, DGLA, ARA, DRA, DTA and DPAn-6 and ω-3 fatty acids such as ALA, STA, ETrA, ETA, EPA, DPA and DHA. This process is well described in the literature (e.g., see Intl. App. Pub. No. WO 2006/052870). Briefly, this process involves elongation of the carbon chain through the addition of carbon atoms and desaturation of the molecule through the addition of double bonds, via a series of special elongation and desaturation enzymes termed "PUFA biosynthetic pathway enzymes" that are present in the endoplasmic reticulum membrane. More specifically, "PUFA biosynthetic pathway enzymes" refer to any of the following enzymes (and genes which encode said enzymes) associated with the biosynthesis of a PUFA, including: Δ4 desaturase, Δ5 desaturase, Δ6 desaturase, Δ12 desaturase, Δ15 desaturase, Δ17 desaturase, Δ9 desaturase, Δ8 desaturase, Δ9 elongase, $C_{14/16}$ elongase, $C_{16/18}$ elongase, $C_{18/20}$ elongase and/or $C_{20/22}$ elongase.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are Δ8 desaturases, Δ5 desaturases, Δ17 desaturases, Δ12 desaturases, Δ15 desaturases, Δ9 desaturases, Δ6 desaturases and Δ4 desaturases. Δ17 desaturases, and also Δ15 desaturases, are also occasionally referred to as "omega-3 desaturases", "w-3 desaturases", and/or "ω-3 desaturases", based on their ability to convert ω-6 fatty acids into their ω-3 counterparts.

The term "elongase" refers to a polypeptide that can elongate a fatty acid carbon chain to produce an acid 2 carbons longer than the fatty acid substrate that the elongase acts upon. This process of elongation occurs in a multi-step mechanism in association with fatty acid synthase, as described in Intl. App. Pub. No. WO 2005/047480. Examples of reactions catalyzed by elongase systems are the conversion of GLA to DGLA, STA to ETA, ARA to DTA and EPA to DPA. In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., LA, ALA, GLA, STA) and a $C_{20/22}$ elongase (also known as a Δ5 elongase as the terms can be used interchangeably) will utilize a $C_{20}$ substrate (e.g., ARA, EPA). For the purposes herein, two distinct types of $C_{18/20}$ elongases can be defined: a Δ6 elongase will catalyze conversion of GLA and STA to DGLA and ETA, respectively, while a Δ9 elongase is able to catalyze the conversion of LA and ALA to EDA and ETrA, respectively.

The terms "conversion efficiency" and "percent substrate conversion" refer to the efficiency by which a particular enzyme, such as a desaturase or elongase, can convert substrate to product. The conversion efficiency is measured according to the following formula: ([product]/[substrate+ product])*100, where 'product' includes the immediate product and all products in the pathway derived from it.

The terms "Δ9 elongation conversion efficiency" and "Δ9 elongase conversion efficiency" refer to the efficiency by which Δ9 elongase can convert $C_{18}$ substrates (i.e., LA, ALA) to $C_{20}$ products (i.e., EDA, ETrA).

The terms "Δ4 desaturation conversion efficiency" and "Δ4 desaturase conversion efficiency" refer to the efficiency by which Δ4 desaturase can convert substrates (i.e., DTA, DPAn-3) to products (i.e., DPAn-6, DHA).

The term "oleaginous" refers to those organisms that tend to store their energy source in the form of oil (Weete, In: Fungal Lipid Biochemistry, $2^{nd}$ Ed., Plenum, 1980). Generally, the cellular oil content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil. The term "oleaginous yeast" refers to those microorganisms classified as yeasts that can make oil. Examples of oleaginous yeast include, but are no means limited to, the following genera: *Yarrowia, Candida, Rhodotorula, Rhodosporidium, Cryptococcus, Trichosporon* and *Lipomyces*.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), which is hereby incorporated herein by reference, particularly Chapter 11 and Table 11.1. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability, corresponding to higher Tm, of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The disclosure herein teaches the complete amino acid and nucleotide sequence encoding particular fungal proteins. The skilled artisan, having the benefit of the sequences as reported herein, may now use all or a substantial portion of the disclosed sequences for purposes known to those skilled in this art. Accordingly, the complete sequences as reported in the accompanying Sequence Listing, as well as substantial portions of those sequences as defined above, are encompassed in the present disclosure.

The term "complementary" is used to describe the relationship between nucleotide bases that are capable of hybridizing to one another. For example, with respect to DNA, adenosine is complementary to thymine and cytosine is complementary to guanine. Accordingly, isolated nucleic acid fragments that are complementary to the complete sequences as reported in the accompanying Sequence Listing, as well as those substantially similar nucleic acid sequences, are encompassed in the present disclosure.

As used herein, the terms "homology" and "homologous" are used interchangeably. They refer to nucleic acid fragments wherein changes in one or more nucleotide bases do not affect the ability of the nucleic acid fragment to mediate gene expression or produce a certain phenotype. These terms also refer to modifications of the nucleic acid fragments such as deletion or insertion of one or more nucleotides that do not substantially alter the functional properties of the resulting nucleic acid fragment relative to the initial, unmodified fragment.

Moreover, the skilled artisan recognizes that homologous nucleic acid sequences are also defined by their ability to hybridize, under moderately stringent conditions, e.g., 0.5× SSC, 0.1% SDS, 60° C., with the sequences exemplified herein, or to any portion of the nucleotide sequences disclosed herein and which are functionally equivalent thereto. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. An extensive guide to the hybridization of nucleic acids is found in Tijssen, *Laboratory Techniques in Biochemistry and Molecular Biology-Hybridization with Nucleic Acid Probes*, Part I, Chapter 2 "Overview of principles of hybridization and the strategy of nucleic acid probe assays", Elsevier, NY (1993); and *Current Protocols in Molecular Biology*, Chapter 2, Ausubel et al., Eds., Greene Publishing and Wiley-Interscience, New York (1995).

The term "percent identity" refers to a relationship between two or more polypeptide sequences or two or more polynucleotide sequences, as determined by comparing the sequences. "Percent identity" also means the degree of sequence relatedness between polypeptide or polynucleotide sequences, as the case may be, as determined by the percentage of match between compared sequences. "Percent identity" and "percent similarity" can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: NJ (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton, N.Y. (1991).

Preferred methods to determine percent identity are designed to give the best match between the sequences tested. Methods to determine percent identity and percent similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, *CABIOS*, 5:151-153 (1989); Higgins, D. G. et al., *Comput. Appl. Biosci.*, 8:189-191(1992)) and found in the MegAlign™ (version 8.0.2) program of the LASERGENE bioinformatics computing suite (DNASTAR Inc.). After alignment of the sequences using either Clustal program, it is possible to obtain a "percent identity" by viewing the "sequence distances" table in the program.

For multiple alignments using the Clustal V method of alignment, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. Default parameters for multiple alignment using the Clustal W method of alignment correspond to GAP PENALTY=10, GAP LENGTH PENALTY=0.2, Delay Divergent Seqs(%)=30, DNA Transition Weight=0.5, Protein Weight Matrix=Gonnet Series, DNA Weight Matrix=IUB.

It is well understood by one skilled in the art that various measures of sequence percent identity are useful in identifying polypeptides, from other species, wherein such polypeptides have the same or similar function or activity. Suitable nucleic acid fragments, i.e., isolated polynucleotides according to the disclosure herein, encode polypeptides that are at least about 70-85% identical, while more preferred nucleic acid fragments encode amino acid sequences that are at least about 85-95% identical to the amino acid sequences reported herein. Although preferred ranges are described above, useful examples of percent identities include any integer percentage from 44% to 100%, such as 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without affecting the amino acid sequence of an encoded polypeptide. Accordingly, described herein is any nucleic acid fragment that encodes all or a substantial portion of the amino acid sequence encoding the fungal polypeptide substantially as set forth in SEQ ID NO:2. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid fragment that expresses a specific protein, and which may refer to the coding region alone or may include regulatory sequences preceding (5' non-coding sequences) and following (3'non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence which codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequence" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and which can be translated into protein by the cell. "cDNA" refers to a double-stranded DNA that is complementary to, and derived from, mRNA.

The term "operably linked" refers to the association of nucleic acid sequences on a single nucleic acid fragment so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

The term "expression", as used herein, refers to the transcription and stable accumulation of sense (mRNA) or antisense RNA. Expression may also refer to translation of mRNA into a polypeptide. Thus, the term "expression", as used herein, also refers to the production of a functional end-product (e.g., an mRNA or a protein [either precursor or mature]).

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" or "transformant" organisms.

The term "recombinant" refers to an artificial combination of two otherwise separated segments of sequence, e.g., by chemical synthesis or by the manipulation of isolated segments of nucleic acids by genetic engineering techniques.

A "plasmid" or "vector" is an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

"Transformation cassette" refers to a fragment of DNA containing a foreign gene and having elements in addition to the foreign gene that facilitate transformation of a particular host cell.

The term "expression cassette" refers to a fragment of DNA containing a foreign gene and having elements in addition to the foreign gene that allow for enhanced expression of that gene in a foreign host. Generally, an expression cassette will comprise the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence ["ORF"]; and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and culture host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple transformants must be screened in order to obtain strains displaying the desired expression level and pattern. Such screening may be accomplished by Southern analysis of DNA blots, Northern analysis of mRNA expression, Western analysis of protein expression, or phenotypic analysis, among others.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNASTAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within this description, whenever sequence analysis software is used for analysis, the analytical results are based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

Genes encoding LPLATs are found in eukaryotic cells, based on their intimate role in de novo synthesis and remodeling of glycerophospholipids, wherein LPLATs remove acyl-CoA fatty acids from the cellular acyl-CoA pool and acylate various lysophospholipid substrates at the sn-2 position in the phospholipid pool. The present disclosure relates to a nucleotide sequence (SEQ ID NO:1) isolated from *Mortierella alpina*, encoding a LPAAT (SEQ ID NO:2). This nucleotide and corresponding protein sequence, designated herein as "MaLPAAT1", were previously described as SEQ ID NOs:80 and 81, respectively, in U.S. patent application Ser. No. 11/265,761, filed Nov. 2, 2005 (the priority of which is claimed herein), corresponding to U.S. Pat. Appl. Pub. No. 2006-0115881-A1 and Intl. App. Pub. No. WO 2006/052870.

Comparison of the MaLPAAT1 nucleotide base and deduced amino acid sequences to public databases reveals that the most similar known sequences are about 44% identical to the amino acid sequence of MaLPAAT1 reported herein over a length of 314 amino acids using a BLASTP method of alignment (Altschul, S. F., et al., *Nucleic Acids Res.*, 25:3389-3402 (1997) and *FEBS J.*, 272:5101-5109 (2005); provided by the National Center for Biotechnology Information ["NCBI"]).

More preferred amino acid fragments are at least about 70%-80% identical to the sequences herein, where those sequences that are at least about 80%-90% identical are particularly suitable and those sequences that are at least about 90%-95% identical are most preferred. Similarly, preferred MaLPAAT1 encoding nucleic acid sequences corresponding to the ORF are those encoding active proteins and which are at least about 70%-80% identical to the nucleic acid sequences of MaLPAAT1 reported herein, where those sequences that are at least about 80%-90% identical are particularly suitable and those sequences that are at least about 90%-95% identical are most preferred.

In alternate embodiments, the MaLPAAT1 sequence can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins, preferably those expressed in the largest amount, and determining which codons are used with highest frequency. Then, the coding sequence for a polypeptide of interest having e.g., desaturase activity can be synthesized in whole or in part using the codons preferred in the host species.

Thus, MaLPAAT1 was codon-optimized for expression in *Yarrowia lipolytica*. This was possible based on previous determination of the *Y. lipolytica* codon usage profile, identification of those codons that were preferred, and determination of the consensus sequence around the 'ATG' initiation codon (see U.S. Pat. No. 7,238,482 and U.S. Pat. No. 7,125,672). The codon-optimized synthetic gene (SEQ ID NO:3), designated herein as "MaLPAAT1S", encoded the protein as set forth in SEQ ID NO:4. SEQ ID NO:4 identical to that of the wildtype protein sequence (i.e., SEQ ID NO:2).

One skilled in the art would be able to use the teachings herein to create various other codon-optimized LPAAT proteins suitable for optimal expression in alternate hosts (i.e., other than *Yarrowia lipolytica*), based on the wildtype MaLPAAT1 sequence. Accordingly, the disclosure herein relates to any codon-optimized LPAAT protein that is derived from the wildtype MaLPAAT1, that is, encoded by SEQ ID NO:2. This includes, but is not limited to, the nucleotide sequence set forth in SEQ ID NO:3, which encodes a synthetic LPAAT protein (i.e., MaLPAAT1S as set forth in SEQ ID NO:4) that was codon-optimized for expression in *Y. lipolytica*.

Any of the instant LPAAT sequences (i.e., MaLPAAT, MaLPAAT1S) or portions thereof may be used to search for LPLAT homologs in the same or other bacterial, algal, fungal, oomycete, yeast, stramenopiles, euglenoid, plant or animal species using sequence analysis software. In general, such computer software matches similar sequences by assigning degrees of homology to various substitutions, deletions, and other modifications. Use of software algorithms, such as the BLASTP method of alignment with a low complexity filter and the following parameters: Expect value=10, matrix=Blosum 62 (Altschul, et al., *Nucleic Acids Res.* 25:3389-3402 (1997)), is well-known for comparing any LPAAT protein against a database of nucleic or protein sequences and thereby identifying similar known sequences within a preferred host organism.

Use of a software algorithm to comb through databases of known sequences is particularly suitable for the isolation of homologs having a relatively low percent identity to publicly available LPAAT sequences, such as those described in SEQ ID NO:2. It is predictable that isolation would be relatively easier for LPAAT homologs of at least about 70%-85% identity to publicly available LPAAT sequences. Further, those sequences that are at least about 85%-90% identical would be particularly suitable for isolation and those sequences that are at least about 90%-95% identical would be the most facilely isolated.

LPAAT homologs can also be identified by the use of motifs unique to the LPLAT enzymes. These motifs likely represent regions of the LPLAT protein that are essential to the structure, stability or activity of the protein and these motifs are useful as diagnostic tools for the rapid identification of novel LPLAT genes.

A variety of LPLAT motifs have been proposed, with slight variation based on the specific species that are included in analyzed alignments. For example, Lewin, T. W. et al. (*Biochemistry*, 38:5764-5771 (1999) and Yamashita et al., (*Biochim, Biophys. Acta*, 1771:1202-1215 (2007)) proposed the following 1-acyl-sn-glycerol-3-phosphate acyltransferase [("LPAAT"] family motifs to be important for LPLAT activity, based on alignment of sequences from bacteria, yeast, nematodes and mammals: NHxxxxD (SEQ ID NO:38), GxxFI-[D/R]-R (SEQ ID NO:65), EGTR (SEQ ID NO:39) and either [V/I]-[P/X]-[I/V/L]-[I/V]-P-[V/I] (SEQ ID NO:66) or IVPIVM (SEQ ID NO:67). The NHxxxxD and EGTR motifs are present in MaLPAAT1 (SEQ ID NO:2), but the other motifs are not. Based on the presence of these motifs, MaLPAAT1 (SEQ ID NO:2) is expected to have LPAAT activity.

Alternatively, any of the instant LPAAT sequences or portions thereof may be hybridization reagents for the identification of homologs. The basic components of a nucleic acid hybridization test include a probe, a sample suspected of containing the gene or gene fragment of interest and a specific hybridization method. Probes are typically single-stranded nucleic acid sequences that are complementary to the nucleic acid sequences to be detected. Probes are hybridizable to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added, such as guanidinium chloride, guanidinium thiocyanate, sodium thiocyanate, lithium tetrachloroacetate, sodium perchlorate, rubidium tetrachloroacetate, potassium iodide or cesium trifluoroacetate. If desired, one can add formamide to the hybridization mixture, typically 30-50% (v/v) ["by volume"].

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol ["weight by volume"] glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Any of the LPAAT nucleic acid fragments or any identified homologs may be used to isolate genes encoding homologous proteins from the same or other bacterial, algal, fungal, oomycete, yeast, stramenopiles, euglenoid, plant or animal species. Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies such as polymerase chain reaction ["PCR"] (U.S. Pat. No.4,683,202); ligase chain reaction ["LCR"] (Tabor, S. et al., *Proc. Natl. Acad. Sci. U.S.A.*, 82:1074 (1985)); or strand displacement amplification ["SDA"] (Walker, et al., *Proc. Natl. Acad. Sci. U.S.A.*, 89:392 (1992)); and, 3) methods of library construction and screening by complementation.

For example, genes encoding similar proteins or polypeptides to the LPAATs described herein could be isolated directly by using all or a portion of the nucleic acid fragments as DNA hybridization probes to screen libraries from any desired organism using well known methods. Specific oligonucleotide probes based upon the nucleic acid sequences can be designed and synthesized by methods known in the art (Maniatis, supra). Moreover, the entire sequences can be used directly to synthesize DNA probes by methods known to the skilled artisan, such as random primers DNA labeling, nick translation or end-labeling techniques, or RNA probes using available in vitro transcription systems. In addition, specific primers can be designed and used to amplify a part of or the full length of the LPAAT sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the LPAAT sequences may be used in PCR protocols to amplify longer nucleic acid fragments encoding homologous genes from DNA or RNA. PCR may also be performed on a library of cloned nucleic acid fragments wherein the sequence of one primer is derived from the disclosed nucleic acid fragments. The sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *Proc. Natl Acad. Sci. U.S.A.*, 85:8998 (1988)) to generate cDNAs by using PCR to amplify copies of the region between a single point in the transcript and the 3' or 5' end. Primers oriented in the 3' and 5' directions can be designed from the disclosed sequences. Using commercially available 3' RACE or 5' RACE systems (e.g., Gibco/BRL, Gaithersburg, Md.), specific 3' or 5' cDNA fragments can be isolated (Ohara et al., *Proc. Natl Acad. Sci. U.S.A.*, 86:5673 (1989); Loh et al., *Science*, 243:217 (1989)).

Alternately, any of the LPAAT nucleic acid fragments described herein (or any homologs identified thereof) may be used for creation of new and improved LPLATs. As is well known in the art, in vitro mutagenesis and selection, chemical mutagenesis, "gene shuffling" methods or other means can be employed to obtain mutations of naturally occurring acyltransferase genes. Furthermore, improved LPAATs may be synthesized by domain swapping, wherein a functional domain from any of the LPAAT nucleic acid fragments described herein is exchanged with a functional domain in an alternate LPLAT gene to thereby result in a novel protein.

Based on any of these well-known methods just discussed, it would be possible to identify and/or isolate LPLAT gene homologs in any preferred eukaryotic organism of choice. The activity of any putative LPAAT gene can readily be confirmed by expression of the gene within a LC-PUFA-producing host organism, since the $C_{18}$ to $C_{20}$ elongation and/or Δ4 desaturation are increased relative to those within an organism lacking the LPAAT transgene.

Methods useful for manipulating biochemical pathways are well known to those skilled in the art. It is expected that introduction of chimeric genes encoding the LPAATs described herein (i.e., MaLPAAT1, MaLPAAT1S or other mutant enzymes, codon-optimized enzymes or homologs thereof, under the control of the appropriate promoters, will be useful for manipulating LC-PUFA biosynthesis in various host cells.

It has been previously hypothesized that LPCATs could be important in the accumulation of EPA in the TAG fraction of *Yarrowia lipolytica* (U.S. Pat. Appl. Pub. No. 2006-0115881-A1). As described therein, this hypothesis was based on the following studies: 1) Stymne S. and A. K. Stobart (*Biochem J.* 223(2):305-14(1984)), who hypothesized that the exchange between the acyl-CoA pool and PC pool may be attributed to the forward and backward reaction of LPCAT; 2) Domergue, F. et al. (*J. Bio. Chem* 278:35115 (2003)), who suggested that accumulation of GLA at the sn-2 position of PC and the inability to efficiently synthesize ARA in yeast was a result of the elongation step involved in PUFA biosynthesis occurring within the acyl-CoA pool, while Δ5 and Δ6 desaturation steps occurred predominantly at the sn-2 position of PC; 3) Abbadi, A. et al. (*The Plant Cell*, 16:2734-2748 (2004)), who suggested that LPCAT plays a critical role in the successful reconstitution of a Δ6 desaturase/Δ6 elongase pathway, based on analysis on the constraints of PUFA accumulation in transgenic oilseed plants; and, 4) Intl. App. Pub. No. WO 2004/076617 A2 (Renz, A. et al.), who provided a gene encoding LPCAT from *Caenorhabditis elegans* (T06E8.1) that substantially improved the efficiency of elongation in a genetically introduced Δ6 desaturase/Δ6 elongase pathway in *S. cerevisiae* fed with exogenous fatty acid substrates suitable for Δ6 elongation. Renz, A. et al. concluded that LPCAT allowed efficient and continuous exchange of the newly synthesized fatty acids between phospholipids and the acyl-CoA pool, since desaturases catalyze the introduction of double bonds in PC-coupled fatty acids while elongases exclusively catalyze the elongation of CoA esterified fatty acids (acyl-CoAs).

Herein, it is demonstrated that LPAAT is indeed important in the accumulation of EPA and DHA in the TAG fraction of *Yarrowia lipolytica*. Surprisingly, it was found that over-expression of MaLPAAT1S can result in an improvement in both the Δ9 elongase conversion efficiency and Δ4 desaturase conversion efficiency. As previously defined, conversion efficiency is a term that refers to the efficiency by which a particular enzyme, such as a Δ4 desaturase or Δ9 elongase, can convert substrate to product. Thus, improvement in Δ9 elongase and/or Δ4 desaturase conversion efficiency in a strain engineered to produce DHA was demonstrated to result in increased EPA % TFAs, DHA % TFAs and the ratio of DHA % TFAs to DPA % TFAs.

PUFA desaturations occur on phospholipids, while fatty acid elongations occur on acyl-CoAs. Based on previous studies, it was therefore expected that LPLAT over-expression would result in improved desaturations due to improved substrate availability in phospholipids, while expression of LPLATs was not expected to result in improved elongations that require improved substrate availability in the CoA pool.

Despite these assumptions, Example 6 demonstrates that MaLPAAT1S expression did not improve the conversion efficiency of all desaturations in strains of *Yarrowia* producing DHA, in a comparable manner. Specifically, the conversion efficiency of Δ4 desaturase was selectively improved (118% improvement with respect to the control), while similar improvements were not found in Δ8, Δ5 or Δ17 desaturations. It is hypothesized that Δ4 desaturase was therefore limiting as a result of limited availability of the DPA substrate in phospholipids.

Additionally, Example 6 demonstrates that MaLPAAT1S expression improved the Δ9 elongase conversion efficiency in strains of *Yarrowia* producing DHA (104% improvement with respect to the control). Surprisingly, however, MaLPAAT1S did not also result in a comparable improvement in the efficiency of the $C_{20/22}$ elongation of EPA to DPA.

On the basis of the above discussion, methods for improving either $C_{18}$ to $C_{20}$ elongation conversion efficiency or $\Delta 4$ desaturation conversion efficiency in a LC-PUFA-producing recombinant oleaginous microbial host cell are described in Applicant's Assignee's co-filed U.S. Patent Application No. 61,XXXXXX.

Based on the above improvements, one of skill in the art will appreciate the value of expressing a LPLAT, such as MaLPAAT1 or MaLPAAT1S or other mutant enzymes, codon-optimized enzymes or homologs thereof, in a recombinant host cell that is producing LC-PUFAs, such EDA, DGLA, ARA, DTA, DPAn-6, ETrA, ETA, EPA, DPA and DHA, if it is desirable to optimize the production of these fatty acids.

In alternative embodiments, it may be useful to disrupt a host organism's native LPAAT, based on the complete sequences described herein, the complement of those complete sequences, substantial portions of those sequences, codon-optimized desaturases derived therefrom and those sequences that are substantially homologous thereto.

It is necessary to create and introduce a recombinant construct comprising an open reading frame encoding an LPLAT (i.e., MaLPAAT, MaLPAAT1S or other mutant enzymes, codon-optimized enzymes or homologs thereof into a suitable host cell. One of skill in the art is aware of standard resource materials that describe: 1) specific conditions and procedures for construction, manipulation and isolation of macromolecules, such as DNA molecules, plasmids, etc.; 2) generation of recombinant DNA fragments and recombinant expression constructs; and, 3) screening and isolating of clones. See, Sambrook, J., Fritsch, E. F. and Maniatis, T., Molecular Cloning: A Laboratory Manual, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience, Hoboken, N.J. (1987).

In general, the choice of sequences included in the construct depends on the desired expression products, the nature of the host cell and the proposed means of separating transformed cells versus non-transformed cells. The skilled artisan is aware of the genetic elements that must be present on the plasmid vector to successfully transform, select and propagate host cells containing the chimeric gene. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation, i.e., a promoter, the gene coding sequence, and a region 3' of the DNA fragment that controls transcriptional termination, i.e., a terminator. It is most preferred when both control regions are derived from genes from the transformed host cell, although they need not be derived from genes native to the production host.

Transcription initiation control regions or promoters useful for driving expression of heterologous genes or portions of them in the desired host cell are numerous and well known. These control regions may comprise a promoter, enhancer, silencer, intron sequences, 3' UTR and/or 5' UTR regions, and protein and/or RNA stabilizing elements. Such elements may vary in their strength and specificity. Virtually any promoter, i.e., native, synthetic, or chimeric, capable of directing expression of these genes in the selected host cell is suitable, although transcriptional and translational regions from the host species are particularly useful. Expression in a host cell can occur in an induced or constitutive fashion. Induced expression occurs by inducing the activity of a regulatable promoter operably linked to the LPLAT gene of interest, while constitutive expression occurs by the use of a constitutive promoter.

3' non-coding sequences encoding transcription termination regions may be provided in a recombinant construct and may be from the 3' region of the gene from which the initiation region was obtained or from a different gene. A large number of termination regions are known and function satisfactorily in a variety of hosts when utilized in both the same and different genera and species from which they were derived. Termination regions may also be derived from various genes native to the preferred hosts. The termination region is usually selected more for convenience rather than for any particular property.

Particularly useful termination regions for use in yeast are derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. The 3'-region can also be synthetic, as one of skill in the art can utilize available information to design and synthesize a 3'-region sequence that functions as a transcription terminator. A termination region may be unnecessary, but is highly preferred.

The vector may also comprise a selectable and/or scorable marker, in addition to the regulatory elements described above. Preferably, the marker gene is an antibiotic resistance gene such that treating cells with the antibiotic results in growth inhibition, or death, of untransformed cells and uninhibited growth of transformed cells. For selection of yeast transformants, any marker that functions in yeast is useful with resistance to kanamycin, hygromycin and the amino glycoside G418 and the ability to grow on media lacking uracil, lysine, histine or leucine being particularly useful.

Merely inserting a gene (e.g., encoding a LPLAT such as MaLPAAT1, MaLPAAT1S or other mutant enzymes, codon-optimized enzymes or homologs thereof) into a cloning vector does not ensure its expression at the desired rate, concentration, amount, etc. In response to the need for a high expression rate, many specialized expression vectors have been created by manipulating a number of different genetic elements that control transcription, RNA stability, translation, protein stability and location, oxygen limitation, and secretion from the host cell. Some of the manipulated features include: the nature of the relevant transcriptional promoter and terminator sequences, the number of copies of the cloned gene and whether the gene is plasmid-borne or integrated into the genome of the host cell, the final cellular location of the synthesized protein, the efficiency of translation and correct folding of the protein in the host organism, the intrinsic stability of the mRNA and protein of the cloned gene within the host cell and the codon usage within the cloned gene, such that its frequency approaches the frequency of preferred codon usage of the host cell. Each of these may be used in the methods and host cells described herein to further optimize expression of LPLAT genes.

For example, LPLAT expression can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Alternately, additional copies of the LPLAT genes may be introduced into the recombinant host cells to thereby increase LC-PUFA production and accumulation, either by cloning additional copies of genes within a single expression construct or by introducing additional copies into the host cell by increasing the plasmid copy number or by multiple integration of the cloned gene into the genome.

After a recombinant construct is created comprising at least one chimeric gene comprising a promoter, a LPLAT open reading frame ["ORF"] and a terminator, it is placed in a plasmid vector capable of autonomous replication in the host cell or is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When two or more genes are expressed from separate replicating vectors, each vector may have a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene(s) of interest may be introduced into a host cell by any standard technique. These techniques include transformation, e.g., lithium acetate transformation (*Methods in Enzymology*, 194:186-187 (1991)), biolistic impact, electroporation, microinjection, vacuum filtration or any other method that introduces the gene of interest into the host cell.

For convenience, a host cell that has been manipulated by any method to take up a DNA sequence, for example, in an expression cassette, is referred to herein as "transformed" or "recombinant" or "transformant". The transformed host will have at least one copy of the expression construct and may have two or more, depending upon whether the gene is integrated into the genome, amplified, or is present on an extrachromosomal element having multiple copy numbers.

The transformed host cell can be identified by selection for a marker contained on the introduced construct. Alternatively, a separate marker construct may be co-transformed with the desired construct, as many transformation techniques introduce many DNA molecules into host cells.

Typically, transformed hosts are selected for their ability to grow on selective media, which may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. Additional selection techniques are described in U.S. Pat. Nos. 7,238,482 and 7,259,255.

Following transformation, substrates suitable for LPLATs (and, optionally other LC-PUFA enzymes that are co-expressed within the host cell) may be produced by the host either naturally or transgenically, or they may be provided exogenously.

Regardless of the selected host or expression construct, multiple transformants must be screened to obtain a strain displaying the desired expression level and pattern. For example, Juretzek et al. (*Yeast*, 18:97-113 (2001)) note that the stability of an integrated DNA fragment in *Yarrowia lipolytica* is dependent on the individual transformants, the recipient strain and the targeting platform used. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618(1-2):133-145 (1993)), Western analysis of protein expression, phenotypic analysis or GC analysis of the PUFA products.

A variety of eukaryotic organisms are suitable as host, to thereby yield a transformant comprising a LPAAT as described herein, including bacteria, yeast, algae, stramenopile, oomycete, euglenoid and/or fungus. This is contemplated because transcription, translation and the protein biosynthetic apparatus is highly conserved. Thus, suitable hosts may include those that grow on a variety of feedstocks, including simple or complex carbohydrates, fatty acids, organic acids, oils, glycerols and alcohols, and/or hydrocarbons over a wide range of temperature and pH values.

Preferred microbial hosts are oleaginous organisms. These oleaginous organisms are naturally capable of oil synthesis and accumulation, wherein the total oil content can comprise greater than about 25% of the dry cell weight, more preferably greater than about 30% of the dry cell weight, and most preferably greater than about 40% of the dry cell weight. Various bacteria, algae, euglenoids, moss, fungi, yeast and stramenopiles are naturally classified as oleaginous. In alternate embodiments, a non-oleaginous organism can be genetically modified to become oleaginous, e.g., yeast such as *Saccharomyces cerevisiae*.

In more preferred embodiments, the microbial host cells are oleaginous yeast. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*). Most preferred is the oleaginous yeast *Yarrowia lipolytica*; and, in a further embodiment, most preferred are the *Y. lipolytica* strains designated as ATCC #76982, ATCC #20362, ATCC #8862, ATCC #18944 and/or LGAM S(7)1 (Papanikolaou S., and Aggelis G., *Bioresour. Technol.*, 82(1):43-9 (2002)).

Most preferably, the host organism will be capable of producing LC-PUFAs, comprising at least one of the biosynthetic pathways described below (although this pathway can be native to the host cell or can be genetically engineered), in addition to being oleaginous.

The metabolic process wherein oleic acid is converted to LC-PUFAs involves elongation of the carbon chain through the addition of carbon atoms and desaturation of the molecule through the addition of double bonds. This requires a series of special desaturation and elongation enzymes present in the endoplasmic reticulum membrane. However, as seen in FIG. 1 and as described below, multiple alternate pathways exist for LC-PUFA production.

Specifically, FIG. 1 depicts the pathways described below. All pathways require the initial conversion of oleic acid to linoleic acid ["LA"], the first of the ω-6 fatty acids, by a Δ12 desaturase. Then, using the "Δ9 elongase/Δ8 desaturase pathway" and LA as substrate, long-chain ω-6 fatty acids are formed as follows: 1) LA is converted to eicosadienoic acid ["EDA"] by a Δ9 elongase; 2) EDA is converted to dihomo- γ-linolenic acid ["DGLA"] by a Δ8 desaturase; 3) DGLA is converted to arachidonic acid ["ARA"] by a Δ5 desaturase; 4) ARA is converted to docosatetraenoic acid ["DTA"] by a $C_{20/22}$ elongase; and, 5) DTA is converted to docosapentaenoic acid ["DPAn-6"] by a Δ4 desaturase.

The "Δ9 elongase/Δ8 desaturase pathway" can also use α-linolenic acid ["ALA"] as substrate to produce long-chain ω-3 fatty acids as follows: 1) LA is converted to ALA, the first of the ω-3 fatty acids, by a Δ15 desaturase; 2) ALA is converted to eicosatrienoic acid ["ETrA"] by a Δ9 elongase; 3) ETrA is converted to eicosatetraenoic acid ["ETA"] by a Δ8 desaturase; 4) ETA is converted to eicosapentaenoic acid ["EPA"] by a Δ5 desaturase; 5) EPA is converted to docosapentaenoic acid ["DPA"] by a $C_{20/22}$ elongase; and, 6) DPA is converted to docosahexaenoic acid ["DHA"] by a Δ4 desaturase. Optionally, ω-6 fatty acids may be converted to ω-3 fatty acids. For example, ETA and EPA are produced from DGLA and ARA, respectively, by Δ17 desaturase activity.

Alternate pathways for the biosynthesis of ω-3/ω-6 fatty acids utilize a Δ6 desaturase and $C_{18/20}$ elongase, that is, the "Δ6 desaturase/Δ6 elongase pathway". More specifically, LA and ALA may be converted to GLA and stearidonic acid ["STA"], respectively, by a Δ6 desaturase; then, a Δ6 elongase converts GLA to DGLA and/or STA to ETA. Downstream PUFAs are subsequently formed as described above.

The LC-PUFA-producing oleaginous host cell will preferably be capable of producing at least about 2-5% LC-PUFAs in the total lipids of the recombinant host cell, more preferably at least about 5-15% LC-PUFAs in the total lipids, more preferably at least about 15-35% LC-PUFAs in the total lipids, more preferably at least about 35-50% LC-PUFAs in the total lipids, more preferably at least about 50-65% LC-PUFAs in the total lipids and most preferably at least about 65-75% LC-PUFAs in the total lipids. The structural form of the LC-PUFAs is not limiting; thus, for example, the EPA or DHA may exist in the total lipids as free fatty acids or in esterified forms such as acylglycerols, phospholipids, sulfolipids or glycolipids.

A variety of organisms naturally produce LC-PUFAs. For example, ARA, EPA and/or DHA is produced via *Cyclotella* sp., *Crypthecodinium* sp., *Mortierella* sp., *Nitzschia* sp., *Pythium, Thraustochytrium* sp. and *Schizochytrium* sp. Thus, for example, transformation of *Mortierella alpina*, which is commercially used for production of ARA, with MaLPAAT1 or MaLPAAT1S under the control of inducible or regulated promoters could yield a transformant capable of synthesizing increased quantities of ARA. The method of transformation of *M. alpina* is described by Mackenzie et al. (*Appl. Environ. Microbiol.*, 66:4655 (2000)). Similarly, methods for transformation of Thraustochytriales microorganisms (e.g., *Thraustochytrium, Schizochytrium*) are disclosed in U.S. Pat. No. 7,001,772.

Alternately, the preferred host cell can be engineered to produce LC-PUFAs. For example, specific teachings applicable for engineering ARA, EPA and DHA production in the oleaginous yeast, *Yarrowia lipolytica*, are provided in U.S. Pat. Appl. Pub. No. 2006-0094092-A1, U.S. Pat. Appl. Pub. No. 2006-0115881-A1, U.S. Pat. Appl. Pub. No. 2009-0093543-A1 and U.S. Pat. Appl. Pub. No. 2006-0110806-A1, respectively. These references also describe the preferred method of expressing genes in *Y. lipolytica* by integration of a linear DNA fragment into the genome of the host, preferred promoters, termination regions, integration loci and disruptions, and preferred selection methods when using this particular host species.

One of skill in the art would be able to use the cited teachings in U.S. Pat. Appl. Pub. Nos. 2006-0094092-A1, 2006-0115881-A1, 2009-0093543-A1 and 2006-0110806-A1 to recombinantly engineer other host cells for LC-PUFA production.

In alternate embodiments, suitable hosts may be plants or other animals. For example, oilseed plants that can be readily engineered for LC-PUFA production include: soybean (*Glycine* and *Soja* sp.), corn (*Zea mays*), flax (*Linum* sp.), rapeseed (*Brassica* sp.), primrose, canola, maize, cotton, safflower (*Carthamus* sp.) and sunflower (*Helianthus* sp.). See, for example, U.S. Pat. Appl. Pub. No. 2007-0237876 A1. One of skill in the art will appreciate the value of co-expressing a LPLAT (i.e., MaLPAAT1, MaLPAAT1S or other mutant enzymes, codon-optimized enzymes or homologs thereof), with genes encoding a LC-PUFA biosynthetic pathway, based on the disclosure herein.

The transformed recombinant host cell is grown under conditions that optimize expression of chimeric genes (e.g., encoding LPLATs, etc.) and preferably produce the greatest and the most economical yield of LC-PUFA(s). In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest.

Microorganisms of interest, such as oleaginous yeast, are generally grown in a complex media such as yeast extract-peptone-dextrose broth (YPD) or a defined minimal media that lacks a component necessary for growth and thereby forces selection of the desired expression cassettes (e.g., Yeast Nitrogen Base (DIFCO Laboratories, Detroit, Mich.)).

Fermentation media for the methods and host cells described herein must contain a suitable carbon source, such as are taught in U.S. Pat. No. 7,238,482. Although it is contemplated that the source of carbon utilized may encompass a wide variety of carbon-containing sources, preferred carbon sources are sugars, glycerol and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of LC-PUFA(s)-producing host cells and the promotion of the enzymatic pathways for LC-PUFA production. Particular attention is given to several metal ions, such as $Fe^{+2}$, $Cu^{+2}$, $Mn^{+2}$, $Co^{+2}$, $Zn^{+2}$ and $Mg^{+2}$, that promote synthesis of lipids and PUFAs (Nakahara, T. et al., *Ind. Appl. Single Cell Oils*, D. J. Kyle and R. Colin, eds. pp 61-97 (1992)).

Preferred growth media for the methods and host cells described herein are common commercially prepared media, such as Yeast Nitrogen Base (DIFCO Laboratories, Detroit, Mich.). Other defined or synthetic growth media may also be used and the appropriate medium for growth of *Yarrowia lipolytica* will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of LC-PUFAs in oleaginous yeast cells requires a two-stage process, since the metabolic state must be "balanced" between growth and synthesis/storage of fats. Thus, most preferably, a two-stage fermentation process is necessary for the production of LC-PUFAs in *Yarrowia lipolytica*. This approach is described in U.S. Pat. No. 7,238,482, as are various suitable fermentation process designs (i.e., batch, fed-batch and continuous) and considerations during growth.

In some aspects, the primary product is oleaginous yeast biomass. As such, isolation and purification of the LC-PUFA-containing oils from the biomass may not be necessary (i.e., wherein the whole cell biomass is the product).

However, certain end uses and/or product forms may require partial and/or complete isolation/purification of the LC-PUFA-containing oil from the biomass, to result in partially purified biomass, purified oil, and/or purified LC-PUFAs. Fatty acids, including PUFAs, may be found in the host microorganisms as free fatty acids or in esterified forms such as acylglycerols, phospholipids, sulfolipids or glycolipids. These fatty acids may be extracted from the host cells through a variety of means well-known in the art. One review of extraction techniques, quality analysis and acceptability standards for yeast lipids is that of Z. Jacobs (*Critical Reviews in Biotechnology*, 12(5/6):463-491 (1992)). A brief review of downstream processing is also available by A. Singh and O. Ward (*Adv. Appl. Microbiol.*, 45:271-312 (1997)).

In general, means for the purification of fatty acids (including LC-PUFAs) may include extraction (e.g., U.S. Pat. Nos. 6,797,303 and 5,648,564) with organic solvents, sonication, supercritical fluid extraction (e.g., using carbon dioxide), saponification and physical means such as presses, or combinations thereof. See U.S. Pat. No. 7,238,482.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and, 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

*E. coli* TOP10 cells were obtained from Invitrogen (Carlsbad, Calif.). *E. coli* (XL1-Blue) competent cells were purchased from the Stratagene Company (San Diego, Calif.). *E. coil* strains were typically grown at 37° C. on Luria Bertani (LB) plates.

General molecular cloning was performed according to standard methods (Sambrook et al., supra). Oligonucleotides were synthesized by Sigma-Genosys (Spring, Tex.). PCR products were cloned into Promega's pGEM-T-easy vector (Madison, Wis.).

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR, Inc., (Madison, Wis.).

The meaning of abbreviations is as follows: "sec" means second(s), "min" means minute(s), "h" means hour(s), "d" means day(s), "µl" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Nomenclature for Expression Cassettes

The structure of an expression cassette will be represented by a simple notation system of "X::Y::Z", wherein X describes the promoter fragment, Y describes the gene fragment, and Z describes the terminator fragment, which are all operably linked to one another.

Transformation and Cultivation of *Yarrowia lipolytica*

*Yarrowia lipolytica* strain ATCC #20362 was purchased from the American Type Culture Collection (Rockville, Md.). *Yarrowia lipolytica* strains were routinely grown at 28-30° C. in several media (e.g., YPD agar medium, Basic Minimal Media ["MM"], Minimal Media+5-Fluoroorotic Acid ["MM+5-FOA"], High Glucose Media ["HGM"] and Fermentation medium ["FM"]), as described in U.S. Pat. Appl. Pub. No. 2009-0093543-A1.

Transformation of *Y. lipolytica* was performed as described in U.S. Pat. Appl. Pub. No. 2009-0093543-A1.

Fatty Acid Analysis of *Yarrowia lipolytica*

For fatty acid ["FA"] analysis, cells were collected by centrifugation and lipids were extracted as described in Bligh, E. G. & Dyer, W. J. (*Can. J. Biochem. Physiol.*, 37:911-917 (1959)). Fatty acid methyl esters ["FAMEs"] were prepared by transesterification of the lipid extract with sodium methoxide (Roughan, G., and Nishida I. *Arch Biochem Biophys.*, 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* cells (0.5 mL culture) were harvested, washed once in distilled water, and dried under vacuum in a Speed-Vac for 5-10 min. Sodium methoxide (100 µl of 1%) and a known amount of C15:0 triacylglycerol (C15:0 TAG; Cat. No. T-145, Nu-Check Prep, Elysian, Minn.) was added to the sample, and then the sample was vortexed and rocked for 30 min at 50° C. After adding 3 drops of 1 M NaCl and 400 µl hexane, the sample was vortexed and spun. The upper layer was removed and analyzed by GC.

FAME peaks recorded via GC analysis were identified by their retention times, when compared to that of known fatty acids, and quantitated by comparing the FAME peak areas with that of the internal standard (C15:0 TAG) of known amount. Thus, the approximate amount (µg) of any fatty acid FAME ["µg FAME"] is calculated according to the formula: (area of the FAME peak for the specified fatty acid/area of the standard FAME peak)*(µg of the standard C15:0 TAG), while the amount (µg) of any fatty acid ["µg FA"] is calculated according to the formula: (area of the FAME peak for the specified fatty acid/area of the standard FAME peak)*(µg of the standard C15:0 TAG)*0.9503, since 1 µg of C15:0 TAG is equal to 0.9503 µg fatty acids. Note that the 0.9503 conversion factor is an approximation of the value determined for most fatty acids, which range between 0.95 and 0.96.

The lipid profile, summarizing the amount of each individual fatty acid as a weight percent of TFAs, was determined by dividing the individual FAME peak area by the sum of all FAME peak areas and multiplying by 100.

Example 1

Construction of *Mortierella alpina* cDNA

The construction of cDNA from *Mortierella alpina* strain ATCC #16266 using the BD-Clontech Creator Smart® cDNA library kit (Mississauga, ON, Canada) is described in U.S. Pat. No. 7,189,559, although the newly created cDNA was not subjected to digestion with SfiI for the purposes herein.

Example 2

Identification of a Partial Internal Lysophosphatidic Acid Acyltransferase Sequence from *Mortierella alpina*

The present Example describes the identification of an internal 211 bp cDNA fragment (SEQ ID NO:5) of a *M. alpina* lysophosphatidic acid acyltransferase ["LPAAT"] using degenerate oligonucleotides and PCR.

Based on an amino acid alignment of fungal LPAAT homologs, 5' degenerate oligonucleotide primers MaLP1_5-1 (SEQ ID NO:6) and MaLP2_5_1 (SEQ ID NO:7) and 3' degenerate oligonucleotide primers MaLP1_3-2 (SEQ ID NO:8) and MaLP2_3-2 (SEQ ID NO:9) were synthesized.

The cDNA (2 µl) described in Example 1 was used as the template for PCR amplification with all combinations of the degenerate oligonucleotide primers described above. In addition to 1 µl each of 100 µM 5' and 3' degenerate primers, 1 µL of PCR nucleotide mix (10 mM, Promega, Madison, Wis.), 5 µL of 10× PCR buffer (Invitrogen), 1.5 µL of MgCl$_2$ (50 mM, Invitrogen), 0.5 µL of Taq polymerase (Invitrogen) and water to 50 µL was added to each of the 4 PCR reactions. Amplification was carried out as follows: initial denaturation at 94° C. for 3 min, followed by 35 cycles of denaturation at 94° C. for 45 sec, annealing at 50° C. for 45 sec and elongation at 72° C. for 1 min. A final elongation cycle at 72° C. for 7 min was carried out, followed by reaction termination at 4° C. The PCR products were separated by agarose gel electrophoresis and each DNA band was purified using the Zymoclean™ Gel DNA Recovery Kit (Zymo Research, Orange, Calif.) following the manufacturer's protocol. The resulting DNA was cloned into the pGEM®-T Easy Vector (Promega) following the manufacturer's protocol. Multiple clones were sequenced using T7 (SEQ ID NO:10) and M13-28Rev (SEQ ID NO:11) primers. A consensus sequence combining all of the individual sequences obtained (after removing sequence resulting from the degenerate oligonucleotides themselves) is shown in SEQ ID NO:5. This sequence was determined to be an internal cDNA fragment of a *M. alpina* lysophosphatidic acid acyltransferase, designated herein as "MaLPAAT1".

Example 3

Identification of the 3' End Sequence of a Lysophosphatidic Acid Acyltransferase from *Mortierella alpina*

The present Example describes the identification of the 3' end sequence of the *M. alpina* lysophosphatidic acid acyltransferase ["MaLPAAT1"] identified in Example 2, via PCR.

Oligonucleotide primers MaLP3R1-1 (SEQ ID NO:12) and MaLP3R1-2 (SEQ ID NO:13) were designed for PCR of the 3' end of MaLPAAT1, based on the internal sequence fragment obtained in Example 2 (SEQ ID NO:5). These two primers were alternately paired with the CDS III/3' PCR Primer (SEQ ID NO:14), used in creation of the library (BD-Clontech, Mississauga, ON, Canada) for the PCR. Specifically, 2 separate reactions were prepared comprising either MaLP3R1-1 (SEQ ID NO:12) and CDS III/3' PCR Primer (SEQ ID NO:14) or MaLP3R1-2 (SEQ ID NO:13) and CDS III/3' PCR Primer (SEQ ID NO:14).

Thus, each PCR reaction contained: 2 µl of cDNA (Example 1), 1 µl of 100 µM of each primer, 1 µL of PCR nucleotide mix (10 mM, Promega), 5 µL of 10× PCR buffer (Invitrogen), 1.5 µL of MgCl$_2$ (50 mM, Invitrogen), 0.5 µL of Taq polymerase (Invitrogen) and water to 50 µL. Amplification, purification of each PCR product, cloning and sequencing using T7 (SEQ ID NO:10) and M13-28Rev (SEQ ID NO:11) primers was carried out according to the conditions described in Example 2. A 669 bp consensus sequence for the 3' end of MaLPAAT1 combining all of the individual sequences obtained (after removing sequence resulting from the oligonucleotides themselves) is shown in SEQ ID NO:15.

Example 4

Identification of the 5' End Sequence of a Lysophosphatidic Acid Acyltransferase from *Mortierella alpina*

The present Example describes the identification of the 5' end sequence of the *M. alpina* lysophosphatidic acid acyltransferase ["MaLPAAT1"] identified in Example 2, using genome walking.

Preparation of Genomic DNA from *Mortierella alpina*

Genomic DNA was isolated from *Mortierella alpina* (ATCC #16266) using a QiaPrep Spin Miniprep Kit (Qiagen, Catalog #627106). Cells grown on a YPD agar plate (2% Bacto-yeast extract, 3% Bactor-peptone, 2% glucose, 2.5% bacto-agar) were scraped off and resuspended in 1.2 mL of kit buffer P1. The resuspended cells were placed in two 2.0 mL screw cap tubes, each containing 0.6 mL glass beads (0.5 mm diameter). The cells were homogenized at the HOMOGENIZE setting on a Biospec (Bartlesville, Okla.) mini bead beater for 2 min. The tubes were then centrifuged at 14,000 rpm in an Eppendorf microfuge for 2 min. The supernatant (0.75 mL) was transferred to three 1.5 mL microfuge tubes. Equal volumes of kit buffer P2 were added to each tube. After mixing the tubes by inversion three times, 0.35 mL of buffer N3 was added to each tube. The contents of each tube were again mixed by inversion for a total of five times. The mixture was centrifuged at 14,000 rpm in an Eppendorf microfuge for 5 min. The supernatant from each tube was transferred individually into 3 separate kit spin columns. The columns were then subjected to the following steps: centrifugation (1 min at 14,000 rpm), wash once with buffer PE, centrifugation (1 min at 14,000 rpm), and then a final centrifugation (1 min at 14,000 rpm). Buffer EB (50 µl) was added to each column and let stand for 1 min. The genomic DNA was then eluted by centrifugation at 14,000 rpm for 1 min.

Genome Walking

A Clontech Universal GenomeWalker™ kit was used to obtain a piece of genomic DNA corresponding to the 5'-end region of MaLPAAT1. Briefly, 2.5 µg each of *M. alpina* genomic DNA was digested with DraI, EcoRV, PvuII or StuI individually, the digested DNA samples were purified using Qiagen Qiaquick PCR purification kits and eluted with 30 µl each of kit buffer EB, and the purified samples were then ligated with Genome Walker adaptor (SEQ ID NOs:16 [top strand] and 17 [bottom strand]).

Each ligation reaction mixture contained 1.9 µl of 25 µM Genome Walker adaptor, 1.6 µl 10× ligation buffer, 0.5 µl T4 DNA ligase and 4 µl of one of the purified digested genomic DNA samples. The reaction mixtures were incubated at 16° C. overnight. The reaction was terminated by incubation at 70° C. for 5 min. Then, 72 µl of 10 mM TrisHCl, 1 mM EDTA, pH 7.4 buffer was added to each ligation reaction mix.

Four separate PCR reactions were performed, each using one of the four ligation mixtures as template. The PCR reaction mixtures contained 1 µl of ligation mixture, 0.5 µl of 20 µM MaLPAT2-5-1 (SEQ ID NO:18), 1 µl of 10 µM kit primer AP1 (SEQ ID NO:19), 22.5 µl water, and 25 µl ExTaq premix Taq 2× PCR solution (TaKaRa Bio Inc., Otsu, Shiga, 520-2193, Japan). The PCR reactions were carried out for 30 cycles using the following conditions: denaturation at 94° C. for 30 sec, annealing at 55° C. for 30 sec, and elongation at 72° C. for 180 sec. A final elongation cycle at 72° C. for 7 min was carried out, followed by reaction termination at 4° C.

The products of each PCR reaction were diluted 1:50 individually and used as templates for a second round of PCR. Each reaction mixture contained 1 µl of one of the diluted PCR products as template, 0.5 µl of 20 µM MaLPAT2-5-2 (SEQ ID NO:20), 1 µl of 10 µM kit primer AP2 (SEQ ID NO:21), 22.5 µl water and 25 µl of ExTaq premix Taq 2× PCR solution (TaKaRa). PCR reactions were carried out for 30 cycles using the same thermocycler conditions described above.

A DNA fragment was obtained from the second round of PCR with the StuI digested genomic DNA template. This fragment was purified and cloned into pCR2.1-TOPO and sequenced. Sequence analysis showed that the 1947 bp fragment (SEQ ID NO:22) was the 5'-end of the *M. alpina* LPAAT1. This fragment extends beyond the start of the ORF and includes 1401 bp of the 5' untranslated region.

Separately, double-stranded cDNA of *M. alpina* was used as the template for amplification of the 5'-end of the MaLPAAT1 cDNA. In the first round of PCR amplification, the oligonucleotide primers consisted of MaLPAT2-5-1 (SEQ ID NO:18) and the generic oligonucleotide 5'-CDSIII primer (SEQ ID NO:23) from the BD-Clontech Creator™ SMART™ cDNA Library Kit. The PCR amplifications were carried out in a 50 µl total volume, comprising: 1 µl of 1:10 diluted *M. alpina* cDNA as template (Example 1), 1 µl of each primer (20 µM), 22 µl water and 25 µl ExTaq 2× premix (TaKaRa). Amplification was carried out as follows: initial denaturation at 94° C. for 90 sec, followed by 30 cycles of denaturation at 94° C. for 30 sec, annealing at 55° C. for 30 sec and elongation at 72 ° C. for 1 min. A final elongation cycle at 72° C. for 7 min was carried out.

The second round of PCR amplification used 1 µl of diluted product (1:50) from the first round PCR reaction as template. Primers consisted of a gene specific oligonucleotide, i.e., MaLPAT2-5-2 (SEQ ID NO:20) and the oligonucleotide 5'-CDSIII (SEQ ID NO:23). Amplification was conducted as described above.

The products of the second round PCR reaction were electrophoresed in 1% (w/v) agarose and appeared as a diffused band spanning the size range of ~500 bp. It was purified using the Qiagen Gel purification kit according to the manufacturer's protocol, cloned into pCR2.1-TOPO (Invitrogen), and transformed into *E. coli*. Transformants were selected on LB agar containing ampicillin (100 µg/mL).

Sequence analysis of the plasmid DNA from one transformant revealed a fragment of 502 bp (SEQ ID NO:24). This fragment extends beyond the start of the ORF and includes 156 bp of the 5' untranslated region.

Comparison of the sequences of the 1947 bp genomic fragment (SEQ ID NO:22) and the 502 bp cDNA fragment (SEQ ID NO:24) revealed the presence of a 189 bp intron (SEQ ID NO:25, corresponding to bases 1412-1600 of SEQ ID NO:22), excised from within the $4^{th}$ codon of the translated protein.

Example 5

Identification of a Full-Length Lysophosphatidic Acid Acyltransferase cDNA Sequence from *Mortierella alpina*

The present Example describes the identification of the complete cDNA sequence of the *M. alpina* lysophosphatidic acid acyltransferase ["MaLPAAT1"].

The 5' genomic sequence (SEQ ID NO:22, Example 4), the internal cDNA sequence (SEQ ID NO:5, Example 2) and the 3' cDNA sequence (SEQ ID NO:15, Example 3) were aligned using Sequencher™ (Version 4.2, Gene Codes Corporation, Ann Arbor, Mich.). The complete 2756 bp hybrid sequence is shown in SEQ ID NO:26. Bases 1-1401 of SEQ ID NO:26 correspond to the 5' untranslated region, the 'ATG' translation initiation codon is located at bases 1402-1404, the intron corresponds to bases 1412-1600 of the hybrid sequence, the 'TAG' termination codon is located at bases 2533-2535, and the remaining 221 bases of the sequence correspond to 3' untranslated region.

Oligonucleotide primers MaLP1__5NotI (SEQ ID NO:27) and MaLP1__3NotI (SEQ ID NO:28) were designed to PCR the complete MaLPAAT1 coding sequence from the cDNA. MaLP1__5NotI (SEQ ID NO:27) spans the predicted intron in the 5' genomic sequence.

The composition of the PCR reaction was as described in Example 3. Amplification, purification of the cDNA product and cloning into pGEM®-T Easy Vector was carried out according to the conditions described in Example 2.

Multiple clones were sequenced using T7 (SEQ ID NO:10) and M13-28Rev (SEQ ID NO:11) primers. The done designated as "pLF109" (SEQ ID NO:29) confirmed the coding sequence and corresponding amino acid sequence for MaLPAAT1 to be as set forth in SEQ ID NO:1 and SEQ ID NO:2, respectively.

Identity of the MaLPAAT1 sequence was confirmed by conducting BLAST (Basic Local Alignment Search Tool) searches of the MaLPAAT1 sequence for similarity to all publicly available protein sequences contained in the BLAST non-redundant "nr" protein sequences database. Specifically, SEQ ID NO:2 was compared for similarity to the "nr" database, using the BLASTP 2.2.20+ algorithm (Altschul, S. F., et al., *Nucleic Acids Res.*, 25:3389-3402 (1997) and *FEBS J.*, 272:5101-5109 (2005)) provided by the National Center for Biotechnology Information ["NCBI"].

The results of the BLAST comparison summarizing the sequence to which SEQ ID NO:2 has the most similarity are reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance. Thus, the amino acid sequence of SEQ ID NO:2 had 44% identity and 62% similarity with the hypothetical protein UM06426.1 sequence of *Ustilago maydis* 521 (GenBank Accession No. XP_762573.1), with an expectation value of 2e-59; additionally, SEQ ID NO:2 had 44% identity and 62% similarity with a 1-acylglycerol-3-phosphate O-acyltransferase from *Cryptococcus neoformans* var. *neoformans* JEC21 (GenBank Accession No. XP_567944.1), with an expectation value of 7e-59.

As several variant LPAAT-like sequences have been isolated from *Mortierella alpina*, in addition to the sequence described herein as SEQ ID NO:2, a multiple sequence alignment was performed using default parameters [gap opening penalty=10, gap extension penalty=0.05, and gap separation penalty range=8] of Vector NTI® Advance 9.1.0 AlignX program (Invitrogen Corporation, Carlsbad, Calif.). Specifically, the following additional sequences were aligned: SEQ ID NO:17 of Intl. App. Pub. No. WO 2004/087902, corresponding to SEQ ID NO:31 herein, and having 417 amino acids ["AAs"] in length; SEQ ID NO:19 of Intl. App. Pub. No. WO 2004/087902, corresponding to SEQ ID NO:33 herein, and having 389 AAs in length; SEQ ID NO:2 of Intl. App. Pub. No. WO 2008/146745, corresponding to SEQ ID NO:34 herein, and having 329 AAs in length; SEQ ID NO:4 of Intl. App. Pub. No. WO 2008/146745, corresponding to SEQ ID NO:35 herein, and having 313 AAs in length; and, SEQ ID NO:2 of U.S. Pat. No. 7,189,559, corresponding to SEQ ID NO:37 herein, and having 308 AAs in length.

As was noted above, the nucleotide sequence (SEQ ID NO:1) isolated from *Mortierella alpina*, and the encoded LPAAT (SEQ ID NO:2), designated herein as "MaLPAAT1", were previously described as SEQ ID NOs:80 and 81, respectively, in U.S. patent application Ser. No. 11/265,761, filed Nov. 2, 2005 (the priority of which is claimed herein), corresponding to U.S. Pat. Appl. Pub. No. 2006-0115881-A1 and Intl. App. Pub. No. WO 2006/052870. Accordingly, it should be clear that these sequences, SEQ ID NO:1 and SEQ ID NO:2, are entitled to a priority date that is well before the disclosure of SEQ ID NO:2 of Intl. App. Pub. No. WO 2008/146745, corresponding to SEQ ID NO:34 herein, and SEQ ID NO:4 of Intl. App. Pub. No. WO 2008/146745, corresponding to SEQ ID NO:35 herein.

The resulting alignment is shown in FIG. 2. Those amino acid residues that are conserved in all 6 of the aligned proteins are highlighted in bold text. The 1-acyl-sn-glycerol-3-phosphate acyltransferase ["LPAAT"] family motifs NHxxxxD (SEQ ID NO:38) and EGTR (SEQ ID NO:39), proposed by Lewin, T. W. et al. (*Biochemistry*, 38:5764-5771 (1999) and Yamashita et al., (*Biochim, Biophys. Acta*, 1771:1202-1215 (2007)) as important for LPLAT activity, are indicated with a double underline. The NHxxxxD motif was completely conserved in all 6 of the sequences aligned, while the EGTR motif was only partially conserved. Based on the presence of both motifs in MaLPAAT1 (SEQ ID NO:2), it was concluded that is likely a LPAAT having lysophosphatidic acid acyltransferase activity.

To analyze the percent identity between and among each of the variant LPAAT-like sequences isolated from *Mortierella alpina* (supra), the sequences were aligned using the method of Clustal W (slow, accurate, Gonnet option; Thompson et al., *Nucleic Acids Res.*, 22:4673-4680 (1994)) of the MegAlign™ program (version 8.0.2) of the LASERGENE bioinformatics computing suite (DNASTAR, Inc., Madison, Wis.). The percent identities are shown in Table 4.

TABLE 4

Percent Identity Between And Among Various LPAAT Sequences Isolated From *Mortierella alpina*

| | SEQ ID NO: 17 of WO 2004/087902 | SEQ ID NO: 19 of WO 2004/087902 | SEQ ID NO: 2 of U.S. Pat. No. 7,189,559 | SEQ ID NO: 2 of WO 2008/146745 | SEQ ID NO: 2 (MaLPAAT1) | SEQ ID NO: 4 of WO 2008/146745 |
|---|---|---|---|---|---|---|
| SEQ ID NO: 17 of WO 2004/087902 | — | 100 | 20.3 | 14.9 | 14.6 | 14.3 |
| SEQ ID NO: 19 of WO 2004/087902 | | — | 20.3 | 14.6 | 14.4 | 14.1 |
| SEQ ID NO: 2 of U.S. Pat. No. 7,189,559 | | | — | 14.9 | 15.0 | 14.7 |
| SEQ ID NO: 2 of WO 2008/146745 | | | | — | 73.2 | 73.2 |
| SEQ ID NO: 2 (MaLPAAT1) | | | | | — | 95.2 |
| SEQ ID NO: 4 of WO 2008/146745 | | | | | | — |

Example 6

Expression of a Codon-Optimized Lysophosphatidic Acid Acyltransferase Gene ("MaLPAAT1S") in *Yarrowia lipolytica*

*Yarrowia lipolytica* strain Y5037U, a Ura3– strain of Y5037 producing about 18.6% EPA, 22.8% DPA and 9.7% DHA relative to the total lipids, was used to functionally characterize the effects of overexpression of the *Mortierella alpina* LPAAT1, following its integration into the *Yarrowia* host chromosome. This was in spite of the host containing its native LPLATs, i.e., Ale1 and LPAAT1.

Construction of PY201, comprising a Codon-Optimized *Saccharomyces cerevisiae* Ale1 Gene The *Saccharomyces cerevisiae* ORF designated as "ScAle1" (SEQ ID NO:40; ORF "YOR175C"; GenBank Accession No. NP_014818; Pat. Appl. Pub. No. US-20080145867 and corresponding to Intl. App. Pub. No. WO 2008/076377; Intl. App. Pub. No. WO 2009/001315) was optimized for expression in *Yarrowia lipolytica*, by DNA 2.0 (Menlo Park, Calif.). In addition to codon optimization, 5' Pci1 and 3' Not1 cloning sites were introduced within the synthetic gene (i.e., ScAle1S; SEQ ID NO:42). None of the modifications in the ScAle1S gene changed the amino acid sequence of the encoded protein (i.e., the protein sequence encoded by the codon-optimized gene [i.e., SEQ ID NO:43] is identical to that of the wildtype protein sequence [i.e., SEQ ID NO:41]). ScAle1S was cloned into pJ201 (DNA 2.0) to result in pJ201:ScAle1S.

Figure 3A:
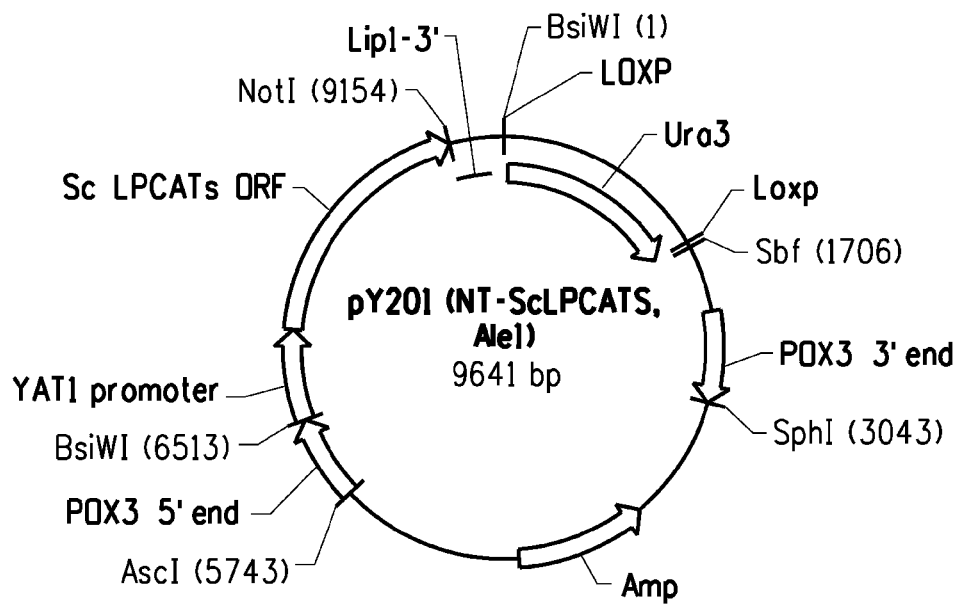
Figure 3B:
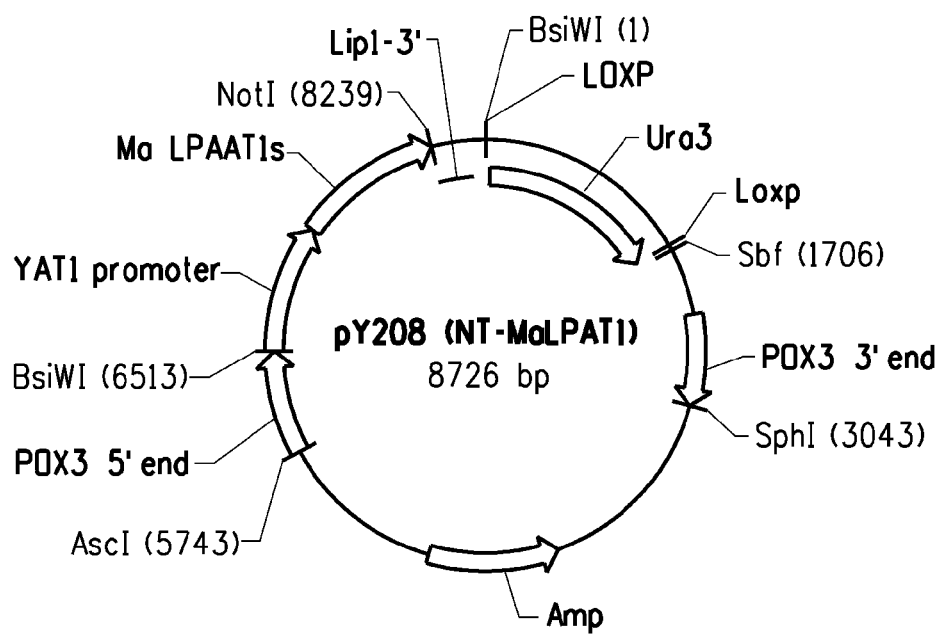

A 1863 bp Pci1/Not1 fragment comprising ScAle1S was excised from pJ201:ScAle1S and used to create pY201 (SEQ ID NO:44; Table 5; FIG. 3A). In addition to comprising a chimeric YAT1::ScAle1S::Lip1 gene, pY201 also contains a *Yarrowia lipolytica* URA3 selection marker flanked by LoxP sites for subsequent removal, if needed, by Cre recombinase-mediated recombination. Both the YAT1::ScAle1S::Lip1 chimeric gene and the URA3 gene were flanked by fragments having homology to 5' and 3' regions of the *Yarrowia lipolytica* Pox3 gene to facilitate integration by double homologous recombination, although integration into *Y. lipolytica* is known to usually occur without homologous recombination. Thus, construct pY201 thereby contained the following components:

TABLE 5

Description of Plasmid pY201 (SEQ ID NO: 44)

| RE Sites And Nucleotides Within SEQ ID NO: 44 | Description Of Fragment And Chimeric Gene Components |
|---|---|
| BsiW1/Sbf1 (1-1706 bp) | LoxP::Ura3::LoxP, comprising: LoxP sequence (SEQ ID NO: 45) *Yarrowia lipolytica* Ura3 gene (GenBank Accession No. AJ306421); LoxP sequence (SEQ ID NO: 45) |
| Sbf1/Sph1 (1706-3043 bp) | 3' portion of *Yarrowia lipolytica* POX3 Acyl-CoA oxidase 3 (GenBank Accession No. YALI0D24750g) (i.e., bp 2215-3038 in pY201) |
| Sph1/Asc1 (3043-5743 bp) | ColE1 plasmid origin of replication; Ampicillin-resistance gene ($Amp^R$) for selection in *E. coli* (i.e., bp 3598-4758 [complementary] in pY201); *E. coli* f1 origin of replication |
| AscI/BsiWI (5743-6513 bp) | 5' portion of *Yarrowia lipolytica* POX3 Acyl-CoA oxidase 3 (GenBank Accession No. YALI0D24750g) (i.e., bp 5743-6512 in pY201) |
| BsiWI/BsiWI (6514-1 bp) [a Not1 site, located between ScAle1S and Lip1 is present at bp 9154 bp] | YAT1::ScAle1S::Lip1, comprising: YAT1: *Yarrowia lipolytica* YAT1 promoter (Pat. Appl. Pub. No. US 2006/0094102-A1) (i.e., bp 6514-7291 in pY201) ScAle1S: codon-optimized Ale1 (SEQ ID NO: 42) derived from *Saccharomyces cerevisiae* YOR175C (i.e., bp 7292-9151 in pY201; labeled as "Sc LPCATs ORF" in Figure); Lip1: Lip1 terminator sequence from *Yarrowia* Lip1 gene (GenBank Accession No. Z50020) (i.e., bp 9160-9481 pY201; labeled as "Lip1-3'" in Figure) |

Construction of pY208, comprising a Codon-Optimized *Mortierella alpina* LPAAT1

The *Mortierella alpina* ORF designated as MaLPAAT1 (SEQ ID NO:1) was optimized for expression in *Yarrowia lipolytica*, by DNA 2.0 (Menlo Park, Calif.). In addition to codon optimization, 5' Pci1 and 3' Not1 cloning sites were introduced within the synthetic gene (i.e., MaLPAAT1S; SEQ ID NO:3). None of the modifications in the MaLPAAT1S gene changed the amino acid sequence of the encoded protein (i.e., the protein sequence encoded by the codon-optimized gene [i.e., SEQ ID NO:4] is identical to that of the wildtype protein sequence [i.e., SEQ ID NO:2]). MaLPAAT1S was cloned into pJ201 (DNA 2.0) to result in pJ201: MaLPAAT1S.

A 945 bp Pci1/Not1 fragment comprising MaLPAAT1S was excised from pJ201:MaLPAAT1S and used to create pY208 (SEQ ID NO:46), in a 3-way ligation with two fragments of pY201 (SEQ ID NO:44). Specifically, the MaLPAAT1 fragment was ligated with a 3530 bp Sph-NotI pY201 fragment and a 4248 bp NcoI-SphI pY201 fragment to result in pY208. The components present in pY208 (FIG. 3B; SEQ ID NO:46) are identical to those present in pY201, with the exception of the YAT1::MaLPAAT1S::Lip1 gene in pY208, instead of the YAT1::ScAle1S::Lip1 gene in pY201 (FIG. 3A).

Functional Characterization of MaLPAAT1S in DHA-Producing *Y. lipolytica* Strain Y5037U

*Yarrowia lipolytica* strain Y5037U (construction described in Example 7, infra) was individually transformed with linear SphI-AscI fragments of pY208 (YAT::MaLPAAT1S::Lip1) according to the General Methods.

The transformation mix was plated on MM agar plates and clone #6 of strain Y5037U transformed with expression vector pY208 (designated as "Y5037U::MaLPAAT1S") was selected to examine the effect of MaLPAAT1S overexpression on lipid content, fatty acid composition and conversion efficiencies. Additionally, strain Y5037 (a Ura+ strain that was parent to strain Y5037 (Ura−)) was used as a control.

More specifically, control strain Y5037 was compared to strain Y5037U::MaLPAAT1S after 2 days of growth in FM medium (Biomyx Cat. No. CM4681, Biomyx Technology, San Diego, Calif.) containing per L: 6.7 g Difco Yeast Nitrogen Base without amino acids, 5 g Yeast Extract, 6 g $KH_2PO_4$, 2 g $K_2HPO_4$, 1.5 g $MgSO_4.7H_2O$, 1.5 mg thiamine.HCl, and 20 g glucose) on a shaker at 200 rpm and 30° C., followed by 3 days of incubation in 3 mL HGM medium.

One mL aliquots of the cultures were then harvested by centrifugation and analyzed by GC. Specifically, the cultured cells were collected by centrifugation for 1 min at 13,000 rpm, total lipids were extracted, and fatty acid methyl esters ["FAMEs"] were prepared by trans-esterification, and subsequently analyzed with a Hewlett-Packard 6890 GC (General Methods).

The lipid content and fatty acid composition was quantified for the control Y5037 strain and the transformant Y5037U strain. Additionally, data is presented as a % of the Y5037 control. Table 6 below summarizes the concentration of each fatty acid as a weight percent of TFAs ["% TFAs"]. More specifically, fatty acids are identified as 16:0 (palmitate), 16:1 (palmitoleic acid), 18:0 (stearic acid), 18:1 (oleic acid), 18:2 (LA), ALA, EDA, DGLA, ARA, ETrA, ETA, EPA, DPA, DHA and EDD (corresponding to the sum of EPA plus DPA plus DHA). Additionally, the ratio of DHA % TFAs/DPA % TFAs is provided.

Table 7 summarizes the conversion efficiency of each desaturase and elongase functioning in the PUFA biosynthetic pathway and which are required for DHA production. Specifically, the Δ12 desaturase conversion efficiency ["Δ12 CE"], Δ8 desaturase conversion efficiency ["Δ8 CE"], Δ5 desaturase conversion efficiency ["Δ5 CE"], Δ17 desaturase conversion efficiency ["Δ17 CE"], Δ4 desaturase conversion efficiency ["Δ4 CE"], Δ9 elongase conversion efficiency ["Δ9e CE"] and Δ5 elongase conversion efficiency ["Δ5e CE"] are provided for the control Y5037 strain and strain Y5037U::MaLPAAT1S; data for strain Y5037U::MaLPAAT1S is also presented as a % of the Y5037 control. Conversion efficiency was calculated according to the formula: product(s)/(product(s)+substrate)*100, where product includes both product and product derivatives.

TABLE 6

Lipid Content and Composition In MaLPAAT1 Transformant Strains Of *Yarrowia lipolytica* Y5037

| Strain | Replicates | % TFAs | | | | | | | | | | | | | | | DHA/DPA |
|---|---|---|---|---|---|---|---|---|---|---|---|---|---|---|---|---|---|
| | | 16:0 | 16:1 | 18:0 | 18:1 | 18:2 | ALA | EDA | DGLA | ARA | ETrA | ETA | EPA | DPA | DHA | EDD | |
| Y5037* | 1 | 5.1 | 1.3 | 1.6 | 4.7 | 22.5 | 2.7 | 3.9 | 1.9 | 1.4 | 1.3 | 1.7 | 20.4 | 20.7 | 8.9 | 50.1 | 0.4 |
| Y5037U:: MaLPAT1 | 1 | 6.1 | 1.5 | 1.8 | 4.5 | 21.1 | 2.2 | 4.0 | 2.1 | 1.5 | 1.2 | 1.7 | 23.4 | 19.5 | 10.7 | 53.7 | 0.6 |
| | % Ctrl | 120 | 115 | 113 | 96 | 94 | 81 | 103 | 111 | 107 | 92 | 100 | 115 | 94 | 120 | 107 | 150 |

*Note: The lipid profile for Y5037 in this Table is not identical to that described in Example 7, based on different growth conditions.

TABLE 7

Desaturase And Elongase Conversion Efficiency In MaLPAAT1 Transformant Strains Of *Yarrowia lipolytica* Y5037

| Strain | Replicates | Δ12 CE | Δ9e CE | Δ8 CE | Δ5 CE | Δ17 CE | Δ5e CE | Δ4 CE |
|---|---|---|---|---|---|---|---|---|
| Y5037 | 1 | 95 | 70 | 91 | 93 | 88 | 59 | 30 |
| Y5037U:: MaLPAT1 | 1 | 95 | 73 | 92 | 93 | 88 | 56 | 36 |
| | % Ctrl | 100 | 104 | 101 | 100 | 100 | 95 | 118 |

Based on the data in Table 6 and Table 7, overexpression of MaLPAAT1S in DHA strain Y5037U::MaLPAAT1S resulted in reduction of the concentration of LA as a weight % of TFAs ["LA % TFAs"], an increase in the concentration of EPA as a weight % of TFAs ["EPA % TFAs"], an increase in the concentration of DHA as a weight % of TFAs ["DHA % TFAs"], an increase in the concentration of EPA+DPA+DHA as a weight % of TFAs ["EDD % TFAs"], an increase in the ratio of DHA % TFAs to DPA % TFAs ["DHA/DPA"], and an increase in the conversion efficiencies of the Δ9 elongation and Δ4 desaturation.

More specifically, overexpression of MaLPAAT1 in Y5037U::MaLPAAT1S can reduce LA % TFAs to 94%, increase EPA % TFAs to 115%, increase DHA % TFAs to 120%, increase Δ9e CE to 104%, and increase Δ4 desaturation CE to 118%, as compared to the control.

Example 7

Generation of *Yarrowia lipolytica* Strain Y5037 to Produce about 18.6% EPA, 22.8% DPA and 9.7% DHA of Total Fatty Acids The present Example describes the construction of strain Y5037, derived from *Yarrowia lipolytica* ATCC #20362, capable of producing about 18.6% EPA, 22.8% DPA and 9.7% DHA relative to the total lipids via expression of a Δ9 elongase/Δ8 desaturase pathway.

Briefly, as diagrammed in FIG. 4, strain Y5037 was derived from *Yarrowia lipolytica* ATCC #20362 via construction of strain Y2224 (a FOA resistant mutant from an autonomous mutation of the Ura3 gene of wildtype *Yarrowia* strain ATCC #20362), strain Y4001 (producing 17% EDA with a Leu– phenotype), strain Y4001U1 (Leu– and Ura–), strain Y4036 (producing 18% DGLA with a Leu– phenotype), strain Y4036U (Leu– and Ura–), strain Y4070 (producing 12% ARA with a Ura– phenotype), strain Y4086 (producing 14% EPA), strain Y4086U1 (Ura3–), strain Y4128 (producing 37% EPA; deposited with the American Type Culture Collection on Aug. 23, 2007, bearing the designation ATCC PTA-8614), strain Y4128U3 (Ura–), strain Y4217 (producing 42% EPA), strain Y4217U2 (Ura–), strain Y4259 (producing 46.5% EPA), strain Y4259U2 (Ura–), strain Y4305 (producing 53.2% EPA), strain Y4305U3 (Ura–), strain Y5004 (producing 17% EPA, 18.7% DPA and 6.4% DHA), strain Y5004U1 (Ura–), strain Y5018 (producing 25.4% EPA, 11.4% DPA and 9.4% DHA), strain Y5018U1 (Ura–) and strain Y5037 (producing 18.6% EPA, 22.8% DPA and 9.7% DHA relative to the total TFAs). Further details regarding the construction of strains Y2224, Y4001, Y4001U, Y4036, Y4036U, Y4070, Y4086, Y4086U1, Y4128, Y4128U3, Y4217, Y4217U2, Y4259, Y4259U2, Y4305 and Y4305U3 are described in the General Methods of U.S. Pat. App. Pub. No. 2008-0254191 and in Examples 1-3 of U.S. Pat. App. Pub. No. 2009-0093543, hereby incorporated herein by reference.

The complete lipid profile of strain Y4305, was as follows: 16:0 (2.8%), 16:1 (0.7%), 18:0 (1.3%), 18:1 (4.9%), 18:2 (17.6%), ALA (2.3%), EDA (3.4%), DGLA (2.0%), ARA (0.6%), ETA (1.7%), and EPA (53.2%). The total lipid content of cells ["TFAs % DCW"] was 27.5.

The final genotype of strain Y4305 with respect to wild type *Yarrowia lipolytica* ATCC #20362 was SCP2-(YALI0E01298g), YALI0C18711g-, Pex10-, YALI0F24167g-, unknown 1-, unknown 3-, unknown 8-, GPD::FmD12::Pex20, YAT1::FmD12::OCT, GPM/FBAIN::FmD12S::OCT, EXP1::FmD12S::Aco, YAT1::FmD12S::Lip2, YAT1::ME3S::Pex16, EXP1::ME3S::Pex20 (3 copies), GPAT::EgD9e::Lip2, EXP1::EgD9eS::Lip1, FBAINm::EgD9eS::Lip2, FBA:: EgD9eS::Pex20, GPD::EgD9eS::Lip2, YAT1::EgD9eS::Lip2, YAT1::E389D9eS::OCT, FBAINm::EgD8M::Pex20, FBAIN::EgD8M::Lip1 (2 copies), EXP1::EgD8M::Pex16, GPDIN::EgD8M::Lip1, YAT1::EgD8M::Aco, FBAIN::EgD5::Aco, EXP1::EgD5S::Pex20, YAT1::EgD5S::Aco, EXP1::EgD5S::ACO, YAT1::RD5S::OCT, YAT1::PaD17S::Lip1, EXP1::PaD17::Pex16, FBAINm::PaD17::Aco, YAT1::YICPT1::ACO, GPD::YICPT1::ACO (wherein FmD12 is a *Fusarium moniliforme* Δ12 desaturase gene [U.S. Pat. No. 7,504,259]; FmD12S is a codon-optimized Δ12 desaturase gene, derived from *Fusarium moniliforme* [U.S. Pat. No. 7,504,259]; ME3S is a codon-optimized $C_{16/18}$ elongase gene, derived from *Mortierella alpina* [U.S. Pat. No. 7,470,532]; EgD9e is a *Euglena gracilis* Δ9 elongase gene [Intl. App. Pub. No. WO 2007/061742]; EgD9eS is a codon-optimized Δ9 elongase gene, derived from *Euglena gracilis* [Intl. App. Pub. No. WO 2007/061742]; E389D9eS is a codon-optimized Δ9 elongase gene, derived from *Eutreptiella* sp. CCMP389 [Intl. App. Pub. No. WO 2007/061742]; EgD8M is a synthetic mutant Δ8 desaturase [Intl. App. Pub. No. WO 2008/073271], derived from *Euglena gracilis* [U.S. Pat. No. 7,256,033]; EgD5 is a *Euglena gracilis* Δ5 desaturase [U.S. Pat. App. Pub. US 2007-0292924-A1]; EgD5S is a codon-optimized Δ5 desaturase gene, derived from *Euglena gracilis* [U.S. Pat. App. Pub. No. 2007-0292924]; RD5S is a codon-optimized Δ5 desaturase, derived from *Pendinium* sp. CCMP626 [U.S. Pat. App. Pub. No. 2007-0271632]; PaD17 is a *Pythium aphanidermatum* Δ17 desaturase [Intl. App. Pub. No. WO 2008/054565]; PaD17S is a codon-optimized Δ17 desaturase, derived from *Pythium aphanidermatum* [Intl. App. Pub. No. WO 2008/054565]; and, YICPT1 is a *Yarrowia lipolytica* diacylglycerol cholinephosphotransferase gene [Intl. App. Pub. No. WO 2006/052870]).

Strain Y4305U3 (Ura3-) was generated via integrating a Ura3 mutant gene into the Ura3 gene of strain Y4305.

Figure 5A:
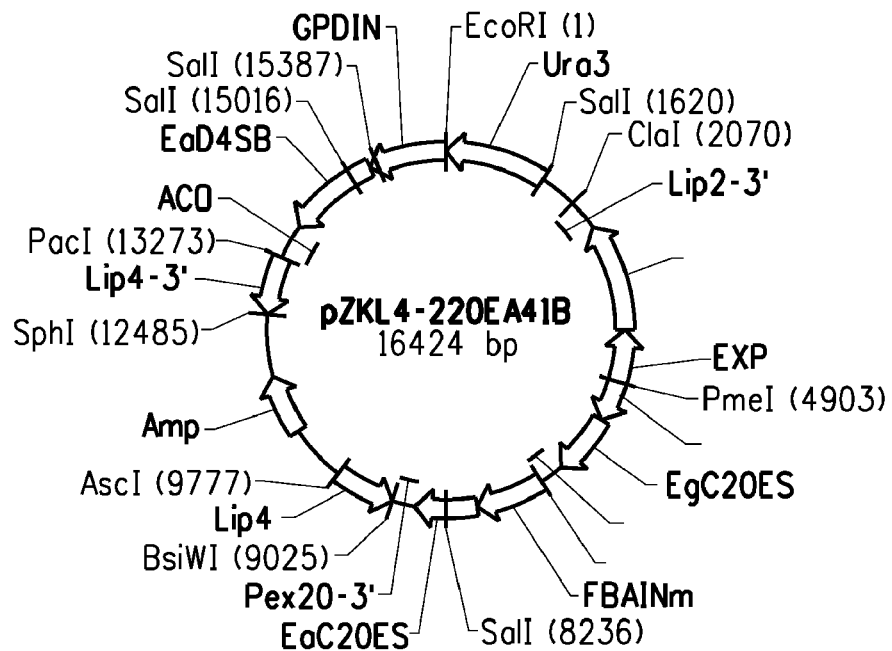

Generation of Y5004 Strain to Produce about 17.0% EPA, 18.7% DPA and 6.4% DHA of TFAs Construct pZKL4-220EA41B (FIG. 5A; SEQ ID NO:47) was constructed to integrate two $C_{20/22}$ elongase genes and two Δ4 desaturase genes into the lipase 4-like locus (GenBank Accession No. XM_503825) of strain Y4305U3. The pZKL4-220EA41B plasmid contained the following components:

TABLE 8

Components Of Plasmid pZKL4-220EA41B (SEQ ID NO: 47)

| RE Sites And Nucleotides Within SEQ ID NO: 47 | Description Of Fragment And Chimeric Gene Components |
|---|---|
| Asc I/BsiW I (9777-9025) | 745 bp 5' portion of the *Yarrowia* Lipase 4-like gene (GenBank Accession No. XM_503825; labeled as "Lip4" in Figure) |
| PacI/SphI (13273-12485) | 782 bp 3' portion of Yarrowia Lipase 4 like gene (GenBank Accession No. XM_503825; labeled as "Lip4-3'" in Figure) |
| SwaI/BsiW I (6882-9025) | FBAINm::EaC20ES::Pex20, comprising: FBAINm: *Yarrowia lipolytica* FBAINm promoter (U.S. Pat. No. 7,202,356) EaC20ES: codon-optimized C20 elongase gene (SEQ ID NO: 48), derived from *Euglena anabaena* (U.S. Pat. Appl. Pub. No. 2008/0254191-A1); Pex20: Pex20 terminator sequence from *Yarrowia* Pex20 gene (GenBank Accession No. AF054613) |
| Pme I/Swa I (4903-6882) | YAT1::EgC20ES::Lip1, comprising: YAT1: *Yarrowia lipolytica* YAT1 promoter (U.S. Pat. Appl. Pub. No. 2006/0094102-A1); EgC20ES: codon-optimized C20 elongase gene (SEQ ID NO: 50), derived from *Euglena gracilis* (U.S. Pat. Appl. Pub. No. 2008/0254191-A1); Lip1: Lip1 terminator sequence from *Yarrowia* Lip1 gene (GenBank Accession No. Z50020) |
| Pme I/Cla I (4903-2070) | EXP1::EaD4S-1::Lip2, comprising: EXP1: *Yarrowia lipolytica* export protein (EXP1) promoter (Intl. App. Pub. No. WO 2006/052870); EaD4S-1: codon-optimized truncated Δ4 desaturase (SEQ ID NO: 52), derived from *Euglena anabaena* (U.S. Pat. Appl. Pub. No. 2008/0254191-A1); Lip2: Lip2 terminator sequence from *Yarrowia* Lip2 gene (GenBank Accession No. AJ012632) |
| Sal I/EcoR I (1620-1) | *Yarrowia* Ura3 gene (GenBank Accession No. AJ306421) |
| EcoR I/Pac I (1-14039) | GPDIN::EaD4SB::Aco, comprising: GPDIN: *Yarrowia lipolytica* GPDIN promoter (U.S. Pat. No. 7,459,546); EaD4SB: codon-optimized truncated Δ4 desaturase version B (SEQ ID NO: 54), derived from *Euglena anabaena* (U.S. Pat. Appl. Pub. No. 2008/0254191-A1); Aco: Aco terminator sequence from *Yarrowia* Aco gene (GenBank Accession No. AJ001300) |

The pZKL4-220EA41 B plasmid was digested with AscI/SphI, and then used for transformation of strain Y4305U3 (supra), according to the General Methods. The transformants were selected on MM plates. After 5 days growth at 30° C., 72 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, resuspended in HGM and then shaken at 250 rpm/min for 5 days. The cells were collected by centrifugation, lipids were extracted, and FAMEs were prepared by trans-esterification, and subsequently analyzed with a Hewlett-Packard 6890 GC.

GC analyses showed the presence of DHA in the transformants with pZKL4-220EA41B, but not in the parent Y4305U strain. Most of the selected 72 strains produced about 22% EPA, 18% DPA and 5% DHA of TFAs. Strain #2 produced 17% EPA, 18.7% DPA and 6.4% DHA, while strain #33 produced 21.5% EPA, 21% DPA and 5.5% DHA. These two strains were designated as Y5004 and Y5005, respectively.

Knockout of the lipase 4-like locus (GenBank Accession No. XM_503825) was not confirmed in either strain Y5004 or Y5005.

Generation of Strain Y5004U (Ura3−)

Figure 5B:
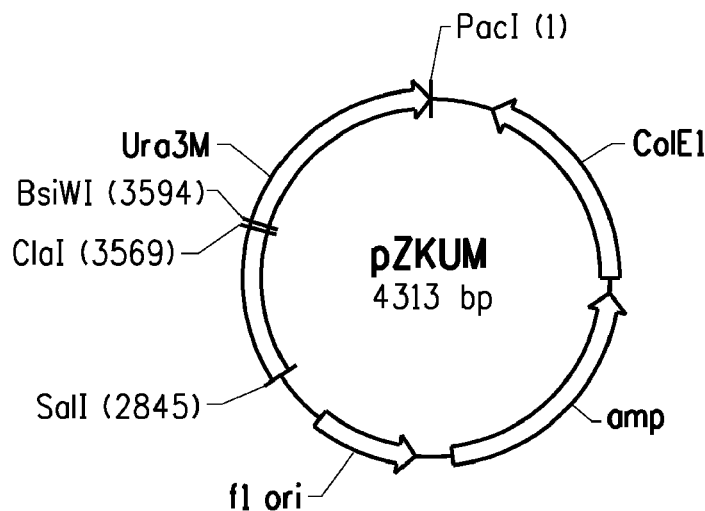

In order to disrupt the Ura3 gene in strain Y5004, construct pZKUM (FIG. 5B; SEQ ID NO:56; described in Table 15 of U.S. Pat. App. Pub. No. 2009-0093543, hereby incorporated herein by reference) was used to integrate a Ura3 mutant gene into the Ura3 gene of strain Y5004. Plasmid pZKUM was digested with SalI/PacI, and then used to transform strain Y5004 according to the General Methods. Following transformation, cells were plated onto MM+5-FOA selection plates and maintained at 30° C. for 4 to 5 days.

A total of 8 transformants grown on MM+5-FOA plates were picked and re-streaked onto MM plates and MM+5-FOA plates, separately. All 8 strains had a Ura− phenotype (i.e., cells could grow on MM+5-FOA plates, but not on MM plates). The cells were scraped from the MM+5-FOA plates, lipids were extracted, and FAMEs were prepared by trans-esterification, and subsequently analyzed with a Hewlett-Packard 6890 GC.

GC analyses showed the presence of 14.8% EPA, 17.4% DPA and 0.4% DHA of TFAs in transformant #5 and 15.3% EPA, 17.2% DPA and 0.4% DHA in transformant #8. These two strains were designated as strains Y5004U1 and Y5004U2, respectively (collectively, Y5004U).

Figure 6A:
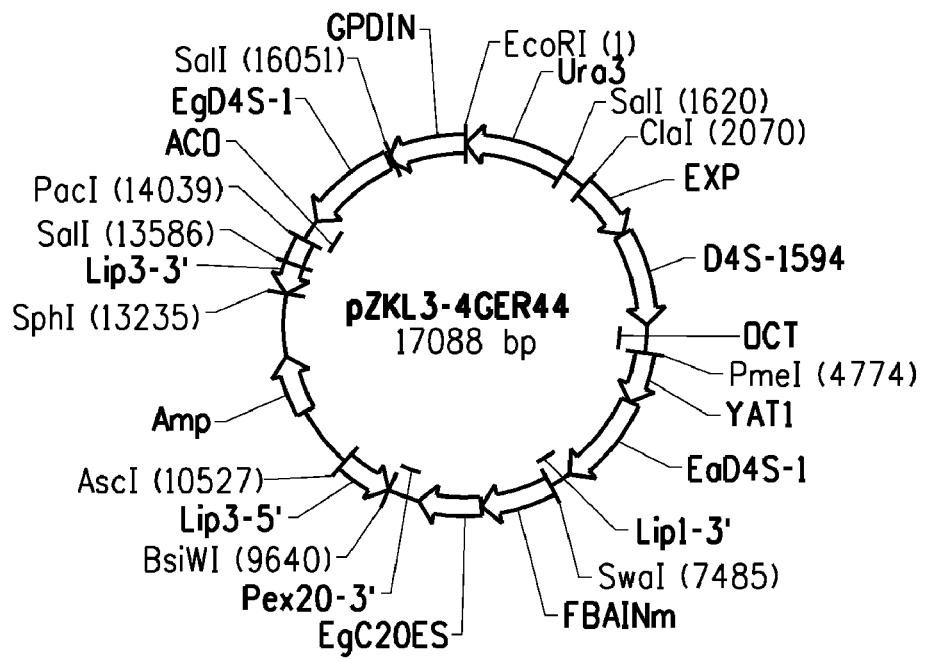

Generation of Y5018 Strain to Produce about 25.4% EPA, 11.4% DPA and 9.4% DHA of TFAs Construct pZKL3-4GER44 (FIG. 6A; SEQ ID NO:57) was constructed to integrate one $C_{20/22}$ elongase gene and three Δ4 desaturase genes into the lipase 3-like locus (GenBank Accession No. XP_506121) of strain Y5004U1. The pZKL3-4GER44 plasmid contained the following components:

TABLE 9

Components Of Plasmid pZKL3-4GER44 (SEQ ID NO: 57)

| RE Sites And Nucleotides Within SEQ ID NO: 57 | Description Of Fragment And Chimeric Gene Components |
|---|---|
| Asc I/BsiW I (10527-9640) | 887 bp 5' portion of the *Yarrowia* Lipase 3-like gene (GenBank Accession No. XP_506121) |
| Pac I/Sph I (14039-13235) | 804 bp 3' portion of *Yarrowia* Lipase 3-like gene (GenBank Accession No. XP_506121) |
| Swa I/BsiW I (7485-9640) | FBAINm::EgC20ES::Pex20, comprising:<br>FBAINm: *Yarrowia lipolytica* FBAINm promoter (U.S. Pat. No. 7,202,356);<br>EgC20ES: codon-optimized C20 elongase gene (SEQ ID NO: 50), derived from *Euglena gracilis* (U.S. Pat. Appl. Pub. No. 2008-0254191-A1),<br>Pex20: Pex20 terminator sequence from *Yarrowia* Pex20 gene (GenBank Accession No. AF054613) |
| Pme I/Swa I (4774-7485) | YAT1::EaD4S-1::Lip1, comprising:<br>YAT1: *Yarrowia lipolytica* YAT1 promoter (U.S. Pat. Appl. Pub. No. 2006/0094102-A1);<br>EaD4S-1: codon-optimized truncated Δ4 desaturase (SEQ ID NO: 52), derived from *Euglena anabaena* (U.S. Pat. Appl. Pub. No. 2008/0254191-A1);<br>Lip1: Lip1 terminator sequence from *Yarrowia* Lip1 gene (GenBank Accession No. Z50020) |
| Cla I/Pme I (2070-4774) | EXP1::E1594D4S::Oct, comprising:<br>EXP1: *Yarrowia lipolytica* export protein promoter (Intl. App. Pub. No. WO 2006/052870);<br>E1594D4S: codon-optimized Δ4 desaturase (SEQ ID NO: 58), derived from *Eutreptiella* cf_gymnastica CCMP1594 (U.S. Patent Application No. 12/408,860) (labeled as "D4S-1594" in Figure);<br>OCT: OCT terminator sequence of *Yarrowia* OCT gene (GenBank Accession No. X69988) |
| Sal I/EcoR I (1620-1) | *Yarrowia* Ura3 gene (GenBank Accession No. AJ306421) |
| EcoR I/Pac I (1-14039) | GPDIN::EgD4S-1::Aco, comprising:<br>GPDIN: *Yarrowia lipolytica* GPDIN promoter (U.S. Pat. No. 7,459,546);<br>EgD4S-1: codon-optimized truncated Δ4 desaturase (SEQ ID NO: 60), derived from *Euglena gracilis* (U.S. Pat. Appl. Pub. No. 2008/0254191-A1);<br>Aco: Aco terminator sequence from *Yarrowia* Aco gene (GenBank Accession No. AJ001300) |

The pZKL3-4GER44 plasmid was digested with AscI/SphI, and then used for transformation of strain Y5004U1, according to the General Methods. The transformants were selected on MM plates. After 5 days growth at 30° C., 96 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, resuspended in HGM and then shaken at 250 rpm/min for 5 days. The cells were subjected to fatty acid analysis, according to the General Methods.

GC analyses showed that most of the selected 96 strains produced about 19% EPA, 22% DPA and 7% DHA of TFAs. Strain #1 produced 23.3% EPA, 13.7% DPA and 8.9% DHA, while strain #49 produced 25.2% EPA, 11.4% DPA and 9.4% DHA. These two strains were designated as Y5011 and Y5018, respectively.

Knockout of the lipase 3-like locus (GenBank Accession No. XP_506121) was not confirmed in strains Y5011 and Y5018.

Generation of Strain Y5018U (Ura3−)

In order to disrupt. the Ura3 gene in strain Y5018, construct pZKUM (FIG. 5B; SEQ ID NO:56; described in Table 15 of U.S. Pat. App. Pub. No. 2009-0093543-A1) was used to integrate a Ura3 mutant gene into the Ura3 gene of strain Y5018, in a manner similar to that described for pZKUM transformation of strain Y5004. A total of 18 transformants were grown and identified to possess a Ura− phenotype.

GC analyses showed the presence of 16.6% EPA, 10.4% DPA and 0.0% DHA of TFAs in pZKUM-transformant strain #2 and 17.0% EPA, 10.8% DPA and 0.0% DHA in pZKUM-transformant strain #4. These two strains were designated as strains Y5018U1 and Y5018U2, respectively (collectively, Y5018U).

Figure 6B:
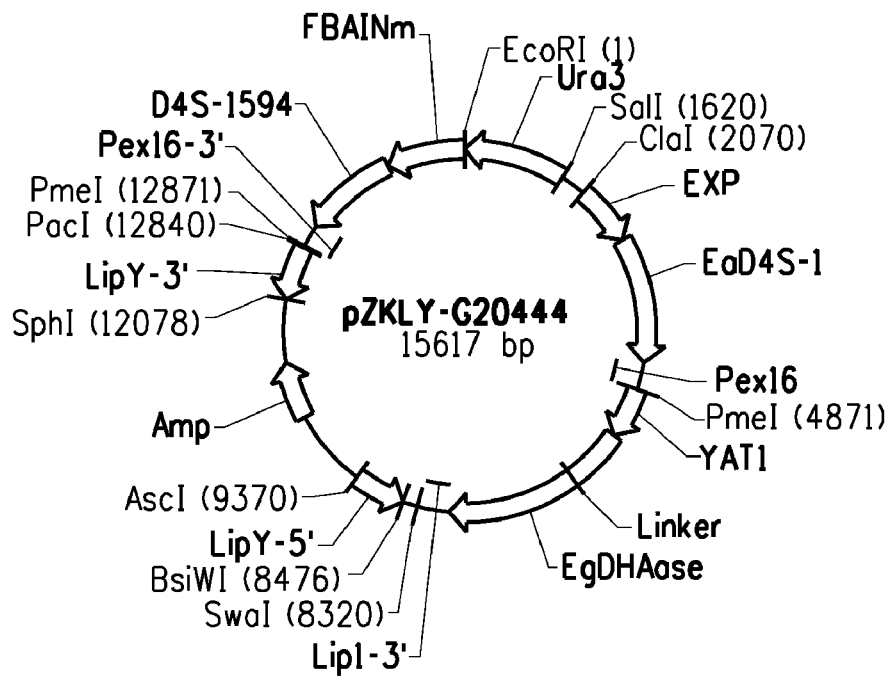

Generation of Y5037 Strain to Produce about 18.6% EPA, 22.8% DPA and 9.7% DHA of TFAs Construct pZKLY-G20444 (FIG. 6B; SEQ ID NO:62) was constructed to integrate one DHA synthase and two Δ4 desaturase genes into the lipase 7-like locus (GenBank Accession No. AJ549519) of strain Y5018U1. A DHA synthase is a multizyme comprising a C20 elongase linked to a Δ4 desaturase (U.S. Pat. Appl. Pub. No. 2008/0254191-A1). The pZKLY-G20444 plasmid contained the following components:

FmD12S::OCT, EXP1::FmD12S::Aco, YAT1::FmD12S::Lip2, YAT1::ME3S::Pex16, EXP1::ME3S::Pex20 (3 copies), GPAT::EgD9e::Lip2, EXP1::EgD9eS::Lip1, FBAINm::EgD9eS::Lip2, FBA::EgD9eS::Pex20, GPD::EgD9eS::Lip2,

TABLE 10

Components Of Plasmid pZKLY-G20444 (SEQ ID NO: 62)

| RE Sites And Nucleotides Within SEQ ID NO: 62 | Description Of Fragment And Chimeric Gene Components |
|---|---|
| Asc I/BsiW I (9370-8476) | 887 bp 5' portion of the *Yarrowia* Lipase 7-like gene (labeled as "LipY-5'" in Figure; GenBank Accession No. AJ549519) |
| Pac I/Sph I (12840-12078) | 756 bp 3' portion of *Yarrowia* Lipase 7-like gene (labeled as "LipY-3'" in Figure; GenBank Accession No. AJ549519) |
| Pme I/Swa I (4871-8320) | YAT1::EgDHAsyn1S::Lip1, comprising: YAT1: *Yarrowia lipolytica* YAT1 promoter (U.S. Pat. Appl. Pub. No. 2006/0094102-A1); EgDHAsyn1S: codon-optimized DHA synthase (SEQ ID NO: 63), derived from *Euglena gracilis* (labeled as "EgDHAase" in Figure; U.S. Pat. Appl. Pub. No. 2008/0254191-A1); Lip1: Lip1 terminator sequence from *Yarrowia* Lip1 gene (GenBank Accession No. Z50020) |
| Cla I/Pme I (2070-4871) | EXP1::EaD4S-1::Pex16, comprising: EXP1: *Yarrowia lipolytica* export protein (EXP1) promoter (Intl. App. Pub. No. WO 2006/052870); EaD4S-1: codon-optimized truncated Δ4 desaturase (SEQ ID NO: 52), derived from *Euglena anabaena* (U.S. Pat. Appl. Pub. No. 2008/0254191-A1); Pex16: Pex16 terminator sequence from *Yarrowia* Pex16 gene (GenBank Accession No. U75433) |
| Sal I/EcoR I (1620-1) | *Yarrowia* Ura3 gene (GenBank Accession No. AJ306421) |
| EcoR I/Pme I (1-12871) | FBAINm::E1594D4S::Pex16, comprising: FBAINm: *Yarrowia lipolytica* FBAINm promoter (U.S. Pat. No. 7,202,356); E1594D4S: codon-optimized Δ4 desaturase (SEQ ID NO: 58), derived from *Eutreptiella* cf._*gymnastica* CCMP1594 (U.S. Patent Application No. 12/408,860) (labeled as "D4S-1594" in Figure); Pex16: Pex16 terminator sequence from *Yarrowia* Pex16 gene (GenBank Accession No. U75433) |

The pZKLY-G20444 plasmid was digested with AscI/SphI, and then used for transformation of strain Y5018U1, according to the General Methods. The transformants were selected on MM plates. After 5 days growth at 30° C., 96 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, resuspended in HGM and then shaken at 250 rpm/min for 5 days. The cells were subjected to fatty acid analysis, according to the General Methods.

GC analyses showed that most of the selected 96 strains produced about 19% EPA, 22% DPA and 9% DHA of TFAs. Strain #3 produced 18.6% EPA, 22.8% DPA and 9.7% DHA; strain #9 produced 18.4% EPA, 21% DPA and 9.6% DHA; strain #27 produced 17.8% EPA, 20.6% DPA and 10% DHA; and strain #40 produced 18.8% EPA, 21.2% DPA and 9.6% DHA. These four strains were designated as Y5037, Y5038, Y5039 and Y5040, respectively.

Knockout of the lipase 7-like locus (GenBank Accession No, AJ549519) was not confirmed in strains Y5037, Y5038, Y5039 or Y5040.

The final genotype of strains Y5037, Y5038, Y5039 and Y5040 with respect to wild type *Yarrowia lipolytica* ATCC #20362 was SCP2-(YALI1E01298g), YALI1C18711g-, Pex10-, YALI0F24167g-, unknown 1-, unknown 3-, unknown 8-, unknown 9-, unknown 10-, unknown 11-, GPD::FmD12::Pex20, YAT1::FmD12::OCT, GPM/FBAIN::FmD12S::OCT, EXP1::FmD12S::Aco, YAT1::FmD12S::Lip2, YAT1::ME3S::Pex16, EXP1::ME3S::Pex20 (3 copies), GPAT::EgD9e::Lip2, EXP1::EgD9eS::Lip1, FBAINm::EgD9eS::Lip2, FBA::EgD9eS::Pex20, GPD::EgD9eS::Lip2, YAT1::EgD9eS::Lip2, YAT1::E389D9eS::OCT, FBAINm::EgD8M::Pex20, FBAIN::EgD8M::Lip1 (2 copies), EXP1::EgD8M::Pex16, GPDIN::EgD8M::Lip1, YAT1::EgD8M::Aco, FBAIN::EgD5::Aco, EXP1::EgD5S::Pex20, YAT1::EgD5S::Aco, EXP1::EgD5S::ACO, YAT1::RD5S::OCT, YAT1::PaD17S::Lip1, EXP1::PaD17::Pex16, FBAINm::PaD17::Aco, YAT1::YICPT1::ACO, GPD::YICPT1::ACO, FBAINm::EaC20ES::Pex20, YAT1::EgC20ES::Lip1, FBAINm::EgC20ES::Pex20, EXP1::EaD4S-1::Lip2, EXP1::EaD4S-1::Pex16, YAT1::EaD4S-1::Lip1, GPDIN::EaD4SB::Aco, EXP1::E1594D4S::Oct, FBAINm::E1594D4S::Pex16, GPDIN::EgD4S-1::Aco, YAT::EgDHAsyn1S::Lip1.

Generation of Strain Y5037U (Ura3–)

In order to disrupt the Ura3 gene in strain Y5037, construct pZKUM (FIG. 5B; SEQ ID NO:56; described in Table 15 of U.S. Pat. App. Pub. No. 2009-0093543-A1) was used to integrate a Ura3 mutant gene into the Ura3 gene of strain Y5037, in a manner similar to that described for pZKUM transformation of strain Y5004. A total of 12 transformants were grown and identified to possess a Ura– phenotype.

GC analyses showed the presence of 12.1% EPA, 10.2% DPA and 3.3% DHA or TFAs in pZKUM-transformant strain #4 and 12.4% EPA, 10.3% DPA and 3.5% DHA in pZKUM-transformant strain #11. These two strains were designated as strains Y5037U1 and Y5037U2, respectively (collectively, Y5037U).

What is claimed is:

1. An isolated nucleic acid molecule encoding a polypeptide having lysophosphatidic acid acyltransferase activity, selected from the group consisting of:
   (a) an isolated nucleic acid molecule encoding the amino acid sequence as set forth in SEQ ID NO:2;
   (b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or,
   (c) an isolated nucleic acid molecule that is completely complementary to (a) or (b).

2. The isolated nucleic acid molecule of claim 1 selected from the group consisting of SEQ ID NO:1 and SEQ ID NO:3.

3. An isolated nucleic acid molecule comprising at least one nucleotide sequence selected from the group consisting of:
   (a) a nucleotide sequence encoding a lysophosphatidic acid acyltransferase enzyme of at least 314 amino acids that has at least 90% identity based on the BLAST method of alignment when compared to a polypeptide having the sequence as set forth in SEQ ID NO:2; and,
   (b) a nucleotide sequence comprising the complement of (a).

4. A recombinant DNA construct comprising the isolated nucleic acid molecule of claim 1 operably linked to at least one regulatory sequence.

5. A transformed host cell comprising the recombinant DNA construct of claim 4.

6. The transformed host cell of claim 5, selected from the group consisting of bacteria, yeast, algae, stramenopiles, oomycetes, euglenoids, fungi and plants.

7. The transformed host cell of claim 6, wherein the yeast is an oleaginous yeast.

8. The transformed host cell of claim 7, wherein the oleaginous yeast is selected from the group consisting of: *Yarrowia, Candida, Rhodotorula, Rhodosporidium, Cryptococcus, Trichosporon* and *Lipomyces*.

9. The transformed host cell of claim 8, wherein the host cell is *Yarrowia lipolytica*.

* * * * *

SEQUENCE LISTING

<160> NUMBER OF SEQ ID NOS: 67

<210> SEQ ID NO 1
<211> LENGTH: 945
<212> TYPE: DNA
<213> ORGANISM: Mortierella alpina
<220> FEATURE:
<221> NAME/KEY: CDS
<222> LOCATION: (1)..(945)
<300> PUBLICATION INFORMATION:
<302> TITLE: HIGH EICOSAPENTAENOIC ACID PRODUCING STRAINS OF YARROWIA
      LIPOLYTICA
<310> PATENT DOCUMENT NUMBER: US-2006-0115881-A1
<311> PATENT FILING DATE: 2005-11-02
<312> PUBLICATION DATE: 2006-06-01
<313> RELEVANT RESIDUES IN SEQ ID NO: (1)..(945)
<300> PUBLICATION INFORMATION:
<302> TITLE: HIGH EICOSAPENTAENOIC ACID PRODUCING STRAINS OF YARROWIA
      LIPOLYTICA
<310> PATENT DOCUMENT NUMBER: WO 2006/052870
<311> PATENT FILING DATE: 2005-11-03
<312> PUBLICATION DATE: 2006-05-18
<313> RELEVANT RESIDUES IN SEQ ID NO: (1)..(945)

<400> SEQUENCE: 1

```
atg tcc ata ggt tct tcc aat cct gtc ctg ctg gca gcg atc ccc ttc      48
Met Ser Ile Gly Ser Ser Asn Pro Val Leu Leu Ala Ala Ile Pro Phe
 1               5                  10                  15 gtc tac ctc ttc gtc ctc cct cgt gtc ctc gcc ttc ctc cct caa aag      96
Val Tyr Leu Phe Val Leu Pro Arg Val Leu Ala Phe Leu Pro Gln Lys
            20                  25                  30 gcc cag ttc ctc gca aaa tgc atc gtg gtc ttg atc gcc acc ctt atc     144
Ala Gln Phe Leu Ala Lys Cys Ile Val Val Leu Ile Ala Thr Leu Ile
        35                  40                  45 atg tcc gtc gca ggc tgc ttc att tcc atc gtc tgt gcg ctc ctc gat     192
Met Ser Val Ala Gly Cys Phe Ile Ser Ile Val Cys Ala Leu Leu Asp
    50                  55                  60 aaa cgc tat gtg atc aac tac gtc gtc tca aga ctc ttc tca ttc ctc     240
Lys Arg Tyr Val Ile Asn Tyr Val Val Ser Arg Leu Phe Ser Phe Leu
65                  70                  75                  80 gct gca aga ccc tgc ggt gtc acc tac aag atc gtc ggc gag gaa cat     288
Ala Ala Arg Pro Cys Gly Val Thr Tyr Lys Ile Val Gly Glu Glu His
                85                  90                  95 ctg gac aag tac ccc gcc att gtc gtc tgc aac cac cag agc tcc atg     336
Leu Asp Lys Tyr Pro Ala Ile Val Val Cys Asn His Gln Ser Ser Met
            100                 105                 110 gac atg atg gtc ctg gga cgc gtc ttc cca aag cac tgt gtc gtc atg     384
Asp Met Met Val Leu Gly Arg Val Phe Pro Lys His Cys Val Val Met
        115                 120                 125 gca aag aag gaa ctt ctt tac ttt ccg ttc ctg ggc atg ttt atg aag     432
Ala Lys Lys Glu Leu Leu Tyr Phe Pro Phe Leu Gly Met Phe Met Lys
    130                 135                 140 ctg agt aac gcc atc ttc att gac cgc aag aac cac aag aag gcg atc     480
Leu Ser Asn Ala Ile Phe Ile Asp Arg Lys Asn His Lys Lys Ala Ile
145                 150                 155                 160 gag tcc acc acc caa gct gtc gcc gac atg aag aag cac aac tct gga     528
Glu Ser Thr Thr Gln Ala Val Ala Asp Met Lys Lys His Asn Ser Gly
                165                 170                 175 atc tgg att ttc ccc gaa gga aca cgt tcc cgc ttg gac aag gcc gat     576
Ile Trp Ile Phe Pro Glu Gly Thr Arg Ser Arg Leu Asp Lys Ala Asp
            180                 185                 190 ctc ttg ccc ttc aag aag gga gcc ttc cac ctc gcc att caa gcc caa     624
Leu Leu Pro Phe Lys Lys Gly Ala Phe His Leu Ala Ile Gln Ala Gln
```

```
                195                 200                    205
ctc ccg atc ctc ccc atc atc tcg caa gga tac tca cac atc tac gat    672
Leu Pro Ile Leu Pro Ile Ile Ser Gln Gly Tyr Ser His Ile Tyr Asp
210                 215                     220 tcg tca aaa cgc tac ttc ccc ggt gga gag ctc gag atc aga gtc ctg    720
Ser Ser Lys Arg Tyr Phe Pro Gly Gly Glu Leu Glu Ile Arg Val Leu
225                 230                     235                 240 gaa cct atc ccc acc acg gga ttg acc aca gac gat gtg aac gac ctg    768
Glu Pro Ile Pro Thr Thr Gly Leu Thr Thr Asp Asp Val Asn Asp Leu
                245                 250                     255 atg gac aag act cgc aac ctg atg ctg aag cac ctc aag gag atg gat    816
Met Asp Lys Thr Arg Asn Leu Met Leu Lys His Leu Lys Glu Met Asp
            260                 265                     270 tct caa tac tcc tcc tcc acc gct gaa aac gga tcg acc cat att gac    864
Ser Gln Tyr Ser Ser Ser Thr Ala Glu Asn Gly Ser Thr His Ile Asp
        275                 280                     285 gcc gat atc gca aag tca act gcc aca tcg atc gga aac acg gac gat    912
Ala Asp Ile Ala Lys Ser Thr Ala Thr Ser Ile Gly Asn Thr Asp Asp
290                 295                     300 gct atc aca aag agg agg aca cca aaa gag tag                         945
Ala Ile Thr Lys Arg Arg Thr Pro Lys Glu
305                 310
```

<210> SEQ ID NO 2
<211> LENGTH: 314
<212> TYPE: PRT
<213> ORGANISM: Mortierella alpina

<400> SEQUENCE: 2

```
Met Ser Ile Gly Ser Ser Asn Pro Val Leu Ala Ala Ile Pro Phe
1               5                   10                  15

Val Tyr Leu Phe Val Leu Pro Arg Val Leu Ala Phe Leu Pro Gln Lys
            20                  25                  30

Ala Gln Phe Leu Ala Lys Cys Ile Val Val Leu Ile Ala Thr Leu Ile
        35                  40                  45

Met Ser Val Ala Gly Cys Phe Ile Ser Ile Val Cys Ala Leu Leu Asp
    50                  55                  60

Lys Arg Tyr Val Ile Asn Tyr Val Ser Arg Leu Phe Ser Phe Leu
65              70                  75                  80

Ala Ala Arg Pro Cys Gly Val Thr Tyr Lys Ile Val Gly Glu Glu His
            85                  90                  95

Leu Asp Lys Tyr Pro Ala Ile Val Val Cys Asn His Gln Ser Ser Met
        100                 105                 110

Asp Met Met Val Leu Gly Arg Val Phe Pro Lys His Cys Val Val Met
    115                 120                 125

Ala Lys Lys Glu Leu Leu Tyr Phe Pro Phe Leu Gly Met Phe Met Lys
130                 135                 140

Leu Ser Asn Ala Ile Phe Ile Asp Arg Lys Asn His Lys Lys Ala Ile
145                 150                 155                 160

Glu Ser Thr Thr Gln Ala Val Ala Asp Met Lys Lys His Asn Ser Gly
            165                 170                 175

Ile Trp Ile Phe Pro Glu Gly Thr Arg Ser Arg Leu Asp Lys Ala Asp
        180                 185                 190

Leu Leu Pro Phe Lys Lys Gly Ala Phe His Leu Ala Ile Gln Ala Gln
    195                 200                 205

Leu Pro Ile Leu Pro Ile Ile Ser Gln Gly Tyr Ser His Ile Tyr Asp
210                 215                 220
```

```
Ser Ser Lys Arg Tyr Phe Pro Gly Gly Glu Leu Glu Ile Arg Val Leu
225                 230                 235                 240

Glu Pro Ile Pro Thr Thr Gly Leu Thr Thr Asp Asp Val Asn Asp Leu
            245                 250                 255

Met Asp Lys Thr Arg Asn Leu Met Leu Lys His Leu Lys Glu Met Asp
        260                 265                 270

Ser Gln Tyr Ser Ser Ser Thr Ala Glu Asn Gly Ser Thr His Ile Asp
            275                 280                 285

Ala Asp Ile Ala Lys Ser Thr Ala Thr Ser Ile Gly Asn Thr Asp Asp
    290                 295                 300

Ala Ile Thr Lys Arg Arg Thr Pro Lys Glu
305                 310

<210> SEQ ID NO 3
<211> LENGTH: 955
<212> TYPE: DNA
<213> ORGANISM: Mortierella alpina
<220> FEATURE:
<221> NAME/KEY: CDS
<222> LOCATION: (3)..(947)
<223> OTHER INFORMATION: synthetic LPAAT1 (codon-optimized for Yarrowia
      lipolytica)

<400> SEQUENCE: 3 ac atg tct att ggt tcg tcc aac ccc gtg ctc ttg gct gcg att ccc      47
   Met Ser Ile Gly Ser Ser Asn Pro Val Leu Leu Ala Ala Ile Pro
   1               5                  10                  15 ttc gtc tac ctg ttt gtc ctc cca cga gtc ctg gct ttc ctg cct cag    95
Phe Val Tyr Leu Phe Val Leu Pro Arg Val Leu Ala Phe Leu Pro Gln
                20                  25                  30 aag gct cag ttc ctg gcc aaa tgt att gtg gtc ctg att gcc acg ctt   143
Lys Ala Gln Phe Leu Ala Lys Cys Ile Val Val Leu Ile Ala Thr Leu
            35                  40                  45 atc atg tcc gtt gca ggc tgc ttc atc tcg atc gtg tgc gct ctt ctg   191
Ile Met Ser Val Ala Gly Cys Phe Ile Ser Ile Val Cys Ala Leu Leu
        50                  55                  60 gac aag aga tac gtc atc aat tac gtt gtg tcg cga ttg ttc tcc ttc   239
Asp Lys Arg Tyr Val Ile Asn Tyr Val Val Ser Arg Leu Phe Ser Phe
65                  70                  75 ctt gcc gct cga ccg tgt ggt gtg acc tat aag att gtt ggt gag gaa   287
Leu Ala Ala Arg Pro Cys Gly Val Thr Tyr Lys Ile Val Gly Glu Glu
80                  85                  90                  95 cac ctc gat aag tac cct gct atc gtg gtc tgt aac cat caa tcc tct   335
His Leu Asp Lys Tyr Pro Ala Ile Val Val Cys Asn His Gln Ser Ser
                100                 105                 110 atg gat atg atg gtt ttg gga cga gtt ttt cca aag cac tgc gtt gtc   383
Met Asp Met Met Val Leu Gly Arg Val Phe Pro Lys His Cys Val Val
            115                 120                 125 atg gcg aag aag gaa ctc ctg tac ttt ccc ttt ttg gga atg ttt atg   431
Met Ala Lys Lys Glu Leu Leu Tyr Phe Pro Phe Leu Gly Met Phe Met
        130                 135                 140 aaa ctg agc aac gct atc ttc atc gac cgg aag aac cac aag aaa gcc   479
Lys Leu Ser Asn Ala Ile Phe Ile Asp Arg Lys Asn His Lys Lys Ala
145                 150                 155 atc gag tct acc acc caa gcc gtg gcg gac atg aag aag cac aac tct   527
Ile Glu Ser Thr Thr Gln Ala Val Ala Asp Met Lys Lys His Asn Ser
160                 165                 170                 175 gga atc tgg att ttc cca gag ggc acc cgg tct aga ctg gac aag gca   575
Gly Ile Trp Ile Phe Pro Glu Gly Thr Arg Ser Arg Leu Asp Lys Ala
                180                 185                 190
```

```
gac ctg ctg ccc ttc aag aaa ggt gcc ttt cat ctt gca att cag gcc        623
Asp Leu Leu Pro Phe Lys Lys Gly Ala Phe His Leu Ala Ile Gln Ala
            195                 200                 205 cag ctc cct att ctc ccc att atc tcg cag ggc tat tcc cat atc tac        671
Gln Leu Pro Ile Leu Pro Ile Ile Ser Gln Gly Tyr Ser His Ile Tyr
        210                 215                 220 gac tct tcg aag cgg tac ttc ccc ggt gga gag ctc gag atc aga gtc        719
Asp Ser Ser Lys Arg Tyr Phe Pro Gly Gly Glu Leu Glu Ile Arg Val
225                 230                 235 ctg gag ccc att cct aca act ggc ctc act act gat gat gtg aac gac        767
Leu Glu Pro Ile Pro Thr Thr Gly Leu Thr Thr Asp Asp Val Asn Asp
240                 245                 250                 255 ctg atg gac aag aca cga aac ctt atg ctc aag cac ttg aag gag atg        815
Leu Met Asp Lys Thr Arg Asn Leu Met Leu Lys His Leu Lys Glu Met
                260                 265                 270 gat tcc cag tat tcg tcg agc act gct gaa aat gga tcc acg cac atc        863
Asp Ser Gln Tyr Ser Ser Ser Thr Ala Glu Asn Gly Ser Thr His Ile
            275                 280                 285 gac gcc gat att gcc aag tct aca gcc acc agc att ggc aac act gac        911
Asp Ala Asp Ile Ala Lys Ser Thr Ala Thr Ser Ile Gly Asn Thr Asp
        290                 295                 300 gac gca att aca aaa cgt cgt acc cct aag gaa taa gcggccgc              955
Asp Ala Ile Thr Lys Arg Arg Thr Pro Lys Glu
305                 310

<210> SEQ ID NO 4
<211> LENGTH: 314
<212> TYPE: PRT
<213> ORGANISM: Mortierella alpina

<400> SEQUENCE: 4

Met Ser Ile Gly Ser Ser Asn Pro Val Leu Ala Ala Ile Pro Phe
1               5                   10                  15

Val Tyr Leu Phe Val Leu Pro Arg Val Leu Ala Phe Leu Pro Gln Lys
            20                  25                  30

Ala Gln Phe Leu Ala Lys Cys Ile Val Val Leu Ile Ala Thr Leu Ile
        35                  40                  45

Met Ser Val Ala Gly Cys Phe Ile Ser Ile Val Cys Ala Leu Leu Asp
    50                  55                  60

Lys Arg Tyr Val Ile Asn Tyr Val Val Ser Arg Leu Phe Ser Phe Leu
65                  70                  75                  80

Ala Ala Arg Pro Cys Gly Val Thr Tyr Lys Ile Val Gly Glu Glu His
                85                  90                  95

Leu Asp Lys Tyr Pro Ala Ile Val Val Cys Asn His Gln Ser Ser Met
            100                 105                 110

Asp Met Met Val Leu Gly Arg Val Phe Pro Lys His Cys Val Val Met
        115                 120                 125

Ala Lys Lys Glu Leu Leu Tyr Phe Pro Phe Leu Gly Met Phe Met Lys
    130                 135                 140

Leu Ser Asn Ala Ile Phe Ile Asp Arg Lys Asn His Lys Lys Ala Ile
145                 150                 155                 160

Glu Ser Thr Thr Gln Ala Val Ala Asp Met Lys Lys His Asn Ser Gly
                165                 170                 175

Ile Trp Ile Phe Pro Glu Gly Thr Arg Ser Arg Leu Asp Lys Ala Asp
            180                 185                 190

Leu Leu Pro Phe Lys Lys Gly Ala Phe His Leu Ala Ile Gln Ala Gln
        195                 200                 205
```

```
Leu Pro Ile Leu Pro Ile Ile Ser Gln Gly Tyr Ser His Ile Tyr Asp
        210                 215                 220

Ser Ser Lys Arg Tyr Phe Pro Gly Gly Glu Leu Glu Ile Arg Val Leu
225                 230                 235                 240

Glu Pro Ile Pro Thr Thr Gly Leu Thr Thr Asp Asp Val Asn Asp Leu
                245                 250                 255

Met Asp Lys Thr Arg Asn Leu Met Leu Lys His Leu Lys Glu Met Asp
            260                 265                 270

Ser Gln Tyr Ser Ser Ser Thr Ala Glu Asn Gly Ser Thr His Ile Asp
        275                 280                 285

Ala Asp Ile Ala Lys Ser Thr Ala Thr Ser Ile Gly Asn Thr Asp Asp
    290                 295                 300

Ala Ile Thr Lys Arg Arg Thr Pro Lys Glu
305                 310

<210> SEQ ID NO 5
<211> LENGTH: 211
<212> TYPE: DNA
<213> ORGANISM: Mortierella alpina

<400> SEQUENCE: 5
gagctccatg gacatgatgg tcctgggacg cgtcttccca aagcactgtg tcgtcatggc      60
aaagaaggaa cttctttact ttccgttcct gggcatgttt atgaagctga gtaacgccat     120
cttcattgac cgcaagaacc acaagaaggc gatcgagtcc accacccaag ctgtcgccga     180
catgaagaag cacaactctg gaatctggat t                                    211

<210> SEQ ID NO 6
<211> LENGTH: 26
<212> TYPE: DNA
<213> ORGANISM: Artificial Sequence
<220> FEATURE:
<223> OTHER INFORMATION: Primer MaLP1_5-1
<220> FEATURE:
<221> NAME/KEY: misc_feature
<222> LOCATION: (18)..(18)
<223> OTHER INFORMATION: n is a, c, g, or t

<400> SEQUENCE: 6
cccgccgtct acgtcdsnaa ycayca                                           26

<210> SEQ ID NO 7
<211> LENGTH: 20
<212> TYPE: DNA
<213> ORGANISM: Artificial Sequence
<220> FEATURE:
<223> OTHER INFORMATION: Primer MaLP2_5-1

<400> SEQUENCE: 7
gtcatgatct gcaaycayca                                                  20

<210> SEQ ID NO 8
<211> LENGTH: 23
<212> TYPE: DNA
<213> ORGANISM: Artificial Sequence
<220> FEATURE:
<223> OTHER INFORMATION: Primer MaLP1_3-2
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
```

<222> LOCATION: (18)..(18)
<223> OTHER INFORMATION: n is a, c, g, or t

<400> SEQUENCE: 8
taaggagcgg tnccytcngg raa                                              23

<210> SEQ ID NO 9
<211> LENGTH: 24
<212> TYPE: DNA
<213> ORGANISM: Artificial Sequence
<220> FEATURE:
<223> OTHER INFORMATION: Primer MaLP2_3-2
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 9
ggagcagttg gtnccytcng graa                                             24

<210> SEQ ID NO 10
<211> LENGTH: 22
<212> TYPE: DNA
<213> ORGANISM: Artificial Sequence
<220> FEATURE:
<223> OTHER INFORMATION: Primer T7

<400> SEQUENCE: 10
gtaatacgac tcactatagg gc                                               22

<210> SEQ ID NO 11
<211> LENGTH: 19
<212> TYPE: DNA
<213> ORGANISM: Artificial Sequence
<220> FEATURE:
<223> OTHER INFORMATION: Primer M13-28Rev

<400> SEQUENCE: 11
ggaaacagct atgaccatg                                                   19

<210> SEQ ID NO 12
<211> LENGTH: 18
<212> TYPE: DNA
<213> ORGANISM: Artificial Sequence
<220> FEATURE:
<223> OTHER INFORMATION: Primer MaLP3R1-1

<400> SEQUENCE: 12
cgagtccacc acccaagc                                                    18

<210> SEQ ID NO 13
<211> LENGTH: 18
<212> TYPE: DNA
<213> ORGANISM: Artificial Sequence
<220> FEATURE:
<223> OTHER INFORMATION: Primer MaLP3R1-2

<400> SEQUENCE: 13
aagaaggcga tcgagtcc                                                    18

<210> SEQ ID NO 14
<211> LENGTH: 59
<212> TYPE: DNA

```
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's
      SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 14
attctagagg ccgaggcggc cgacatgttt tttttttttt tttttttttt ttttttvn      59

<210> SEQ ID NO 15
<211> LENGTH: 669
<212> TYPE: DNA
<213> ORGANISM: Mortierella alpina
<220> FEATURE:
<221> NAME/KEY: misc_feature
<222> LOCATION: (635)..(635)
<223> OTHER INFORMATION: n is a, c, g, or t

<400> SEQUENCE: 15
tgtcgccgac atgaagaagc acaactctgg aatctggatt ttccccgaag gaacacgttc     60
ccgcttggac aaggccgatc tcttgccctt caagaaggga gccttccacc tcgccattca    120
agcccaactc ccgatcctcc ccatcatctc gcaaggatac tcacacatct acgattcgtc    180
aaaacgctac ttccccggtg agagctcga gatcagagtc ctggaaccta tccccaccac     240
gggattgacc acagacgatg tgaacgacct gatggacaag actcgcaacc tgatgctgaa    300
gcacctcaag gagatggatt ctcaatactc ctcctccacc gctgaaaacg gatcgaccca    360
tattgacgcc gatatcgcaa agtcaactgc cacatcgatc ggaaacacgg acgatgctat    420
cacaaagagg aggacaccaa aagagtagtg gttatgcaac agcagcaata acaatattaa    480
caacaaacaa caacctgaac agcaaccaca acaacaaca acaacaacaa caacaacaac    540
cctgcaggat tctctgatcc tgcacatcgc atccccatgc ctgtaatgta ctttttcaaa    600
agaataacat gattaaatcg atagagctgt acccncctta aaaaaaaaaa aaaaaaaaa    660 aaaaaaaaa                                                            669

<210> SEQ ID NO 16
<211> LENGTH: 44
<212> TYPE: DNA
<213> ORGANISM: Artificial Sequence
<220> FEATURE:
<223> OTHER INFORMATION: Genome Walker adaptor-1

<400> SEQUENCE: 16
gtaatacgac tatagggcac gcgtggtcga cggcccgggc tggt                      44

<210> SEQ ID NO 17
<211> LENGTH: 8
<212> TYPE: DNA
<213> ORGANISM: Artificial Sequence
<220> FEATURE:
<223> OTHER INFORMATION: Genome Walker adaptor-2
<220> FEATURE:
<221> NAME/KEY: misc_feature
<222> LOCATION: (1)..(1)
<223> OTHER INFORMATION: 5' end is associated with a -PO4 group
<220> FEATURE:
<221> NAME/KEY: misc_feature
<222> LOCATION: (8)..(8)
```

<223> OTHER INFORMATION: 3' end is associated with a -H2N group

<400> SEQUENCE: 17 accagccc                                                                    8

<210> SEQ ID NO 18
<211> LENGTH: 20
<212> TYPE: DNA
<213> ORGANISM: Artificial Sequence
<220> FEATURE:
<223> OTHER INFORMATION: Primer MaLPAT2-5-1

<400> SEQUENCE: 18
gacacagtgc tttgggaaga                                                      20

<210> SEQ ID NO 19
<211> LENGTH: 22
<212> TYPE: DNA
<213> ORGANISM: Artificial Sequence
<220> FEATURE:
<223> OTHER INFORMATION: Primer AP1

<400> SEQUENCE: 19
gtaatacgac tcactatagg gc                                                   22

<210> SEQ ID NO 20
<211> LENGTH: 20
<212> TYPE: DNA
<213> ORGANISM: Artificial Sequence
<220> FEATURE:
<223> OTHER INFORMATION: Primer MaLPAT2-5-2

<400> SEQUENCE: 20
aggaccatca tgtccatgga                                                      20

<210> SEQ ID NO 21
<211> LENGTH: 19
<212> TYPE: DNA
<213> ORGANISM: Artificial Sequence
<220> FEATURE:
<223> OTHER INFORMATION: Primer AP2

<400> SEQUENCE: 21
actatagggc acgcgtggt                                                       19

<210> SEQ ID NO 22
<211> LENGTH: 1947
<212> TYPE: DNA
<213> ORGANISM: Mortierella alpina

<400> SEQUENCE: 22
cgcccttact atagggcacg cgtggtcgac ggcccgggct ggtctgtttt gcatcccatc           60
gactctccca acatatatcc gcattcattc gctcatgtgc acgctatgag aaatggccaa          120
ggaagagtcc ccgtttggcc atttcaactt ttacgcctgt tgtttttcgc cttccgtcat          180
ggtcggtccg tctgtttgcg ccttgtcgac agtgtcgaca tggcgcacaa ttgcaagcaa          240
agcagaacga gaaaaccaca ggaaaggacg cgaggcgtgc tttcatccgt gcatgccaca          300
gcattcctgc ctgtctcttt gcgcccaaac gttattattg ctcgcactgt ctgtactgtg          360
cagtttgcac tctagaagcg aaggtggata agagagtgta tggccttttca agacccaata         420
cgctgcttga atgtttttcc cagcctaatc cgatctccgc ggcggatgtt cttattgctg          480
tcaatcgtcg ttccgcatat caatcataca gttagcaccg atcgagacct gtatatgagc          540

-continued

```
cagtgcctta catcagagaa catggctacc atgtgagtac cggacgcagc atctgcgagc    600
ctgcctttgc gcgcgcaata acgaatggaa ggcgttacga gtttgctcgc catattcgga    660
caaggttgat cggacagcaa atcaaaaatg catgtgagaa caattggacc tggctctggc    720
ttgttggctt gtatcacagc actcttgcac ccaaacagat agcaaatctg tcactccacc    780
ccgatcaggt tgacattgcc cacctccatt cctctgagca gtcaagtctc tgcagcagaa    840
cgcatgcatt cgaccttggt gaattgcatt gggctactga actgtagcac aggcactttg    900
ctggccctga gagtgacctc cccctctgcg gtgtgtggtgc agtgaggcac gcgatgggcc    960
attgagcaat tcatcccctg atcctaaagt ggagatgatc atgacaaaca caaaaaaaa    1020
ggtgaaaagg ggattgctgc tgctgctgct gtgtctgtgc ttatgcgatg tatccgaaat    1080
gcatggcaat ggccgccttc ctttggggca aggaccaacc ccaaaattgt tttgggctgc    1140
catatgggca agagcgtcgt ccgccgtatt tcttttgcga ctccgtcggc gactcagctc    1200
tgcatctttt tcttcttttt tttttttttt ttttgtcttc ctgaatcaat cctcctgtcg    1260
tccattcctc cagtcgtcct cgtcctgcat tcaacgcccg cttcgcaacc accgtctgtg    1320
ctgtctaccg tgctcgctcc tttgcaaaac tcctttcatt cgacgattgt tcccatctcc    1380
agcacaaccc tttcgtcaga catgtccata ggtatgttgt gtcttctcgg cggtaccacc    1440
tttgttcttt ctttttttttt ttttgtaatg ctcaattcac tttgcaaatg ttactcaaag    1500
cgtcaatgga aactggctcc attccaccct tgcaacaacg caatcgtctg tcttcattct    1560
aaaccgcctg tatgtgctgt gcttgcctga ccctccctag gttcttccaa tcctgtcctg    1620
ctggcagcga tccccttcgt ctacctcttc gtcctccctc gtgtcctcgc cttcctccct    1680
caaaaggccc agttcctcgc aaaatgcatc gtggtcttga tcgccaccct tatcatgtcc    1740
gtcgcaggct gcttcatttc catcgtctgt gcgctcctcg ataaacgcta tgtgatcaac    1800
tacgtcgtct caagactctt ctcattcctc gctgcaagac cctgcggtgt cacctacaag    1860
atcgtcggcg aggaacatct ggacaagtac cccgccattg tcgtctgcaa ccaccagagc    1920
tccatggaca tgatggtcct aagggcg                                         1947
```

<210> SEQ ID NO 23
<211> LENGTH: 23
<212> TYPE: DNA
<213> ORGANISM: Artificial Sequence
<220> FEATURE:
<223> OTHER INFORMATION: 5'-CDSIII Primer

<400> SEQUENCE: 23

```
aagcagtggt atcaacgcag agt                                              23
```

<210> SEQ ID NO 24
<211> LENGTH: 502
<212> TYPE: DNA
<213> ORGANISM: Mortierella alpina

<400> SEQUENCE: 24

```
tcaatcctcc tgtcgtccat tcctccagtc gtcctcgtcc tgcattcaac gcccacttca     60
caaccaccgt ctgtgctgtc taccgtgctc gctcctttgc aaaactcctt tcattcgacg    120
attgttccca tctccagcac aaccctttcg tcagacatgt ccataggttc ttccaatcct    180
gtcctgctgg cagcgatccc cttcgtctac ctcttcgtcc tccctcgtgt cctgccttc    240
ctccctcaaa aggcccagtt cctcgcaaaa tgcatcgtgg tcttgatcgc cacccttatc    300
```

```
atgtccgtcg caggctgctt catttccatc gtctgtgcgc tcctcgataa acgctatgtg     360
atcaactacg tcgtctcaag actcttctca ttcctcgctg caagaccctg cggtgtcacc     420
tacaagatcg tcggcgagga acatctggac aagtaccccg ccattgtcgt ctgcaaccac     480
cagagctcca tggacatgat gg                                              502

<210> SEQ ID NO 25
<211> LENGTH: 189
<212> TYPE: DNA
<213> ORGANISM: Mortierella alpina
<220> FEATURE:
<221> NAME/KEY: Intron
<222> LOCATION: (1)..(189)

<400> SEQUENCE: 25
gtatgttgtg tcttctcggc ggtaccacct ttgttctttc tttttttttt tttgtaatgc      60
tcaattcact ttgcaaatgt tactcaaagc gtcaatggaa actggctcca ttccacccttt   120 gcaacaacgc aatcgtctgt cttcattcta aaccgcctgt atgtgctgtg cttgcctgac    180
cctccctag                                                            189

<210> SEQ ID NO 26
<211> LENGTH: 2756
<212> TYPE: DNA
<213> ORGANISM: Mortierella alpina
<220> FEATURE:
<221> NAME/KEY: 5'UTR
<222> LOCATION: (1)..(1401)
<220> FEATURE:
<221> NAME/KEY: Intron
<222> LOCATION: (1412)..(1600)
<220> FEATURE:
<221> NAME/KEY: 3'UTR
<222> LOCATION: (2536)..(2756)
<220> FEATURE:
<221> NAME/KEY: misc_feature
<222> LOCATION: (2722)..(2722)
<223> OTHER INFORMATION: n is a, c, g, or t

<400> SEQUENCE: 26
cgcccttact atagggcacg cgtggtcgac ggcccgggct ggtctgtttt gcatcccatc      60
gactctccca acatatatcc gcattcattc gctcatgtgc acgctatgag aaatggccaa    120
ggaagagtcc ccgtttggcc atttcaactt ttacgcctgt tgttttttcgc cttccgtcat   180 ggtcggtccg tctgtttgcg ccttgtcgac agtgtcgaca tggcgcacaa ttgcaagcaa    240
agcagaacga gaaaaccaca ggaaaggacg cgaggcgtgc tttcatccgt gcatgccaca    300
gcattcctgc ctgtctcttt gcgcccaaac gttattattg ctcgcactgt ctgtactgtg    360 cagttttgcac tctagaagcg aaggtggata agagagtgta tggccttttca agacccaata  420 cgctgcttga atgttttttcc cagcctaatc cgatctccgc ggcggatgtt cttattgctg   480
tcaatcgtcg ttccgcatat caatcataca gttagcaccg atcgagacct gtatatgagc    540
cagtgcctta catcagagaa catggctacc atgtgagtac cggacgcagc atctgcgagc    600
ctgcctttgc gcgcgcaata acgaatgcaa ggcgttacga gtttgctcgc catattcgga    660
caaggttgat cggacagcaa atcaaaaatg catgtgagaa caattggacc tggctctggc    720
ttgttggctt gtatcacagc actcttgcac ccaaacagat agcaaatctg tcactccacc    780
ccgatcaggt tgacattgcc cacctccatt cctctgagca gtcaagtctc tgcagcagaa    840
cgcatgcatt cgaccttggt gaattgcatt gggctactga actgtagcac aggcactttg    900
ctggccctga gagtgaccctc cccctctgcg ggtgtggtgc agtgaggcac gcgatgggcc    960
```

-continued

```
attgagcaat tcatcccctg atcctaaagt ggagatgatc atgacaaaca caaaaaaaaa    1020
ggtgaaaagg ggattgctgc tgctgctgct gtgtctgtgc ttatgcgatg tatccgaaat    1080
gcatggcaat ggccgccttc ctttggggca aggaccaacc ccaaaattgt tttgggctgc    1140
catatgggca agagcgtcgt ccgccgtatt tcttttgcga ctccgtcggc gactcagctc    1200
tgcatctttt tcttctttt ttttttttt tttgtcttc ctgaatcaat cctcctgtcg    1260
tccattcctc cagtcgtcct cgtcctgcat tcaacgcccg cttcgcaacc accgtctgtg    1320
ctgtctaccg tgctcgctcc tttgcaaaac tcctttcatt cgacgattgt tcccatctcc    1380
agcacaaccc tttcgtcaga catgtccata ggtatgttgt gtcttctcgg cggtaccacc    1440
tttgttcttt ctttttttt ttttgtaatg ctcaattcac tttgcaaatg ttactcaaag    1500
cgtcaatgga aactggctcc attccaccct tgcaacaacg caatcgtctg tcttcattct    1560
aaaccgcctg tatgtgctgt gcttgcctga ccctccctag gttcttccaa tcctgtcctg    1620
ctggcagcga tccccttcgt ctacctcttc gtcctccctc gtgtcctcgc cttcctccct    1680
caaaaggccc agttcctcgc aaaatgcatc gtggtcttga tcgccaccct tatcatgtcc    1740
gtcgcaggct gcttcatttc catcgtctgt gcgctcctcg ataaacgcta tgtgatcaac    1800
tacgtcgtct caagactctt ctcattcctc gctgcaagac cctgcggtgt cacctacaag    1860
atcgtcggcg aggaacatct ggacaagtac cccgccattg tcgtctgcaa ccaccagagc    1920
tccatggaca tgatggtcct gggacgcgtc ttcccaaagc actgtgtcgt catggcaaag    1980
aaggaacttc tttactttcc gttcctgggc atgtttatga agctgagtaa cgccatcttc    2040
attgaccgca agaaccacaa gaaggcgatc gagtccacca cccaagctgt cgccgacatg    2100
aagaagcaca actctggaat ctggattttc cccgaaggaa cacgttcccg cttggacaag    2160
gccgatctct tgcccttcaa gaagggagcc ttccacctcg ccattcaagc ccaactcccg    2220
atcctcccca tcatctcgca aggatactca cacatctacg attcgtcaaa cgctacttc     2280 cccggtggag agctcgagat cagagtcctg gaacctatcc ccaccacggg attgaccaca    2340
gacgatgtga acgacctgat ggacaagact cgcaacctga tgctgaagca cctcaaggag    2400
atggattctc aatactcctc ctccaccgct gaaaacggat cgacccatat tgacgccgat    2460
atcgcaaagt caactgccac atcgatcgga aacacggacg atgctatcac aaagaggagg    2520
acaccaaaag agtagtggtt atgcaacagc agcaataaca atattaacaa caaacaacaa    2580
cctgaacagc aaccacaaac aacaacaaca caacaacaa caacacccct gcaggattct    2640
ctgatcctgc acatcgcatc cccatgcctg taatgtactt tttcaaaaga ataacatgat    2700
taaatcgata gagctgtacc cnccttaaaa aaaaaaaaaa aaaaaaaaaa aaaaaa       2756
```

```
<210> SEQ ID NO 27
<211> LENGTH: 29
<212> TYPE: DNA
<213> ORGANISM: Artificial Sequence
<220> FEATURE:
<223> OTHER INFORMATION: Primer MaLP1_5NotI

<400> SEQUENCE: 27
gcggccgcaa catgtccata ggttcttcc                                        29

<210> SEQ ID NO 28
<211> LENGTH: 28
<212> TYPE: DNA
<213> ORGANISM: Artificial Sequence
<220> FEATURE:
```

<223> OTHER INFORMATION: MaLP1_3NotI

<400> SEQUENCE: 28
gcggccgcct actcttttgg tgtcctcc  28

<210> SEQ ID NO 29
<211> LENGTH: 3981
<212> TYPE: DNA
<213> ORGANISM: Artificial Sequence
<220> FEATURE:
<223> OTHER INFORMATION: Plasmid pLF109

<400> SEQUENCE: 29

| | | | | | |
|---|---|---|---|---|---|
| atcactagtg | aattcgcggc | cgcctgcagg | tcgaccatat | gggagagctc | ccaacgcgtt | 60 |
| ggatgcatag | cttgagtatt | ctatagtgtc | acctaaatag | cttggcgtaa | tcatggtcat | 120 |
| agctgtttcc | tgtgtgaaat | tgttatccgc | tcacaattcc | acacaacata | cgagccggaa | 180 |
| gcataaagtg | taaagcctgg | ggtgcctaat | gagtgagcta | actcacatta | attgcgttgc | 240 |
| gctcactgcc | cgctttccag | tcgggaaacc | tgtcgtgcca | gctgcattaa | tgaatcggcc | 300 |
| aacgcgcggg | gagaggcggt | ttgcgtattg | ggcgctcttc | cgcttcctcg | ctcactgact | 360 |
| cgctgcgctc | ggtcgttcgg | ctgcggcgag | cggtatcagc | tcactcaaag | gcggtaatac | 420 |
| ggttatccac | agaatcaggg | gataacgcag | gaaagaacat | gtgagcaaaa | ggccagcaaa | 480 |
| aggccaggaa | ccgtaaaaag | gccgcgttgc | tggcgttttt | ccataggctc | cgcccccctg | 540 |
| acgagcatca | caaaaatcga | cgctcaagtc | agaggtggcg | aaacccgaca | ggactataaa | 600 |
| gataccaggc | gtttccccct | ggaagctccc | tcgtgcgctc | tcctgttccg | accctgccgc | 660 |
| ttaccggata | cctgtccgcc | tttctccctt | cgggaagcgt | ggcgctttct | catagctcac | 720 |
| gctgtaggta | tctcagttcg | gtgtaggtcg | ttcgctccaa | gctgggctgt | gtgcacgaac | 780 |
| cccccgttca | gcccgaccgc | tgcgccttat | ccggtaacta | tcgtcttgag | tccaacccgg | 840 |
| taagacacga | cttatcgcca | ctggcagcag | ccactggtaa | caggattagc | agagcgaggt | 900 |
| atgtaggcgg | tgctacagag | ttcttgaagt | ggtggcctaa | ctacggctac | actagaagaa | 960 |
| cagtatttgg | tatctgcgct | ctgctgaagc | cagttacctt | cggaaaaaga | gttggtagct | 1020 |
| cttgatccgg | caaacaaacc | accgctggta | gcggtggttt | ttttgtttgc | aagcagcaga | 1080 |
| ttacgcgcag | aaaaaaagga | tctcaagaag | atcctttgat | cttttctacg | gggtctgacg | 1140 |
| ctcagtggaa | cgaaaactca | cgttaaggga | ttttggtcat | gagattatca | aaaaggatct | 1200 |
| tcacctagat | ccttttaaat | taaaaatgaa | gttttaaatc | aatctaaagt | atatatgagt | 1260 |
| aaacttggtc | tgacagttac | caatgcttaa | tcagtgaggc | acctatctca | gcgatctgtc | 1320 |
| tatttcgttc | atccatagtt | gcctgactcc | ccgtcgtgta | gataactacg | atacgggagg | 1380 |
| gcttaccatc | tggccccagt | gctgcaatga | taccgcgaga | cccacgctca | ccggctccag | 1440 |
| atttatcagc | aataaaccag | ccagccggaa | gggccgagcg | cagaagtggt | cctgcaactt | 1500 |
| tatccgcctc | catccagtct | attaattgtt | gccgggaagc | tagagtaagt | agttcgccag | 1560 |
| ttaatagttt | gcgcaacgtt | gttgccattg | ctacaggcat | cgtggtgtca | cgctcgtcgt | 1620 |
| ttggtatggc | ttcattcagc | tccggttccc | aacgatcaag | gcgagttaca | tgatccccca | 1680 |
| tgttgtgcaa | aaaagcggtt | agctccttcg | gtcctccgat | cgttgtcaga | agtaagttgg | 1740 |
| ccgcagtgtt | atcactcatg | gttatggcag | cactgcataa | ttctcttact | gtcatgccat | 1800 |
| ccgtaagatg | cttttctgtg | actggtgagt | actcaaccaa | gtcattctga | gaatagtgta | 1860 |
| tgcggcgacc | gagttgctct | tgcccggcgt | caatacggga | taataccgcg | ccacatagca | 1920 |

-continued

```
gaactttaaa agtgctcatc attggaaaac gttcttcggg gcgaaaactc tcaaggatct    1980
taccgctgtt gagatccagt tcgatgtaac ccactcgtgc acccaactga tcttcagcat    2040
cttttacttt caccagcgtt tctgggtgag caaaaacagg aaggcaaaat gccgcaaaaa    2100
agggaataag ggcgacacgg aaatgttgaa tactcatact cttccttttt caatattatt    2160
gaagcattta tcagggttat tgtctcatga gcggatacat atttgaatgt atttagaaaa    2220
ataaacaaat aggggttccg cgcacatttc cccgaaaagt gccacctgat gcggtgtgaa    2280
ataccgcaca gatgcgtaag gagaaaatac cgcatcagga aattgtaagc gttaatattt    2340
tgttaaaatt cgcgttaaat ttttgttaaa tcagctcatt ttttaaccaa taggccgaaa    2400
tcggcaaaat cccttataaa tcaaaagaat agaccgagat agggttgagt gttgttccag    2460
tttggaacaa gagtccacta ttaaagaacg tggactccaa cgtcaaaggg cgaaaaaccg    2520
tctatcaggg cgatggccca ctacgtgaac catcaccta atcaagtttt ttggggtcga    2580
ggtgccgtaa agcactaaat cggaacccta aagggagccc ccgatttaga gcttgacggg    2640
gaaagccggc gaacgtggcg agaaaggaag ggaagaaagc gaaaggagcg ggcgctaggg    2700
cgctggcaag tgtagcggtc acgctgcgcg taaccaccac acccgccgcg cttaatgcgc    2760
cgctacaggg cgcgtccatt cgccattcag gctgcgcaac tgttgggaag ggcgatcggt    2820
gcgggcctct tcgctattac gccagctggc gaaaggggga tgtgctgcaa ggcgattaag    2880
ttgggtaacg ccaggttttt cccagtcacg acgttgtaaa acgacggcca gtgaattgta    2940
atacgactca ctatagggcg aattgggccc gacgtcgcat gctcccggcc gccatggcgg    3000
ccgcgggaat tcgatatgtc cataggttct tccaatcctg tcctgctggc agcgatcccc    3060
ttcgtctacc tcttcgtcct ccctcgtgtc ctcgccttcc tccctcaaaa ggcccagttc    3120
ctcgcaaaat gcatcgtggt cttgatcgcc acccttatca tgtccgtcgc aggctgcttc    3180
atttccatcg tctgtgcgct cctcgataaa cgctatgtga tcaactacgt cgtctcaaga    3240
ctcttctcat tcctcgctgc aagaccctgc ggtgtcacct acaagatcgt cggcgaggaa    3300
catctggaca agtaccccgc cattgtcgtc tgcaaccacc agagctccat ggacatgatg    3360
gtcctgggac gcgtcttccc aaagcactgt gtcgtcatgg caaagaagga acttctttac    3420
tttccgttcc tgggcatgtt tatgaagctg agtaacgcca tcttcattga ccgcaagaac    3480
cacaagaagg cgatcgagtc caccacccaa gctgtcgccg acatgaagaa gcacaactct    3540
ggaatctgga ttttccccga aggaacacgt tcccgcttgg acaaggccga tctcttgccc    3600
ttcaagaagg gagccttcca cctcgccatt caagcccaac tcccgatcct ccccatcatc    3660
tcgcaaggat actcacacat ctacgattcg tcaaaacgct acttccccgg tggagagctc    3720
gagatcagag tcctggaacc tatccccacc acgggattga ccacagacga tgtgaacgac    3780
ctgatggaca agactcgcaa cctgatgctg aagcacctca aggagatgga ttctcaatac    3840
tcctcctcca ccgctgaaaa cggatcgacc catattgacg ccgatatcgc aaagtcaact    3900
gccacatcga tcgaaacac ggacgatgct atcacaaaga ggaggacacc aaaagagtag    3960
tggttatgca acaacagcaa t                                              3981
```

<210> SEQ ID NO 30
<211> LENGTH: 1254
<212> TYPE: DNA
<213> ORGANISM: Mortierella alpina
<220> FEATURE:
<221> NAME/KEY: CDS
<222> LOCATION: (1)..(1254)

<223> OTHER INFORMATION: GenBank Accession No. CQ891250
<300> PUBLICATION INFORMATION:
<302> TITLE: Novel plant acyltransferases specific for long-chained, multiply unsaturated fatty acids
<310> PATENT DOCUMENT NUMBER: WO 2004/087902
<311> PATENT FILING DATE: 2004-03-26
<312> PUBLICATION DATE: 2004-10-14
<313> RELEVANT RESIDUES IN SEQ ID NO: (1)..(1254)

<400> SEQUENCE: 30

```
atg gat gaa tcc acc acg acc acc acg cac cac tca gag acc agc agc       48
Met Asp Glu Ser Thr Thr Thr Thr Thr His His Ser Glu Thr Ser Ser
1               5                   10                  15 aag acg tcc tcg cac ccc cgc cgg ctc ggt ccc gag atg aac cct atc       96
Lys Thr Ser Ser His Pro Arg Arg Leu Gly Pro Glu Met Asn Pro Ile
                20                  25                  30 tac aag ggt ctg cga gcc att gtc tgg gcc ttt tac ttc aac ctg gga      144
Tyr Lys Gly Leu Arg Ala Ile Val Trp Ala Phe Tyr Phe Asn Leu Gly
            35                  40                  45 gcg tcg ctt ata tcg atc acg cag gtg ctg tcg ctg cct ctg gcg ttg      192
Ala Ser Leu Ile Ser Ile Thr Gln Val Leu Ser Leu Pro Leu Ala Leu
        50                  55                  60 att gct cca ggg gtc tac cag tgg cac atc agc aaa aca cag ggt cac      240
Ile Ala Pro Gly Val Tyr Gln Trp His Ile Ser Lys Thr Gln Gly His
65                  70                  75                  80 ttt gga gct ttc ctg ctc cgg atg aac cag ctc ttt gcg ccg tca gat      288
Phe Gly Ala Phe Leu Leu Arg Met Asn Gln Leu Phe Ala Pro Ser Asp
                85                  90                  95 att gtc ttg aca ggg gac gag agt gtc agg gga atc gtc aag gtc tac      336
Ile Val Leu Thr Gly Asp Glu Ser Val Arg Gly Ile Val Lys Val Tyr
                100                 105                 110 aaa gga cgg aac ctg aag gag gcc ggt gag cca ggc agc ggt cag gga      384
Lys Gly Arg Asn Leu Lys Glu Ala Gly Glu Pro Gly Ser Gly Gln Gly
            115                 120                 125 gag gac att ctt ctg gat atg ccc gag agg atg gtt ttc att gcg aac      432
Glu Asp Ile Leu Leu Asp Met Pro Glu Arg Met Val Phe Ile Ala Asn
        130                 135                 140 cac cag atc tac tct gac tgg atg tac ctc tgg tgc ttc tcc tat ttt      480
His Gln Ile Tyr Ser Asp Trp Met Tyr Leu Trp Cys Phe Ser Tyr Phe
145                 150                 155                 160 gca gag agg cac agg gca ctg aag att att ctt cgg ggc gac ctg acc      528
Ala Glu Arg His Arg Ala Leu Lys Ile Ile Leu Arg Gly Asp Leu Thr
                165                 170                 175 tgg atc cct gtc ttt ggc tgg ggt atg cgg ttc ttt gac ttt atc ttt      576
Trp Ile Pro Val Phe Gly Trp Gly Met Arg Phe Phe Asp Phe Ile Phe
                180                 185                 190 ttg aaa cgt aat gac tgg gca cac gat cgc cgt gcc att gag gaa aac      624
Leu Lys Arg Asn Asp Trp Ala His Asp Arg Arg Ala Ile Glu Glu Asn
            195                 200                 205 ttg gga cgt gtc aag gaa aag gat ccc ctc tgg ctc gtg gtc ttc ccc      672
Leu Gly Arg Val Lys Glu Lys Asp Pro Leu Trp Leu Val Val Phe Pro
        210                 215                 220 gag gga aca gtc gtc tcc aag gaa acg cgt ctc cga tcc gtt gcc ttt      720
Glu Gly Thr Val Val Ser Lys Glu Thr Arg Leu Arg Ser Val Ala Phe
225                 230                 235                 240 tca aag aag gct agt ctg tcg gat cac cgc cat gtg ctg ctt cca agg      768
Ser Lys Lys Ala Ser Leu Ser Asp His Arg His Val Leu Leu Pro Arg
                245                 250                 255 acc agc ggt ctg ttt gtg tgc atc aac aag ttg cgt gga tct gtc gac      816
Thr Ser Gly Leu Phe Val Cys Ile Asn Lys Leu Arg Gly Ser Val Asp
                260                 265                 270
```

-continued

| | | |
|---|---|---|
| tac ttg tac gat gca acc gtt ggc tac tcg aat gtc gag tat ggc gag<br>Tyr Leu Tyr Asp Ala Thr Val Gly Tyr Ser Asn Val Glu Tyr Gly Glu<br>275 280 285 | 864 |
| att ccg cag gag ctt tac ccg tta cca gga ctg tat atc aac aaa gca<br>Ile Pro Gln Glu Leu Tyr Pro Leu Pro Gly Leu Tyr Ile Asn Lys Ala<br>290 295 300 | 912 |
| cag ccc aag gag atc aac atg cac ctg cgt cga ttt gcg atc aag gat<br>Gln Pro Lys Glu Ile Asn Met His Leu Arg Arg Phe Ala Ile Lys Asp<br>305 310 315 320 | 960 |
| atc ccc acg tca gaa ccc gaa ttt gtg gaa tgg gtc cga gct cgg tgg<br>Ile Pro Thr Ser Glu Pro Glu Phe Val Glu Trp Val Arg Ala Arg Trp<br>325 330 335 | 1008 |
| gtg gag aag gat gag ttg atg gaa gag ttt tat acc aag ggc cga ttt<br>Val Glu Lys Asp Glu Leu Met Glu Glu Phe Tyr Thr Lys Gly Arg Phe<br>340 345 350 | 1056 |
| cca tca caa ctg acg gcc gcc gac att ggt gag aag gag gtc aag acg<br>Pro Ser Gln Leu Thr Ala Ala Asp Ile Gly Glu Lys Glu Val Lys Thr<br>355 360 365 | 1104 |
| gca gga ggt cca acg gag gga cag agt gtc agg atc ccg ctc aag gcg<br>Ala Gly Gly Pro Thr Glu Gly Gln Ser Val Arg Ile Pro Leu Lys Ala<br>370 375 380 | 1152 |
| cga ggc atg atg gac tac ctc atg ccc tcg gtc atg aat ctg atc gcc<br>Arg Gly Met Met Asp Tyr Leu Met Pro Ser Val Met Asn Leu Ile Ala<br>385 390 395 400 | 1200 |
| ctt cct gtg ctg gcg ttt gcg atg aga tat gca gtg cag caa gca tcg<br>Leu Pro Val Leu Ala Phe Ala Met Arg Tyr Ala Val Gln Gln Ala Ser<br>405 410 415 | 1248 |
| ggc tga<br>Gly | 1254 |

<210> SEQ ID NO 31
<211> LENGTH: 417
<212> TYPE: PRT
<213> ORGANISM: Mortierella alpina

<400> SEQUENCE: 31

Met Asp Glu Ser Thr Thr Thr Thr Thr His His Ser Glu Thr Ser Ser
1               5                   10                  15

Lys Thr Ser Ser His Pro Arg Arg Leu Gly Pro Glu Met Asn Pro Ile
            20                  25                  30

Tyr Lys Gly Leu Arg Ala Ile Val Trp Ala Phe Tyr Phe Asn Leu Gly
        35                  40                  45

Ala Ser Leu Ile Ser Ile Thr Gln Val Leu Ser Leu Pro Leu Ala Leu
    50                  55                  60

Ile Ala Pro Gly Val Tyr Gln Trp His Ile Ser Lys Thr Gln Gly His
65                  70                  75                  80

Phe Gly Ala Phe Leu Leu Arg Met Asn Gln Leu Phe Ala Pro Ser Asp
                85                  90                  95

Ile Val Leu Thr Gly Asp Glu Ser Val Arg Gly Ile Val Lys Val Tyr
            100                 105                 110

Lys Gly Arg Asn Leu Lys Glu Ala Gly Glu Pro Gly Ser Gly Gln Gly
        115                 120                 125

Glu Asp Ile Leu Leu Asp Met Pro Glu Arg Met Val Phe Ile Ala Asn
    130                 135                 140

His Gln Ile Tyr Ser Asp Trp Met Tyr Leu Trp Cys Phe Ser Tyr Phe
145                 150                 155                 160

Ala Glu Arg His Arg Ala Leu Lys Ile Ile Leu Arg Gly Asp Leu Thr
                165                 170                 175

-continued

```
Trp Ile Pro Val Phe Gly Trp Gly Met Arg Phe Phe Asp Phe Ile Phe
                180                 185                 190

Leu Lys Arg Asn Asp Trp Ala His Asp Arg Arg Ala Ile Glu Glu Asn
            195                 200                 205

Leu Gly Arg Val Lys Glu Lys Asp Pro Leu Trp Leu Val Val Phe Pro
        210                 215                 220

Glu Gly Thr Val Val Ser Lys Glu Thr Arg Leu Arg Ser Val Ala Phe
225                 230                 235                 240

Ser Lys Lys Ala Ser Leu Ser Asp His Arg His Val Leu Leu Pro Arg
                245                 250                 255

Thr Ser Gly Leu Phe Val Cys Ile Asn Lys Leu Arg Gly Ser Val Asp
            260                 265                 270

Tyr Leu Tyr Asp Ala Thr Val Gly Tyr Ser Asn Val Glu Tyr Gly Glu
        275                 280                 285

Ile Pro Gln Glu Leu Tyr Pro Leu Pro Gly Leu Tyr Ile Asn Lys Ala
    290                 295                 300

Gln Pro Lys Glu Ile Asn Met His Leu Arg Arg Phe Ala Ile Lys Asp
305                 310                 315                 320

Ile Pro Thr Ser Glu Pro Glu Phe Val Glu Trp Val Arg Ala Arg Trp
                325                 330                 335

Val Glu Lys Asp Glu Leu Met Glu Glu Phe Tyr Thr Lys Gly Arg Phe
            340                 345                 350

Pro Ser Gln Leu Thr Ala Ala Asp Ile Gly Glu Lys Glu Val Lys Thr
        355                 360                 365

Ala Gly Gly Pro Thr Glu Gly Gln Ser Val Arg Ile Pro Leu Lys Ala
    370                 375                 380

Arg Gly Met Met Asp Tyr Leu Met Pro Ser Val Met Asn Leu Ile Ala
385                 390                 395                 400

Leu Pro Val Leu Ala Phe Ala Met Arg Tyr Ala Val Gln Gln Ala Ser
                405                 410                 415

Gly
```

<210> SEQ ID NO 32
<211> LENGTH: 1170
<212> TYPE: DNA
<213> ORGANISM: Mortierella alpina
<220> FEATURE:
<221> NAME/KEY: CDS
<222> LOCATION: (1)..(1170)
<223> OTHER INFORMATION: Gen Bank Accession No. CQ891252
<300> PUBLICATION INFORMATION:
<302> TITLE: Novel plant acyltransferases specific for long-chained, multiply unsaturated fatty acids
<310> PATENT DOCUMENT NUMBER: WO 2004/087902
<311> PATENT FILING DATE: 2004-03-26
<312> PUBLICATION DATE: 2004-10-14
<313> RELEVANT RESIDUES IN SEQ ID NO: (1)..(1170)

<400> SEQUENCE: 32

```
atg aac cct atc tac aag ggt ctg cga gcc att gtc tgg gcc ttt tac    48
Met Asn Pro Ile Tyr Lys Gly Leu Arg Ala Ile Val Trp Ala Phe Tyr
1               5                   10                  15 ttc aac ctg gga gcg tcg ctt ata tcg atc acg cag gtg ctg tcg ctg    96
Phe Asn Leu Gly Ala Ser Leu Ile Ser Ile Thr Gln Val Leu Ser Leu
            20                  25                  30 cct ctg gcg ttg att gct cca ggg gtc tac cag tgg cac atc agc aaa   144
Pro Leu Ala Leu Ile Ala Pro Gly Val Tyr Gln Trp His Ile Ser Lys
        35                  40                  45
```

| | | |
|---|---|---|
| aca cag ggt cac ttt gga gct ttc ctg ctc cgg atg aac cag ctc ttt<br>Thr Gln Gly His Phe Gly Ala Phe Leu Leu Arg Met Asn Gln Leu Phe<br>50                            55                         60 | | 192 |
| gcg ccg tca gat att gtc ttg aca ggg gac gag agt gtc agg gga atc<br>Ala Pro Ser Asp Ile Val Leu Thr Gly Asp Glu Ser Val Arg Gly Ile<br>65                    70                        75                        80 | | 240 |
| gtc aag gtc tac aaa gga cgg aac ctg aag gag gcc ggt gag cca ggc<br>Val Lys Val Tyr Lys Gly Arg Asn Leu Lys Glu Ala Gly Glu Pro Gly<br>                     85                        90                        95 | | 288 |
| agc ggt cag gga gag gac att ctt ctg gat atg ccc gag agg atg gtt<br>Ser Gly Gln Gly Glu Asp Ile Leu Leu Asp Met Pro Glu Arg Met Val<br>              100                       105                     110 | | 336 |
| ttc att gcg aac cac cag atc tac tct gac tgg atg tac ctc tgg tgc<br>Phe Ile Ala Asn His Gln Ile Tyr Ser Asp Trp Met Tyr Leu Trp Cys<br>        115                       120                     125 | | 384 |
| ttc tcc tat ttt gca gag agg cac agg gca ctg aag att att ctt cgg<br>Phe Ser Tyr Phe Ala Glu Arg His Arg Ala Leu Lys Ile Ile Leu Arg<br>130                         135                     140 | | 432 |
| ggc gac ctg acc tgg atc cct gtc ttt ggc tgg ggt atg cgg ttc ttt<br>Gly Asp Leu Thr Trp Ile Pro Val Phe Gly Trp Gly Met Arg Phe Phe<br>145                         150                     155                     160 | | 480 |
| gac ttt atc ttt ttg aaa cgt aat gac tgg gca cac gat cgc cgt gcc<br>Asp Phe Ile Phe Leu Lys Arg Asn Asp Trp Ala His Asp Arg Arg Ala<br>                     165                     170                     175 | | 528 |
| att gag gaa aac ttg gga cgt gtc aag gaa aag gat ccc ctc tgg ctc<br>Ile Glu Glu Asn Leu Gly Arg Val Lys Glu Lys Asp Pro Leu Trp Leu<br>                  180                     185                     190 | | 576 |
| gtg gtc ttc ccc gag gga aca gtc gtc tcc aag gaa acg cgt ctc cga<br>Val Val Phe Pro Glu Gly Thr Val Val Ser Lys Glu Thr Arg Leu Arg<br>               195                     200                     205 | | 624 |
| tcc gtt gcc ttt tca aag aag gct agt ctg tcg gat cac cgc cat gtg<br>Ser Val Ala Phe Ser Lys Lys Ala Ser Leu Ser Asp His Arg His Val<br>210                         215                     220 | | 672 |
| ctg ctt cca agg acc agc ggt ctg ttt gtg tgc atc aac aag ttg cgt<br>Leu Leu Pro Arg Thr Ser Gly Leu Phe Val Cys Ile Asn Lys Leu Arg<br>225                         230                     235                     240 | | 720 |
| gga tct gtc gac tac ttg tac gat gca acc gtt ggc tac tcg aat gtc<br>Gly Ser Val Asp Tyr Leu Tyr Asp Ala Thr Val Gly Tyr Ser Asn Val<br>                     245                     250                     255 | | 768 |
| gag tat ggc gag att ccg cag gag ctt tac ccg tta cca gga ctg tat<br>Glu Tyr Gly Glu Ile Pro Gln Glu Leu Tyr Pro Leu Pro Gly Leu Tyr<br>               260                     265                     270 | | 816 |
| atc aac aaa gca cag ccc aag gag atc aac atg cac ctg cgt cga ttt<br>Ile Asn Lys Ala Gln Pro Lys Glu Ile Asn Met His Leu Arg Arg Phe<br>        275                       280                     285 | | 864 |
| gcg atc aag gat atc ccc acg tca gaa ccc gaa ttt gtg gaa tgg gtc<br>Ala Ile Lys Asp Ile Pro Thr Ser Glu Pro Glu Phe Val Glu Trp Val<br>290                         295                     300 | | 912 |
| cga gct cgg tgg gtg gag aag gat gag ttg atg gaa gag ttt tat acc<br>Arg Ala Arg Trp Val Glu Lys Asp Glu Leu Met Glu Glu Phe Tyr Thr<br>305                         310                     315                     320 | | 960 |
| aag ggc cga ttt cca tca caa ctg acg gcc gcc gac att ggt gag aag<br>Lys Gly Arg Phe Pro Ser Gln Leu Thr Ala Ala Asp Ile Gly Glu Lys<br>                     325                     330                     335 | | 1008 |
| gag gtc aag acg gca gga ggt cca acg gag gga cag agt gtc agg atc<br>Glu Val Lys Thr Ala Gly Gly Pro Thr Glu Gly Gln Ser Val Arg Ile<br>                     340                     345                     350 | | 1056 |
| ccg ctc aag gcg cga ggc atg atg gac tac ctc atg ccc tcg gtc atg<br>Pro Leu Lys Ala Arg Gly Met Met Asp Tyr Leu Met Pro Ser Val Met<br>355                         360                     365 | | 1104 |

```
aat ctg atc gcc ctt cct gtg ctg gcg ttt gcg atg aga tat gca gtg    1152
Asn Leu Ile Ala Leu Pro Val Leu Ala Phe Ala Met Arg Tyr Ala Val
    370                 375                 380 cag caa gca tcg ggc tga                                            1170
Gln Gln Ala Ser Gly
385

<210> SEQ ID NO 33
<211> LENGTH: 389
<212> TYPE: PRT
<213> ORGANISM: Mortierella alpina

<400> SEQUENCE: 33

Met Asn Pro Ile Tyr Lys Gly Leu Arg Ala Ile Val Trp Ala Phe Tyr
1               5                   10                  15

Phe Asn Leu Gly Ala Ser Leu Ile Ser Ile Thr Gln Val Leu Ser Leu
            20                  25                  30

Pro Leu Ala Leu Ile Ala Pro Gly Val Tyr Gln Trp His Ile Ser Lys
        35                  40                  45

Thr Gln Gly His Phe Gly Ala Phe Leu Leu Arg Met Asn Gln Leu Phe
    50                  55                  60

Ala Pro Ser Asp Ile Val Leu Thr Gly Asp Glu Ser Val Arg Gly Ile
65                  70                  75                  80

Val Lys Val Tyr Lys Gly Arg Asn Leu Lys Glu Ala Gly Glu Pro Gly
                85                  90                  95

Ser Gly Gln Gly Glu Asp Ile Leu Leu Asp Met Pro Glu Arg Met Val
            100                 105                 110

Phe Ile Ala Asn His Gln Ile Tyr Ser Asp Trp Met Tyr Leu Trp Cys
        115                 120                 125

Phe Ser Tyr Phe Ala Glu Arg His Arg Ala Leu Lys Ile Ile Leu Arg
    130                 135                 140

Gly Asp Leu Thr Trp Ile Pro Val Phe Gly Trp Gly Met Arg Phe Phe
145                 150                 155                 160

Asp Phe Ile Phe Leu Lys Arg Asn Asp Trp Ala His Asp Arg Arg Ala
                165                 170                 175

Ile Glu Glu Asn Leu Gly Arg Val Lys Glu Lys Asp Pro Leu Trp Leu
            180                 185                 190

Val Val Phe Pro Glu Gly Thr Val Val Ser Lys Glu Thr Arg Leu Arg
        195                 200                 205

Ser Val Ala Phe Ser Lys Lys Ala Ser Leu Ser Asp His Arg His Val
    210                 215                 220

Leu Leu Pro Arg Thr Ser Gly Leu Phe Val Cys Ile Asn Lys Leu Arg
225                 230                 235                 240

Gly Ser Val Asp Tyr Leu Tyr Asp Ala Thr Val Gly Tyr Ser Asn Val
                245                 250                 255

Glu Tyr Gly Glu Ile Pro Gln Glu Leu Tyr Pro Leu Pro Gly Leu Tyr
            260                 265                 270

Ile Asn Lys Ala Gln Pro Lys Glu Ile Asn Met His Leu Arg Arg Phe
        275                 280                 285

Ala Ile Lys Asp Ile Pro Thr Ser Glu Pro Glu Phe Val Glu Trp Val
    290                 295                 300

Arg Ala Arg Trp Val Glu Lys Asp Glu Leu Met Glu Glu Phe Tyr Thr
305                 310                 315                 320

Lys Gly Arg Phe Pro Ser Gln Leu Thr Ala Ala Asp Ile Gly Glu Lys
                325                 330                 335
```

Glu Val Lys Thr Ala Gly Gly Pro Thr Glu Gly Gln Ser Val Arg Ile
                340                 345                 350

Pro Leu Lys Ala Arg Gly Met Met Asp Tyr Leu Met Pro Ser Val Met
            355                 360                 365

Asn Leu Ile Ala Leu Pro Val Leu Ala Phe Ala Met Arg Tyr Ala Val
        370                 375                 380

Gln Gln Ala Ser Gly
385

<210> SEQ ID NO 34
<211> LENGTH: 329
<212> TYPE: PRT
<213> ORGANISM: Mortierella alpina
<300> PUBLICATION INFORMATION:
<302> TITLE: Novel Lysophosphatidate Acyltransferase Gene
<310> PATENT DOCUMENT NUMBER: WO 2008/146745
<311> PATENT FILING DATE: 2008-05-23
<312> PUBLICATION DATE: 2008-12-04
<313> RELEVANT RESIDUES IN SEQ ID NO: (1)..(329)

<400> SEQUENCE: 34

Met Ser Ser Met Ser Ser Ile Glu Pro Ala Leu Ser Ser Phe Pro Gly
1               5                   10                  15

Asn Leu Ala Val Ile Leu Val Phe Tyr Leu Ala Leu Pro Arg Leu Leu
            20                  25                  30

Ala Val Leu Pro Gln Lys Ile Gln Phe Ile Ala Lys Cys Leu Ile Val
        35                  40                  45

Leu Thr Ala Thr Phe Leu Met Ser Val Ala Gly Cys Phe Val Ala Ile
    50                  55                  60

Val Cys Ala Leu Leu Gln Lys Arg Tyr Ala Ile Asn Tyr Val Val Ala
65                  70                  75                  80

Arg Ile Phe Ser Tyr Ile Ala Cys Arg Pro Cys Gly Val Thr Phe Asn
                85                  90                  95

Ile Val Gly Glu Glu His Leu Glu Asn Thr Pro Ala Ile Val Val Cys
            100                 105                 110

Asn His Gln Ser Ser Met Asp Met Met Val Leu Gly Arg Val Phe Pro
        115                 120                 125

Met Arg Cys Val Val Met Ala Lys Lys Glu Leu Gln Tyr Phe Pro Phe
    130                 135                 140

Leu Gly Ile Phe Met Thr Leu Ser Asn Ala Ile Phe Ile Asp Arg Lys
145                 150                 155                 160

Asn His Lys Lys Ala Ile Glu Ser Thr Thr Gln Ala Val Ala Asp Met
                165                 170                 175

Lys Lys His Asn Ser Gly Ile Trp Ile Phe Pro Glu Gly Thr Arg Ser
            180                 185                 190

Arg Leu Asp Thr Ala Asp Leu Leu Pro Phe Lys Lys Gly Ala Phe His
        195                 200                 205

Leu Ala Ile Gln Ser Gly Leu Pro Ile Leu Pro Ile Val Ser Ala Gly
    210                 215                 220

Tyr Asn His Ile Tyr Asp Ser Ala Lys Arg Ser Phe Pro Gly Gly Glu
225                 230                 235                 240

Leu Glu Ile Arg Val Leu Glu Pro Ile Pro Thr Thr Gly Met Thr Ala
                245                 250                 255

Asp Asp Val Asn Asp Leu Met Glu Arg Thr Arg Ala Val Met Leu Lys
            260                 265                 270

Asn Leu Lys Glu Met Asp Val Asn Ser Leu Ala Val Ser Ser Lys Pro

```
                   275                 280                 285
Ser Leu Ser Val Asp Glu Leu Lys Ser Ala Pro Ala Leu Lys Gln Glu
    290                 295                 300

Ala Lys Ser Thr Ala Val Val Glu Glu Glu Gly Val Ser Tyr Asp Ser
305                 310                 315                 320

Val Lys Lys Arg Lys Thr Val Lys Ala
                325

<210> SEQ ID NO 35
<211> LENGTH: 313
<212> TYPE: PRT
<213> ORGANISM: Mortierella alpina
<300> PUBLICATION INFORMATION:
<302> TITLE: Novel Lysophosphatidate Acyltransferase Gene
<310> PATENT DOCUMENT NUMBER: WO 2008/146745
<311> PATENT FILING DATE: 2008-05-23
<312> PUBLICATION DATE: 2008-12-04
<313> RELEVANT RESIDUES IN SEQ ID NO: (1)..(313)

<400> SEQUENCE: 35

Met Ser Ile Gly Ser Ser Asn Pro Val Leu Leu Ala Ala Ile Pro Phe
1               5                   10                  15

Val Tyr Leu Phe Val Leu Pro Arg Ile Leu Ala Phe Leu Pro Gln Lys
                20                  25                  30

Ala Gln Phe Leu Ala Lys Cys Ile Val Val Leu Ile Ala Thr Leu Ile
            35                  40                  45

Met Ser Val Ala Gly Cys Leu Ile Ser Ile Val Cys Ala Leu Leu Asp
    50                  55                  60

Lys Arg Tyr Val Ile Asn Tyr Val Val Ser Arg Leu Phe Ser Phe Leu
65                  70                  75                  80

Ala Ala Arg Pro Cys Gly Val Thr Tyr Lys Ile Val Gly Glu Glu His
                85                  90                  95

Leu Asp Lys Tyr Pro Ala Ile Val Val Cys Asn His Gln Ser Ser Met
            100                 105                 110

Asp Met Met Val Leu Gly Arg Val Phe Pro Lys His Cys Val Val Met
    115                 120                 125

Ala Lys Lys Glu Leu Leu Tyr Phe Pro Phe Leu Gly Met Phe Met Lys
130                 135                 140

Leu Ser Asn Ala Ile Phe Ile Asp Arg Lys Asn His Lys Lys Ala Ile
145                 150                 155                 160

Glu Ser Thr Thr Gln Ala Val Ala Asp Met Lys Lys His Asn Ser Gly
                165                 170                 175

Ile Trp Ile Phe Pro Glu Gly Thr Arg Ser Arg Leu Asp Lys Ala Asp
            180                 185                 190

Leu Leu Pro Phe Lys Lys Gly Ala Phe His Leu Ala Ile Gln Ala Gln
    195                 200                 205

Leu Pro Ile Leu Pro Ile Val Ser Gln Gly Tyr Ser His Ile Tyr Asp
210                 215                 220

Ser Ser Lys Arg Tyr Phe Pro Gly Gly Glu Leu Glu Ile Arg Val Leu
225                 230                 235                 240

Glu Pro Ile Pro Thr Lys Gly Leu Thr Thr Asp Val Asn Asp Leu
                245                 250                 255

Met Asp Lys Thr Arg Asn Leu Met Leu Lys His Leu Lys Asp Met Asp
            260                 265                 270

Ser His Cys Ser Ser Ala Val Gly Asn Gly Ser Leu Pro Leu Asp Ala
    275                 280                 285
```

```
Asp Ile Ala Lys Ser Thr Ala Thr Ser Ile Gly Asn Thr Asp Asp Ala
    290                 295                 300

Val Thr Lys Arg Arg Thr Leu Lys Glu
305                 310

<210> SEQ ID NO 36
<211> LENGTH: 1086
<212> TYPE: DNA
<213> ORGANISM: Mortierella alpina
<220> FEATURE:
<221> NAME/KEY: CDS
<222> LOCATION: (22)..(948)
<300> PUBLICATION INFORMATION:
<302> TITLE: A MORTIERELLA ALPINA LYSOPHOSPHATIDIC ACID ACYLTRANSFERASE
      HOMOLOG FOR ALTERATION OF POLYUNSATURATED FATTY ACIDS AND OIL
      CONTENT IN OLEAGINOUS ORGANISMS
<310> PATENT DOCUMENT NUMBER: U.S. Patent 7,189,559
<311> PATENT FILING DATE: 2005-10-14
<312> PUBLICATION DATE: 2007-03-13
<313> RELEVANT RESIDUES IN SEQ ID NO: (1)..(1086)

<400> SEQUENCE: 36
gggattcccc cgcttcccgg c atg ctc ggg tcc gtc acc cga ccc aca aag        51
                       Met Leu Gly Ser Val Thr Arg Pro Thr Lys
                         1               5                  10 gcc ctg ctc tat gga tca gcc ctc ttc agt ttc tgc tca ttg ctc aat        99
Ala Leu Leu Tyr Gly Ser Ala Leu Phe Ser Phe Cys Ser Leu Leu Asn
             15                  20                  25 gtg gtc cag gtg ttc tcc ata ctc ctg cag ccg ttc tcg aag cgt ctc       147
Val Val Gln Val Phe Ser Ile Leu Leu Gln Pro Phe Ser Lys Arg Leu
         30                  35                  40 ttc ttt gaa gtg aac gct cgc gtg gcc ggc tcc atg tgg aag gtt atg       195
Phe Phe Glu Val Asn Ala Arg Val Ala Gly Ser Met Trp Lys Val Met
     45                  50                  55 cag ctg att atg gag aaa aag cac aag gcc gcc atc acc ttc tca gga       243
Gln Leu Ile Met Glu Lys Lys His Lys Ala Ala Ile Thr Phe Ser Gly
 60                  65                  70 gac aag atc cct cac cac gag agt gcc atc gtc ttt ggc aac cac cgg       291
Asp Lys Ile Pro His His Glu Ser Ala Ile Val Phe Gly Asn His Arg
 75                  80                  85                  90 tcc ttt gtc gac ttt tac atg ttt cac acc gtt gct gct cgg aga ggc       339
Ser Phe Val Asp Phe Tyr Met Phe His Thr Val Ala Ala Arg Arg Gly
                 95                 100                 105 atg ctc aac tat atg aag tac ttt gcc aag gac tct ctg aaa tac att       387
Met Leu Asn Tyr Met Lys Tyr Phe Ala Lys Asp Ser Leu Lys Tyr Ile
            110                 115                 120 cca ttc tat gga tgg ggc atg tgg atc atg gga atg cta ttc atc aat       435
Pro Phe Tyr Gly Trp Gly Met Trp Ile Met Gly Met Leu Phe Ile Asn
        125                 130                 135 cgc aac tgg cag cag gat cag ctc aag atc aac aag atg ttt gca cgg       483
Arg Asn Trp Gln Gln Asp Gln Leu Lys Ile Asn Lys Met Phe Ala Arg
    140                 145                 150 ata ttg gac atc caa gcg ccc gtt tgg gtc gcc agt ttc ttg gag ggc       531
Ile Leu Asp Ile Gln Ala Pro Val Trp Val Ala Ser Phe Leu Glu Gly
155                 160                 165                 170 tct cgg ttg acg ccc agc aaa ctg gct gcc tct caa aag ttc atg ctg       579
Ser Arg Leu Thr Pro Ser Lys Leu Ala Ala Ser Gln Lys Phe Met Leu
                175                 180                 185 gga cgc gga ttg cct ctg ctg tca aac gtc atg atg ccc agg acc aag       627
Gly Arg Gly Leu Pro Leu Leu Ser Asn Val Met Met Pro Arg Thr Lys
            190                 195                 200 gga ttc att gcc tgt gtc aac aaa ttc cgg gga act cat gtg aaa tgt       675
Gly Phe Ile Ala Cys Val Asn Lys Phe Arg Gly Thr His Val Lys Cys
        205                 210                 215
```

-continued

```
              205                 210                 215
gtt tat gat ttc acg ttc gcc tac tac cac aag acc aag ggc ttt gga    723
Val Tyr Asp Phe Thr Phe Ala Tyr Tyr His Lys Thr Lys Gly Phe Gly
    220                 225                 230 gtg cct cca gat ctg gtc cgt gtt cac act ggc cag ctc agc ccc gag    771
Val Pro Pro Asp Leu Val Arg Val His Thr Gly Gln Leu Ser Pro Glu
235                 240                 245                 250 tac aaa ttc cat gtt cat gtg aga cgc tat cag ctc gac gat ctg ccc    819
Tyr Lys Phe His Val His Val Arg Arg Tyr Gln Leu Asp Asp Leu Pro
                255                 260                 265 acg gat gag gag aag ctg agc gag tgg gtg gtc caa aag tat gtg gag    867
Thr Asp Glu Glu Lys Leu Ser Glu Trp Val Val Gln Lys Tyr Val Glu
            270                 275                 280 aag gac gcc ttt ttg gag cag atg aag gag aat tgg aca gat ggt att    915
Lys Asp Ala Phe Leu Glu Gln Met Lys Glu Asn Trp Thr Asp Gly Ile
        285                 290                 295 gat ggg ggt gtg tgg tca gag aac tgg atg tga gcgagatgca ccgcaaactg    968
Asp Gly Gly Val Trp Ser Glu Asn Trp Met
    300                 305 tgtacagcgt cttagaggga taagaaagga ttgatatatt taaagaaagg aaacctatcg    1028
ccgattacaa gtaaaaacct ccataatgaa aaaaaaaaaa aaaaaaaaaa aaaaaaa       1086
```

<210> SEQ ID NO 37
<211> LENGTH: 308
<212> TYPE: PRT
<213> ORGANISM: Mortierella alpina

<400> SEQUENCE: 37

```
Met Leu Gly Ser Val Thr Arg Pro Thr Lys Ala Leu Leu Tyr Gly Ser
1               5                   10                  15

Ala Leu Phe Ser Phe Cys Ser Leu Leu Asn Val Val Gln Val Phe Ser
                20                  25                  30

Ile Leu Leu Gln Pro Phe Ser Lys Arg Leu Phe Glu Val Asn Ala
            35                  40                  45

Arg Val Ala Gly Ser Met Trp Lys Val Met Gln Leu Ile Met Glu Lys
        50                  55                  60

Lys His Lys Ala Ala Ile Thr Phe Ser Gly Asp Lys Ile Pro His His
65                  70                  75                  80

Glu Ser Ala Ile Val Phe Gly Asn His Arg Ser Phe Val Asp Phe Tyr
                85                  90                  95

Met Phe His Thr Val Ala Ala Arg Arg Gly Met Leu Asn Tyr Met Lys
            100                 105                 110

Tyr Phe Ala Lys Asp Ser Leu Lys Tyr Ile Pro Phe Tyr Gly Trp Gly
        115                 120                 125

Met Trp Ile Met Gly Met Leu Phe Ile Asn Arg Asn Trp Gln Gln Asp
    130                 135                 140

Gln Leu Lys Ile Asn Lys Met Phe Ala Arg Ile Leu Asp Ile Gln Ala
145                 150                 155                 160

Pro Val Trp Val Ala Ser Phe Leu Glu Gly Ser Arg Leu Thr Pro Ser
                165                 170                 175

Lys Leu Ala Ala Ser Gln Lys Phe Met Leu Gly Arg Gly Leu Pro Leu
            180                 185                 190

Leu Ser Asn Val Met Met Pro Arg Thr Lys Gly Phe Ile Ala Cys Val
        195                 200                 205

Asn Lys Phe Arg Gly Thr His Val Lys Cys Val Tyr Asp Phe Thr Phe
    210                 215                 220
```

```
Ala Tyr Tyr His Lys Thr Lys Gly Phe Gly Val Pro Pro Asp Leu Val
225                 230                 235                 240

Arg Val His Thr Gly Gln Leu Ser Pro Glu Tyr Lys Phe His Val His
            245                 250                 255

Val Arg Arg Tyr Gln Leu Asp Asp Leu Pro Thr Asp Glu Glu Lys Leu
        260                 265                 270

Ser Glu Trp Val Val Gln Lys Tyr Val Glu Lys Asp Ala Phe Leu Glu
            275                 280                 285

Gln Met Lys Glu Asn Trp Thr Asp Gly Ile Asp Gly Gly Val Trp Ser
        290                 295                 300

Glu Asn Trp Met
305

<210> SEQ ID NO 38
<211> LENGTH: 7
<212> TYPE: PRT
<213> ORGANISM: Artificial Sequence
<220> FEATURE:
<223> OTHER INFORMATION: 1-acyl-sn-glycerol-3-phosphate acyltransferase
      motif
<220> FEATURE:
<221> NAME/KEY: misc_feature
<222> LOCATION: (3)..(6)
<223> OTHER INFORMATION: Xaa can be any naturally occurring amino acid

<400> SEQUENCE: 38

Asn His Xaa Xaa Xaa Xaa Asp
1               5

<210> SEQ ID NO 39
<211> LENGTH: 4
<212> TYPE: PRT
<213> ORGANISM: Artificial Sequence
<220> FEATURE:
<223> OTHER INFORMATION: 1-acyl-sn-glycerol-3-phosphate acyltransferase
      motif

<400> SEQUENCE: 39

Glu Gly Thr Arg
1

<210> SEQ ID NO 40
<211> LENGTH: 1860
<212> TYPE: DNA
<213> ORGANISM: Saccharomyces cerevisiae
<220> FEATURE:
<221> NAME/KEY: CDS
<222> LOCATION: (1)..(1860)
<223> OTHER INFORMATION: GenBank Accession No. NP_014818; "YOR175C"
<300> PUBLICATION INFORMATION:
<302> TITLE: Genes encoding a novel type of lysophophatidylcholine
      acyltransferases and their use to increase triacylglycerol
      production and/or modify fatty acid composition
<310> PATENT DOCUMENT NUMBER: US-2008-0145867-A1
<311> PATENT FILING DATE: 2007-06-15
<312> PUBLICATION DATE: 2008-06-19
<313> RELEVANT RESIDUES IN SEQ ID NO: (1)..(1860)
<300> PUBLICATION INFORMATION:
<302> TITLE: Genes encoding a novel type of lysophophatidylcholine
      acyltransferases and their use to increase triacylglycerol
      production and/or modify fatty acid composition
<310> PATENT DOCUMENT NUMBER: WO 2008/076377
<311> PATENT FILING DATE: 2007-12-13
<312> PUBLICATION DATE: 2008-06-26
<313> RELEVANT RESIDUES IN SEQ ID NO: (1)..(1860)
<300> PUBLICATION INFORMATION:
<302> TITLE: USE OF A CLASS OF GENES ENCODING LYSOPHOSPHOLIPID ACYL
      TRANSFERASES FOR APPLICATION IN AGRICULTURE, BIOTECHNOLOGY AND
```

-continued

MEDICINE
<310> PATENT DOCUMENT NUMBER: WO 2009/001315
<311> PATENT FILING DATE: 2008-06-25
<312> PUBLICATION DATE: 2008-12-31
<313> RELEVANT RESIDUES IN SEQ ID NO: (1)..(1860)

<400> SEQUENCE: 40

```
atg tac aat cct gtg gac gct gtt tta aca aag ata att acc aac tat      48
Met Tyr Asn Pro Val Asp Ala Val Leu Thr Lys Ile Ile Thr Asn Tyr
 1               5                  10                  15 ggg att gat agt ttt aca ctg cga tat gct atc tgc tta ttg gga tcg      96
Gly Ile Asp Ser Phe Thr Leu Arg Tyr Ala Ile Cys Leu Leu Gly Ser
             20                  25                  30 ttc cca ctg aat gct att ttg aag aga att ccc gag aag cgt ata ggt     144
Phe Pro Leu Asn Ala Ile Leu Lys Arg Ile Pro Glu Lys Arg Ile Gly
         35                  40                  45 tta aaa tgt tgt ttt atc att tct atg tcg atg ttt tac tta ttc ggt     192
Leu Lys Cys Cys Phe Ile Ile Ser Met Ser Met Phe Tyr Leu Phe Gly
     50                  55                  60 gtg ctg aat cta gta agt gga ttc agg acc ctg ttt att agt acc atg     240
Val Leu Asn Leu Val Ser Gly Phe Arg Thr Leu Phe Ile Ser Thr Met
 65                  70                  75                  80 ttt act tac ttg atc tca aga ttt tac cgt tcc aag ttt atg cca cac     288
Phe Thr Tyr Leu Ile Ser Arg Phe Tyr Arg Ser Lys Phe Met Pro His
                 85                  90                  95 ttg aat ttc atg ttt gtt atg ggt cat ttg gca ata aat cat ata cac     336
Leu Asn Phe Met Phe Val Met Gly His Leu Ala Ile Asn His Ile His
            100                 105                 110 gcc caa ttc ctt aac gaa cag act caa act acc gtt gac att aca agt     384
Ala Gln Phe Leu Asn Glu Gln Thr Gln Thr Thr Val Asp Ile Thr Ser
        115                 120                 125 tca caa atg gtt tta gcc atg aaa cta act tct ttt gca tgg tcg tac     432
Ser Gln Met Val Leu Ala Met Lys Leu Thr Ser Phe Ala Trp Ser Tyr
    130                 135                 140 tat gat ggt tca tgc act agc gaa agc gat ttc aaa gat ttg act gag     480
Tyr Asp Gly Ser Cys Thr Ser Glu Ser Asp Phe Lys Asp Leu Thr Glu
145                 150                 155                 160 cat caa aaa tct cgt gct gtc aga ggt cat cca ccc tta tta aag ttc     528
His Gln Lys Ser Arg Ala Val Arg Gly His Pro Pro Leu Leu Lys Phe
                165                 170                 175 ctg gca tat gca ttt ttc tat tca acg ttg cta act ggc cca agt ttc     576
Leu Ala Tyr Ala Phe Phe Tyr Ser Thr Leu Leu Thr Gly Pro Ser Phe
            180                 185                 190 gat tat gcc gat ttt gac agc tgg ttg aat tgt gag atg ttc cgt gac     624
Asp Tyr Ala Asp Phe Asp Ser Trp Leu Asn Cys Glu Met Phe Arg Asp
        195                 200                 205 ttg cct gaa agc aaa aag cct atg aga aga cac cac cct ggt gaa aga     672
Leu Pro Glu Ser Lys Lys Pro Met Arg Arg His His Pro Gly Glu Arg
    210                 215                 220 aga cag att cca aag aat ggt aaa ctt gca tta tgg aaa gtt gtt caa     720
Arg Gln Ile Pro Lys Asn Gly Lys Leu Ala Leu Trp Lys Val Val Gln
225                 230                 235                 240 ggt ctt gct tgg atg att tta agt aca cta gga atg aag cac ttc ccc     768
Gly Leu Ala Trp Met Ile Leu Ser Thr Leu Gly Met Lys His Phe Pro
                245                 250                 255 gta aaa tac gtt ttg gac aaa gat ggc ttc cca acg aga tct ttt ata     816
Val Lys Tyr Val Leu Asp Lys Asp Gly Phe Pro Thr Arg Ser Phe Ile
            260                 265                 270 ttc aga atc cat tac tta ttc ttg ctt ggt ttc atc cat aga ttc aag     864
Phe Arg Ile His Tyr Leu Phe Leu Leu Gly Phe Ile His Arg Phe Lys
        275                 280                 285
```

```
tac tac gct gcc tgg act att tcg gaa gga tct tgt att ttg tgc ggt      912
Tyr Tyr Ala Ala Trp Thr Ile Ser Glu Gly Ser Cys Ile Leu Cys Gly
    290                 295                 300 ttg ggt tat aat ggt tat gat tca aag aca caa aag atc aga tgg gat      960
Leu Gly Tyr Asn Gly Tyr Asp Ser Lys Thr Gln Lys Ile Arg Trp Asp
305                 310                 315                 320 cgt gtc aga aat att gac att tgg acc gta gaa acg gcg cag aat acg     1008
Arg Val Arg Asn Ile Asp Ile Trp Thr Val Glu Thr Ala Gln Asn Thr
                325                 330                 335 cgt gaa atg ttg gaa gca tgg aat atg aat act aac aag tgg cta aaa     1056
Arg Glu Met Leu Glu Ala Trp Asn Met Asn Thr Asn Lys Trp Leu Lys
            340                 345                 350 tac tct gtt tat tta cgt gtc aca aag aag ggc aaa aaa cct ggt ttc     1104
Tyr Ser Val Tyr Leu Arg Val Thr Lys Lys Gly Lys Lys Pro Gly Phe
        355                 360                 365 cgc tca act ttg ttt act ttc cta act tcc gca ttt tgg cat ggt acc     1152
Arg Ser Thr Leu Phe Thr Phe Leu Thr Ser Ala Phe Trp His Gly Thr
    370                 375                 380 aga cct ggg tac tat ctg act ttt gcg aca ggg gct ttg tac caa aca     1200
Arg Pro Gly Tyr Tyr Leu Thr Phe Ala Thr Gly Ala Leu Tyr Gln Thr
385                 390                 395                 400 tgt ggt aaa atc tac aga cgc aat ttt aga cca att ttc ttg cga gaa     1248
Cys Gly Lys Ile Tyr Arg Arg Asn Phe Arg Pro Ile Phe Leu Arg Glu
                405                 410                 415 gat ggt gtc act cct ttg cct tct aaa aaa atc tac gat tta gtt ggc     1296
Asp Gly Val Thr Pro Leu Pro Ser Lys Lys Ile Tyr Asp Leu Val Gly
            420                 425                 430 ata tat gca att aaa cta gca ttt ggt tac atg gtg caa cca ttt att     1344
Ile Tyr Ala Ile Lys Leu Ala Phe Gly Tyr Met Val Gln Pro Phe Ile
        435                 440                 445 atc ctt gat ttg aag cca tct tta atg gta tgg ggc tct gtt tat ttc     1392
Ile Leu Asp Leu Lys Pro Ser Leu Met Val Trp Gly Ser Val Tyr Phe
    450                 455                 460 tat gtt cat att att gtt gct ttc tca ttt ttc cta ttc aga gga cca     1440
Tyr Val His Ile Ile Val Ala Phe Ser Phe Phe Leu Phe Arg Gly Pro
465                 470                 475                 480 tat gct aaa caa gtt act gaa ttt ttt aaa tcc aaa caa cct aaa gaa     1488
Tyr Ala Lys Gln Val Thr Glu Phe Phe Lys Ser Lys Gln Pro Lys Glu
                485                 490                 495 ata ttc att aga aaa caa aag aag ttg gaa aaa gat att tct gca agc     1536
Ile Phe Ile Arg Lys Gln Lys Lys Leu Glu Lys Asp Ile Ser Ala Ser
            500                 505                 510 tct cca aac ttg ggt ggt ata ttg aag gca aag att gaa cat gaa aag     1584
Ser Pro Asn Leu Gly Gly Ile Leu Lys Ala Lys Ile Glu His Glu Lys
        515                 520                 525 gga aag aca gca gaa gaa gaa gaa atg aac tta ggt att cca cca att     1632
Gly Lys Thr Ala Glu Glu Glu Glu Met Asn Leu Gly Ile Pro Pro Ile
    530                 535                 540 gag tta gaa aag tgg gac aat gct aag gaa gat tgg gaa gat ttc tgc     1680
Glu Leu Glu Lys Trp Asp Asn Ala Lys Glu Asp Trp Glu Asp Phe Cys
545                 550                 555                 560 aaa gat tac aaa gaa tgg aga aat aaa aat ggt ctt gaa ata gaa gag     1728
Lys Asp Tyr Lys Glu Trp Arg Asn Lys Asn Gly Leu Glu Ile Glu Glu
                565                 570                 575 gaa aac ctt tct aaa gct ttt gaa aga ttc aag cag gaa ttt tct aac     1776
Glu Asn Leu Ser Lys Ala Phe Glu Arg Phe Lys Gln Glu Phe Ser Asn
            580                 585                 590 gct gca agt gga tca ggt gaa cgt gtg aga aaa atg agt ttt agt ggt     1824
Ala Ala Ser Gly Ser Gly Glu Arg Val Arg Lys Met Ser Phe Ser Gly
```

-continued

```
                 595                 600                 605
tac tca cca aag cct att tca aaa aag gaa gag tag                        1860
Tyr Ser Pro Lys Pro Ile Ser Lys Lys Glu Glu
        610                 615
```

<210> SEQ ID NO 41
<211> LENGTH: 619
<212> TYPE: PRT
<213> ORGANISM: Saccharomyces cerevisiae

<400> SEQUENCE: 41

| | | | | | | | | | | | | |
|---|---|---|---|---|---|---|---|---|---|---|---|---|
| Met | Tyr | Asn | Pro | Val | Asp | Ala | Val | Leu | Thr | Lys | Ile | Ile | Thr | Asn | Tyr |
| 1 | | | | 5 | | | | | 10 | | | | | 15 | |
| Gly | Ile | Asp | Ser | Phe | Thr | Leu | Arg | Tyr | Ala | Ile | Cys | Leu | Leu | Gly | Ser |
| | | | 20 | | | | | 25 | | | | | 30 | | |
| Phe | Pro | Leu | Asn | Ala | Ile | Leu | Lys | Arg | Ile | Pro | Glu | Lys | Arg | Ile | Gly |
| | | | | 35 | | | | | 40 | | | | | 45 | |
| Leu | Lys | Cys | Cys | Phe | Ile | Ile | Ser | Met | Ser | Met | Phe | Tyr | Leu | Phe | Gly |
| | 50 | | | | | 55 | | | | | 60 | | | | |
| Val | Leu | Asn | Leu | Val | Ser | Gly | Phe | Arg | Thr | Leu | Phe | Ile | Ser | Thr | Met |
| 65 | | | | | 70 | | | | | 75 | | | | | 80 |
| Phe | Thr | Tyr | Leu | Ile | Ser | Arg | Phe | Tyr | Arg | Ser | Lys | Phe | Met | Pro | His |
| | | | | 85 | | | | | 90 | | | | | 95 | |
| Leu | Asn | Phe | Met | Phe | Val | Met | Gly | His | Leu | Ala | Ile | Asn | His | Ile | His |
| | | | 100 | | | | | 105 | | | | | 110 | | |
| Ala | Gln | Phe | Leu | Asn | Glu | Gln | Thr | Gln | Thr | Thr | Val | Asp | Ile | Thr | Ser |
| | | | | 115 | | | | | 120 | | | | | 125 | |
| Ser | Gln | Met | Val | Leu | Ala | Met | Lys | Leu | Thr | Ser | Phe | Ala | Trp | Ser | Tyr |
| | 130 | | | | | 135 | | | | | 140 | | | | |
| Tyr | Asp | Gly | Ser | Cys | Thr | Ser | Glu | Ser | Asp | Phe | Lys | Asp | Leu | Thr | Glu |
| 145 | | | | | 150 | | | | | 155 | | | | | 160 |
| His | Gln | Lys | Ser | Arg | Ala | Val | Arg | Gly | His | Pro | Pro | Leu | Leu | Lys | Phe |
| | | | | 165 | | | | | 170 | | | | | 175 | |
| Leu | Ala | Tyr | Ala | Phe | Phe | Tyr | Ser | Thr | Leu | Leu | Thr | Gly | Pro | Ser | Phe |
| | | | 180 | | | | | 185 | | | | | 190 | | |
| Asp | Tyr | Ala | Asp | Phe | Asp | Ser | Trp | Leu | Asn | Cys | Glu | Met | Phe | Arg | Asp |
| | | | | 195 | | | | | 200 | | | | | 205 | |
| Leu | Pro | Glu | Ser | Lys | Lys | Pro | Met | Arg | Arg | His | His | Pro | Gly | Glu | Arg |
| | 210 | | | | | 215 | | | | | 220 | | | | |
| Arg | Gln | Ile | Pro | Lys | Asn | Gly | Lys | Leu | Ala | Leu | Trp | Lys | Val | Val | Gln |
| 225 | | | | | 230 | | | | | 235 | | | | | 240 |
| Gly | Leu | Ala | Trp | Met | Ile | Leu | Ser | Thr | Leu | Gly | Met | Lys | His | Phe | Pro |
| | | | | 245 | | | | | 250 | | | | | 255 | |
| Val | Lys | Tyr | Val | Leu | Asp | Lys | Asp | Gly | Phe | Pro | Thr | Arg | Ser | Phe | Ile |
| | | | 260 | | | | | 265 | | | | | 270 | | |
| Phe | Arg | Ile | His | Tyr | Leu | Phe | Leu | Leu | Gly | Phe | Ile | His | Arg | Phe | Lys |
| | | | | 275 | | | | | 280 | | | | | 285 | |
| Tyr | Tyr | Ala | Ala | Trp | Thr | Ile | Ser | Glu | Gly | Ser | Cys | Ile | Leu | Cys | Gly |
| | 290 | | | | | 295 | | | | | 300 | | | | |
| Leu | Gly | Tyr | Asn | Gly | Tyr | Asp | Ser | Lys | Thr | Gln | Lys | Ile | Arg | Trp | Asp |
| 305 | | | | | 310 | | | | | 315 | | | | | 320 |
| Arg | Val | Arg | Asn | Ile | Asp | Ile | Trp | Thr | Val | Glu | Thr | Ala | Gln | Asn | Thr |
| | | | | 325 | | | | | 330 | | | | | 335 | |
| Arg | Glu | Met | Leu | Glu | Ala | Trp | Asn | Met | Asn | Thr | Asn | Lys | Trp | Leu | Lys |
| | | | 340 | | | | | 345 | | | | | 350 | | |

```
Tyr Ser Val Tyr Leu Arg Val Thr Lys Lys Gly Lys Pro Gly Phe
            355                 360                 365

Arg Ser Thr Leu Phe Thr Phe Leu Thr Ser Ala Phe Trp His Gly Thr
    370                 375                 380

Arg Pro Gly Tyr Tyr Leu Thr Phe Ala Thr Gly Ala Leu Tyr Gln Thr
385                 390                 395                 400

Cys Gly Lys Ile Tyr Arg Arg Asn Phe Arg Pro Ile Phe Leu Arg Glu
                405                 410                 415

Asp Gly Val Thr Pro Leu Pro Ser Lys Lys Ile Tyr Asp Leu Val Gly
            420                 425                 430

Ile Tyr Ala Ile Lys Leu Ala Phe Gly Tyr Met Val Gln Pro Phe Ile
            435                 440                 445

Ile Leu Asp Leu Lys Pro Ser Leu Met Val Trp Gly Ser Val Tyr Phe
        450                 455                 460

Tyr Val His Ile Ile Val Ala Phe Ser Phe Phe Leu Phe Arg Gly Pro
465                 470                 475                 480

Tyr Ala Lys Gln Val Thr Glu Phe Phe Lys Ser Lys Gln Pro Lys Glu
                485                 490                 495

Ile Phe Ile Arg Lys Gln Lys Lys Leu Glu Lys Asp Ile Ser Ala Ser
            500                 505                 510

Ser Pro Asn Leu Gly Gly Ile Leu Lys Ala Lys Ile Glu His Glu Lys
        515                 520                 525

Gly Lys Thr Ala Glu Glu Glu Met Asn Leu Gly Ile Pro Pro Ile
    530                 535                 540

Glu Leu Glu Lys Trp Asp Asn Ala Lys Glu Asp Trp Glu Asp Phe Cys
545                 550                 555                 560

Lys Asp Tyr Lys Glu Trp Arg Asn Lys Asn Gly Leu Glu Ile Glu Glu
                565                 570                 575

Glu Asn Leu Ser Lys Ala Phe Glu Arg Phe Lys Gln Gly Phe Ser Asn
            580                 585                 590

Ala Ala Ser Gly Ser Gly Glu Arg Val Arg Lys Met Ser Phe Ser Gly
        595                 600                 605

Tyr Ser Pro Lys Pro Ile Ser Lys Lys Glu Glu
    610                 615

<210> SEQ ID NO 42
<211> LENGTH: 1870
<212> TYPE: DNA
<213> ORGANISM: Saccharomyces cerevisiae
<220> FEATURE:
<221> NAME/KEY: CDS
<222> LOCATION: (3)..(1862)
<223> OTHER INFORMATION: synthetic Ale1 (codon-optimized for Yarrowia
      lipolytica)

<400> SEQUENCE: 42 ac atg tac aac ccc gtg gac gca gtg ttg act aag att att aca aac        47
   Met Tyr Asn Pro Val Asp Ala Val Leu Thr Lys Ile Ile Thr Asn
     1               5                  10                  15 tac gga att gat tct ttt acc ctg cga tat gcc att tgt ctg ttg gga      95
Tyr Gly Ile Asp Ser Phe Thr Leu Arg Tyr Ala Ile Cys Leu Leu Gly
                20                  25                  30 tct ttt cct ctt aac gct att ctg aag cgg att cct gaa aag cga atc     143
Ser Phe Pro Leu Asn Ala Ile Leu Lys Arg Ile Pro Glu Lys Arg Ile
            35                  40                  45 ggc ctg aag tgt tgt ttt atc att tct atg tcc atg ttt tat ctc ttc     191
Gly Leu Lys Cys Cys Phe Ile Ile Ser Met Ser Met Phe Tyr Leu Phe
```

-continued

```
                 50                  55                  60
ggc gtt ctg aat ctc gtg agc gga ttt cga acc ctc ttc att tcc aca      239
Gly Val Leu Asn Leu Val Ser Gly Phe Arg Thr Leu Phe Ile Ser Thr
     65                  70                  75 atg ttc aca tac ctt atc tct cgg ttc tac cga tcc aag ttt atg ccc      287
Met Phe Thr Tyr Leu Ile Ser Arg Phe Tyr Arg Ser Lys Phe Met Pro
 80                  85                  90                  95 cat ctc aac ttc atg ttc gtc atg ggc cac ttg gct atc aac cac att      335
His Leu Asn Phe Met Phe Val Met Gly His Leu Ala Ile Asn His Ile
                100                 105                 110 cat gct cag ttc ctg aac gaa caa act caa acg acc gtc gat att aca      383
His Ala Gln Phe Leu Asn Glu Gln Thr Gln Thr Thr Val Asp Ile Thr
            115                 120                 125 tcc tcg cag atg gtc ctg gct atg aag ctg aca agc ttt gcc tgg tct      431
Ser Ser Gln Met Val Leu Ala Met Lys Leu Thr Ser Phe Ala Trp Ser
        130                 135                 140 tac tat gac ggt tcg tgt acg agc gag tcc gac ttc aag gac ctt acc      479
Tyr Tyr Asp Gly Ser Cys Thr Ser Glu Ser Asp Phe Lys Asp Leu Thr
    145                 150                 155 gaa cac cag aag tcc cga gcc gtc cga ggc cat cct ccc ctt ctg aaa      527
Glu His Gln Lys Ser Arg Ala Val Arg Gly His Pro Pro Leu Leu Lys
160                 165                 170                 175 ttt ttg gct tac gcc ttt ttc tac tct acc ctt ctc acc ggt ccc tcc      575
Phe Leu Ala Tyr Ala Phe Phe Tyr Ser Thr Leu Leu Thr Gly Pro Ser
                180                 185                 190 ttc gat tac gct gat ttc gac tct tgg ctg aac tgc gaa atg ttc cgg      623
Phe Asp Tyr Ala Asp Phe Asp Ser Trp Leu Asn Cys Glu Met Phe Arg
            195                 200                 205 gac ctt ccc gag tcc aag aaa ccc atg cga aga cat cat cct ggt gag      671
Asp Leu Pro Glu Ser Lys Lys Pro Met Arg Arg His His Pro Gly Glu
        210                 215                 220 cgg cgt cag att ccc aag aac ggc aag ctc gcc ctg tgg aag gtt gtc      719
Arg Arg Gln Ile Pro Lys Asn Gly Lys Leu Ala Leu Trp Lys Val Val
    225                 230                 235 cag ggc ctc gcc tgg atg att ctg agc acg ttg ggt atg aag cac ttc      767
Gln Gly Leu Ala Trp Met Ile Leu Ser Thr Leu Gly Met Lys His Phe
240                 245                 250                 255 ccc gtg aag tac gtg ctg gac aag gac gga ttt cct acc cgt tcc ttt      815
Pro Val Lys Tyr Val Leu Asp Lys Asp Gly Phe Pro Thr Arg Ser Phe
                260                 265                 270 atc ttc cgt att cat tat ctg ttt ctg ctg gga ttc atc cac cga ttt      863
Ile Phe Arg Ile His Tyr Leu Phe Leu Leu Gly Phe Ile His Arg Phe
            275                 280                 285 aag tat tac gct gcg tgg acg att agc gaa ggt tcg tgc att ctc tgt      911
Lys Tyr Tyr Ala Ala Trp Thr Ile Ser Glu Gly Ser Cys Ile Leu Cys
        290                 295                 300 ggt ctt ggt tat aat gga tac gat tct aag acc cag aag atc cgg tgg      959
Gly Leu Gly Tyr Asn Gly Tyr Asp Ser Lys Thr Gln Lys Ile Arg Trp
    305                 310                 315 gat cga gtg cgg aat att gat att tgg aca gtg gag act gca caa aac     1007
Asp Arg Val Arg Asn Ile Asp Ile Trp Thr Val Glu Thr Ala Gln Asn
320                 325                 330                 335 acc cga gag atg ctg gaa gcg tgg aac atg aat act aac aaa tgg ctg     1055
Thr Arg Glu Met Leu Glu Ala Trp Asn Met Asn Thr Asn Lys Trp Leu
                340                 345                 350 aag tat agc gtg tat ctt aga gtg act aag aag ggt aag aag cca ggt     1103
Lys Tyr Ser Val Tyr Leu Arg Val Thr Lys Lys Gly Lys Lys Pro Gly
            355                 360                 365 ttt cga tct acc ctg ttt acc ttc ctg acc tcc gcc ttt tgg cac ggt     1151
Phe Arg Ser Thr Leu Phe Thr Phe Leu Thr Ser Ala Phe Trp His Gly
```

```
Phe Arg Ser Thr Leu Phe Thr Phe Leu Thr Ser Ala Phe Trp His Gly
        370                 375                 380 acc cgt cct gga tac tac ctt acc ttc gca act ggt gcc ctg tac caa   1199
Thr Arg Pro Gly Tyr Tyr Leu Thr Phe Ala Thr Gly Ala Leu Tyr Gln
385                 390                 395 acc tgt gga aag atc tat aga cga aac ttt cgt ccc atc ttt ctg aga   1247
Thr Cys Gly Lys Ile Tyr Arg Arg Asn Phe Arg Pro Ile Phe Leu Arg
400                 405                 410                 415 gaa gat ggc gtg aca cct ctc ccg tcc aag aag att tac gac ctg gtc   1295
Glu Asp Gly Val Thr Pro Leu Pro Ser Lys Lys Ile Tyr Asp Leu Val
                420                 425                 430 ggc att tac gct att aag ctg gcc ttt ggt tac atg gtt caa ccc ttc   1343
Gly Ile Tyr Ala Ile Lys Leu Ala Phe Gly Tyr Met Val Gln Pro Phe
            435                 440                 445 att atc ctt gac ctg aag ccc tct ctt atg gtt tgg gga tcc gtg tat   1391
Ile Ile Leu Asp Leu Lys Pro Ser Leu Met Val Trp Gly Ser Val Tyr
        450                 455                 460 ttc tac gtg cat att att gtg gcc ttc tcg ttc ttt ctg ttc cga gga   1439
Phe Tyr Val His Ile Ile Val Ala Phe Ser Phe Phe Leu Phe Arg Gly
    465                 470                 475 cca tac gct aag cag gtt act gaa ttt ttc aaa agc aag caa ccg aag   1487
Pro Tyr Ala Lys Gln Val Thr Glu Phe Phe Lys Ser Lys Gln Pro Lys
480                 485                 490                 495 gag atc ttc atc cga aag cag aag aag ttg gaa aaa gac atc tct gcc   1535
Glu Ile Phe Ile Arg Lys Gln Lys Lys Leu Glu Lys Asp Ile Ser Ala
                500                 505                 510 tct tcc ccc aac ctc gga ggt att ctt aag gca aaa atc gaa cat gag   1583
Ser Ser Pro Asn Leu Gly Gly Ile Leu Lys Ala Lys Ile Glu His Glu
            515                 520                 525 aag gga aag acg gca gag gag gaa gag atg aac ttg ggc att cca ccc   1631
Lys Gly Lys Thr Ala Glu Glu Glu Glu Met Asn Leu Gly Ile Pro Pro
        530                 535                 540 atc gaa ctg gag aag tgg gac aac gcc aag gag gac tgg gag gat ttc   1679
Ile Glu Leu Glu Lys Trp Asp Asn Ala Lys Glu Asp Trp Glu Asp Phe
    545                 550                 555 tgc aag gac tac aag gag tgg cgg aac aag aac gga ctg gaa att gaa   1727
Cys Lys Asp Tyr Lys Glu Trp Arg Asn Lys Asn Gly Leu Glu Ile Glu
560                 565                 570                 575 gag gag aac ctg tcc aag gcc ttc gag cga ttt aag cag gaa ttt tcc   1775
Glu Glu Asn Leu Ser Lys Ala Phe Glu Arg Phe Lys Gln Glu Phe Ser
                580                 585                 590 aac gct gcg tcg ggc tct ggt gaa cgg gtt cgg aaa atg tcc ttc tcc   1823
Asn Ala Ala Ser Gly Ser Gly Glu Arg Val Arg Lys Met Ser Phe Ser
            595                 600                 605 gga tat tct cct aaa ccc atc tcg aag aaa gaa gaa tag gcggccgc      1870
Gly Tyr Ser Pro Lys Pro Ile Ser Lys Lys Glu Glu
        610                 615

<210> SEQ ID NO 43
<211> LENGTH: 619
<212> TYPE: PRT
<213> ORGANISM: Saccharomyces cerevisiae

<400> SEQUENCE: 43

Met Tyr Asn Pro Val Asp Ala Val Leu Thr Lys Ile Ile Thr Asn Tyr
1               5                   10                  15

Gly Ile Asp Ser Phe Thr Leu Arg Tyr Ala Ile Cys Leu Leu Gly Ser
            20                  25                  30

Phe Pro Leu Asn Ala Ile Leu Lys Arg Ile Pro Glu Lys Arg Ile Gly
        35                  40                  45
```

-continued

```
Leu Lys Cys Cys Phe Ile Ile Ser Met Ser Met Phe Tyr Leu Phe Gly
     50                  55                  60

Val Leu Asn Leu Val Ser Gly Phe Arg Thr Leu Phe Ile Ser Thr Met
 65                  70                  75                  80

Phe Thr Tyr Leu Ile Ser Arg Phe Tyr Arg Ser Lys Phe Met Pro His
                 85                  90                  95

Leu Asn Phe Met Phe Val Met Gly His Leu Ala Ile Asn His Ile His
            100                 105                 110

Ala Gln Phe Leu Asn Glu Gln Thr Gln Thr Thr Val Asp Ile Thr Ser
            115                 120                 125

Ser Gln Met Val Leu Ala Met Lys Leu Thr Ser Phe Ala Trp Ser Tyr
        130                 135                 140

Tyr Asp Gly Ser Cys Thr Ser Glu Ser Asp Phe Lys Asp Leu Thr Glu
145                 150                 155                 160

His Gln Lys Ser Arg Ala Val Arg Gly His Pro Pro Leu Leu Lys Phe
                165                 170                 175

Leu Ala Tyr Ala Phe Phe Tyr Ser Thr Leu Leu Thr Gly Pro Ser Phe
            180                 185                 190

Asp Tyr Ala Asp Phe Asp Ser Trp Leu Asn Cys Glu Met Phe Arg Asp
        195                 200                 205

Leu Pro Glu Ser Lys Lys Pro Met Arg Arg His His Pro Gly Glu Arg
210                 215                 220

Arg Gln Ile Pro Lys Asn Gly Lys Leu Ala Leu Trp Lys Val Val Gln
225                 230                 235                 240

Gly Leu Ala Trp Met Ile Leu Ser Thr Leu Gly Met Lys His Phe Pro
                245                 250                 255

Val Lys Tyr Val Leu Asp Lys Asp Gly Phe Pro Thr Arg Ser Phe Ile
            260                 265                 270

Phe Arg Ile His Tyr Leu Phe Leu Leu Gly Phe Ile His Arg Phe Lys
        275                 280                 285

Tyr Tyr Ala Ala Trp Thr Ile Ser Glu Gly Ser Cys Ile Leu Cys Gly
290                 295                 300

Leu Gly Tyr Asn Gly Tyr Asp Ser Lys Thr Gln Lys Ile Arg Trp Asp
305                 310                 315                 320

Arg Val Arg Asn Ile Asp Ile Trp Thr Val Glu Thr Ala Gln Asn Thr
                325                 330                 335

Arg Glu Met Leu Glu Ala Trp Asn Met Asn Thr Asn Lys Trp Leu Lys
            340                 345                 350

Tyr Ser Val Tyr Leu Arg Val Thr Lys Lys Gly Lys Lys Pro Gly Phe
        355                 360                 365

Arg Ser Thr Leu Phe Thr Phe Leu Thr Ser Ala Phe Trp His Gly Thr
370                 375                 380

Arg Pro Gly Tyr Tyr Leu Thr Phe Ala Thr Gly Ala Leu Tyr Gln Thr
385                 390                 395                 400

Cys Gly Lys Ile Tyr Arg Arg Asn Phe Arg Pro Ile Phe Leu Arg Glu
                405                 410                 415

Asp Gly Val Thr Pro Leu Pro Ser Lys Lys Ile Tyr Asp Leu Val Gly
            420                 425                 430

Ile Tyr Ala Ile Lys Leu Ala Phe Gly Tyr Met Val Gln Pro Phe Ile
        435                 440                 445

Ile Leu Asp Leu Lys Pro Ser Leu Met Val Trp Gly Ser Val Tyr Phe
450                 455                 460
```

```
Tyr Val His Ile Ile Val Ala Phe Ser Phe Phe Leu Phe Arg Gly Pro
465                 470                 475                 480

Tyr Ala Lys Gln Val Thr Glu Phe Phe Lys Ser Lys Gln Pro Lys Glu
            485                 490                 495

Ile Phe Ile Arg Lys Gln Lys Lys Leu Glu Lys Asp Ile Ser Ala Ser
                500                 505                 510

Ser Pro Asn Leu Gly Gly Ile Leu Lys Ala Lys Ile Glu His Glu Lys
            515                 520                 525

Gly Lys Thr Ala Glu Glu Glu Met Asn Leu Gly Ile Pro Pro Ile
        530                 535                 540

Glu Leu Glu Lys Trp Asp Asn Ala Lys Glu Asp Trp Glu Asp Phe Cys
545                 550                 555                 560

Lys Asp Tyr Lys Glu Trp Arg Asn Lys Asn Gly Leu Glu Ile Glu Glu
                565                 570                 575

Glu Asn Leu Ser Lys Ala Phe Glu Arg Phe Lys Gln Glu Phe Ser Asn
            580                 585                 590

Ala Ala Ser Gly Ser Gly Glu Arg Val Arg Lys Met Ser Phe Ser Gly
        595                 600                 605

Tyr Ser Pro Lys Pro Ile Ser Lys Lys Glu Glu
    610                 615

<210> SEQ ID NO 44
<211> LENGTH: 9641
<212> TYPE: DNA
<213> ORGANISM: Artificial Sequence
<220> FEATURE:
<223> OTHER INFORMATION: Plasmid pY201

<400> SEQUENCE: 44
gtacgataac ttcgtatagc atacattata cgaagttatc gcgtcgacga gtatctgtct    60
gactcgtcat tgccgccttt ggagtacgac tccaactatg agtgtgcttg atcactttg    120 acgatacatt cttcgttgga ggctgtgggt ctgacagctg cgttttcggc gcggttggcc   180
gacaacaata tcagctgcaa cgtcattgct ggctttcatc atgatcacat ttttgtcggc   240
aaaggcgacg cccagagagc cattgacgtt ctttctaatt tggaccgata gccgtatagt   300
ccagtctatc tataagttca actaactcgt aactattacc ataacatata cttcactgcc   360
ccagataagg ttccgataaa aagttctgca gactaaattt atttcagtct cctcttcacc   420
accaaaatgc cctcctacga agctcgagct aacgtccaca agtccgcctt tgccgctcga   480
gtgctcaagc tcgtggcagc caagaaaacc aacctgtgtg cttctctgga tgttaccacc   540
accaaggagc tcattgagct tgccgataag gtcggacctt atgtgtgcat gatcaaaacc   600
catatcgaca tcattgacga cttcacctac gccggcactg tgctcccccct caaggaactt   660 gctcttaagc acggtttctt cctgttcgag gacagaaagt tcgcagatat tggcaacact   720
gtcaagcacc agtaccggtg tcaccgaatc gccgagtggc ccgatatcac caacgcccac   780
ggtgtacccg gaaccggaat cattgctggc ctgcgagctg gtgccgagga actgtctct   840 gaacagaaga aggaggacgt ctctgactac gagaactccc agtacaagga gttcctagtc   900
ccctctccca acgagaagct ggccagaggt ctgctcatgc tggccgagct gtcttgcaag   960
ggctctctgg ccactggcga gtactccaag cagaccattg agcttgcccg atccgacccc  1020
gagtttgtgg ttggcttcat tgcccagaac cgacctaagg gcgactctga ggactggctt  1080
attctgaccc ccggggtggg tcttgacgac aaggagacg ctctcggaca gcagtaccga  1140
actgttgagg atgtcatgtc taccggaacg gatatcataa ttgtcggccg aggtctgtac  1200
```

```
ggccagaacc gagatcctat tgaggaggcc aagcgatacc agaaggctgg ctgggaggct    1260
taccagaaga ttaactgtta gaggttagac tatggatatg taatttaact gtgtatatag    1320
agagcgtgca agtatggagc gcttgttcag cttgtatgat ggtcagacga cctgtctgat    1380
cgagtatgta tgatactgca caacctgtgt atccgcatga tctgtccaat ggggcatgtt    1440
gttgtgtttc tcgatacgga gatgctgggt acagtgctaa tacgttgaac tacttatact    1500
tatatgaggc tcgaagaaag ctgacttgtg tatgacttat tctcaactac atccccagtc    1560
acaataccac cactgcacta ccactacacc aaaaccatga tcaaaccacc catggacttc    1620
ctggaggcag aagaacttgt tatggaaaag ctcaagagag agatcataac ttcgtatagc    1680
atacattata cgaagttatc ctgcaggtaa aggaattcag gagagaccgg ttggcggcg     1740 tatttgtgtc ccaaaaaaca gccccaattg ccccaattga ccccaaattg acccagtagc    1800
gggcccaacc ccggcgagag cccccttcac cccacatatc aaacctcccc cggttcccac    1860
acttgccgtt aagggcgtag ggtactgcag tctggaatct acgcttgttc agactttgta    1920
ctagtttctt tgtctggcca tccgggtaac ccatgccgga cgcaaaatag actactgaaa    1980
atttttttgc tttgtggttg ggactttagc caagggtata aaagaccacc gtccccgaat    2040
tacctttcct cttcttttct ctctctcctt gtcaactcac acccgaaatc gttaagcatt    2100
tccttctgag tataagaatc attcaccatg gacttcctgg aggcagaaga acttgttatg    2160
gaaaagctca agagagagaa gccaagatac tatcaagaca tgtgtcgcaa cttaattaag    2220
atgacgacat ttgcgagctg gacgaggaat agatggagcg tgtgttctga gtcgatgttt    2280
tctatggagt tgtgagtgtt agtagacatg atgggtttat atatgatgaa tgaatagatg    2340 tgatttttgat ttgcacgatg gaattgagaa ctttgtaaac gtacatggga atgtatgaat    2400
gtggggtttt tgtgactgga taactgacgg tcagtggacg ccgttgttca aatatccaag    2460
agatgcgaga aactttgggt caagtgaaca tgtcctctct gttcaagtaa accatcaact    2520
atgggtagta tatttagtaa ggacaagagt tgagattctt ggagtcccta gaaacgtatt    2580
ttcgcgttcc aagatcaaat tagtagagta atacgggcac gggaatccat tcatagtctc    2640
aattttccca taggtgtgct acaaggtgtt gagatgtggt acagtaccac catgattcga    2700
ggtaaagagc ccagaagtca ttgatgaggt caagaaatac acagatctac agctcaatac    2760
aatgaatatc ttctttcata ttcttcaggt gacaccaagg gtgtctattt tccccagaaa    2820
tgcgtgaaaa ggcgcgtgtg tagcgtggag tatgggttcg gttggcgtat ccttcatata    2880
tcgacgaaat agtagggcaa gagatgacaa aaagtatcta tatgtagaca gcgtagaata    2940
tggatttgat tggtataaat tcatttattg cgtgtctcac aaatactctc gataagttgg    3000
ggttaaactg gagatggaac aatgtcgata tctcgacgca tgcgacgtcg ggcccaattc    3060
gccctatagt gagtcgtatt acaattcact ggccgtcgtt ttacaacgtc gtgactggga    3120
aaaccctggc gttacccaac ttaatcgcct tgcagcacat ccccctttcg ccagctggcg    3180
taatagcgaa gaggcccgca ccgatcgccc ttcccaacag ttgcgcagcc tgaatggcga    3240
atggacgcgc cctgtagcgg cgcattaagc gcggcgggtg tggtggttac gcgcagcgtg    3300
accgctacac ttgccagcgc cctagcgccc gctcctttcg ctttcttccc ttcctttctc    3360
gccacgttcg ccggctttcc ccgtcaagct ctaaatcggg ggctcccttt agggttccga    3420
tttagtgctt tacggcacct cgaccccaaa aaacttgatt agggtgatgg ttcacgtagt    3480
gggccatcgc cctgatagac ggtttttcgc cctttgacgt tggagtccac gttctttaat    3540
```

```
agtggactct tgttccaaac tggaacaaca ctcaaccctc tctcggtcta ttcttttgat      3600
ttataaggga ttttgccgat ttcggcctat tggttaaaaa atgagctgat ttaacaaaaa      3660
tttaacgcga atttaacaa atattaacg cttacaattt cctgatgcgg tattttctcc       3720
ttacgcatct gtgcggtatt tcacaccgca tcaggtggca cttttcgggg aaatgtgcgc      3780
ggaacccctc tttgtttatt tttctaaata cattcaaata tgtatccgct catgagacaa      3840
taaccctgat aaatgcttca ataatattga aaaggaaga gtatgagtat tcaacatttc      3900
cgtgtcgccc ttattccctt ttttgcggca ttttgccttc ctgttttgc tcacccagaa       3960
acgctggtga agtaaaaga tgctgaagat cagttgggtg cacgagtggg ttacatcgaa       4020
ctggatctca acagcggtaa gatccttgag agttttcgcc ccgaagaacg ttttccaatg      4080
atgagcactt ttaaagttct gctatgtggc gcggtattat cccgtattga cgccgggcaa      4140
gagcaactcg gtcgccgcat acactattct cagaatgact tggttgagta ctcaccagtc     4200
acagaaaagc atcttacgga tggcatgaca gtaagagaat tatgcagtgc tgccataacc     4260
atgagtgata acactgcggc caacttactt ctgacaacga tcggaggacc gaaggagcta     4320
accgcttttt tgcacaacat gggggatcat gtaactcgcc ttgatcgttg ggaaccggag     4380
ctgaatgaag ccataccaaa cgacgagcgt gacaccacga tgcctgtagc aatggcaaca     4440
acgttgcgca aactattaac tggcgaacta cttactctag cttcccggca acaattaata     4500
gactggatgg aggcggataa agttgcagga ccacttctgc gctcggccct tccggctggc     4560
tggtttattg ctgataaatc tggagccggt gagcgtgggt ctcgcggtat cattgcagca     4620
ctggggccag atggtaagcc ctcccgtatc gtagttatct acacgacggg gagtcaggca     4680
actatggatg aacgaaatag acagatcgct gagataggtg cctcactgat taagcattgg     4740
taactgtcag accaagttta ctcatatata ctttagattg atttaaaact tcattttaa     4800
tttaaaagga tctaggtgaa gatcctttt gataatctca tgaccaaaat cccttaacgt     4860
gagttttcgt tccactgagc gtcagacccc gtagaaaaga tcaaaggatc ttcttgagat     4920
ccttttttc tgcgcgtaat ctgctgcttg caaacaaaaa aaccaccgct accagcggtg     4980
gtttgtttgc cggatcaaga gctaccaact ctttttccga aggtaactgg cttcagcaga      5040
gcgcagatac caaatactgt tcttctagtg tagccgtagt taggccacca cttcaagaac      5100
tctgtagcac cgcctacata cctcgctctg ctaatcctgt taccagtggc tgctgccagt      5160
ggcgataagt cgtgtcttac cgggttggac tcaagacgat agttaccgga taaggcgcag      5220
cggtcgggct gaacggggggg ttcgtgcaca cagcccagct tggagcgaac gacctacacc     5280
gaactgagat acctacagcg tgagctatga gaaagcgcca cgcttcccga agggagaaag      5340
gcggacaggt atccggtaag cggcagggtc ggaacaggag agcgcacgag ggagcttcca      5400
gggggaaacg cctggtatct ttatagtcct gtcgggttc gccacctctg acttgagcgt      5460
cgatttttgt gatgctcgtc agggggggcgg agcctatgga aaaacgccag caacgcggcc      5520
ttttttacggt tcctggcctt ttgctggcct tttgctcaca tgttctttcc tgcgttatcc     5580
cctgattctg tggataaccg tattaccgcc tttgagtgag ctgataccgc tcgccgcagc     5640
cgaacgaccg agcgcagcga gtcagtgagc gaggaagcgg aagagcgccc aatacgcaaa     5700
ccgcctctcc ccgcgcgttg gccgattcat taatgcagct ggcgcgccac caatcacaat     5760
tctgaaaagc acatcttgat ctcctcattg cggggagtcc aacggtggtc ttattcccc     5820
gaatttcccg ctcaatctcg ttccagaccc accggacac agtgcttaac gccgttccga     5880
aactctaccg cagatatgct ccaacggact gggctgcata gatgtgatcc tcggcttgga     5940
```

```
gaaatggata aaagccggcc aaaaaaaaag cggaaaaaag cggaaaaaaa gagaaaaaaa    6000
atcgcaaaat ttgaaaaata gggggaaaag acgcaaaaac gcaaggaggg gggagtatat    6060
gacactgata agcaagctca caacggttcc tcttattttt ttcctcatct tctgcctagg    6120
ttcccaaaat cccagatgct tctctccagt gccaaaagta agtaccccac aggttttcgg    6180
ccgaaaattc cacgtgcagc aacgtcgtgt ggggtgttaa aatgtggggg gggggaacca    6240
ggacaagagg ctcttgtggg agccgaatga gagcacaaag cgggcgggtg tgataagggc    6300
atttttgccc attttccctt ctcctgtctc tccgacggtg atggcgttgt gcgtcctcta    6360
tttctttttta tttcttttttg ttttatttct ctgactaccg atttggtttg atttcctcaa    6420
ccccacacaa ataagctcgg gccgaggaat atatatatac acggacacag tcgccctgtg    6480
gacaacacgt cactacctct acgatacaca ccgtacgata gttagtagac aacaatcgat    6540
agttggagca agggagaaat gtagagtgtg aaagactcac tatggtccgg gcttatctcg    6600
accaatagcc aaagtctgga gtttctgaga gaaaaaggca agatacgtat gtaacaaagc    6660
gacgcatggt acaataatac cggaggcatg tatcatagag agttagtggt tcgatgatgg    6720
cactggtgcc tggtatgact ttatacggct gactacatat ttgtcctcag acatacaatt    6780
acagtcaagc acttacccctt ggacatctgt aggtaccccc cggccaagac gatctcagcg    6840
tgtcgtatgt cggattggcg tagctccctc gctcgtcaat tggctcccat ctactttctt    6900
ctgcttggct acaccagca tgtctgctat ggctcgtttt cgtgccttat ctatcctccc    6960
agtattacca actctaaatg acatgatgtg attgggtcta cactttcata tcagagataa    7020
ggagtagcac agttgcataa aaagcccaac tctaatcagc ttcttccttt cttgtaatta    7080
gtacaaaggt gattagcgaa atctggaagc ttagttggcc ctaaaaaaat caaaaaaagc    7140
aaaaaacgaa aaacgaaaaa ccacagtttt gagaacaggg aggtaacgaa ggatcgtata    7200
tatatatata tatatatata cccacggatc ccgagaccgg cctttgattc ttccctacaa    7260
ccaaccattc tcaccaccct aattcacaac catgtacaac cccgtggacg cagtgttgac    7320
taagattatt acaaactacg gaattgattc ttttaccctg cgatatgcca tttgtctgtt    7380
gggatctttt cctcttaacg ctattctgaa gcggattcct gaaaagcgaa tcggcctgaa    7440
gtgttgtttt atcatttcta tgtccatgtt ttatctcttc ggcgttctga atctcgtgag    7500
cggatttcga accctcttca tttccacaat gttcacatac cttatctctc ggttctaccg    7560
atccaagttt atgccccatc tcaacttcat gttcgtcatg gccacttgg ctatcaacca    7620
cattcatgct cagttcctga acgaacaaac tcaaacgacc gtcgatatta catcctcgca    7680
gatggtcctg gctatgaagc tgacaagctt tgcctggtct tactatgacg gttcgtgtac    7740
gagcgagtcc gacttcaagg accttaccga acaccagaag tcccgagccg tccgaggcca    7800
tcctcccctt ctgaaatttt tggcttacgc ctttttctac tctacccttc tcaccggtcc    7860
ctccttcgat tacgctgatt tcgactcttg gctgaactgc gaaatgttcc gggaccttcc    7920
cgagtccaag aaacccatgc gaagacatca tcctggtgag cggcgtcaga ttcccaagaa    7980
cggcaagctc gccctgtgga aggttgtcca gggcctcgcc tggatgattc tgagcacgtt    8040
gggtatgaag cacttccccg tgaagtacgt gctggacaag gacggatttc ctacccgttc    8100
ctttatcttc cgtattcatt atctgtttct gctgggattc atccaccgat ttaagtatta    8160
cgctgcgtgg acgattagcg aaggttcgtg cattctctgt ggtcttggtt ataatggata    8220
cgattctaag acccagaaga tccggtggga tcgagtgcgg aatattgata tttggacagt    8280
```

-continued

```
ggagactgca caaaacaccc gagagatgct ggaagcgtgg aacatgaata ctaacaaatg    8340
gctgaagtat agcgtgtatc ttagagtgac taagaagggt aagaagccag gttttcgatc    8400
taccctgttt accttcctga cctccgcctt ttggcacggt acccgtcctg gatactacct    8460
taccttcgca actggtgccc tgtaccaaac ctgtggaaag atctatagac gaaactttcg    8520
tcccatcttt ctgagagaag atggcgtgac acctctcccg tccaagaaga tttacgacct    8580
ggtcggcatt tacgctatta agctggcctt tggttacatg gttcaaccct tcattatcct    8640
tgacctgaag ccctctctta tggtttgggg atccgtgtat ttctacgtgc atattattgt    8700
ggccttctcg ttctttctgt tccgaggacc atacgctaag caggttactg aattttttcaa   8760
aagcaagcaa ccgaaggaga tcttcatccg aaagcagaag aagttggaaa aagacatctc    8820
tgcctcttcc cccaacctcg gaggtattct taaggcaaaa atcgaacatg agaagggaaa    8880
gacggcagag gaggaagaga tgaacttggg cattccaccc atcgaactgg agaagtggga    8940
caacgccaag gaggactggg aggatttctg caaggactac aaggagtggc ggaacaagaa    9000
cggactggaa attgaagagg agaacctgtc caaggccttc gagcgattta agcaggaatt    9060
ttccaacgct gcgtcgggct ctggtgaacg ggttcggaaa atgtccttct ccggatattc    9120
tcctaaaccc atctcgaaga aagaagaata ggcggccgca tgagaagata aatatataaa    9180
tacattgaga tattaaatgc gctagattag agagcctcat actgctcgga gagaagccaa    9240
gacgagtact caaaggggat tacaccatcc atatccacag acacaagctg gggaaaggtt    9300
ctatatacac tttccggaat accgtagttt ccgatgttat caatgggggc agccaggatt    9360
tcaggcactt cggtgtctcg gggtgaaatg gcgttcttgg cctccatcaa gtcgtaccat    9420
gtcttcattt gcctgtcaaa gtaaaacaga agcagatgaa gaatgaactt gaagtgaagg    9480
aatttaaatg taacgaaact gaaatttgac cagatattgt gtccgcggtg gagctccagc    9540
ttttgttccc tttagtgagg gttaatttcg agcttggcgt aatcatggtc atagctgttt    9600
cctgtgtgaa attgttatcc gctcacaagc ttccacacaa c                        9641

<210> SEQ ID NO 45
<211> LENGTH: 34
<212> TYPE: DNA
<213> ORGANISM: Escherichia coli

<400> SEQUENCE: 45
ataacttcgt ataatgtatg ctatacgaag ttat                                34

<210> SEQ ID NO 46
<211> LENGTH: 8726
<212> TYPE: DNA
<213> ORGANISM: Artificial Sequence
<220> FEATURE:
<223> OTHER INFORMATION: Plasmid pY208

<400> SEQUENCE: 46
gtacgataac ttcgtatagc atacattata cgaagttatc gcgtcgacga gtatctgtct     60
gactcgtcat tgccgccttt ggagtacgac tccaactatg agtgtgcttg gatcactttg    120
acgatacatt cttcgttgga ggctgtgggt ctgacagctg cgttttcggc gcggttggcc    180
gacaacaata tcagctgcaa cgtcattgct ggctttcatc atgatcacat ttttgtcggc    240
aaaggcgacg cccagagagc cattgacgtt ctttctaatt tggaccgata gccgtatagt    300
ccagtctatc tataagttca actaactcgt aactattacc ataacatata cttcactgcc    360
ccagataagg ttccgataaa aagttctgca gactaaattt atttcagtct cctcttcacc    420
```

```
accaaaatgc cctcctacga agctcgagct aacgtccaca agtccgcctt tgccgctcga   480
gtgctcaagc tcgtggcagc caagaaaacc aacctgtgtg cttctctgga tgttaccacc   540
accaaggagc tcattgagct tgccgataag gtcggacctt atgtgtgcat gatcaaaacc   600
catatcgaca tcattgacga cttcacctac gccggcactg tgctccccct caaggaactt   660
gctcttaagc acgtttctt cctgttcgag gacagaaagt tcgcagatat tggcaacact   720
gtcaagcacc agtaccggtg tcaccgaatc gccgagtggt ccgatatcac caacgcccac   780
ggtgtacccg aaccggaat cattgctggc ctgcgagctg tgccgagga aactgtctct   840
gaacagaaga aggaggacgt ctctgactac gagaactccc agtacaagga gttcctagtc   900
ccctctccca acgagaagct ggccagaggt ctgctcatgc tggccgagct gtcttgcaag   960
ggctctctgg ccactggcga gtactccaag cagaccattg agcttgcccg atccgacccc  1020
gagtttgtgg ttggcttcat tgcccagaac cgacctaagg cgactctga ggactggctt   1080
attctgaccc ccggggtggg tcttgacgac aagggagacg ctctcggaca gcagtaccga  1140
actgttgagg atgtcatgtc taccggaacg gatatcataa ttgtcggccg aggtctgtac  1200
ggccagaacc gagatcctat tgaggaggcc aagcgatacc agaaggctgg ctgggaggct  1260
taccagaaga ttaactgtta gaggttagac tatggatatg taatttaact gtgtatatag  1320
agagcgtgca agtatggagc gcttgttcag cttgtatgat ggtcagacga cctgtctgat  1380
cgagtatgta tgatactgca caacctgtgt atccgcatga tctgtccaat ggggcatgtt  1440
gttgtgtttc tcgatacgga gatgctgggt acagtgctaa tacgttgaac tacttatact  1500
tatatgaggc tcgaagaaag ctgacttgtg tatgacttat tctcaactac atccccagtc  1560
acaataccac cactgcacta ccactacacc aaaaccatga tcaaaccacc catggacttc  1620
ctggaggcag aagaacttgt tatggaaaag ctcaagagag agatcataac ttcgtatagc  1680
atacattata cgaagttatc ctgcaggtaa aggaattcag gagagaccgg ttggcggcg  1740
tatttgtgtc ccaaaaaaca gccccaattg ccccaattga ccccaaattg acccagtagc  1800
gggcccaacc ccggcgagag ccccccttcac cccacatatc aaacctcccc cggttcccac  1860
acttgccgtt aagggcgtag ggtactgcag tctggaatct acgcttgttc agactttgta  1920
ctagtttctt tgtctggcca tccgggtaac ccatgccgga cgcaaaatag actactgaaa  1980
atttttttgc tttgtggttg ggactttagc caagggtata aagaccacc gtccccgaat   2040
tacctttcct cttcttttct ctctctcctt gtcaactcac acccgaaatc gttaagcatt  2100
tccttctgag tataagaatc attcaccatg gacttcctgg aggcagaaga acttgttatg  2160
gaaaagctca agagagagaa gccaagatac tatcaagaca tgtgtcgcaa cttaattaag  2220
atgacgacat ttgcgagctg gacgaggaat agatggagcg tgtgttctga gtcgatgttt  2280
tctatggagt tgtgagtgtt agtagacatg atgggtttat atatgatgaa tgaatagatg  2340
tgatttttgat ttgcacgatg gaattgagaa ctttgtaaac gtacatggga atgtatgaat  2400
gtgggggttt tgtgactgga taactgacgg tcagtggacg ccgttgttca aatatccaag  2460
agatgcgaga aactttgggt caagtgaaca tgtcctctct gttcaagtaa accatcaact  2520
atgggtagta tatttagtaa ggacaagagt tgagattctt tggagtccta gaaacgtatt  2580
ttcgcgttcc aagatcaaat tagtagagta atacgggcac gggaatccat tcatagtctc  2640
aattttccca taggtgtgct acaaggtgtt gagatgtggt acagtaccac catgattcga  2700
ggtaaagagc ccagaagtca ttgatgaggt caagaaatac acagatctac agctcaatac  2760
```

```
aatgaatatc ttctttcata ttcttcaggt gacaccaagg gtgtctattt tccccagaaa    2820
tgcgtgaaaa ggcgcgtgtg tagcgtggag tatgggttcg gttggcgtat ccttcatata    2880
tcgacgaaat agtagggcaa gagatgacaa aaagtatcta tatgtagaca gcgtagaata    2940
tggatttgat tggtataaat tcatttattg cgtgtctcac aaatactctc gataagttgg    3000
ggttaaactg gagatggaac aatgtcgata tctcgacgca tgcgacgtcg ggcccaattc    3060
gccctatagt gagtcgtatt acaattcact ggccgtcgtt ttacaacgtc gtgactggga    3120
aaaccctggc gttacccaac ttaatcgcct tgcagcacat ccccctttcg ccagctggcg    3180
taatagcgaa gaggcccgca ccgatcgccc ttcccaacag ttgcgcagcc tgaatggcga    3240
atggacgcgc cctgtagcgg cgcattaagc gcggcgggtg tggtggttac gcgcagcgtg    3300
accgctacac ttgccagcgc cctagcgccc gctcctttcg ctttcttccc ttcctttctc    3360
gccacgttcg ccggctttcc ccgtcaagct ctaaatcggg gctccctttt agggttccga    3420
tttagtgctt tacggcacct cgaccccaaa aaacttgatt agggtgatgg ttcacgtagt    3480
gggccatcgc cctgatagac ggtttttcgc cctttgacgt tggagtccac gttctttaat    3540
agtggactct tgttccaaac tggaacaaca ctcaacccta tctcggtcta ttcttttgat    3600
ttataaggga ttttgccgat ttcggcctat tggttaaaaa atgagctgat ttaacaaaaa    3660
tttaacgcga attttaacaa aatattaacg cttacaattt cctgatgcgg tattttctcc    3720
ttacgcatct gtgcggtatt tcacaccgca tcaggtggca cttttcgggg aaatgtgcgc    3780
ggaaccccta tttgtttatt tttctaaata cattcaaata tgtatccgct catgagacaa    3840
taaccctgat aaatgcttca ataatattga aaaggaaga gtatgagtat tcaacatttc    3900
cgtgtcgccc ttattccctt ttttgcggca ttttgccttc ctgtttttgc tcacccagaa    3960
acgctggtga agtaaaaga tgctgaagat cagttgggtg cacgagtggg ttacatcgaa    4020
ctggatctca acagcggtaa gatccttgag agttttcgcc ccgaagaacg ttttccaatg    4080
atgagcactt ttaaagttct gctatgtggc gcggtattat cccgtattga cgccgggcaa    4140
gagcaactcg gtcgccgcat acactattct cagaatgact tggttgagta ctcaccagtc    4200
acagaaaagc atcttacgga tggcatgaca gtaagagaat tatgcagtgc tgccataacc    4260
atgagtgata acactgcggc caacttactt ctgacaacga tcggaggacc gaaggagcta    4320
accgcttttt tgcacaacat gggggatcat gtaactcgcc ttgatcgttg ggaaccggag    4380
ctgaatgaag ccataccaaa cgacgagcgt gacaccacga tgcctgtagc aatggcaaca    4440
acgttgcgca aactattaac tggcgaacta cttactctag cttcccggca acaattaata    4500
gactggatgg aggcggataa agttgcagga ccacttctgc gctcggccct tccggctggc    4560
tggtttattg ctgataaatc tggagccggt gagcgtgggt ctcgcggtat cattgcagca    4620
ctggggccag atggtaagcc ctcccgtatc gtagttatct acacgacggg gagtcaggca    4680 actatgatg aacgaaatag acagatcgct gagataggtg cctcactgat taagcattgg    4740
taactgtcag accaagttta ctcatatata ctttagattg atttaaaact tcatttttaa    4800
tttaaaagga tctaggtgaa gatcctttt gataatctca tgaccaaaat cccttaacgt    4860
gagttttcgt tccactgagc gtcagacccc gtagaaaaga tcaaaggatc ttcttgagat    4920 ccttttttc tgcgcgtaat ctgctgcttg caaacaaaaa aaccaccgct accagcggtg    4980
gtttgtttgc cggatcaaga gctaccaact ctttttccga aggtaactgg cttcagcaga    5040
gcgcagatac caaatactgt tcttctagtg tagccgtagt taggccacca cttcaagaac    5100
tctgtagcac cgcctacata cctcgctctg ctaatcctgt taccagtggc tgctgccagt    5160
```

```
ggcgataagt cgtgtcttac cgggttggac tcaagacgat agttaccgga taaggcgcag    5220
cggtcgggct gaacgggggg ttcgtgcaca cagcccagct tggagcgaac gacctacacc    5280
gaactgagat acctcagcg tgagctatga aaagcgcca cgcttcccga agggagaaag      5340
gcggacaggt atccggtaag cggcagggtc ggaacaggag agcgcacgag ggagcttcca    5400
gggggaaacg cctggtatct ttatagtcct gtcgggtttc gccacctctg acttgagcgt    5460 cgattttgt gatgctcgtc aggggggcgg agcctatgga aaaacgccag caacgcggcc     5520
tttttacggt tcctggcctt ttgctggcct tttgctcaca tgttctttcc tgcgttatcc    5580
cctgattctg tggataaccg tattaccgcc tttgagtgag ctgataccgc tcgccgcagc    5640
cgaacgaccg agcgcagcga gtcagtgagc gaggaagcgg aagagcgccc aatacgcaaa    5700
ccgcctctcc ccgcgcgttg gccgattcat taatgcagct ggcgcgccac caatcacaat    5760
tctgaaaagc acatcttgat ctcctcattg cggggagtcc aacggtggtc ttattccccc    5820
gaatttcccg ctcaatctcg ttccagaccg acccggacac agtgcttaac gccgttccga    5880
aactctaccg cagatatgct ccaacggact gggctgcata gatgtgatcc tcggcttgga    5940
gaaatggata aaagccggcc aaaaaaaaag cggaaaaaag cggaaaaaaa gagaaaaaaa    6000
atcgcaaaat ttgaaaaata gggggaaaag acgcaaaaac gcaaggaggg gggagtatat    6060
gacactgata agcaagctca caacggttcc tcttattttt ttcctcatct tctgcctagg    6120
ttcccaaaat cccagatgct tctctccagt gccaaaagta agtacccac aggttttcgg     6180 ccgaaaattc cacgtgcagc aacgtcgtgt ggggtgttaa aatgtggggg ggggaacca     6240 ggacaagagg ctcttgtggg agccgaatga gagcacaaag cggcgggtg tgataagggc     6300 atttttgccc attttcctt ctcctgtctc tccgacggtg atggcgttgt gcgtcctcta     6360
tttcttttta tttcttttg tttatttct ctgactaccg atttggtttg atttcctcaa      6420
ccccacacaa ataagctcgg gccgaggaat atatatatac acggacacag tcgccctgtg    6480
gacaacacgt cactacctct acgatacaca ccgtacgata gttagtagac aacaatcgat    6540
agttggagca agggagaaat gtagagtgtg aaagactcac tatggtccgg gcttatctcg    6600
accaatagcc aaagtctgga gtttctgaga gaaaaaggca agatacgtat gtaacaaagc    6660
gacgcatggt acaataatac cggaggcatg tatcatagag agttagtggt tcgatgatgg    6720
cactggtgcc tggtatgact ttatacggct gactacatat ttgtcctcag acatacaatt    6780
acagtcaagc acttacccct ggacatctgt aggtacccc cggccaagac gatctcagcg     6840
tgtcgtatgt cggattggcg tagctccctc gctcgtcaat tggctcccat ctactttctt    6900
ctgcttggct acacccagca tgtctgctat ggctcgtttt cgtgccttat ctatcctccc    6960
agtattacca actctaaatg acatgatgtg attgggtcta cactttcata tcagagataa    7020
ggagtagcac agttgcataa aaagcccaac tctaatcagc ttcttccttt cttgtaatta    7080
gtacaaaggt gattagcgaa atctggaagc ttagttggcc ctaaaaaaat caaaaaaagc    7140
aaaaaacgaa aaacgaaaaa ccacagtttt gagaacaggg aggtaacgaa ggatcgtata    7200
tatatatata tatatatata cccacggatc ccgagaccgg cctttgattc ttccctacaa    7260
ccaaccattc tcaccaccct aattcacaac catgtctatt ggttcgtcca accccgtgct    7320
cttggctgcg attcccttcg tctacctgtt tgtcctccca cgagtcctgg ctttcctgcc    7380
tcagaaggct cagttcctgg ccaaatgtat tgtggtcctg attgccacgc ttatcatgtc    7440
cgttgcaggc tgcttcatct cgatcgtgtg cgctcttctg gacaagagat acgtcatcaa    7500
```

```
ttacgttgtg tcgcgattgt tctccttcct tgccgctcga ccgtgtggtg tgacctataa    7560
gattgttggt gaggaacacc tcgataagta ccctgctatc gtggtctgta accatcaatc    7620
ctctatggat atgatggttt tgggacgagt ttttccaaag cactgcgttg tcatggcgaa    7680
gaaggaactc ctgtactttc ccttttTggg aatgtttatg aaactgagca acgctatctt    7740
catcgaccgg aagaaccaca agaaagccat cgagtctacc acccaagccg tggcggacat    7800
gaagaagcac aactctggaa tctggatttt cccagagggc accggtcta gactggacaa     7860 ggcagacctg ctgcccttca agaaaggtgc ctttcatctt gcaattcagg cccagctccc    7920
tattctcccc attatctcgc agggctattc ccatatctac gactcttcga agcggtactt    7980
ccccggtgga gagctcgaga tcagagtcct ggagcccatt cctacaactg gcctcactac    8040
tgatgatgtg aacgacctga tggacaagac acgaaacctt atgctcaagc acttgaagga    8100
gatggattcc cagtattcgt cgagcactgc tgaaaatgga tccacgcaca tcgacgccga    8160
tattgccaag tctacagcca ccagcattgg caacactgac gacgcaatta caaaacgtcg    8220
taccccTaag gaataagcgg ccgcatgaga agataaatat ataaatacat tgagatatta    8280
aatgcgctag attagagagc ctcatactgc tcggagagaa gccaagacga gtactcaaag    8340
gggattacac catccatatc cacagacaca agctggggaa aggttctata tacactttcc    8400
ggaataccgt agtttccgat gttatcaatg ggggcagcca ggatttcagg cacttcggtg    8460
tctcggggtg aaatggcgtt cttggcctcc atcaagtcgt accatgtctt catttgcctg    8520
tcaaagtaaa acagaagcag atgaagaatg aacttgaagt gaaggaattt aaatgtaacg    8580
aaactgaaat ttgaccagat attgtgtccg cggtggagct ccagcttttg ttcccttTag    8640
tgagggttaa tttcgagctt ggcgtaatca tggtcatagc tgtttcctgt gtgaaattgt    8700
tatccgctca caagcttcca cacaac                                         8726

<210> SEQ ID NO 47
<211> LENGTH: 16424
<212> TYPE: DNA
<213> ORGANISM: Artificial Sequence
<220> FEATURE:
<223> OTHER INFORMATION: Plasmid pZKL4-220EA41B

<400> SEQUENCE: 47
aattctctct cttgagcttt tccataacaa gttcttctgc ctccaggaag tccatgggtg      60
gtttgatcat ggttttggtg tagtggtagt gcagtggtgg tattgtgact ggggatgtag     120
ttgagaataa gtcatacaca agtcagcttt cttcgagcct catataagta taagtagttc     180
aacgtattag cactgtaccc agcatctccg tatcgagaaa cacaacaaca tgccccattg     240
gacagatcat gcggatacac aggttgtgca gtatcataca tactcgatca gacaggtcgt     300
ctgaccatca tacaagctga acaagcgctc catacttgca cgctctctat atacacagtt     360
aaattacata tccatagtct aacctctaac agttaatctt ctggtaagcc tcccagccag     420
ccttctggta tcgcttggcc tcctcaatag gatctcggtt ctggccgtac agacctcggc     480
cgacaattat gatatccgtt ccggtagaca tgacatcctc aacagttcgg tactgctgtc     540
cgagagcgtc tcccttgtcg tcaagaccca ccccgggggt cagaataagc cagtcctcag     600
agtcgccctt aggtcggttc tggcaatga agccaaccac aaactggggg tcggatcggg      660
caagctcaat ggtctgcttg gagtactcgc cagtggccag agagcccttg caagacagct     720
cggccagcat gagcagacct ctggccagct tctcgtggg agaggggact aggaactcct     780
tgtactggga gttctcgtag tcagagacgt cctccttctt ctgttcagag acagtttcct     840
```

```
cggcaccagc tcgcaggcca gcaatgattc cggttccggg tacaccgtgg gcgttggtga    900
tatcggacca ctcggcgatt cggtgacacc ggtactggtg cttgacagtg ttgccaatat    960
ctgcgaactt tctgtcctcg aacaggaaga aaccgtgctt aagagcaagt tccttgaggg   1020
ggagcacagt gccggcgtag gtgaagtcgt caatgatgtc gatatgggtt ttgatcatgc   1080
acacataagg tccgacctta tcggcaagct caatgagctc cttggtggtg gtaacatcca   1140
gagaagcaca caggttggtt ttcttggctg ccacgagctt gagcactcga gcggcaaagg   1200
cggacttgtg gacgttagct cgagcttcgt aggagggcat tttggtggtg aagaggagac   1260
tgaaataaat ttagtctgca gaacttttta tcggaacctt atctgggca  gtgaagtata   1320
tgttatggta atagttacga gttagttgaa cttatagata gactggacta tacggctatc   1380
ggtccaaatt agaaagaacg tcaatggctc tctgggcgtc gcctttgccg acaaaaatgt   1440
gatcatgatg aaagccagca atgacgttgc agctgatatt ttgtcggcc  aaccgcgccg   1500
aaaacgcagc tgtcagaccc acagcctcca acgaagaatg tatcgtcaaa gtgatccaag   1560
cacactcata gttggagtcg tactccaaag gcggcaatga cgagtcagac agatactcgt   1620
cgaccttttc cttgggaacc accaccgtca gcccttctga ctcacgtatt gtagccaccg   1680
acacaggcaa cagtccgtgg atagcagaat atgtcttgtc ggtccatttc tcaccaactt   1740
taggcgtcaa gtgaatgttg cagaagaagt atgtgccttc attgagaatc ggtgttgctg   1800
atttcaataa agtcttgaga tcagtttggc cagtcatgtt gtgggggta  attggattga   1860
gttatcgcct acagtctgta caggtatact cgctgcccac tttatacttt ttgattccgc   1920
tgcacttgaa gcaatgtcgt ttaccaaaag tgagaatgct ccacagaaca cccccaggg   1980
tatggttgag caaaaaataa acactccgat acggggaatc gaaccccggt ctccacggtt   2040
ctcaagaagt attcttgatg agagcgtatc gatcgaggaa gaggacaagc ggctgcttct   2100
taagtttgtg acatcagtat ccaaggcacc attgcaagga ttcaaggctt tgaacccgtc   2160
atttgccatt cgtaacgctg gtagacaggt tgatcggttc cctacggcct ccacctgtgt   2220
caatcttctc aagctgcctg actatcagga cattgatcaa cttcggaaga aacttttgta   2280
tgccattcga tcacatgctg gtttcgattt gtcttagagg aacgcatata cagtaatcat   2340
agagaataaa cgatattcat ttattaaagt agatagttga ggtagaagtt gtaaagagtg   2400
ataaatagcg gccgcttaag ccagagtggc gacagcagga caaccggcag cagatccgtc   2460
ggtggagccg tcgggttggg cagcaacggc agcagagagc acaggacaaa catcctccag   2520
ggaacctgca gtgggagcaa gcttgtcgtt gtctgcaggt ttggtgccca tagctcgcaa   2580
gtgctcgacc attccgtaca gagcatcgga aaactgagag tagttcttgt agggaagacc   2640
gtattcctcg cacacgccct tgacaacagg agcaatggtg ggatagttgg cgtgagaaat   2700
gctgggaaac aggtgatgct cgatctggtg gttgagtcca ccagaaaggt ggtttgaaaa   2760
gtagccacca gatcgccagt tgacgcaaca cagaacttgg gaggcagccc agtcgttggg   2820
aggtggagtg gggtgcttct gtttcgcctt ggcttcctgc tcggcctgct tgagcatttc   2880
ggtccgtcgg gcagcgataa cggaagaggg attgaggtag tcgcacgact cggaaatgtg   2940
gttgataatg aaacagacgg caaggtactc gccagaaacc agatgagctg taatgaagag   3000
ggccaatccg tgagcgatgc catgcaggta gcagggaagc acaatctgca tgagaaagcc   3060
catgatcttt gcaccccaga acagcatctg accctcgagg ggaacgagtc tggcagagaa   3120
gtcgatggga ccacgtcgct tggcaagaca aaacgtgaaa tcggagataa tgaccttgct   3180
```

```
gatggtcatg agagcgaaca acggaaaggc gtacacgtgt tgcagctgat ggtggggttt    3240
ccaaggagtg tccggatgca tccgcatgag gggataggtt ccgaaaacgt ctggatcgtt    3300
ctcgggaaga gcaaactcgg gatcggacac caggttggtg tactggtgat gaccaatgac    3360
gtgttggtac tcccaggcag tcgaggaggc tccgataacg tccatacccc agccagcaag    3420
acggttgagt cgtccagact tggagaaagc accatgattg ccgtcgtgct ggatgctgag    3480
tccaatgtga gagcctgcca gaccccagac ggcagcccaa agaaggatc cctgtgtcac    3540 catgaggtag aacgaggcag caaaggcagc cataacaagg gctgccttga cagacaggcc    3600
accacgtcga ggttgtccag cctccttgag agtctgaacc actcgctgct tgagctcggc    3660
gtagaaagcg gaggcctgcc agtcgtagaa ggttctgtga tcctgaagtg taccgattcg    3720
gtacttctcc ataaccttgt cgggtcgtcc tgcaggatgg tacgattcga ccagaatagt    3780
ggagtctcgt ccgagaccga gagagataac atctccaccg ggatgcttgc caatgaactc    3840
ggtgatgtcg tacacaccgt cgtgacaggc caaccagcca tcggtgggaa caatgtgtcg    3900
agcgacctct cgcatggtaa actttcggtc ctgtccagta ccggaggtgg ccagagcgtc    3960
gtaataggct gcaggtgggt tgccaacagg tcgaatggga ggtggaagag aagcgatctc    4020
cgagggcttg ccaggtccac cgggtttgac cttggccatg ccattgctg tagatatgtc     4080 ttgtgtgtaa gggggttggg gtggttgttt gtgttcttga cttttgtgtt agcaagggaa    4140
gacgggcaaa aaagtgagtg tggttgggag ggagagacga gccttatata taatgcttgt    4200
ttgtgtttgt gcaagtggac gccgaaacgg gcaggagcca aactaaacaa ggcagacaat    4260
gcgagcttaa ttggattgcc tgatgggcag gggttagggc tcgatcaatg ggggtgcgaa    4320
gtgacaaaat tgggaattag gttcgcaagc aaggctgaca agactttggc ccaaacattt    4380
gtacgcggtg gacaacagga gccacccatc gtctgtcacg ggctagccgg tcgtgcgtcc    4440
tgtcaggctc cacctaggct ccatgccact ccatacaatc ccactagtgt accgctaggc    4500
cgcttttagc tcccatctaa gaccccccca aaacctccac tgtacagtgc actgtactgt    4560
gtggcgatca agggcaaggg aaaaaaggcg caaacatgca cgcatggaat gacgtaggta    4620
aggcgttact agactgaaaa gtggcacatt tcggcgtgcc aaagggtcct aggtgcgttt    4680
cgcgagctgg gcgccaggcc aagccgctcc aaaacgcctc tccgactccc tccagcggcc    4740
tccatatccc catccctctc cacagcaatg ttgttaagcc ttgcaaacga aaaaatagaa    4800
aggctaataa gcttccaata ttgtggtgta cgctgcataa cgcaacaatg agcgccaaac    4860
aacacacaca cacagcacac agcagcatta accacgatgt ttaaacagag tgtgaaagac    4920
tcactatggt ccgggcttat ctcgaccaat agccaaagtc tggagtttct gagagaaaaa    4980
ggcaagatac gtatgtaaca aagcgacgca tggtacaata ataccggagg catgtatcat    5040
agagagttag tggttcgatg atggcactgg tgcctggtat gactttatac ggctgactac    5100
atatttgtcc tcagacatac aattacagtc aagcacttac ccttggacat ctgtaggtac    5160
cccccggcca agacgatctc agcgtgtcgt atgtcggatt ggcgtagctc cctcgctcgt    5220
caattggctc ccatctactt tcttctgctt ggctacaccc agcatgtctg ctatggctcg    5280
ttttcgtgcc ttatctatcc tcccagtatt accaactcta aatgacatga tgtgattggg    5340
tctacacttt catatcagag ataaggagta gcacagttgc ataaaaagcc caactctaat    5400
cagcttcttc ctttcttgta attagtacaa aggtgattag cgaaatctgg aagcttagtt    5460
ggccctaaaa aaatcaaaaa aagcaaaaaa cgaaaaacga aaaccacag ttttgagaac     5520 agggaggtaa cgaaggatcg tatatatata tatatatata tatacccacg gatcccgaga    5580
```

```
ccggcctttg attcttccct acaaccaacc attctcacca ccctaattca caaccatggc    5640
tgactctccc gtcatcaacc tctccaccat gtggaagcct ctgtcgctca tggccttgga    5700
tcttgctgtt ctgggacacg tctggaagca ggcacaacag gagggctcca tctcggctta    5760
cgccgactct gtgtggactc ccctcatcat gtccggtctg tacctctcca tgatcttcgt    5820
gggatgtcga tggatgaaga accgagagcc cttcgaaatc aagacctaca tgtttgccta    5880
caacctgtac cagacccctca tgaacctttg cattgtgctg ggcttcctct accaggtcca    5940
cgctaccggt atgcgattct ggggatctgg cgtggaccga tcgcccaagg gtctgggaat    6000 tggcttttc atctatgccc attaccacaa caagtacgtc gagtacttcg acacactctt    6060
catggtgctg cggaaaaaga caaccagat ttcctttctt cacgtctacc atcacgctct    6120
gctcacctgg gcttggtttg ccgtggtcta cttcgctcct ggaggtgacg gctggtttgg    6180
agcctgctac aattcctcca ttcatgtcct gatgtactct tactatctgc ttgccacctt    6240
cggcatctcc tgtccctgga aaagatcct cacccagctg caaatggttc agttctgctt    6300
ttgcttcacc cactcgatct acgtgtggat ttgcggttcc gaaatctacc ctcgacccctt    6360 gactgctctc cagtccttcg tgatggtcaa catgctggtt ctctttggca acttctacgt    6420
caagcagtat tctcagaaga atggaaagcc cgagaacggt gccactcctg agaacggtgc    6480
caagcctcag ccctgcgaga acggcaccgt cgagaagcga gagaacgaca ctgccaacgt    6540
tcgataagcg gccgcatgag aagataaata tataaataca ttgagatatt aaatgcgcta    6600
gattagagag cctcatactg ctcggagaga agccaagacg agtactcaaa ggggattaca    6660
ccatccatat ccacagacac aagctgggga aaggttctat atacactttc cggaataccg    6720
tagtttccga tgttatcaat gggggcagcc aggatttcag gcacttcggt gtctcggggt    6780
gaaatggcgt tcttggcctc catcaagtcg taccatgtct tcatttgcct gtcaaagtaa    6840
aacagaagca gatgaagaat gaacttgaag tgaaggaatt taaattgccc cggagaagac    6900
ggccaggccg cctagatgac aaattcaaca actcacagct gactttctgc cattgccact    6960
aggggggggc cttttatat ggccaagcca agctctccac gtcggttggg ctgcacccaa    7020
caataaatgg gtagggttgc accaacaaag ggatgggatg gggggtagaa gatacgagga    7080
taacggggct caatggcaca aataagaacg aatactgcca ttaagactcg tgatccagcg    7140
actgacacca ttgcatcatc taagggcctc aaaactacct cggaactgct gcgctgatct    7200
ggacaccaca gaggttccga gcactttagg ttgcaccaaa tgtcccacca ggtgcaggca    7260
gaaaacgctg gaacagcgtg tacagtttgt cttaacaaaa agtgagggcg ctgaggtcga    7320
gcagggtggt gtgacttgtt atagccttta gagctgcgaa agcgcgtatg gatttggctc    7380
atcaggccag attgagggtc tgtggacaca tgtcatgtta gtgtacttca atcgccccct    7440
ggatatagcc ccgacaatag gccgtggcct catttttttg ccttccgcac atttccattg    7500
ctcggtaccc acaccttgct tctcctgcac ttgccaacct taatactggt ttacattgac    7560
caacatctta caagcggggg gcttgtctag ggtatatata aacagtggct ctcccaatcg    7620
gttgccagtc tcttttttcc tttctttccc cacagattcg aaatctaaac tacacatcac    7680
agaactccga gccgtgagta tccacgacaa gatcagtgtc gagacgacgc gttttgtgta    7740
atgacacaat ccgaaagtcg ctagcaacac acactctcta cacaaactaa cccagctctg    7800
gtaccatggc cgagggcaag tccgacggtc ccgtcgttac cctccagtcc atgtggaagc    7860
ccctggctct catggccatc gacgtcggca tcctggtcaa cgtgcgacgg aaggccttca    7920
```

```
ccgagttcga cggacactcg aacgtcttcg ccgatcccgt gtacattccc tttgtcatga   7980
acctgttcta cctcaccatg atctttgctg gctgccgatg gatgaagact cgagaaccct   8040
tcgagatcaa gtcctacatg tttgcctaca acgcttacca gacaatgatg aactttctca   8100
ttgtggtcgg cttcatgtat gaggttcact ccaccggtat gcgatactgg ggatccagaa   8160
tcgacacttc taccaagggc ttgggactgg gtttcctcat ctatgcccat taccacaaca   8220
agtacgtgga gtacgtcgac accctgttca tgattctgcg gaagaaaaac aatcagatct   8280
cgttccttca cgtttaccac cattccctgc tcacttgggc atggtgggct gtggtctact   8340
gggctcctgg cggagatgcc tggttcggtg cctgttacaa ctccttcatc cacgttctca   8400
tgtactccta ctatctgttt gccaccttcg gcattcgatg tccctggaaa agatgctca   8460
cccagttgca atggtccag ttctgctttt gcttcgctca tgccatgtac gttggatggc   8520
ttggtcacga ggtgtaccct cgatggctca ctgctctgca ggcctttgtg atgctcaaca   8580
tgctggtcct ctttggcaac ttctacatga agtcttactc caaggcgagc aagctcgaac   8640
cagcctctcc cgtgtcgcct gcctctcttg ctcagaagcc cttcgagaac gccaaggtca   8700
agtaagcggc cgcaagtgtg gatggggaag tgagtgcccg gttctgtgtg cacaattggc   8760
aatccaagat ggatggattc aacacaggga tatagcgagc tacgtggtgg tgcgaggata   8820
tagcaacgga tatttatgtt tgacacttga gaatgtacga tacaagcact gtccaagtac   8880
aatactaaac atactgtaca tactcatact cgtacccggg caacggtttc acttgagtgc   8940
agtggctagt gctcttactc gtacagtgtg caatactgcg tatcatagtc tttgatgtat   9000
atcgtattca ttcatgttag ttgcgtacgt agggatcagg tgcttaggaa gctcgaccaa   9060
ccacggagac tgttgaaact ggatgtcggt aacagcatct ggaatgctga atgttcctcg   9120
aataacaaca tatttctcct tgttgaggtg atcataagct atgtatccgg tgattgaagt   9180
ggaatagaag tctcctccga agactgagtc caacgtcatg ttcgggaaat accgacaact   9240
ctctccacat gtaaaatcag ttcgtagagg agtgactggc gcattgacac agtaggcgat   9300
gtttgcaatc cgagaaaact tggccgtaaa gttgtacagc tcctgggagg cttgaactcg   9360
agtttttgaa agtgtcgctg gtggctcgcc gaagagggag gcatagaggt acgcaaccac   9420
ttgcccgagc gtgaggttca tgatgccaat agtgaatgtc atttatcacc gtactgcgca   9480
gtatttatat agggctcatc ggtccatgta tagatctgtc cacttatgac accccatgt   9540
ctcattaatg tgtaaaggtg gagacgggtg gagtacaggt acagagttgg aggaaatcag   9600
gatagtgggg ttaagacatg ctccgagtcc aaatttcaac tctccattgt cacaagacct   9660
ctggtttcag agttattaca gatctaggcc tgtttcaagg tgaggggacc tcatctggat   9720
cggcacgacg atcgtcacct tacagaggac gtctgtcgca gggaaaggtg atgtggcgcg   9780
ccagctgcat taatgaatcg gccaacgcgc ggggagaggc ggtttgcgta ttgggcgctc   9840
ttccgcttcc tcgctcactg actcgctgcg ctcggtcgtt cggctgcggc gagcggtatc   9900
agctcactca aaggcggtaa tacggttatc cacagaatca ggggataacg caggaaagaa   9960
catgtgagca aaaggccagc aaaaggccag gaaccgtaaa aaggccgcgt tgctggcgtt  10020
tttccatagg ctccgccccc ctgacgagca tcacaaaaat cgacgctcaa gtcagaggtg  10080
gcgaaacccg acaggactat aaagatacca ggcgtttccc cctggaagct ccctcgtgcg  10140
ctctcctgtt ccgaccctgc cgcttaccgg atacctgtcc gcctttctcc cttcgggaag  10200
cgtggcgctt tctcatagct cacgctgtag gtatctcagt tcggtgtagg tcgttcgctc  10260
caagctgggc tgtgtgcacg aaccccccgt tcagcccgac cgctgcgcct tatccggtaa  10320
```

```
ctatcgtctt gagtccaacc cggtaagaca cgacttatcg ccactggcag cagccactgg   10380
taacaggatt agcagagcga ggtatgtagg cggtgctaca gagttcttga agtggtggcc   10440
taactacggc tacactagaa gaacagtatt tggtatctgc gctctgctga agccagttac   10500
cttcggaaaa agagttggta gctcttgatc cggcaaacaa accaccgctg gtagcggtgg   10560
tttttttgtt tgcaagcagc agattacgcg cagaaaaaaa ggatctcaag aagatccttt   10620
gatcttttct acggggtctg acgctcagtg gaacgaaaac tcacgttaag ggattttggt   10680
catgagatta tcaaaaagga tcttcaccta gatcctttta aattaaaaat gaagttttaa   10740
atcaatctaa agtatatatg agtaaacttg gtctgacagt taccaatgct taatcagtga   10800
ggcacctatc tcagcgatct gtctatttcg ttcatccata gttgcctgac tccccgtcgt   10860
gtagataact acgatacggg agggcttacc atctggcccc agtgctgcaa tgataccgcg   10920
agacccacgc tcaccggctc cagatttatc agcaataaac cagccagccg gaagggccga   10980
gcgcagaagt ggtcctgcaa ctttatccgc ctccatccag tctattaatt gttgccggga   11040
agctagagta gtagttcgc cagttaatag tttgcgcaac gttgttgcca ttgctacagg   11100
catcgtggtg tcacgctcgt cgtttggtat ggcttcattc agctccggtt cccaacgatc   11160
aaggcgagtt acatgatccc ccatgttgtg caaaaaagcg gttagctcct tcggtcctcc   11220
gatcgttgtc agaagtaagt tggccgcagt gttatcactc atggttatgg cagcactgca   11280
taattctctt actgtcatgc catccgtaag atgcttttct gtgactggtg agtactcaac   11340
caagtcattc tgagaatagt gtatgcggcg accgagttgc tcttgcccgg cgtcaatacg   11400
ggataatacc gcgccacata gcagaacttt aaaagtgctc atcattggaa aacgttcttc   11460
ggggcgaaaa ctctcaagga tcttaccgct gttgagatcc agttcgatgt aacccactcg   11520
tgcacccaac tgatcttcag catcttttac tttcaccagc gtttctgggt gagcaaaaac   11580
aggaaggcaa aatgccgcaa aaaagggaat aagggcgaca cggaaatgtt gaatactcat   11640
actcttcctt tttcaatatt attgaagcat ttatcagggt tattgtctca tgagcggata   11700
catatttgaa tgtatttaga aaataaaca aataggggtt ccgcgcacat ttccccgaaa   11760
agtgccacct gatgcggtgt gaaataccgc acagatgcgt aaggagaaaa taccgcatca   11820
ggaaattgta agcgttaata ttttgttaaa attcgcgtta aatttttgtt aaatcagctc   11880
attttttaac caataggccg aaatcggcaa aatcccttat aaatcaaaag aatagaccga   11940
gatagggttg agtgttgttc cagtttggaa caagagtcca ctattaaaga acgtggactc   12000
caacgtcaaa gggcgaaaaa ccgtctatca gggcgatggc ccactacgtg aaccatcacc   12060
ctaatcaagt tttttggggt cgaggtgccg taaagcacta atcggaacc ctaaagggag   12120
cccccgattt agagcttgac ggggaaagcc ggcgaacgtg gcgagaaagg aagggaagaa   12180
agcgaaagga gcggcgcta gggcgctggc aagtgtagcg gtcacgctgc gcgtaaccac   12240
cacacccgcc gcgcttaatg cgccgctaca gggcgcgtcc attcgccatt caggctgcgc   12300
aactgttggg aagggcgatc ggtgcgggcc tcttcgctat tacgccagct ggcgaaaggg   12360
ggatgtgctg caaggcgatt aagttgggta acgccagggt tttcccagtc acgacgttgt   12420
aaaacgacgg ccagtgaatt gtaatacgac tcactatagg gcgaattggg cccgacgtcg   12480
catgccaagg cgtatattag ttggtgggaa ccagtgtacg accgggtcct gtataaccag   12540
gttcagtggc atacttgtag gagttgttcc cgtggtattt gggcatggct aagcatttc   12600
gccgaccaat gttaagtgca caatagccga tgtagtagat gtaagccaga tggttttgga   12660
```

```
gcaggtcgat tcgagaccac agattgaaag tgcctcgatg gcaggcctcg ttttctcctc    12720
cttcacagac agacactttg tcgagtgcag ggtagacgct ttcttggtca atgtacactt    12780
ctccaatggc gtgtgtgtaa ttggaccaat ctggcagtcc aacgaagata tcgttccagt    12840
gggtgagcct gtagtttcgt cgcttgtcgt ttacttcaag gcctgtgtca ttaaaccaca    12900
gctggttgat gtagtttgca aactctgagt ttcctactct cggctggcca aagttgatca    12960
tggtaggatc atgtccaagt aatttgaagt gagttgcgaa aagaagagct tgagcagcgc    13020
ccagcgagtg accagtaaca tacattttgt agtcagtgtg gttggtgagg aacttttcaa    13080
actgaggagc agcattgacc atagtttcgt tgaaggcctt ggcgaaccca tcatggatca    13140
tgcagccttt gcactcacta gttttgatgg gaataagacg ggggtcttca accaccagag    13200
cccgctcttt gaggttgtca agacctttgt tctccacttc caagtctggt cggactgccc    13260
atctctgtta attaactcac ctgcaggatt gagactatga atggattccc gtgcccgtat    13320
tactctacta atttgatctt ggaacgcgaa aatacgtttc taggactcca aagaatctca    13380
actcttgtcc ttactaaata tactacccat agttgatggt ttacttgaac agagaggaca    13440
tgttcacttg acccaaagtt tctcgcatct cttggatatt tgaacaacgg cgtccactga    13500
ccgtcagtta tccagtcaca aaaccccccac attcatacat tcccatgtac gtttacaaag    13560
ttctcaattc catcgtgcaa atcaaaatca catctattca ttcatcatat ataaacccat    13620
catgtctact aacactcaca actccataga aaacatcgac tcagaacaca cgctccatgc    13680
ggccgcttag gcgagagtag caacggcagg acatccagcg gcagagccgt cggtagaacc    13740
gtcgggttgg gcagccacgg cagcagacag aacagggcag acatcctcca aagatccagc    13800
agtaggagca agtttgtcgt tgtccgcagg cttggtaccc attgctcgca ggtgctccac    13860
catgccgtag agggcatcgg agaactgaga gtagttcttg tagggaagtc cgtactcttc    13920
gcacacaccc ttgacaacgg gagcaatggt gggatagttg gcgtggctga tagaaggaaa    13980
cagatggtgc tcgatctgat gattgagacc tcctgacaag tggttcgaga agtaaccgcc    14040
agatcgccag ttgacacagc aaagaacctg ggaagctgcc cagtcgttgg gtggaggtgt    14100
gggatgcttc tgtttcgcct tggcctcctg ttcggcttgc ttgagcatct ccgttcgtct    14160
ggcagcgatg acagaggagg ggttgaggta gtcacaagac tcggaaatgt ggttgataat    14220 gaagcaaaact gccaggtact cgcctgaaac gaggtgggca gtgatgaaca gagccaaacc    14280
atgtgcaatg ccgtgcaggt aacagggaag aacgatctgc atgagaaagc ccatgatctt    14340
tgctccccag aaaagcatct ggccctcgag aggcacaagt cgggcagaaa agtcgatcgg    14400
acctcgacgc ttggcgaggc agaaggtgaa atcgctaatg ataaccttgg agatagtcat    14460
gagggcgaac aggggaaagg catagacgtg ctgcagttgg tgatgaggtt tccacggagt    14520
gtcgggatgc attcgcatga gagggtaggt tccgaacacg tcgggatcgt tctctggaag    14580
ggcaaattcg ggatcggaaa caaggttggt gtattgatgg tggccaatga catgctggta    14640
ctcccaggct gtggacgaag caccaatgac gtccatatccc catccggcca gtcgattgag    14700
acggccagac ttcgaaaagg caccgtggtt tccgtcgtgc tgaatggaga ggccgatgtg    14760
acttccagca agaccccaca cagctgccca gaaaaacgag ccctgagtga ccatgagata    14820
gaaggaagcg gcaaacgcag ccataaccag tgcagccttg actgacagtc cgcctcgtct    14880
gggctgacca gcctccttga gggtttgcac gactcgctgc ttgagttccg cgtaaaaggc    14940
agaagcctgc cagtcgtaga aagttcgatg atcctgaaga gtgccgattc tgtacttctc    15000
cataaccttg tcgggtcgac cagcagggtg gtaggactcc acgagaatgg tagagtctcg    15060
```

-continued

```
acccagtcca agggaaatga catcgccacc gggatgcttt ccgataaact ctgtaatgtc   15120
gtaaacgccg tcgtgacagg ccagccaacc atcggtggga acgatgtgtc gtgcgacttc   15180
tcgcatggtg aactttcggt cctgaccggt tccagaagta gcgagggcgt catagtaggc   15240
agctggaggg tttcccacgg gtcggatggg tggaggcagc gaggcaatct cggagggttt   15300
gccaggacct ccaggcttga ccttggccat gggcaggacc tgtgttagta cattgtcggg   15360
gagtcatcaa ttggttcgac aggttgtcga ctgttagtat gagctcaatt gggctctggt   15420
gggtcgatga cacttgtcat ctgtttctgt tgggtcatgt ttccatcacc ttctatggta   15480
ctcacaattc gtccgattcg cccgaatccg ttaataccga ctttgatggc catgttgatg   15540
tgtgtttaat tcaagaatga atatagaaa gagaagaaga aaaagattc aattgagccg     15600 gcgatgcaga cccttatata aatgttgcct tggacagacg gagcaagccc gcccaaacct   15660
acgttcggta taatatgtta agcttttta cacaaaggtt tggcttgggg taacctgatg    15720
tggtgcaaaa gaccgggcgt tggcgagcca ttgcgcgggc gaatggggcc gtgactcgtc   15780
tcaaattcga gggcgtgcct caattcgtgc cccgtggct ttttcccgcc gtttccgccc    15840
cgtttgcacc actgcagccg cttctttggt tcggacacct tgctgcgagc taggtgcctt   15900
gtgctactta aaaagtggcc tcccaacacc aacatgacat gagtgcgtgg gccaagacac   15960
gttggcgggg tcgcagtcgg ctcaatggcc cggaaaaaac gctgctggag ctggttcgga   16020
cgcagtccgc cgcggcgtat ggatatccgc aaggttccat agcgccattg ccctccgtcg   16080
gcgtctatcc cgcaacctct aaatagagcg ggaatataac ccaagcttct ttttttttcct  16140 ttaacacgca cacccccaac tatcatgttg ctgctgctgt ttgactctac tctgtggagg   16200
ggtgctccca cccaacccaa cctacaggtg gatccggcgc tgtgattggc tgataagtct   16260
cctatccgga ctaattctga ccaatgggac atgcgcgcag gacccaaatg ccgcaattac   16320
gtaaccccaa cgaaatgcct acccctcttt ggagcccagc ggccccaaat ccccccaagc   16380
agcccggttc taccggcttc catctccaag cacaagcagc ccgg                     16424
```

<210> SEQ ID NO 48
<211> LENGTH: 900
<212> TYPE: DNA
<213> ORGANISM: Euglena anabaena
<220> FEATURE:
<221> NAME/KEY: CDS
<222> LOCATION: (1)..(900)
<223> OTHER INFORMATION: synthetic C20 elongase (codon-optimized for
      Yarrowia lipolytica) ("EaC20ES")
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: US-2008-0254191-A1
<311> PATENT FILING DATE: 2008-04-03
<312> PUBLICATION DATE: 2008-10-16
<313> RELEVANT RESIDUES IN SEQ ID NO: (1)..(900)

<400> SEQUENCE: 48

```
atg gcc gag ggc aag tcc gac ggt ccc gtc gtt acc ctc cag tcc atg      48
Met Ala Glu Gly Lys Ser Asp Gly Pro Val Val Thr Leu Gln Ser Met
1               5                   10                  15 tgg aag ccc ctg gct ctc atg gcc atc gac gtc ggc atc ctg gtc aac      96
Trp Lys Pro Leu Ala Leu Met Ala Ile Asp Val Gly Ile Leu Val Asn
            20                  25                  30 gtg cga cgg aag gcc ttc acc gag ttc gac gga cac tcg aac gtc ttc     144
Val Arg Arg Lys Ala Phe Thr Glu Phe Asp Gly His Ser Asn Val Phe
        35                  40                  45
```

```
gcc gat ccc gtg tac att ccc ttt gtc atg aac ctg ttc tac ctc acc      192
Ala Asp Pro Val Tyr Ile Pro Phe Val Met Asn Leu Phe Tyr Leu Thr
    50                  55                  60 atg atc ttt gct ggc tgc cga tgg atg aag act cga gaa ccc ttc gag      240
Met Ile Phe Ala Gly Cys Arg Trp Met Lys Thr Arg Glu Pro Phe Glu
65                  70                  75                  80 atc aag tcc tac atg ttt gcc tac aac gct tac cag aca atg atg aac      288
Ile Lys Ser Tyr Met Phe Ala Tyr Asn Ala Tyr Gln Thr Met Met Asn
                    85                  90                  95 ttt ctc att gtg gtc ggc ttc atg tat gag gtt cac tcc acc ggt atg      336
Phe Leu Ile Val Val Gly Phe Met Tyr Glu Val His Ser Thr Gly Met
                100                 105                 110 cga tac tgg gga tcc aga atc gac act tct acc aag ggc ttg gga ctg      384
Arg Tyr Trp Gly Ser Arg Ile Asp Thr Ser Thr Lys Gly Leu Gly Leu
            115                 120                 125 ggt ttc ctc atc tat gcc cat tac cac aac aag tac gtg gag tac gtc      432
Gly Phe Leu Ile Tyr Ala His Tyr His Asn Lys Tyr Val Glu Tyr Val
        130                 135                 140 gac acc ctg ttc atg att ctg cgg aag aaa aac aat cag atc tcg ttc      480
Asp Thr Leu Phe Met Ile Leu Arg Lys Lys Asn Asn Gln Ile Ser Phe
145                 150                 155                 160 ctt cac gtt tac cac cat tcc ctg ctc act tgg gca tgg tgg gct gtg      528
Leu His Val Tyr His His Ser Leu Leu Thr Trp Ala Trp Trp Ala Val
                    165                 170                 175 gtc tac tgg gct cct ggc gga gat gcc tgg ttc ggt gcc tgt tac aac      576
Val Tyr Trp Ala Pro Gly Gly Asp Ala Trp Phe Gly Ala Cys Tyr Asn
                180                 185                 190 tcc ttc atc cac gtt ctc atg tac tcc tac tat ctg ttt gcc acc ttc      624
Ser Phe Ile His Val Leu Met Tyr Ser Tyr Tyr Leu Phe Ala Thr Phe
            195                 200                 205 ggc att cga tgt ccc tgg aaa aag atg ctc acc cag ttg caa atg gtc      672
Gly Ile Arg Cys Pro Trp Lys Lys Met Leu Thr Gln Leu Gln Met Val
        210                 215                 220 cag ttc tgc ttt tgc ttc gct cat gcc atg tac gtt gga tgg ctt ggt      720
Gln Phe Cys Phe Cys Phe Ala His Ala Met Tyr Val Gly Trp Leu Gly
225                 230                 235                 240 cac gag gtg tac cct cga tgg ctc act gct ctg cag gcc ttt gtg atg      768
His Glu Val Tyr Pro Arg Trp Leu Thr Ala Leu Gln Ala Phe Val Met
                    245                 250                 255 ctc aac atg ctg gtc ctc ttt ggc aac ttc tac atg aag tct tac tcc      816
Leu Asn Met Leu Val Leu Phe Gly Asn Phe Tyr Met Lys Ser Tyr Ser
                260                 265                 270 aag gcg agc aag ctc gaa cca gcc tct ccc gtg tcg cct gcc tct ctt      864
Lys Ala Ser Lys Leu Glu Pro Ala Ser Pro Val Ser Pro Ala Ser Leu
            275                 280                 285 gct cag aag ccc ttc gag aac gcc aag gtc aag taa                      900
Ala Gln Lys Pro Phe Glu Asn Ala Lys Val Lys
        290                 295

<210> SEQ ID NO 49
<211> LENGTH: 299
<212> TYPE: PRT
<213> ORGANISM: Euglena anabaena

<400> SEQUENCE: 49

Met Ala Glu Gly Lys Ser Asp Gly Pro Val Val Thr Leu Gln Ser Met
1               5                   10                  15

Trp Lys Pro Leu Ala Leu Met Ala Ile Asp Val Gly Ile Leu Val Asn
            20                  25                  30

Val Arg Arg Lys Ala Phe Thr Glu Phe Asp Gly His Ser Asn Val Phe
```

```
                35                  40                  45
Ala Asp Pro Val Tyr Ile Pro Phe Val Met Asn Leu Phe Tyr Leu Thr
 50                  55                  60

Met Ile Phe Ala Gly Cys Arg Trp Met Lys Thr Arg Glu Pro Phe Glu
 65                  70                  75                  80

Ile Lys Ser Tyr Met Phe Ala Tyr Asn Ala Tyr Gln Thr Met Met Asn
                 85                  90                  95

Phe Leu Ile Val Val Gly Phe Met Tyr Glu Val His Ser Thr Gly Met
            100                 105                 110

Arg Tyr Trp Gly Ser Arg Ile Asp Thr Ser Thr Lys Gly Leu Gly Leu
        115                 120                 125

Gly Phe Leu Ile Tyr Ala His Tyr His Asn Lys Tyr Val Glu Tyr Val
    130                 135                 140

Asp Thr Leu Phe Met Ile Leu Arg Lys Lys Asn Asn Gln Ile Ser Phe
145                 150                 155                 160

Leu His Val Tyr His His Ser Leu Leu Thr Trp Ala Trp Trp Ala Val
                165                 170                 175

Val Tyr Trp Ala Pro Gly Gly Asp Ala Trp Phe Gly Ala Cys Tyr Asn
            180                 185                 190

Ser Phe Ile His Val Leu Met Tyr Ser Tyr Tyr Leu Phe Ala Thr Phe
        195                 200                 205

Gly Ile Arg Cys Pro Trp Lys Lys Met Leu Thr Gln Leu Gln Met Val
    210                 215                 220

Gln Phe Cys Phe Cys Phe Ala His Ala Met Tyr Val Gly Trp Leu Gly
225                 230                 235                 240

His Glu Val Tyr Pro Arg Trp Leu Thr Ala Leu Gln Ala Phe Val Met
                245                 250                 255

Leu Asn Met Leu Val Leu Phe Gly Asn Phe Tyr Met Lys Ser Tyr Ser
            260                 265                 270

Lys Ala Ser Lys Leu Glu Pro Ala Ser Pro Val Ser Pro Ala Ser Leu
        275                 280                 285

Ala Gln Lys Pro Phe Glu Asn Ala Lys Val Lys
    290                 295

<210> SEQ ID NO 50
<211> LENGTH: 912
<212> TYPE: DNA
<213> ORGANISM: Euglena gracilis
<220> FEATURE:
<221> NAME/KEY: CDS
<222> LOCATION: (1)..(912)
<223> OTHER INFORMATION: synthetic C20 elongase (codon-optimized for
      Yarrowia lipolytica) ("EgC20ES")
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: US-2008-0254191-A1
<311> PATENT FILING DATE: 2008-04-03
<312> PUBLICATION DATE: 2008-10-16
<313> RELEVANT RESIDUES IN SEQ ID NO: (1)..(912)

<400> SEQUENCE: 50 atg gct gac tct ccc gtc atc aac ctc tcc acc atg tgg aag cct ctg    48
Met Ala Asp Ser Pro Val Ile Asn Leu Ser Thr Met Trp Lys Pro Leu
 1               5                  10                  15 tcg ctc atg gcc ttg gat ctt gct gtt ctg gga cac gtc tgg aag cag    96
Ser Leu Met Ala Leu Asp Leu Ala Val Leu Gly His Val Trp Lys Gln
             20                  25                  30 gca caa cag gag ggc tcc atc tcg gct tac gcc gac tct gtg tgg act   144
```

| | | | | | | | | | | | | | | | |
|---|---|---|---|---|---|---|---|---|---|---|---|---|---|---|---|
| Ala | Gln | Gln | Glu | Gly | Ser | Ile | Ser | Ala | Tyr | Ala | Asp | Ser | Val | Trp | Thr |
| | | 35 | | | | 40 | | | | 45 | | | | | |

```
ccc ctc atc atg tcc ggt ctg tac ctc tcc atg atc ttc gtg gga tgt       192
Pro Leu Ile Met Ser Gly Leu Tyr Leu Ser Met Ile Phe Val Gly Cys
 50              55                  60 cga tgg atg aag aac cga gag ccc ttc gaa atc aag acc tac atg ttt       240
Arg Trp Met Lys Asn Arg Glu Pro Phe Glu Ile Lys Thr Tyr Met Phe
65              70                  75                  80 gcc tac aac ctg tac cag acc ctc atg aac ctt tgc att gtg ctg ggc       288
Ala Tyr Asn Leu Tyr Gln Thr Leu Met Asn Leu Cys Ile Val Leu Gly
                85                  90                  95 ttc ctc tac cag gtc cac gct acc ggt atg cga ttc tgg gga tct ggc       336
Phe Leu Tyr Gln Val His Ala Thr Gly Met Arg Phe Trp Gly Ser Gly
            100                 105                 110 gtg gac cga tcg ccc aag ggt ctg gga att ggc ttt ttc atc tat gcc       384
Val Asp Arg Ser Pro Lys Gly Leu Gly Ile Gly Phe Phe Ile Tyr Ala
        115                 120                 125 cat tac cac aac aag tac gtc gag tac ttc gac aca ctc ttc atg gtg       432
His Tyr His Asn Lys Tyr Val Glu Tyr Phe Asp Thr Leu Phe Met Val
    130                 135                 140 ctg cgg aaa aag aac aac cag att tcc ttt ctt cac gtc tac cat cac       480
Leu Arg Lys Lys Asn Asn Gln Ile Ser Phe Leu His Val Tyr His His
145                 150                 155                 160 gct ctg ctc acc tgg gct tgg ttt gcc gtg gtc tac ttc gct cct gga       528
Ala Leu Leu Thr Trp Ala Trp Phe Ala Val Val Tyr Phe Ala Pro Gly
                165                 170                 175 ggt gac ggc tgg ttt gga gcc tgc tac aat tcc tcc att cat gtc ctg       576
Gly Asp Gly Trp Phe Gly Ala Cys Tyr Asn Ser Ser Ile His Val Leu
            180                 185                 190 atg tac tct tac tat ctg ctt gcc acc ttc ggc atc tcc tgt ccc tgg       624
Met Tyr Ser Tyr Tyr Leu Leu Ala Thr Phe Gly Ile Ser Cys Pro Trp
        195                 200                 205 aaa aag atc ctc acc cag ctg caa atg gtt cag ttc tgc ttt tgc ttc       672
Lys Lys Ile Leu Thr Gln Leu Gln Met Val Gln Phe Cys Phe Cys Phe
    210                 215                 220 acc cac tcg atc tac gtg tgg att tgc ggt tcc gaa atc tac cct cga       720
Thr His Ser Ile Tyr Val Trp Ile Cys Gly Ser Glu Ile Tyr Pro Arg
225                 230                 235                 240 ccc ttg act gct ctc cag tcc ttc gtg atg gtc aac atg ctg gtt ctc       768
Pro Leu Thr Ala Leu Gln Ser Phe Val Met Val Asn Met Leu Val Leu
                245                 250                 255 ttt ggc aac ttc tac gtc aag cag tat tct cag aag aat gga aag ccc       816
Phe Gly Asn Phe Tyr Val Lys Gln Tyr Ser Gln Lys Asn Gly Lys Pro
            260                 265                 270 gag aac ggt gcc act cct gag aac ggt gcc aag cct cag ccc tgc gag       864
Glu Asn Gly Ala Thr Pro Glu Asn Gly Ala Lys Pro Gln Pro Cys Glu
        275                 280                 285 aac ggc acc gtc gag aag cga gag aac gac act gcc aac gtt cga taa      912
Asn Gly Thr Val Glu Lys Arg Glu Asn Asp Thr Ala Asn Val Arg
    290                 295                 300
```

```
<210> SEQ ID NO 51
<211> LENGTH: 303
<212> TYPE: PRT
<213> ORGANISM: Euglena gracilis

<400> SEQUENCE: 51
```

| | | | | | | | | | | | | | | | |
|---|---|---|---|---|---|---|---|---|---|---|---|---|---|---|---|
| Met | Ala | Asp | Ser | Pro | Val | Ile | Asn | Leu | Ser | Thr | Met | Trp | Lys | Pro | Leu |
| 1 | | | | 5 | | | | | 10 | | | | | 15 | |
| Ser | Leu | Met | Ala | Leu | Asp | Leu | Ala | Val | Leu | Gly | His | Val | Trp | Lys | Gln |

```
                    20                  25                  30
Ala Gln Gln Glu Gly Ser Ile Ser Ala Tyr Ala Asp Ser Val Trp Thr
                35                  40                  45

Pro Leu Ile Met Ser Gly Leu Tyr Leu Ser Met Ile Phe Val Gly Cys
    50                  55                  60

Arg Trp Met Lys Asn Arg Glu Pro Phe Glu Ile Lys Thr Tyr Met Phe
65                  70                  75                  80

Ala Tyr Asn Leu Tyr Gln Thr Leu Met Asn Leu Cys Ile Val Leu Gly
                85                  90                  95

Phe Leu Tyr Gln Val His Ala Thr Gly Met Arg Phe Trp Gly Ser Gly
            100                 105                 110

Val Asp Arg Ser Pro Lys Gly Leu Gly Ile Gly Phe Ile Tyr Ala
            115                 120                 125

His Tyr His Asn Lys Tyr Val Glu Tyr Phe Asp Thr Leu Phe Met Val
        130                 135                 140

Leu Arg Lys Lys Asn Asn Gln Ile Ser Phe Leu His Val Tyr His His
145                 150                 155                 160

Ala Leu Leu Thr Trp Ala Trp Phe Ala Val Val Tyr Phe Ala Pro Gly
                165                 170                 175

Gly Asp Gly Trp Phe Gly Ala Cys Tyr Asn Ser Ser Ile His Val Leu
            180                 185                 190

Met Tyr Ser Tyr Tyr Leu Leu Ala Thr Phe Gly Ile Ser Cys Pro Trp
        195                 200                 205

Lys Lys Ile Leu Thr Gln Leu Gln Met Val Gln Phe Cys Phe Cys Phe
210                 215                 220

Thr His Ser Ile Tyr Val Trp Ile Cys Gly Ser Glu Ile Tyr Pro Arg
225                 230                 235                 240

Pro Leu Thr Ala Leu Gln Ser Phe Val Met Val Asn Met Leu Val Leu
                245                 250                 255

Phe Gly Asn Phe Tyr Val Lys Gln Tyr Ser Gln Lys Asn Gly Lys Pro
            260                 265                 270

Glu Asn Gly Ala Thr Pro Glu Asn Gly Ala Lys Pro Gln Pro Cys Glu
        275                 280                 285

Asn Gly Thr Val Glu Lys Arg Glu Asn Asp Thr Ala Asn Val Arg
    290                 295                 300

<210> SEQ ID NO 52
<211> LENGTH: 1644
<212> TYPE: DNA
<213> ORGANISM: Euglena anabaena
<220> FEATURE:
<221> NAME/KEY: CDS
<222> LOCATION: (1)..(1644)
<223> OTHER INFORMATION: synthetic truncated delta-4 desaturase
      (codon-optimized for Yarrowia lipolytica)

<400> SEQUENCE: 52 atg gcc aag gtc aaa ccc ggt gga cct ggc aag ccc tcg gag atc gct      48
Met Ala Lys Val Lys Pro Gly Gly Pro Gly Lys Pro Ser Glu Ile Ala
1               5                   10                  15 tct ctt cca cct ccc att cga cct gtt ggc aac cca cct gca gcc tat      96
Ser Leu Pro Pro Pro Ile Arg Pro Val Gly Asn Pro Pro Ala Ala Tyr
                20                  25                  30 tac gac gct ctg gcc acc tcc ggt act gga cag gac cga aag ttt acc     144
Tyr Asp Ala Leu Ala Thr Ser Gly Thr Gly Gln Asp Arg Lys Phe Thr
            35                  40                  45 atg cga gag gtc gct cga cac att gtt ccc acc gat ggc tgg ttg gcc     192
```

```
Met Arg Glu Val Ala Arg His Ile Val Pro Thr Asp Gly Trp Leu Ala
 50                  55                  60 tgt cac gac ggt gtg tac gac atc acc gag ttc att ggc aag cat ccc       240
Cys His Asp Gly Val Tyr Asp Ile Thr Glu Phe Ile Gly Lys His Pro
 65                  70                  75                  80 ggt gga gat gtt atc tct ctc ggt ctc gga cga gac tcc act att ctg       288
Gly Gly Asp Val Ile Ser Leu Gly Leu Gly Arg Asp Ser Thr Ile Leu
                     85                  90                  95 gtc gaa tcg tac cat cct gca gga cga ccc gac aag gtt atg gag aag       336
Val Glu Ser Tyr His Pro Ala Gly Arg Pro Asp Lys Val Met Glu Lys
                100                 105                 110 tac cga atc ggt aca ctt cag gat cac aga acc ttc tac gac tgg cag       384
Tyr Arg Ile Gly Thr Leu Gln Asp His Arg Thr Phe Tyr Asp Trp Gln
            115                 120                 125 gcc tcc gct ttc tac gcc gag ctc aag cag cga gtg gtt cag act ctc       432
Ala Ser Ala Phe Tyr Ala Glu Leu Lys Gln Arg Val Val Gln Thr Leu
            130                 135                 140 aag gag gct gga caa cct cga cgt ggt ggc ctg tct gtc aag gca gcc       480
Lys Glu Ala Gly Gln Pro Arg Arg Gly Gly Leu Ser Val Lys Ala Ala
145                 150                 155                 160 ctt gtt atg gct gcc ttt gct gcc tcg ttc tac ctc atg gtg aca cag       528
Leu Val Met Ala Ala Phe Ala Ala Ser Phe Tyr Leu Met Val Thr Gln
                165                 170                 175 gga tcc ttc ttt tgg gct gcc gtc tgg ggt ctg gca ggc tct cac att       576
Gly Ser Phe Phe Trp Ala Ala Val Trp Gly Leu Ala Gly Ser His Ile
            180                 185                 190 gga ctc agc atc cag cac gac ggc aat cat ggt gct ttc tcc aag tct       624
Gly Leu Ser Ile Gln His Asp Gly Asn His Gly Ala Phe Ser Lys Ser
            195                 200                 205 gga cga ctc aac cgt ctt gct ggc tgg ggt atg gac gtt atc gga gcc       672
Gly Arg Leu Asn Arg Leu Ala Gly Trp Gly Met Asp Val Ile Gly Ala
        210                 215                 220 tcc tcg act gcc tgg gag tac caa cac gtc att ggt cat cac cag tac       720
Ser Ser Thr Ala Trp Glu Tyr Gln His Val Ile Gly His His Gln Tyr
225                 230                 235                 240 acc aac ctg gtg tcc gat ccc gag ttt gct ctt ccc gag aac gat cca       768
Thr Asn Leu Val Ser Asp Pro Glu Phe Ala Leu Pro Glu Asn Asp Pro
                245                 250                 255 gac gtt ttc gga acc tat ccc ctc atg cgg atg cat ccg gac act cct       816
Asp Val Phe Gly Thr Tyr Pro Leu Met Arg Met His Pro Asp Thr Pro
            260                 265                 270 tgg aaa ccc cac cat cag ctg caa cac gtg tac gcc ttt ccg ttg ttc       864
Trp Lys Pro His His Gln Leu Gln His Val Tyr Ala Phe Pro Leu Phe
            275                 280                 285 gct ctc atg acc atc agc aag gtc att atc tcc gat ttc acg ttt tgt       912
Ala Leu Met Thr Ile Ser Lys Val Ile Ile Ser Asp Phe Thr Phe Cys
        290                 295                 300 ctt gcc aag cga cgt ggt ccc atc gac ttc tct gcc aga ctc gtt ccc       960
Leu Ala Lys Arg Arg Gly Pro Ile Asp Phe Ser Ala Arg Leu Val Pro
305                 310                 315                 320 ctc gag ggt cag atg ctg ttc tgg ggt gca aag atc atg ggc ttt ctc      1008
Leu Glu Gly Gln Met Leu Phe Trp Gly Ala Lys Ile Met Gly Phe Leu
                325                 330                 335 atg cag att gtg ctt ccc tgc tac ctg cat ggc atc gct cac gga ttg      1056
Met Gln Ile Val Leu Pro Cys Tyr Leu His Gly Ile Ala His Gly Leu
            340                 345                 350 gcc ctc ttc att aca gct cat ctg gtt tct ggc gag tac ctt gcc gtc      1104
Ala Leu Phe Ile Thr Ala His Leu Val Ser Gly Glu Tyr Leu Ala Val
            355                 360                 365
```

```
tgt ttc att atc aac cac att tcc gag tcg tgc gac tac ctc aat ccc     1152
Cys Phe Ile Ile Asn His Ile Ser Glu Ser Cys Asp Tyr Leu Asn Pro
        370                 375                 380 tct tcc gtt atc gct gcc cga cgg acc gaa atg ctc aag cag gcc gag     1200
Ser Ser Val Ile Ala Ala Arg Arg Thr Glu Met Leu Lys Gln Ala Glu
385                 390                 395                 400 cag gaa gcc aag gcg aaa cag aag cac ccc act cca cct ccc aac gac     1248
Gln Glu Ala Lys Ala Lys Gln Lys His Pro Thr Pro Pro Pro Asn Asp
                405                 410                 415 tgg gct gcc tcc caa gtt ctg tgt tgc gtc aac tgg cga tct ggt ggc     1296
Trp Ala Ala Ser Gln Val Leu Cys Cys Val Asn Trp Arg Ser Gly Gly
            420                 425                 430 tac ttt tca aac cac ctt tct ggt gga ctc aac cac cag atc gag cat     1344
Tyr Phe Ser Asn His Leu Ser Gly Gly Leu Asn His Gln Ile Glu His
        435                 440                 445 cac ctg ttt ccc agc att tct cac gcc aac tat ccc acc att gct cct     1392
His Leu Phe Pro Ser Ile Ser His Ala Asn Tyr Pro Thr Ile Ala Pro
450                 455                 460 gtt gtc aag ggc gtg tgc gag gaa tac ggt ctt ccc tac aag aac tac     1440
Val Val Lys Gly Val Cys Glu Glu Tyr Gly Leu Pro Tyr Lys Asn Tyr
465                 470                 475                 480 tct cag ttt tcc gat gct ctg tac gga atg gtc gag cac ttg cga gct     1488
Ser Gln Phe Ser Asp Ala Leu Tyr Gly Met Val Glu His Leu Arg Ala
                485                 490                 495 atg ggc acc aaa cct gca gac aac gac aag ctt gct ccc act gca ggt     1536
Met Gly Thr Lys Pro Ala Asp Asn Asp Lys Leu Ala Pro Thr Ala Gly
            500                 505                 510 tcc ctg gag gat gtt tgt cct gtg ctc tct gct gcc gtt gct gcc caa     1584
Ser Leu Glu Asp Val Cys Pro Val Leu Ser Ala Ala Val Ala Ala Gln
        515                 520                 525 ccc gac ggc tcc acc gac gga tct gct gcc ggt tgt cct gct gtc gcc     1632
Pro Asp Gly Ser Thr Asp Gly Ser Ala Ala Gly Cys Pro Ala Val Ala
530                 535                 540 act ctg gct taa                                                     1644
Thr Leu Ala
545

<210> SEQ ID NO 53
<211> LENGTH: 547
<212> TYPE: PRT
<213> ORGANISM: Euglena anabaena

<400> SEQUENCE: 53

Met Ala Lys Val Lys Pro Gly Gly Pro Gly Lys Pro Ser Glu Ile Ala
1               5                   10                  15

Ser Leu Pro Pro Pro Ile Arg Pro Val Gly Asn Pro Ala Ala Tyr
            20                  25                  30

Tyr Asp Ala Leu Ala Thr Ser Gly Thr Gly Gln Asp Arg Lys Phe Thr
        35                  40                  45

Met Arg Glu Val Ala Arg His Ile Val Pro Thr Asp Gly Trp Leu Ala
    50                  55                  60

Cys His Asp Gly Val Tyr Asp Ile Thr Glu Phe Ile Gly Lys His Pro
65                  70                  75                  80

Gly Gly Asp Val Ile Ser Leu Gly Leu Gly Arg Asp Ser Thr Ile Leu
                85                  90                  95

Val Glu Ser Tyr His Pro Ala Gly Arg Pro Asp Lys Val Met Glu Lys
            100                 105                 110

Tyr Arg Ile Gly Thr Leu Gln Asp His Arg Thr Phe Tyr Asp Trp Gln
        115                 120                 125
```

-continued

```
Ala Ser Ala Phe Tyr Ala Glu Leu Lys Gln Arg Val Gln Thr Leu
        130                 135                 140
Lys Glu Ala Gly Gln Pro Arg Arg Gly Gly Leu Ser Val Lys Ala Ala
145                 150                 155                 160
Leu Val Met Ala Ala Phe Ala Ala Ser Phe Tyr Leu Met Val Thr Gln
                165                 170                 175
Gly Ser Phe Phe Trp Ala Val Trp Gly Leu Ala Gly Ser His Ile
                180                 185                 190
Gly Leu Ser Ile Gln His Asp Gly Asn His Gly Ala Phe Ser Lys Ser
                195                 200                 205
Gly Arg Leu Asn Arg Leu Ala Gly Trp Gly Met Asp Val Ile Gly Ala
            210                 215                 220
Ser Ser Thr Ala Trp Glu Tyr Gln His Val Ile Gly His His Gln Tyr
225                 230                 235                 240
Thr Asn Leu Val Ser Asp Pro Glu Phe Ala Leu Pro Glu Asn Asp Pro
                245                 250                 255
Asp Val Phe Gly Thr Tyr Pro Leu Met Arg Met His Pro Asp Thr Pro
                260                 265                 270
Trp Lys Pro His His Gln Leu Gln His Val Tyr Ala Phe Pro Leu Phe
            275                 280                 285
Ala Leu Met Thr Ile Ser Lys Val Ile Ile Ser Asp Phe Thr Phe Cys
        290                 295                 300
Leu Ala Lys Arg Arg Gly Pro Ile Asp Phe Ser Ala Arg Leu Val Pro
305                 310                 315                 320
Leu Glu Gly Gln Met Leu Phe Trp Gly Ala Lys Ile Met Gly Phe Leu
                325                 330                 335
Met Gln Ile Val Leu Pro Cys Tyr Leu His Gly Ile Ala His Gly Leu
                340                 345                 350
Ala Leu Phe Ile Thr Ala His Leu Val Ser Gly Glu Tyr Leu Ala Val
            355                 360                 365
Cys Phe Ile Ile Asn His Ile Ser Glu Ser Cys Asp Tyr Leu Asn Pro
        370                 375                 380
Ser Ser Val Ile Ala Ala Arg Arg Thr Glu Met Leu Lys Gln Ala Glu
385                 390                 395                 400
Gln Glu Ala Lys Ala Lys Gln Lys His Pro Thr Pro Pro Asn Asp
                405                 410                 415
Trp Ala Ala Ser Gln Val Leu Cys Cys Val Asn Trp Arg Ser Gly Gly
                420                 425                 430
Tyr Phe Ser Asn His Leu Ser Gly Gly Leu Asn His Gln Ile Glu His
            435                 440                 445
His Leu Phe Pro Ser Ile Ser His Ala Asn Tyr Pro Thr Ile Ala Pro
        450                 455                 460
Val Val Lys Gly Val Cys Glu Glu Tyr Gly Leu Pro Tyr Lys Asn Tyr
465                 470                 475                 480
Ser Gln Phe Ser Asp Ala Leu Tyr Gly Met Val Glu His Leu Arg Ala
                485                 490                 495
Met Gly Thr Lys Pro Ala Asp Asn Asp Lys Leu Ala Pro Thr Ala Gly
                500                 505                 510
Ser Leu Glu Asp Val Cys Pro Val Leu Ser Ala Ala Val Ala Ala Gln
            515                 520                 525
Pro Asp Gly Ser Thr Asp Gly Ser Ala Ala Gly Cys Pro Ala Val Ala
        530                 535                 540
```

Thr Leu Ala
545

<210> SEQ ID NO 54
<211> LENGTH: 1644
<212> TYPE: DNA
<213> ORGANISM: Euglena anabaena
<220> FEATURE:
<221> NAME/KEY: CDS
<222> LOCATION: (1)..(1644)
<223> OTHER INFORMATION: synthetic truncated delta-4 desaturase
      (codon-optimized for Yarrowia lipolytica)

<400> SEQUENCE: 54

```
atg gcc aag gtc aag cct gga ggt cct ggc aaa ccc tcc gag att gcc      48
Met Ala Lys Val Lys Pro Gly Gly Pro Gly Lys Pro Ser Glu Ile Ala
1               5                   10                  15 tcg ctg cct cca ccc atc cga ccc gtg gga aac cct cca gct gcc tac      96
Ser Leu Pro Pro Pro Ile Arg Pro Val Gly Asn Pro Pro Ala Ala Tyr
            20                  25                  30 tat gac gcc ctc gct act tct gga acc ggt cag gac cga aag ttc acc     144
Tyr Asp Ala Leu Ala Thr Ser Gly Thr Gly Gln Asp Arg Lys Phe Thr
        35                  40                  45 atg cga gaa gtc gca cga cac atc gtt ccc acc gat ggt tgg ctg gcc     192
Met Arg Glu Val Ala Arg His Ile Val Pro Thr Asp Gly Trp Leu Ala
    50                  55                  60 tgt cac gac ggc gtt tac gac att aca gag ttt atc gga aag cat ccc     240
Cys His Asp Gly Val Tyr Asp Ile Thr Glu Phe Ile Gly Lys His Pro
65                  70                  75                  80 ggt ggc gat gtc att tcc ctt gga ctg ggt cga gac tct acc att ctc     288
Gly Gly Asp Val Ile Ser Leu Gly Leu Gly Arg Asp Ser Thr Ile Leu
                85                  90                  95 gtg gag tcc tac cac cct gct ggt cga ccc gac aag gtt atg gag aag     336
Val Glu Ser Tyr His Pro Ala Gly Arg Pro Asp Lys Val Met Glu Lys
            100                 105                 110 tac aga atc ggc act ctt cag gat cat cga act ttc tac gac tgg cag     384
Tyr Arg Ile Gly Thr Leu Gln Asp His Arg Thr Phe Tyr Asp Trp Gln
        115                 120                 125 gct tct gcc ttt tac gcg gaa ctc aag cag cga gtc gtg caa acc ctc     432
Ala Ser Ala Phe Tyr Ala Glu Leu Lys Gln Arg Val Val Gln Thr Leu
    130                 135                 140 aag gag gct ggt cag ccc aga cga ggc gga ctg tca gtc aag gct gca     480
Lys Glu Ala Gly Gln Pro Arg Arg Gly Gly Leu Ser Val Lys Ala Ala
145                 150                 155                 160 ctg gtt atg gct gcg ttt gcc gct tcc ttc tat ctc atg gtc act cag     528
Leu Val Met Ala Ala Phe Ala Ala Ser Phe Tyr Leu Met Val Thr Gln
                165                 170                 175 ggc tcg ttt ttc tgg gca gct gtg tgg ggt ctt gct gga agt cac atc     576
Gly Ser Phe Phe Trp Ala Ala Val Trp Gly Leu Ala Gly Ser His Ile
            180                 185                 190 ggc ctc tcc att cag cac gac gga aac cac ggt gcc ttt tcg aag tct     624
Gly Leu Ser Ile Gln His Asp Gly Asn His Gly Ala Phe Ser Lys Ser
        195                 200                 205 ggc cgt ctc aat cga ctg gcc gga tgg ggt atg gac gtc att ggt gct     672
Gly Arg Leu Asn Arg Leu Ala Gly Trp Gly Met Asp Val Ile Gly Ala
    210                 215                 220 tcg tcc aca gcc tgg gag tac cag cat gtc att ggc cac cat caa tac     720
Ser Ser Thr Ala Trp Glu Tyr Gln His Val Ile Gly His His Gln Tyr
225                 230                 235                 240 acc aac ctt gtt tcc gat ccc gaa ttt gcc ctt cca gag aac gat ccc     768
Thr Asn Leu Val Ser Asp Pro Glu Phe Ala Leu Pro Glu Asn Asp Pro
                245                 250                 255
```

```
gac gtg ttc gga acc tac cct ctc atg cga atg cat ccc gac act ccg      816
Asp Val Phe Gly Thr Tyr Pro Leu Met Arg Met His Pro Asp Thr Pro
        260                 265                 270 tgg aaa cct cat cac caa ctg cag cac gtc tat gcc ttt ccc ctg ttc      864
Trp Lys Pro His His Gln Leu Gln His Val Tyr Ala Phe Pro Leu Phe
        275                 280                 285 gcc ctc atg act atc tcc aag gtt atc att agc gat ttc acc ttc tgc      912
Ala Leu Met Thr Ile Ser Lys Val Ile Ile Ser Asp Phe Thr Phe Cys
        290                 295                 300 ctc gcc aag cgt cga ggt ccg atc gac ttt tct gcc cga ctt gtg cct      960
Leu Ala Lys Arg Arg Gly Pro Ile Asp Phe Ser Ala Arg Leu Val Pro
305                 310                 315                 320 ctc gag ggc cag atg ctt ttc tgg gga gca aag atc atg ggc ttt ctc     1008
Leu Glu Gly Gln Met Leu Phe Trp Gly Ala Lys Ile Met Gly Phe Leu
                325                 330                 335 atg cag atc gtt ctt ccc tgt tac ctg cac ggc att gca cat ggt ttg     1056
Met Gln Ile Val Leu Pro Cys Tyr Leu His Gly Ile Ala His Gly Leu
                    340                 345                 350 gct ctg ttc atc act gcc cac ctc gtt tca ggc gag tac ctg gca gtt     1104
Ala Leu Phe Ile Thr Ala His Leu Val Ser Gly Glu Tyr Leu Ala Val
                355                 360                 365 tgc ttc att atc aac cac att tcc gag tct tgt gac tac ctc aac ccc     1152
Cys Phe Ile Ile Asn His Ile Ser Glu Ser Cys Asp Tyr Leu Asn Pro
        370                 375                 380 tcc tct gtc atc gct gcc aga cga acg gag atg ctc aag caa gcc gaa     1200
Ser Ser Val Ile Ala Ala Arg Arg Thr Glu Met Leu Lys Gln Ala Glu
385                 390                 395                 400 cag gag gcc aag gcg aaa cag aag cat ccc aca cct cca ccc aac gac     1248
Gln Glu Ala Lys Ala Lys Gln Lys His Pro Thr Pro Pro Pro Asn Asp
                405                 410                 415 tgg gca gct tcc cag gtt ctt tgc tgt gtc aac tgg cga tct ggc ggt     1296
Trp Ala Ala Ser Gln Val Leu Cys Cys Val Asn Trp Arg Ser Gly Gly
                    420                 425                 430 tac ttc tcg aac cac ttg tca gga ggt ctc aat cat cag atc gag cac     1344
Tyr Phe Ser Asn His Leu Ser Gly Gly Leu Asn His Gln Ile Glu His
                435                 440                 445 cat ctg ttt cct tct atc agc cac gcc aac tat ccc acc att gct ccc     1392
His Leu Phe Pro Ser Ile Ser His Ala Asn Tyr Pro Thr Ile Ala Pro
        450                 455                 460 gtt gtc aag ggt gtg tgc gaa gag tac gga ctt ccc tac aag aac tac     1440
Val Val Lys Gly Val Cys Glu Glu Tyr Gly Leu Pro Tyr Lys Asn Tyr
465                 470                 475                 480 tct cag ttc tcc gat gcc ctc tac ggc atg gtg gag cac ctg cga gca     1488
Ser Gln Phe Ser Asp Ala Leu Tyr Gly Met Val Glu His Leu Arg Ala
                    485                 490                 495 atg ggt acc aag cct gcg gac aac gac aaa ctt gct cct act gct gga     1536
Met Gly Thr Lys Pro Ala Asp Asn Asp Lys Leu Ala Pro Thr Ala Gly
                500                 505                 510 tct ttg gag gat gtc tgc cct gtt ctg tct gct gcc gtg gct gcc caa     1584
Ser Leu Glu Asp Val Cys Pro Val Leu Ser Ala Ala Val Ala Ala Gln
                    515                 520                 525 ccc gac ggt tct acc gac ggc tct gcc gct gga tgt cct gcc gtt gct     1632
Pro Asp Gly Ser Thr Asp Gly Ser Ala Ala Gly Cys Pro Ala Val Ala
530                 535                 540 act ctc gcc taa                                                     1644
Thr Leu Ala
545

<210> SEQ ID NO 55
```

<211> LENGTH: 547
<212> TYPE: PRT
<213> ORGANISM: Euglena anabaena

<400> SEQUENCE: 55

```
Met Ala Lys Val Lys Pro Gly Gly Pro Gly Lys Pro Ser Glu Ile Ala
1               5                   10                  15

Ser Leu Pro Pro Pro Ile Arg Pro Val Gly Asn Pro Pro Ala Ala Tyr
            20                  25                  30

Tyr Asp Ala Leu Ala Thr Ser Gly Thr Gly Gln Asp Arg Lys Phe Thr
        35                  40                  45

Met Arg Glu Val Ala Arg His Ile Val Pro Thr Asp Gly Trp Leu Ala
    50                  55                  60

Cys His Asp Gly Val Tyr Asp Ile Thr Glu Phe Ile Gly Lys His Pro
65                  70                  75                  80

Gly Gly Asp Val Ile Ser Leu Gly Leu Gly Arg Asp Ser Thr Ile Leu
                85                  90                  95

Val Glu Ser Tyr His Pro Ala Gly Arg Pro Asp Lys Val Met Glu Lys
            100                 105                 110

Tyr Arg Ile Gly Thr Leu Gln Asp His Arg Thr Phe Tyr Asp Trp Gln
        115                 120                 125

Ala Ser Ala Phe Tyr Ala Glu Leu Lys Gln Arg Val Val Gln Thr Leu
    130                 135                 140

Lys Glu Ala Gly Gln Pro Arg Arg Gly Gly Leu Ser Val Lys Ala Ala
145                 150                 155                 160

Leu Val Met Ala Ala Phe Ala Ala Ser Phe Tyr Leu Met Val Thr Gln
                165                 170                 175

Gly Ser Phe Phe Trp Ala Ala Val Trp Gly Leu Ala Gly Ser His Ile
            180                 185                 190

Gly Leu Ser Ile Gln His Asp Gly Asn His Gly Ala Phe Ser Lys Ser
        195                 200                 205

Gly Arg Leu Asn Arg Leu Ala Gly Trp Gly Met Asp Val Ile Gly Ala
    210                 215                 220

Ser Ser Thr Ala Trp Glu Tyr Gln His Val Ile Gly His His Gln Tyr
225                 230                 235                 240

Thr Asn Leu Val Ser Asp Pro Glu Phe Ala Leu Pro Glu Asn Asp Pro
                245                 250                 255

Asp Val Phe Gly Thr Tyr Pro Leu Met Arg Met His Pro Asp Thr Pro
            260                 265                 270

Trp Lys Pro His His Gln Leu Gln His Val Tyr Ala Phe Pro Leu Phe
        275                 280                 285

Ala Leu Met Thr Ile Ser Lys Val Ile Ser Asp Phe Thr Phe Cys
    290                 295                 300

Leu Ala Lys Arg Arg Gly Pro Ile Asp Phe Ser Ala Arg Leu Val Pro
305                 310                 315                 320

Leu Glu Gly Gln Met Leu Phe Trp Gly Ala Lys Ile Met Gly Phe Leu
                325                 330                 335

Met Gln Ile Val Leu Pro Cys Tyr Leu His Gly Ile Ala His Gly Leu
            340                 345                 350

Ala Leu Phe Ile Thr Ala His Leu Val Ser Gly Glu Tyr Leu Ala Val
        355                 360                 365

Cys Phe Ile Ile Asn His Ile Ser Glu Ser Cys Asp Tyr Leu Asn Pro
    370                 375                 380

Ser Ser Val Ile Ala Ala Arg Arg Thr Glu Met Leu Lys Gln Ala Glu
```

```
                385                 390                 395                 400
Gln Glu Ala Lys Ala Lys Gln Lys His Pro Thr Pro Pro Asn Asp
                405                 410                 415

Trp Ala Ala Ser Gln Val Leu Cys Cys Val Asn Trp Arg Ser Gly Gly
            420                 425                 430

Tyr Phe Ser Asn His Leu Ser Gly Gly Leu Asn His Gln Ile Glu His
        435                 440                 445

His Leu Phe Pro Ser Ile Ser His Ala Asn Tyr Pro Thr Ile Ala Pro
    450                 455                 460

Val Val Lys Gly Val Cys Glu Glu Tyr Gly Leu Pro Tyr Lys Asn Tyr
465                 470                 475                 480

Ser Gln Phe Ser Asp Ala Leu Tyr Gly Met Val Glu His Leu Arg Ala
            485                 490                 495

Met Gly Thr Lys Pro Ala Asp Asn Asp Lys Leu Ala Pro Thr Ala Gly
        500                 505                 510

Ser Leu Glu Asp Val Cys Pro Val Leu Ser Ala Val Ala Ala Gln
    515                 520                 525

Pro Asp Gly Ser Thr Asp Gly Ser Ala Ala Gly Cys Pro Ala Val Ala
    530                 535                 540

Thr Leu Ala
545

<210> SEQ ID NO 56
<211> LENGTH: 4313
<212> TYPE: DNA
<213> ORGANISM: Artificial Sequence
<220> FEATURE:
<223> OTHER INFORMATION: Plasmid pZKUM

<400> SEQUENCE: 56
taatcgagct tggcgtaatc atggtcatag ctgtttcctg tgtgaaattg ttatccgctc      60
acaattccac acaacatacg agccggaagc ataaagtgta aagcctgggg tgcctaatga     120
gtgagctaac tcacattaat tgcgttgcgc tcactgcccg ctttccagtc gggaaacctg     180
tcgtgccagc tgcattaatg aatcggccaa cgcgcgggga gaggcggttt gcgtattggg     240
cgctcttccg cttcctcgct cactgactcg ctgcgctcgg tcgttcggct gcggcgagcg     300
gtatcagctc actcaaaggc ggtaatacgg ttatccacag aatcagggga taacgcagga     360
aagaacatgt gagcaaaagg ccagcaaaag gccaggaacc gtaaaaaggc cgcgttgctg     420
gcgtttttcc ataggctccg cccccctgac gagcatcaca aaaatcgacg ctcaagtcag     480
aggtggcgaa acccgacagg actataaaga taccaggcgt ttccccctgg aagctccctc     540
gtgcgctctc ctgttccgac cctgccgctt accggatacc tgtccgcctt ctcccttcg     600 ggaagcgtgg cgctttctca tagctcacgc tgtaggtatc tcagttcggt gtaggtcgtt     660
cgctccaagc tgggctgtgt gcacgaaccc cccgttcagc ccgaccgctg cgccttatcc     720
ggtaactatc gtcttgagtc caacccggta agacacgact tatcgccact ggcagcagcc     780
actggtaaca ggattagcag agcgaggtat gtaggcggtg ctacagagtt cttgaagtgg     840
tggcctaact acggctacac tagaaggaca gtatttggta tctgcgctct gctgaagcca     900
gttaccttcg gaaaagagt tggtagctct tgatccggca acaaaccac cgctggtagc     960 ggtggttttt ttgtttgcaa gcagcagatt acgcgcagaa aaaaaggatc tcaagaagat    1020
cctttgatct tttctacggg gtctgacgct cagtggaacg aaaactcacg ttaagggatt    1080
ttggtcatga gattatcaaa aaggatcttc acctagatcc ttttaaatta aaaatgaagt    1140
```

```
tttaaatcaa tctaaagtat atatgagtaa acttggtctg acagttacca atgcttaatc    1200
agtgaggcac ctatctcagc gatctgtcta tttcgttcat ccatagttgc ctgactcccc    1260
gtcgtgtaga taactacgat acgggagggc ttaccatctg gccccagtgc tgcaatgata    1320
ccgcgagacc cacgctcacc ggctccagat ttatcagcaa taaaccagcc agccggaagg    1380
gccgagcgca gaagtggtcc tgcaacttta tccgcctcca tccagtctat taattgttgc    1440
cgggaagcta gagtaagtag ttcgccagtt aatagtttgc gcaacgttgt tgccattgct    1500
acaggcatcg tggtgtcacg ctcgtcgttt ggtatggctt cattcagctc cggttcccaa    1560
cgatcaaggc gagttacatg atcccccatg ttgtgcaaaa aagcggttag ctccttcggt    1620
cctccgatcg ttgtcagaag taagttggcc gcagtgttat cactcatggt tatggcagca    1680
ctgcataatt ctcttactgt catgccatcc gtaagatgct tttctgtgac tggtgagtac    1740
tcaaccaagt cattctgaga atagtgtatg cggcgaccga gttgctcttg cccggcgtca    1800
atacgggata ataccgcgcc acatagcaga actttaaaag tgctcatcat tggaaaacgt    1860 tcttcgggc gaaaactctc aaggatctta ccgctgttga gatccagttc gatgtaaccc    1920
actcgtgcac ccaactgatc ttcagcatct tttactttca ccagcgtttc tgggtgagca    1980
aaaacaggaa ggcaaaatgc cgcaaaaaag gaataaggg cgacacggaa atgttgaata    2040
ctcatactct ccttttttca atattattga agcatttatc agggttattg tctcatgagc    2100
ggatacatat ttgaatgtat ttagaaaaat aaacaaatag gggttccgcg cacatttccc    2160
cgaaaagtgc cacctgacgc gccctgtagc ggcgcattaa gcgcggcggg tgtggtggtt    2220
acgcgcagcg tgaccgctac acttgccagc gccctagcgc ccgctccttt cgctttcttc    2280
ccttcctttc tcgccacgtt cgccggcttt ccccgtcaag ctctaaatcg gggctccct    2340 ttagggttcc gatttagtgc tttacggcac ctcgacccca aaaaacttga ttagggtgat    2400
ggttcacgta gtgggccatc gccctgatag acggtttttc gccctttgac gttggagtcc    2460
acgttcttta atagtggact cttgttccaa actggaacaa cactcaaccc tatctcggtc    2520 tattctttg atttataagg gattttgccg atttcggcct attggttaaa aaatgagctg    2580
atttaacaaa aatttaacgc gaattttaac aaaatattaa cgcttacaat ttccattcgc    2640
cattcaggct gcgcaactgt tgggaagggc gatcggtgcg ggcctcttcg ctattacgcc    2700
agctggcgaa aggggggatgt gctgcaaggc gattaagttg ggtaacgcca gggttttccc    2760
agtcacgacg ttgtaaaacg acggccagtg aattgtaata cgactcacta tagggcgaat    2820
tgggtaccgg gccccccctc gaggtcgacg agtatctgtc tgactcgtca ttgccgcctt    2880
tggagtacga ctccaactat gagtgtgctt ggatcacttt gacgatacat tcttcgttgg    2940
aggctgtggg tctgacagct gcgttttcgg cgcggttggc cgacaacaat atcagctgca    3000
acgtcattgc tggctttcat catgatcaca tttttgtcgg caaaggcgac gcccagagag    3060
ccattgacgt tctttctaat ttggaccgat agccgtatag tccagtctat ctataagttc    3120
aactaactcg taactattac cataacatat acttcactgc cccagataag gttccgataa    3180
aaagttctgc agactaaatt tatttcagtc tcctcttcac caccaaaatg ccctcctacg    3240
aagctcgagt gctcaagctc gtggcagcca agaaaaccaa cctgtgtgct tctctggatg    3300
ttaccaccac caaggagctc attgagcttg ccgataaggt cggaccttat gtgtgcatga    3360
tcaaaaccca tatcgacatc attgacgact caccbacgc cggcactgtg ctccccctca    3420
aggaacttgc tcttaagcac ggtttcttcc tgttcgagga cagaaagttc gcagatattg    3480
```

```
gcaacactgt caagcaccag taccggtgtc accgaatcgc cgagtggtcc gatatcacca    3540
acgcccacgg tgtacccgga accggaatcg attgctggcc tgcgagctgg tgcgtacgag    3600
gaaactgtct ctgaacagaa gaaggaggac gtctctgact acgagaactc ccagtacaag    3660
gagttcctag tccccctctcc caacgagaag ctggccagag gtctgctcat gctggccgag    3720
ctgtcttgca agggctctct ggccactggc gagtactcca agcagaccat tgagcttgcc    3780
cgatccgacc ccgagtttgt ggttggcttc attgcccaga accgacctaa gggcgactct    3840
gaggactggc ttattctgac ccccggggtg ggtcttgacg acaagggaga cgctctcgga    3900
cagcagtacc gaactgttga ggatgtcatg tctaccggaa cggatatcat aattgtcggc    3960
cgaggtctgt acggccagaa ccgagatcct attgaggagg ccaagcgata ccagaaggct    4020
ggctgggagg cttaccagaa gattaactgt tagaggttag actatggata tgtaatttaa    4080
ctgtgtatat agagagcgtg caagtatgga gcgcttgttc agcttgtatg atggtcagac    4140
gacctgtctg atcgagtatg tatgatactg cacaacctgt gtatccgcat gatctgtcca    4200
atggggcatg ttgttgtgtt tctcgatacg gagatgctgg gtacagtgct aatacgttga    4260
actacttata cttatatgag gctcgaagaa agctgacttg tgtatgactt aat          4313

<210> SEQ ID NO 57
<211> LENGTH: 17088
<212> TYPE: DNA
<213> ORGANISM: Artificial Sequence
<220> FEATURE:
<223> OTHER INFORMATION: Plasmid pZKL3-4GER44

<400> SEQUENCE: 57
aattctctct cttgagcttt tccataacaa gttcttctgc ctccaggaag tccatgggtg      60
gtttgatcat ggttttggtg tagtggtagt gcagtggtgg tattgtgact ggggatgtag     120
ttgagaataa gtcatacaca agtcagcttt cttcgagcct catataagta taagtagttc     180
aacgtattag cactgtaccc agcatctccg tatcgagaaa cacaacaaca tgccccattg     240
gacagatcat gcggatacac aggttgtgca gtatcataca tactcgatca gacaggtcgt     300
ctgaccatca tacaagctga acaagcgctc catacttgca cgctctctat atacacagtt     360
aaattacata tccatagtct aacctctaac agttaatctt ctggtaagcc tcccagccag     420
ccttctggta tcgcttggcc tcctcaatag gatctcggtt ctggccgtac agacctcggc     480
cgacaattat gatatccgtt ccggtagaca tgacatcctc aacagttcgg tactgctgtc     540
cgagagcgtc tcccttgtcg tcaagaccca ccccggggggt cagaataagc cagtcctcag     600
agtcgccctt aggtcggttc tgggcaatga agccaaccac aaactcgggg tcggatcggg     660
caagctcaat ggtctgcttg gagtactcgc cagtggccag agagcccttg caagacagct     720
cggccagcat gagcagacct ctggccagct tctcgttggg agaggggact aggaactcct     780
tgtactggga gttctcgtag tcagagacgt cctccttctt ctgttcagag acagtttcct     840
cggcaccagc tcgcaggcca gcaatgattc cggttccggg tacaccgtgg gcgttggtga     900
tatcggacca ctcggcgatt cggtgacacc ggtactggtg cttgacagtg ttgccaatat     960
ctgcgaactt tctgtcctcg aacaggaaga aaccgtgctt aagagcaagt tccttgaggg    1020
ggagcacagt gccggcgtag gtgaagtcgt caatgatgtc gatatgggtt ttgatcatgc    1080
acacataagg tccgaccttg tcggcaagct caatgagctc cttggtggtg gtaacatcca    1140
gagaagcaca caggttggtt ttcttggctg ccacagcgtt gagcactcga gcggcaaagg    1200
cggacttgtg gacgttagct cgagcttcgt aggagggcat tttggtggtg aagaggagac    1260
```

-continued

```
tgaaataaat ttagtctgca gaacttttta tcggaacctt atctggggca gtgaagtata   1320
tgttatggta atagttacga gttagttgaa cttatagata gactggacta tacggctatc   1380
ggtccaaatt agaagaacg tcaatggctc tctgggcgtc gcctttgccg acaaaaatgt    1440
gatcatgatg aaagccagca atgacgttgc agctgatatt gttgtcggcc aaccgcgccg   1500
aaaacgcagc tgtcagaccc acagcctcca acgaagaatg tatcgtcaaa gtgatccaag   1560
cacactcata gttggagtcg tactccaaag gcggcaatga cgagtcagac agatactcgt   1620 cgacctttc cttgggaacc accaccgtca gcccttctga ctcacgtatt gtagccaccg    1680
acacaggcaa cagtccgtgg atagcagaat atgtcttgtc ggtccatttc tcaccaactt   1740
taggcgtcaa gtgaatgttg cagaagaagt atgtgccttc attgagaatc ggtgttgctg   1800
atttcaataa agtcttgaga tcagtttggc cagtcatgtt gtgggggggta attggattga  1860 gttatcgcct acagtctgta caggtatact cgctgcccac tttatacttt ttgattccgc   1920
tgcacttgaa gcaatgtcgt ttaccaaaag tgagaatgct ccacagaaca caccccaggg   1980
tatggttgag caaaaaataa acactccgat acggggaatc gaaccccggt ctccacggtt   2040
ctcaagaagt attcttgatg agagcgtatc gatggttaat gctgctgtgt gctgtgtgtg   2100
tgtgttgttt ggcgctcatt gttgcgttat gcagcgtaca ccacaatatt ggaagcttat   2160
tagcctttct attttttcgt ttgcaaggct taacaacatt gctgtggaga gggatgggga   2220
tatggaggcc gctggaggga gtcggagagg cgttttggag cggcttggcc tggcgcccag   2280
ctcgcgaaac gcacctagga ccctttggca cgccgaaatg tgccactttt cagtctagta   2340
acgccttacc tacgtcattc catgcgtgca tgtttgcgcc tttttcccct gcccttgat    2400 cgccacacag tacagtgcac tgtacagtgg aggttttggg ggggtcttag atgggagcta   2460
aaagcggcct agcggtacac tagtgggatt gtatggagtg gcatggagcc taggtggagc   2520
ctgacaggac gcacgaccgg ctagcccgtg acagacgatg ggtggctcct gttgtccacc   2580
gcgtacaaat gtttgggcca agtcttgtc agccttgctt gcgaacctaa ttcccaattt    2640
tgtcacttcg caccccatt gatcgagccc taacccctgc ccatcaggca atccaattaa    2700
gctcgcattg tctgccttgt ttagtttggc tcctgcccgt ttcggcgtcc acttgcacaa   2760
acacaaacaa gcattatata taaggctcgt ctctccctcc caaccacact cacttttttg   2820
cccgtcttcc cttgctaaca caaaagtcaa gaacacaaac aaccacccca acccccttac   2880
acacaagaca tatctacagc aatggccatg gctcagtcca ccaaggctgc cgacactgct   2940
gccaccgaca agtctctcga caagaaccga ctcatctccc gagacgagct gcggtctcac   3000
aacgttcccc aggatgcctg ggctgccgtc cacggcagag tcatcaacat taccgagttc   3060
gcccgacggc atcctggtgg cgacatcatt ctgcttgccg caggaaagga tgccaccgtg   3120
ctcttcgaga cttaccatcc tcgaggtgtt cccacctcga tcctcgacaa gctgcaggtc   3180
ggcaagatga aggacggaga acttccctcc tcgttctact cgtgggattc cgactttac    3240 aagaccctgc gagctcgagt ggtcgagcga ttggacaagc tcaacctgcc tcgaagaggt   3300
ggctacgaga tttgggtcaa ggcagtattc ctcctggctg gattctggtt cagcctctac   3360
aagatgtccg tcaacgagac ctactgggct gcctcgctgt ggtccgtgtc tatgggagtc   3420
tttgctgcct tcatcggcac ttgcattcaa cacgatggaa accacggtgc cttctcgacc   3480
agccctgctc tcaacaaggt tgcaggctgg actctggaca tgatcggtgc ttctggctt   3540 acatgggaga ttcagcatat gctcggacac catccctaca ccaacgtcct ggacgtggac   3600
```

```
gaagagaagc gaaaggaagc tggcgacgat tgtcctatgg aggacaagga tcaggagtcc    3660
gacccagatg tcttctcttc gtttcctctc atgcgaatgc acccctacca caaggccgag    3720
tggtaccacc gatatcagca cctgtacgca cccgttctct ttgctttcat gactcttgcc    3780
aaggtgttcc aacaggacat cgaagtcgct accactcagc gactgtacca catcgacgcc    3840
aagtgccgat acaattccat tctcaatgtc cttcggtttt ggtcgatgaa ggtgctctcc    3900
atcggctaca tgctggctgt tccctgctac ttccacggaa tccttggtgg ccttggactg    3960
tttctcatcg gccactttgc ctgtggagag cttctggcaa ccatgttcat tgtcaatcac    4020
gtcatcgagg gtgtgtcctt tggcaaaaag ggagaatctc tcggtctgtc caaggacgtg    4080
gagttcaagc ctacaaccgt ttctggacga actccaatgg agcagacccg tgccgaggcc    4140
aaaaaggctg ccaatggagg caacgtcaag gatgttccct acaacgactg ggctgccgtt    4200
cagtgtcaaa cgagcgtcaa ctggtctcct ggatcgtggt tctggaatca cttctccggt    4260
ggcctctccc accagatcga gcaccatctg tttcccagca tttgtcacac caactacgct    4320
cacatccagg acgttgtcca gaagacttgc gaagagtacg tgttccttta ccagtccgaa    4380
ccctctttgt tctccgccta tggcaagatg ctgtctcatc tcaagtacct cggaaacgag    4440
aaaaaggtcg cttaagcggc cgcatgtaca tacaagatta tttatagaaa tgaatcgcga    4500
tcgaacaaag agtacgagtg tacgagtagg ggatgatgat aaaagtggaa gaagttccgc    4560
atctttggat ttatcaacgt gtaggacgat acttcctgta aaaatgcaat gtctttacca    4620
taggttctgc tgtagatgtt attaactacc attaacatgt ctacttgtac agttgcagac    4680
cagttggagt atagaatggt acacttacca aaaagtgttg atggttgtaa ctacgatata    4740
taaaactgtt gacgggatct gcgtacactg tttaaacaga gtgtgaaaga ctcactatgg    4800
tccgggctta tctcgaccaa tagccaaagt ctggagtttc tgagagaaaa aggcaagata    4860
cgtatgtaac aaagcgacgc atggtacaat aataccggag gcatgtatca tagagagtta    4920
gtggttcgat gatggcactg gtgcctggta tgactttata cggctgacta catatttgtc    4980
ctcagacata caattacagt caagcactta cccttggaca tctgtaggta ccccccggcc    5040
aagacgatct cagcgtgtcg tatgtcggat tggcgtagct ccctcgctcg tcaattggct    5100
cccatctact ttcttctgct tggctacacc cagcatgtct gctatggctc gttttcgtgc    5160
cttatctatc ctcccagtat taccaactct aaatgacatg atgtgattgg gtctacactt    5220
tcatatcaga gataaggagt agcacagttg cataaaaagc ccaactctaa tcagcttctt    5280
cctttcttgt aattagtaca aaggtgatta gcgaaatctg gaagcttagt tggccctaaa    5340
aaaatcaaaa aaagcaaaaa acgaaaaacg aaaaaccaca gttttgagaa cagggaggta    5400
acgaaggatc gtatatatat atatatatat atataccccac ggatcccgag accggccttt    5460
gattcttccc tacaaccaac cattctcacc accctaattc acaaccatgg ccaaggtcaa    5520
acccggtgga cctggcaagc cctcggagat cgcttctctt ccacctccca ttcgacctgt    5580
tggcaaccca cctgcagcct attacgacgc tctggccacc tccggtactg acaggaccg    5640 aaagtttacc atgcgagagg tcgctcgaca cattgttccc accgatggct ggttggcctg    5700
tcacgacggt gtgtacgaca tcaccgagtt cattggcaag catcccggtg agatgttat    5760 ctctctcggt ctcggacgag actccactat tctggtcgaa tcgtaccatc ctgcaggacg    5820
acccgacaag gttatggaga agtaccgaat cggtacactt caggatcaca gaaccttcta    5880
cgactggcag gcctccgctt tctacgccga gctcaagcag cgagtggttc agactctcaa    5940
ggaggctgga caacctcgac gtggtggcct gtctgtcaag gcagcccttg ttatggctgc    6000
```

```
ctttgctgcc tcgttctacc tcatggtgac acagggatcc ttcttttggg ctgccgtctg    6060
gggtctggca ggctctcaca ttggactcag catccagcac gacggcaatc atggtgcttt    6120
ctccaagtct ggacgactca accgtcttgc tggctgggt atggacgtta tcggagcctc     6180
ctcgactgcc tgggagtacc aacacgtcat tggtcatcac cagtacacca acctggtgtc    6240
cgatcccgag tttgctcttc ccgagaacga tccagacgtt ttcggaacct atccctcat     6300
gcggatgcat ccggacactc cttggaaacc ccaccatcag ctgcaacacg tgtacgcctt    6360
tccgttgttc gctctcatga ccatcagcaa ggtcattatc tccgatttca cgttttgtct    6420
tgccaagcga cgtggtccca tcgacttctc tgccagactc gttcccctcg agggtcagat    6480
gctgttctgg ggtgcaaaga tcatgggctt tctcatgcag attgtgcttc cctgctacct    6540
gcatggcatc gctcacggat tggccctctt cattacagct catctggttt ctggcgagta    6600
ccttgccgtc tgtttcatta tcaaccacat ttccgagtcg tgcgactacc tcaatccctc    6660
ttccgttatc gctgcccgac ggaccgaaat gctcaagcag gccgagcagg aagccaaggc    6720
gaaacagaag cacccactc cacctcccaa cgactgggct gcctcccaag ttctgtgttg     6780
cgtcaactgg cgatctggtg gctactttc aaaccaccct tctggtggac tcaaccacca    6840
gatcgagcat cacctgtttc ccagcatttc tcacgccaac tatcccacca ttgctcctgt    6900
tgtcaagggc gtgtgcgagg aatacggtct tccctacaag aactactctc agttttccga    6960
tgctctgtac ggaatggtcg agcacttgcg agctatgggc accaaacctg cagacaacga    7020
caagcttgct cccactgcag gttccctgga ggatgtttgt cctgtgctct ctgctgccgt    7080
tgctgcccaa cccgacggct ccaccgacgg atctgctgcc ggttgtcctg ctgtcgccac    7140
tctggcttaa gcggccgcat gagaagataa atatataaat acattgagat attaaatgcg    7200
ctagattaga gagcctcata ctgctcggag agaagccaag acgagtactc aaaggggatt    7260
acaccatcca tatccacaga cacaagctgg ggaaaggttc tatatacact ttccggaata    7320
ccgtagtttc cgatgttatc aatgggggca gccaggattt caggcacttc ggtgtctcgg    7380
ggtgaaatgg cgttcttggc ctccatcaag tcgtaccatg tcttcatttg cctgtcaaag    7440
taaaacagaa gcagatgaag aatgaacttg aagtgaagga atttaaattg ccccggagaa    7500
gacggccagg ccgcctagat gacaaattca acaactcaca gctgactttc tgccattgcc    7560
actagggggg ggccttttta tatggccaag ccaagctctc cacgtcggtt gggctgcacc    7620
caacaataaa tgggtagggt tgcaccaaca aagggatggg atgggggta gaagatacga     7680
ggataacggg gctcaatggc acaaataaga acgaatactg ccattaagac tcgtgatcca    7740
gcgactgaca ccattgcatc atctaagggc ctcaaaacta cctcggaact gctgcgctga    7800
tctggacacc acagaggttc cgagcacttt aggttgcacc aaatgtccca ccaggtgcag    7860
gcagaaaacg ctggaacagc gtgtacagtt tgtcttaaca aaaagtgagg gcgctgaggt    7920
cgagcagggt ggtgtgactt gttatagcct ttagagctgc gaaagcgcgt atggatttgg    7980
ctcatcaggc cagattgagg gtctgtggac acatgtcatg ttagtgtact tcaatcgccc    8040
cctggatata gccccgacaa taggccgtgg cctcattttt ttgccttccg cacatttcca    8100
ttgctcggta cccacacctt gcttctcctg cacttgccaa ccttaatact ggtttacatt    8160
gaccaacatc ttacaagcgg ggggcttgtc tagggtatat ataaacagtg gctctcccaa    8220
tcggttgcca gtctcttttt tccttttctt ccccacagat tcgaaatcta aactacacat    8280
cacagaactc cgagccgtga gtatccacga caagatcagt gtcgagacga cgcgttttgt    8340
```

```
gtaatgacac aatccgaaag tcgctagcaa cacacactct ctacacaaac taacccagct    8400
ctggtaccat ggctgactct cccgtcatca acctctccac catgtggaag cctctgtcgc    8460
tcatggcctt ggatcttgct gttctgggac acgtctggaa gcaggcacaa caggagggct    8520
ccatctcggc ttacgccgac tctgtgtgga ctcccctcat catgtccggt ctgtacctct    8580
ccatgatctt cgtgggatgt cgatggatga agaaccgaga gcccttcgaa atcaagacct    8640
acatgtttgc ctacaacctg taccagaccc tcatgaacct ttgcattgtg ctgggcttcc    8700
tctaccaggt ccacgctacc ggtatgcgat tctggggatc tggcgtggac cgatcgccca    8760
agggtctggg aattggcttt ttcatctatg cccattacca caacaagtac gtcgagtact    8820
tcgacacact cttcatggtg ctgcggaaaa agaacaacca gatttccttt cttcacgtct    8880
accatcacgc tctgctcacc tgggcttggt ttgccgtggt ctacttcgct cctggaggtg    8940
acggctggtt tggagcctgc tacaattcct ccattcatgt cctgatgtac tcttactatc    9000
tgcttgccac cttcggcatc tcctgtccct ggaaaaagat cctcacccag ctgcaaatgg    9060
ttcagttctg cttttgcttc acccactcga tctacgtgtg gatttgcggt tccgaaatct    9120
accctcgacc cttgactgct ctccagtcct tcgtgatggt caacatgctg gttctctttg    9180
gcaacttcta cgtcaagcag tattctcaga agaatggaaa gcccgagaac ggtgccactc    9240
ctgagaacgg tgccaagcct cagccctgcg agaacggcac cgtcgagaag cgagagaacg    9300
acactgccaa cgttcgataa gcggccgcaa gtgtggatgg ggaagtgagt gcccggttct    9360
gtgtgcacaa ttggcaatcc aagatggatg gattcaacac agggatatag cgagctacgt    9420
ggtggtgcga ggatatagca acggatattt atgtttgaca cttgagaatg tacgatacaa    9480
gcactgtcca agtacaatac taaacatact gtacatactc atactcgtac ccgggcaacg    9540
gtttcacttg agtgcagtgg ctagtgctct tactcgtaca gtgtgcaata ctgcgtatca    9600
tagtctttga tgtatatcgt attcattcat gttagttgcg tacggattgt gtatgtccct    9660
gtacctgcat cttgatggag agagctccgg aaagcggatc aggagctgtc caattttaat    9720
tttataacat ggaaacgagt ccttggagct agaagaccat ttttcaact gcccctatcga   9780 ctatatttat ctactccaaa accgactgct tcccaagaat cttcagccaa ggcttccaaa    9840 gtaaccctc gcttcccgac acttaattga aaccttagat gcagtcactg cgagtgaagt    9900
ggactctaac atctccaaca tagcgacgat attgcgaggg tttgaatata actaagatgc    9960
atgatccatt acatttgtag aaatatcata acaacgaag cacatagaca gaatgctgtt   10020
ggttgttaca tctgaagccg aggtaccgat gtcatttca gctgtcactg cagagacagg   10080
ggtatgtcac atttgaagat catacaaccg acgtttatga aaaccagaga tatagagaat   10140
gtattgacgg ttgtggctat gtcataagtg cagtgaagtg cagtgattat aggtatagta   10200
cacttactgt agctacaagt acatactgct acagtaatac tcatgtatgc aaaccgtatt   10260
ctgtgtctac agaaggcgat acggaagagt caatctctta tgtagagcca tttctataat   10320
cgaaggggcc ttgtaatttc caaacgagta attgagtaat tgaagagcat cgtagacatt   10380
acttatcatg tattgtgaga gggaggagat gcagctgtag ctactgcaca tactgtactc   10440
gcccatgcag ggataatgca tagcgagact tggcagtagg tgacagttgc tagctgctac   10500
ttgtagtcgg gtgggtgata gcatggcgcg ccagctgcat taatgaatcg gccaacgcgc   10560
ggggagaggc ggtttgcgta ttgggcgctc ttccgcttcc tcgctcactg actcgctgcg   10620
ctcggtcgtt cggctgcggc gagcggtatc agctcactca aaggcggtaa tacgttatc    10680 cacagaatca ggggataacg caggaaagaa catgtgagca aaaggccagc aaaaggccag   10740
```

```
gaaccgtaaa aaggccgcgt tgctggcgtt tttccatagg ctccgccccc ctgacgagca    10800
tcacaaaaat cgacgctcaa gtcagaggtg gcgaaacccg acaggactat aaagatacca    10860 ggcgttccc cctggaagct ccctcgtgcg ctctcctgtt ccgaccctgc cgcttaccgg     10920
atacctgtcc gcctttctcc cttcgggaag cgtggcgctt tctcatagct cacgctgtag    10980
gtatctcagt tcggtgtagg tcgttcgctc caagctgggc tgtgtgcacg aaccccccgt    11040
tcagcccgac cgctgcgcct tatccggtaa ctatcgtctt gagtccaacc cggtaagaca    11100
cgacttatcg ccactggcag cagccactgg taacaggatt agcagagcga ggtatgtagg    11160
cggtgctaca gagttcttga agtggtggcc taactacggc tacactagaa gaacagtatt    11220
tggtatctgc gctctgctga agccagttac cttcggaaaa agagttggta gctcttgatc    11280
cggcaaacaa accaccgctg gtagcggtgg tttttttgtt tgcaagcagc agattacgcg    11340
cagaaaaaaa ggatctcaag aagatccttt gatcttttct acggggtctg acgctcagtg    11400
gaacgaaaac tcacgttaag ggattttggt catgagatta tcaaaaagga tcttcaccta    11460 gatccttta aattaaaaat gaagttttaa atcaatctaa agtatatatg agtaaacttg    11520
gtctgacagt taccaatgct taatcagtga ggcacctatc tcagcgatct gtctatttcg    11580
ttcatccata gttgcctgac tccccgtcgt gtagataact acgatacggg agggcttacc    11640
atctggcccc agtgctgcaa tgataccgcg agacccacgc tcaccggctc cagatttatc    11700
agcaataaac cagccagccg gaagggccga gcgcagaagt ggtcctgcaa ctttatccgc    11760
ctccatccag tctattaatt gttgccggga agctagagta agtagttcgc cagttaatag    11820
tttgcgcaac gttgttgcca ttgctacagg catcgtggtg tcacgctcgt cgtttggtat    11880
ggcttcattc agctccggtt cccaacgatc aaggcgagtt acatgatccc ccatgttgtg    11940
caaaaaagcg gttagctcct tcggtcctcc gatcgttgtc agaagtaagt tggccgcagt    12000
gttatcactc atggttatgg cagcactgca taattctctt actgtcatgc catccgtaag    12060
atgcttttct gtgactggtg agtactcaac caagtcattc tgagaatagt gtatgcggcg    12120
accgagttgc tcttgcccgg cgtcaatacg ggataatacc gcgccacata gcagaacttt    12180
aaaagtgctc atcattggaa acgttcttc ggggcgaaaa ctctcaagga tcttaccgct     12240
gttgagatcc agttcgatgt aacccactcg tgcacccaac tgatcttcag catcttttac    12300
tttcaccagc gtttctgggt gagcaaaaac aggaaggcaa aatgccgcaa aaaagggaat    12360
aagggcgaca cggaaatgtt gaatactcat actcttcctt tttcaatatt attgaagcat    12420
ttatcagggt tattgtctca tgagcggata catatttgaa tgtatttaga aaaataaaca    12480
aataggggtt ccgcgcacat ttccccgaaa agtgccacct gatgcggtgt gaaataccgc    12540
acagatgcgt aaggagaaaa taccgcatca ggaaattgta agcgttaata ttttgttaaa    12600 attgcgtta aattttgtt aaatcagctc attttttaac caataggccg aaatcggcaa     12660
aatcccttat aaatcaaaag aatagaccga gatagggttg agtgttgttc cagtttggaa    12720
caagagtcca ctattaaaga acgtggactc caacgtcaaa gggcgaaaaa ccgtctatca    12780
gggcgatggc ccactacgtg aaccatcacc ctaatcaagt ttttggggt cgaggtgccg     12840 taaagcacta atcggaacc ctaaagggag cccccgattt agagcttgac ggggaaagcc     12900
ggcgaacgtg gcgagaaagg aagggaagaa agcgaaagga gcgggcgcta gggcgctggc    12960
aagtgtagcg gtcacgctgc gcgtaaccac cacacccgcc gcgcttaatg cgccgctaca    13020
gggcgcgtcc attcgccatt caggctgcgc aactgttggg aagggcgatc ggtgcgggcc    13080
```

```
tcttcgctat tacgccagct ggcgaaaggg ggatgtgctg caaggcgatt aagttgggta    13140
acgccagggt tttcccagtc acgacgttgt aaaacgacgg ccagtgaatt gtaatacgac    13200
tcactatagg gcgaattggg cccgacgtcg catgcaggaa tagacatctt caataggagc    13260
attaatacct gtgggatcac tgatgtaaac ttctcccaga gtatgtgaat aaccagcggg    13320
ccatccaaca aagaagtcgt tccagtgagt gactcggtac atccgtcttt cggggttgat    13380
ggtaagtccg tcgtctcctt gcttaaagaa cagagcgtcc acgtagtctg caaaagcctt    13440
gtttccaagt cgaggctgcc catagttgat tagcgttgga tcatatccaa gattcttcag    13500
gttgatgccc atgaatagag cagtgacagc tcctagagag tggccagtta cgatcaattt    13560
gtagtcagtg ttgtttccaa ggaagtcgac cagacgatcc tgtacgttca ccatagtctc    13620
tctgtatgcc ttctgaaagc catcatgaac ttggcagcca ggacaattga tactggcaga    13680
agggtttgtg gagtttatgt cagtagtgtt aagaggaggg atactggtca tgtagggttg    13740
ttggatcgtt tggatgtcag taatagcgtc tgcaatggag aaagtgcctc ggaaaacaat    13800
atacttttcc ttttggtgt gatcgtgggc caaaaatcca gtaactgaag tcgagaagaa    13860
atttcctcca aactggtagt caagagtcac atcgggaaaa tgagcgcaag agtttccaca    13920
ggtaaaatcg ctctgcaggg caaatgggcc aggggctctg acacaatagg ccacgttaga    13980
tagccatccg tacttgagaa caaagtcgta tgtctcctgg gtgataggag ccgttaatta    14040
actcacctgc aggattgaga ctatgaatgg attcccgtgc ccgtattact ctactaattt    14100
gatcttggaa cgcgaaaata cgtttctagg actccaaaga atctcaactc ttgtccttac    14160
taaatatact acccatagtt gatggtttac ttgaacagag aggacatgtt cacttgaccc    14220
aaagtttctc gcatctcttg gatatttgaa caacggcgtc cactgaccgt cagttatcca    14280
gtcacaaaac ccccacattc atacattccc atgtacgttt acaaagttct caattccatc    14340
gtgcaaatca aaatcacatc tattcattca tcatatataa acccatcatg tctactaaca    14400
ctcacaactc catagaaaac atcgactcag aacacacgct ccatgcggcc gcttaggact    14460
ttttgtcgcc gttggtaggc acgggaggag cacccatgag tcgcagatgc tgaaccatgc    14520
cacacacggc atcccagaac gtaacgtagt tcttgtaggg caatccgtat tcctcgcaca    14580
cttccttgac aactcgagca atgatgggat agttcgcgtg agagatgctg ggaaacagat    14640
ggtgctcgat ctgatggttg aggccaccgg agaggtgatt ggccagcacg cctccagatc    14700
gccagtgac acagcactgg acttgtgtca cagcccaatc gttgggtgga ggagtgggct    14760
tgacctttt cgcctcggct gcctgatgag ctgcctggag catctcggtc cgtcgggcag    14820
cagtttgaaa ggaggtattc ataaattcgc aagactcgga gatgtggtta atgatgaaac    14880
agatggccag gtactctcca gacacaaggt gggcaacaga gaacagagca aggcccatag    14940
cagttccgtg gaggtagcag ggcagcacaa tctgcaagag aaagttcgcc agcttggctc    15000
cccagaacaa cagctggcct tcgagtggaa ccagtctgga cgaacagtcg atagaaccct    15060
ttttcatgga gagacaaaca gcaaagtcgc tggtgagcac cttggaaatg gtcataagag    15120
cgaagagagg aaaggcgaac aggtgttgaa atcggtgatg aggctgccaa gcagtgtcgg    15180
gatgcattcg catgagagga tagctggaaa acacatctgg gtcgttctcg ggaaggctga    15240
acagcgtatc ggaaacgaga ttcgtgtact gatggtgtcc aatgacatgc tggtactccc    15300
acacggtgga cgaggcaccg atcaagtcca tgccccatcc tgcgagtctg ttgaccaggg    15360
tggatcgaga gaaagcaccg tggttgccat cgtgttgaat gctcagtccg acatgcgaac    15420
cggcaaagcc ccagacggca gcccacagga aagacttgtg ggcaacccac atgtaccagg    15480
```

-continued

```
agacaaagaa gagggtaagc accaggagag ccttgactcc cagtccacct cgacgtgcct    15540
gtccagcctc cttgagtcgt gcaagagccc gtcgtttgag ctcagggtaa aagtccgatt    15600
ctccccaagc gtagaaagtc ttgggatcct ggagtgtgcc gatacggtac ttctccatga    15660
ccttgtctgg tcgtccagcg ggatggtagg actcgaccag aatggtgcag tctcgaccaa    15720
gtccgagagt gatgacgcca cctccaggat gcttggccag gaaatcggtg acgtcgtaca    15780
caccttcgtg acaggtgagc atccatcgg tgggaagaat gtgtcgtctg acctcgtctg     15840
tggtgaacag tcgctccttg ccctgtcccg acacggcgag agagtcatag taagttgcgg    15900
gtggaagacc ggcaggtcta gcgggtcgaa cattggcggt gtcgttttct cgcttctcca    15960
cggtaccgtt ctcgcaaggt tgcggtttgg ccatgggcag gacctgtgtt agtacattgt    16020
cggggagtca tcaattggtt cgacaggttg tcgactgtta gtatgagctc aattgggctc    16080
tggtgggtcg atgacacttg tcatctgttt ctgttgggtc atgtttccat caccttctat    16140
ggtactcaca attcgtccga ttcgcccgaa tccgttaata ccgactttga tggccatgtt    16200
gatgtgtgtt taattcaaga atgaatatag agaagagaag aagaaaaaag attcaattga    16260
gccggcgatg cagacccttta tataaatgtt gccttggaca gacggagcaa gcccgcccaa    16320
acctacgttc ggtataatat gttaagcttt ttaacacaaa ggtttggctt ggggtaacct    16380
gatgtggtgc aaaagaccgg gcgttggcga gccattgcgc gggcgaatgg ggccgtgact    16440
cgtctcaaat tcgagggcgt gcctcaattc gtgccccgt ggcttttttcc cgccgttttcc    16500 gccccgtttg caccactgca gccgcttctt tggttcggac accttgctgc gagctaggtg    16560
ccttgtgcta cttaaaaagt ggcctcccaa caccaacatg acatgagtgc gtgggccaag    16620
acacgttggc ggggtcgcag tcggctcaat ggcccggaaa aaacgctgct ggagctggtt    16680
cggacgcagt ccgccgcggc gtatggatat ccgcaaggtt ccatagcgcc attgccctcc    16740
gtcggcgtct atcccgcaac ctctaaatag agcgggaata taacccaagc ttcttttttt    16800
tcctttaaca cgcacacccc caactatcat gttgctgctg ctgtttgact ctactctgtg    16860 gagggggtgct cccacccaac ccaacctaca ggtggatccg gcgctgtgat tggctgataa    16920
gtctcctatc cggactaatt ctgaccaatg ggacatgcgc gcaggaccca aatgccgcaa    16980
ttacgtaacc ccaacgaaat gcctaccct ctttggagcc cagcggcccc aaatcccccc     17040
aagcagcccg gttctaccgg cttccatctc caagcacaag cagcccgg                 17088
```

```
<210> SEQ ID NO 58
<211> LENGTH: 1548
<212> TYPE: DNA
<213> ORGANISM: Eutreptiella cf_gymnastica CCMP1594
<220> FEATURE:
<221> NAME/KEY: CDS
<222> LOCATION: (1)..(1548)
<223> OTHER INFORMATION: synthetic delta-4 desaturase (codon-optimized
      for Yarrowia lipolytica) ("E1594D4S")

<400> SEQUENCE: 58
```

```
atg gct cag tcc acc aag gct gcc gac act gct gcc acc gac aag tct        48
Met Ala Gln Ser Thr Lys Ala Ala Asp Thr Ala Ala Thr Asp Lys Ser
1               5                   10                  15 ctc gac aag aac cga ctc atc tcc cga gac gag ctg cgg tct cac aac        96
Leu Asp Lys Asn Arg Leu Ile Ser Arg Asp Glu Leu Arg Ser His Asn
            20                  25                  30 gtt ccc cag gat gcc tgg gct gcc gtc cac ggc aga gtc atc aac att       144
Val Pro Gln Asp Ala Trp Ala Ala Val His Gly Arg Val Ile Asn Ile
        35                  40                  45
```

| | | |
|---|---|---|
| acc gag ttc gcc cga cgg cat cct ggt ggc gac atc att ctg ctt gcc<br>Thr Glu Phe Ala Arg Arg His Pro Gly Gly Asp Ile Ile Leu Leu Ala<br> 50                          55                      60 | | 192 |
| gca gga aag gat gcc acc gtg ctc ttc gag act tac cat cct cga ggt<br>Ala Gly Lys Asp Ala Thr Val Leu Phe Glu Thr Tyr His Pro Arg Gly<br>65                      70                      75                      80 | | 240 |
| gtt ccc acc tcg atc ctc gac aag ctg cag gtc ggc aag atg aag gac<br>Val Pro Thr Ser Ile Leu Asp Lys Leu Gln Val Gly Lys Met Lys Asp<br>                    85                      90                      95 | | 288 |
| gga gaa ctt ccc tcc tcg ttc tac tcg tgg gat tcc gac ttt tac aag<br>Gly Glu Leu Pro Ser Ser Phe Tyr Ser Trp Asp Ser Asp Phe Tyr Lys<br>            100                     105                     110 | | 336 |
| acc ctg cga gct cga gtg gtc gag cga ttg gac aag ctc aac ctg cct<br>Thr Leu Arg Ala Arg Val Val Glu Arg Leu Asp Lys Leu Asn Leu Pro<br>            115                     120                     125 | | 384 |
| cga aga ggt ggc tac gag att tgg gtc aag gca gta ttc ctc ctg gct<br>Arg Arg Gly Gly Tyr Glu Ile Trp Val Lys Ala Val Phe Leu Leu Ala<br>            130                     135                     140 | | 432 |
| gga ttc tgg ttc agc ctc tac aag atg tcc gtc aac gag acc tac tgg<br>Gly Phe Trp Phe Ser Leu Tyr Lys Met Ser Val Asn Glu Thr Tyr Trp<br>145                     150                     155                     160 | | 480 |
| gct gcc tcg ctg tgg tcc gtg tct atg gga gtc ttt gct gcc ttc atc<br>Ala Ala Ser Leu Trp Ser Val Ser Met Gly Val Phe Ala Ala Phe Ile<br>                     165                     170                     175 | | 528 |
| ggc act tgc att caa cac gat gga aac cac ggt gcc ttc tcg acc agc<br>Gly Thr Cys Ile Gln His Asp Gly Asn His Gly Ala Phe Ser Thr Ser<br>            180                     185                     190 | | 576 |
| cct gct ctc aac aag gtt gca ggc tgg act ctg gac atg atc ggt gct<br>Pro Ala Leu Asn Lys Val Ala Gly Trp Thr Leu Asp Met Ile Gly Ala<br>            195                     200                     205 | | 624 |
| tct ggc ttt aca tgg gag att cag cat atg ctc gga cac cat ccc tac<br>Ser Gly Phe Thr Trp Glu Ile Gln His Met Leu Gly His His Pro Tyr<br>            210                     215                     220 | | 672 |
| acc aac gtc ctg gac gtg gac gaa gag aag cga aag gaa gct ggc gac<br>Thr Asn Val Leu Asp Val Asp Glu Glu Lys Arg Lys Glu Ala Gly Asp<br>225                   230                     235                     240 | | 720 |
| gat tgt cct atg gag gac aag gat cag gag tcc gac cca gat gtc ttc<br>Asp Cys Pro Met Glu Asp Lys Asp Gln Glu Ser Asp Pro Asp Val Phe<br>            245                     250                     255 | | 768 |
| tct tcg ttt cct ctc atg cga atg cac ccc tac cac aag gcc gag tgg<br>Ser Ser Phe Pro Leu Met Arg Met His Pro Tyr His Lys Ala Glu Trp<br>            260                     265                     270 | | 816 |
| tac cac cga tat cag cac ctg tac gca ccc gtt ctc ttt gct ttc atg<br>Tyr His Arg Tyr Gln His Leu Tyr Ala Pro Val Leu Phe Ala Phe Met<br>            275                     280                     285 | | 864 |
| act ctt gcc aag gtg ttc caa cag gac atc gaa gtc gct acc act cag<br>Thr Leu Ala Lys Val Phe Gln Gln Asp Ile Glu Val Ala Thr Thr Gln<br>            290                     295                     300 | | 912 |
| cga ctg tac cac atc gac gcc aag tgc cga tac aat tcc att ctc aat<br>Arg Leu Tyr His Ile Asp Ala Lys Cys Arg Tyr Asn Ser Ile Leu Asn<br>305                   310                     315                     320 | | 960 |
| gtc ctt cgg ttt tgg tcg atg aag gtg ctc tcc atc ggc tac atg ctg<br>Val Leu Arg Phe Trp Ser Met Lys Val Leu Ser Ile Gly Tyr Met Leu<br>            325                     330                     335 | | 1008 |
| gct gtt ccc tgc tac ttc cac gga atc ctt ggt ggc ctt gga ctg ttt<br>Ala Val Pro Cys Tyr Phe His Gly Ile Leu Gly Gly Leu Gly Leu Phe<br>            340                     345                     350 | | 1056 |
| ctc atc ggc cac ttt gcc tgt gga gag ctt ctg gca acc atg ttc att<br>Leu Ile Gly His Phe Ala Cys Gly Glu Leu Leu Ala Thr Met Phe Ile | | 1104 |

```
                 355                 360                 365
gtc aat cac gtc atc gag ggt gtg tcc ttt ggc aaa aag gga gaa tct      1152
Val Asn His Val Ile Glu Gly Val Ser Phe Gly Lys Lys Gly Glu Ser
        370                 375                 380 ctc ggt ctg tcc aag gac gtg gag ttc aag cct aca acc gtt tct gga      1200
Leu Gly Leu Ser Lys Asp Val Glu Phe Lys Pro Thr Thr Val Ser Gly
385                 390                 395                 400 cga act cca atg gag cag acc cgt gcc gag gcc aaa aag gct gcc aat      1248
Arg Thr Pro Met Glu Gln Thr Arg Ala Glu Ala Lys Lys Ala Ala Asn
                405                 410                 415 gga ggc aac gtc aag gat gtt ccc tac aac gac tgg gct gcc gtt cag      1296
Gly Gly Asn Val Lys Asp Val Pro Tyr Asn Asp Trp Ala Ala Val Gln
            420                 425                 430 tgt caa acg agc gtc aac tgg tct cct gga tcg tgg ttc tgg aat cac      1344
Cys Gln Thr Ser Val Asn Trp Ser Pro Gly Ser Trp Phe Trp Asn His
        435                 440                 445 ttc tcc ggt ggc ctc tcc cac cag atc gag cac cat ctg ttt ccc agc      1392
Phe Ser Gly Gly Leu Ser His Gln Ile Glu His His Leu Phe Pro Ser
450                 455                 460 att tgt cac acc aac tac gct cac atc cag gac gtt gtc cag aag act      1440
Ile Cys His Thr Asn Tyr Ala His Ile Gln Asp Val Val Gln Lys Thr
465                 470                 475                 480 tgc gaa gag tac ggt gtt cct tac cag tcc gaa ccc tct ttg ttc tcc      1488
Cys Glu Glu Tyr Gly Val Pro Tyr Gln Ser Glu Pro Ser Leu Phe Ser
                485                 490                 495 gcc tat ggc aag atg ctg tct cat ctc aag tac ctc gga aac gag aaa      1536
Ala Tyr Gly Lys Met Leu Ser His Leu Lys Tyr Leu Gly Asn Glu Lys
            500                 505                 510 aag gtc gct taa                                                      1548
Lys Val Ala
        515

<210> SEQ ID NO 59
<211> LENGTH: 515
<212> TYPE: PRT
<213> ORGANISM: Eutreptiella cf_gymnastica CCMP1594

<400> SEQUENCE: 59

Met Ala Gln Ser Thr Lys Ala Ala Asp Thr Ala Ala Thr Asp Lys Ser
1               5                   10                  15

Leu Asp Lys Asn Arg Leu Ile Ser Arg Asp Glu Leu Arg Ser His Asn
            20                  25                  30

Val Pro Gln Asp Ala Trp Ala Ala Val His Gly Arg Val Ile Asn Ile
        35                  40                  45

Thr Glu Phe Ala Arg Arg His Pro Gly Gly Asp Ile Ile Leu Leu Ala
    50                  55                  60

Ala Gly Lys Asp Ala Thr Val Leu Phe Glu Thr Tyr His Pro Arg Gly
65                  70                  75                  80

Val Pro Thr Ser Ile Leu Asp Lys Leu Gln Val Gly Lys Met Lys Asp
                85                  90                  95

Gly Glu Leu Pro Ser Ser Phe Tyr Ser Trp Asp Ser Asp Phe Tyr Lys
            100                 105                 110

Thr Leu Arg Ala Arg Val Val Glu Arg Leu Asp Lys Leu Asn Leu Pro
        115                 120                 125

Arg Arg Gly Gly Tyr Glu Ile Trp Val Lys Ala Val Phe Leu Leu Ala
    130                 135                 140

Gly Phe Trp Phe Ser Leu Tyr Lys Met Ser Val Asn Glu Thr Tyr Trp
145                 150                 155                 160
```

Ala Ala Ser Leu Trp Ser Val Ser Met Gly Val Phe Ala Ala Phe Ile
            165                 170                 175

Gly Thr Cys Ile Gln His Asp Gly Asn His Gly Ala Phe Ser Thr Ser
            180                 185                 190

Pro Ala Leu Asn Lys Val Ala Gly Trp Thr Leu Asp Met Ile Gly Ala
            195                 200                 205

Ser Gly Phe Thr Trp Glu Ile Gln His Met Leu Gly His His Pro Tyr
            210                 215                 220

Thr Asn Val Leu Asp Val Asp Glu Glu Lys Arg Lys Glu Ala Gly Asp
225                 230                 235                 240

Asp Cys Pro Met Glu Asp Lys Asp Gln Glu Ser Asp Pro Asp Val Phe
                245                 250                 255

Ser Ser Phe Pro Leu Met Arg Met His Pro Tyr His Lys Ala Glu Trp
                260                 265                 270

Tyr His Arg Tyr Gln His Leu Tyr Ala Pro Val Leu Phe Ala Phe Met
            275                 280                 285

Thr Leu Ala Lys Val Phe Gln Gln Asp Ile Glu Val Ala Thr Thr Gln
        290                 295                 300

Arg Leu Tyr His Ile Asp Ala Lys Cys Arg Tyr Asn Ser Ile Leu Asn
305                 310                 315                 320

Val Leu Arg Phe Trp Ser Met Lys Val Leu Ser Ile Gly Tyr Met Leu
                325                 330                 335

Ala Val Pro Cys Tyr Phe His Gly Ile Leu Gly Gly Leu Gly Leu Phe
            340                 345                 350

Leu Ile Gly His Phe Ala Cys Gly Glu Leu Leu Ala Thr Met Phe Ile
        355                 360                 365

Val Asn His Val Ile Glu Gly Val Ser Phe Gly Lys Lys Gly Glu Ser
            370                 375                 380

Leu Gly Leu Ser Lys Asp Val Glu Phe Lys Pro Thr Thr Val Ser Gly
385                 390                 395                 400

Arg Thr Pro Met Glu Gln Thr Arg Ala Glu Ala Lys Lys Ala Ala Asn
                405                 410                 415

Gly Gly Asn Val Lys Asp Val Pro Tyr Asn Asp Trp Ala Ala Val Gln
            420                 425                 430

Cys Gln Thr Ser Val Asn Trp Ser Pro Gly Ser Trp Phe Trp Asn His
        435                 440                 445

Phe Ser Gly Gly Leu Ser His Gln Ile Glu His His Leu Phe Pro Ser
    450                 455                 460

Ile Cys His Thr Asn Tyr Ala His Ile Gln Asp Val Val Gln Lys Thr
465                 470                 475                 480

Cys Glu Glu Tyr Gly Val Pro Tyr Gln Ser Glu Pro Ser Leu Phe Ser
                485                 490                 495

Ala Tyr Gly Lys Met Leu Ser His Leu Lys Tyr Leu Gly Asn Glu Lys
            500                 505                 510

Lys Val Ala
        515

<210> SEQ ID NO 60
<211> LENGTH: 1542
<212> TYPE: DNA
<213> ORGANISM: Euglena gracilis
<220> FEATURE:
<221> NAME/KEY: CDS
<222> LOCATION: (1)..(1542)
<223> OTHER INFORMATION: synthetic truncated delta-4 desaturase -continued

```
         (codon-optimized for Yarrowia lipolytica)
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: U.S. Pat. Pub. No. 2008-0254191-A1
<311> PATENT FILING DATE: 2008-04-03
<312> PUBLICATION DATE: 2008-10-16
<313> RELEVANT RESIDUES IN SEQ ID NO: (1)..(1542)
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: WO 2008/124048
<311> PATENT FILING DATE: 2008-04-03
<312> PUBLICATION DATE: 2008-10-16
<313> RELEVANT RESIDUES IN SEQ ID NO: (1)..(1542)

<400> SEQUENCE: 60 atg gcc aaa ccg caa cct tgc gag aac ggt acc gtg gag aag cga gaa      48
Met Ala Lys Pro Gln Pro Cys Glu Asn Gly Thr Val Glu Lys Arg Glu
1               5                   10                  15 aac gac acc gcc aat gtt cga ccc gct aga cct gcc ggt ctt cca ccc      96
Asn Asp Thr Ala Asn Val Arg Pro Ala Arg Pro Ala Gly Leu Pro Pro
                20                  25                  30 gca act tac tat gac tct ctc gcc gtg tcg gga cag ggc aag gag cga     144
Ala Thr Tyr Tyr Asp Ser Leu Ala Val Ser Gly Gln Gly Lys Glu Arg
            35                  40                  45 ctg ttc acc aca gac gag gtc aga cga cac att ctt ccc acc gat gga     192
Leu Phe Thr Thr Asp Glu Val Arg Arg His Ile Leu Pro Thr Asp Gly
        50                  55                  60 tgg ctc acc tgt cac gaa ggt gtg tac gac gtc acc gat ttc ctg gcc     240
Trp Leu Thr Cys His Glu Gly Val Tyr Asp Val Thr Asp Phe Leu Ala
65                  70                  75                  80 aag cat cct gga ggt ggc gtc atc act ctc gga ctt ggt cga gac tgc     288
Lys His Pro Gly Gly Gly Val Ile Thr Leu Gly Leu Gly Arg Asp Cys
                85                  90                  95 acc att ctg gtc gag tcc tac cat ccc gct gga cga cca gac aag gtc     336
Thr Ile Leu Val Glu Ser Tyr His Pro Ala Gly Arg Pro Asp Lys Val
            100                 105                 110 atg gag aag tac cgt atc ggc aca ctc cag gat ccc aag act ttc tac     384
Met Glu Lys Tyr Arg Ile Gly Thr Leu Gln Asp Pro Lys Thr Phe Tyr
        115                 120                 125 gct tgg gga gaa tcg gac ttt tac cct gag ctc aaa cga cgg gct ctt     432
Ala Trp Gly Glu Ser Asp Phe Tyr Pro Glu Leu Lys Arg Arg Ala Leu
    130                 135                 140 gca cga ctc aag gag gct gga cag gca cgt cga ggt gga ctg gga gtc     480
Ala Arg Leu Lys Glu Ala Gly Gln Ala Arg Arg Gly Gly Leu Gly Val
145                 150                 155                 160 aag gct ctc ctg gtg ctt acc ctc ttt gtc tcc tgg tac atg tgg         528
Lys Ala Leu Leu Val Leu Thr Leu Phe Phe Val Ser Trp Tyr Met Trp
                165                 170                 175 gtt gcc cac aag tct ttc ctg tgg gct gcc gtc tgg ggc ttt gcc ggt     576
Val Ala His Lys Ser Phe Leu Trp Ala Ala Val Trp Gly Phe Ala Gly
            180                 185                 190 tcg cat gtc gga ctg agc att caa cac gat ggc aac cac ggt gct ttc     624
Ser His Val Gly Leu Ser Ile Gln His Asp Gly Asn His Gly Ala Phe
        195                 200                 205 tct cga tcc acc ctg gtc aac aga ctc gca gga tgg ggc atg gac ttg     672
Ser Arg Ser Thr Leu Val Asn Arg Leu Ala Gly Trp Gly Met Asp Leu
    210                 215                 220 atc ggt gcc tcg tcc acc gtg tgg gag tac cag cat gtc att gga cac     720
Ile Gly Ala Ser Ser Thr Val Trp Glu Tyr Gln His Val Ile Gly His
225                 230                 235                 240 cat cag tac acg aat ctc gtt tcc gat acg ctg ttc agc ctt ccc gag     768
```

| | | |
|---|---|---|
| His Gln Tyr Thr Asn Leu Val Ser Asp Thr Leu Phe Ser Leu Pro Glu<br>245 250 255 | | |
| aac gac cca gat gtg ttt tcc agc tat cct ctc atg cga atg cat ccc<br>Asn Asp Pro Asp Val Phe Ser Ser Tyr Pro Leu Met Arg Met His Pro<br>260 265 270 | | 816 |
| gac act gct tgg cag cct cat cac cga ttt caa cac ctg ttc gcc ttt<br>Asp Thr Ala Trp Gln Pro His His Arg Phe Gln His Leu Phe Ala Phe<br>275 280 285 | | 864 |
| cct ctc ttc gct ctt atg acc att tcc aag gtg ctc acc agc gac ttt<br>Pro Leu Phe Ala Leu Met Thr Ile Ser Lys Val Leu Thr Ser Asp Phe<br>290 295 300 | | 912 |
| gct gtt tgt ctc tcc atg aaa aag ggt tct atc gac tgt tcg tcc aga<br>Ala Val Cys Leu Ser Met Lys Lys Gly Ser Ile Asp Cys Ser Ser Arg<br>305 310 315 320 | | 960 |
| ctg gtt cca ctc gaa ggc cag ctg ttg ttc tgg gga gcc aag ctg gcg<br>Leu Val Pro Leu Glu Gly Gln Leu Leu Phe Trp Gly Ala Lys Leu Ala<br>325 330 335 | | 1008 |
| aac ttt ctc ttg cag att gtg ctg ccc tgc tac ctc cac gga act gct<br>Asn Phe Leu Leu Gln Ile Val Leu Pro Cys Tyr Leu His Gly Thr Ala<br>340 345 350 | | 1056 |
| atg ggc ctt gct ctg ttc tct gtt gcc cac ctt gtg tct gga gag tac<br>Met Gly Leu Ala Leu Phe Ser Val Ala His Leu Val Ser Gly Glu Tyr<br>355 360 365 | | 1104 |
| ctg gcc atc tgt ttc atc att aac cac atc tcc gag tct tgc gaa ttt<br>Leu Ala Ile Cys Phe Ile Ile Asn His Ile Ser Glu Ser Cys Glu Phe<br>370 375 380 | | 1152 |
| atg aat acc tcc ttt caa act gct gcc cga cgg acc gag atg ctc cag<br>Met Asn Thr Ser Phe Gln Thr Ala Ala Arg Arg Thr Glu Met Leu Gln<br>385 390 395 400 | | 1200 |
| gca gct cat cag gca gcc gag gcg aaa aag gtc aag ccc act cct cca<br>Ala Ala His Gln Ala Ala Glu Ala Lys Lys Val Lys Pro Thr Pro Pro<br>405 410 415 | | 1248 |
| ccc aac gat tgg gct gtg aca caa gtc cag tgc tgt gtc aac tgg cga<br>Pro Asn Asp Trp Ala Val Thr Gln Val Gln Cys Cys Val Asn Trp Arg<br>420 425 430 | | 1296 |
| tct gga ggc gtg ctg gcc aat cac ctc tcc ggt ggc ctc aac cat cag<br>Ser Gly Gly Val Leu Ala Asn His Leu Ser Gly Gly Leu Asn His Gln<br>435 440 445 | | 1344 |
| atc gag cac cat ctg ttt ccc agc atc tct cac gcg aac tat ccc atc<br>Ile Glu His His Leu Phe Pro Ser Ile Ser His Ala Asn Tyr Pro Ile<br>450 455 460 | | 1392 |
| att gct cga gtt gtc aag gaa gtg tgc gag gaa tac gga ttg ccc tac<br>Ile Ala Arg Val Val Lys Glu Val Cys Glu Glu Tyr Gly Leu Pro Tyr<br>465 470 475 480 | | 1440 |
| aag aac tac gtt acg ttc tgg gat gcc gtg tgt ggc atg gtt cag cat<br>Lys Asn Tyr Val Thr Phe Trp Asp Ala Val Cys Gly Met Val Gln His<br>485 490 495 | | 1488 |
| ctg cga ctc atg ggt gct cct ccc gtg cct acc aac ggc gac aaa aag<br>Leu Arg Leu Met Gly Ala Pro Pro Val Pro Thr Asn Gly Asp Lys Lys<br>500 505 510 | | 1536 |
| tcc taa<br>Ser | | 1542 |

<210> SEQ ID NO 61
<211> LENGTH: 513
<212> TYPE: PRT
<213> ORGANISM: Euglena gracilis

<400> SEQUENCE: 61

Met Ala Lys Pro Gln Pro Cys Glu Asn Gly Thr Val Glu Lys Arg Glu

-continued

```
1               5               10              15
Asn Asp Thr Ala Asn Val Arg Pro Ala Arg Pro Ala Gly Leu Pro Pro
                20              25              30
Ala Thr Tyr Tyr Asp Ser Leu Ala Val Ser Gly Gln Gly Lys Glu Arg
                35              40              45
Leu Phe Thr Thr Asp Glu Val Arg Arg His Ile Leu Pro Thr Asp Gly
 50              55              60
Trp Leu Thr Cys His Glu Gly Val Tyr Asp Val Thr Asp Phe Leu Ala
 65              70              75              80
Lys His Pro Gly Gly Val Ile Thr Leu Gly Leu Gly Arg Asp Cys
                85              90              95
Thr Ile Leu Val Glu Ser Tyr His Pro Ala Gly Arg Pro Asp Lys Val
                100             105             110
Met Glu Lys Tyr Arg Ile Gly Thr Leu Gln Asp Pro Lys Thr Phe Tyr
                115             120             125
Ala Trp Gly Glu Ser Asp Phe Tyr Pro Glu Leu Lys Arg Arg Ala Leu
                130             135             140
Ala Arg Leu Lys Glu Ala Gly Gln Ala Arg Arg Gly Gly Leu Gly Val
145             150             155             160
Lys Ala Leu Leu Val Leu Thr Leu Phe Phe Val Ser Trp Tyr Met Trp
                165             170             175
Val Ala His Lys Ser Phe Leu Trp Ala Ala Val Trp Gly Phe Ala Gly
                180             185             190
Ser His Val Gly Leu Ser Ile Gln His Asp Gly Asn His Gly Ala Phe
                195             200             205
Ser Arg Ser Thr Leu Val Asn Arg Leu Ala Gly Trp Gly Met Asp Leu
                210             215             220
Ile Gly Ala Ser Ser Thr Val Trp Glu Tyr Gln His Val Ile Gly His
225             230             235             240
His Gln Tyr Thr Asn Leu Val Ser Asp Thr Leu Phe Ser Leu Pro Glu
                245             250             255
Asn Asp Pro Asp Val Phe Ser Ser Tyr Pro Leu Met Arg Met His Pro
                260             265             270
Asp Thr Ala Trp Gln Pro His His Arg Phe Gln His Leu Phe Ala Phe
                275             280             285
Pro Leu Phe Ala Leu Met Thr Ile Ser Lys Val Leu Thr Ser Asp Phe
                290             295             300
Ala Val Cys Leu Ser Met Lys Lys Gly Ser Ile Asp Cys Ser Ser Arg
305             310             315             320
Leu Val Pro Leu Glu Gly Gln Leu Leu Phe Trp Gly Ala Lys Leu Ala
                325             330             335
Asn Phe Leu Leu Gln Ile Val Leu Pro Cys Tyr Leu His Gly Thr Ala
                340             345             350
Met Gly Leu Ala Leu Phe Ser Val Ala His Leu Val Ser Gly Glu Tyr
                355             360             365
Leu Ala Ile Cys Phe Ile Ile Asn His Ile Ser Glu Ser Cys Glu Phe
                370             375             380
Met Asn Thr Ser Phe Gln Thr Ala Ala Arg Thr Glu Met Leu Gln
385             390             395             400
Ala Ala His Gln Ala Ala Glu Ala Lys Lys Val Lys Pro Thr Pro Pro
                405             410             415
Pro Asn Asp Trp Ala Val Thr Gln Val Gln Cys Cys Val Asn Trp Arg
                420             425             430
```

```
Ser Gly Gly Val Leu Ala Asn His Leu Ser Gly Gly Leu Asn His Gln
            435                 440                 445

Ile Glu His His Leu Phe Pro Ser Ile Ser His Ala Asn Tyr Pro Ile
        450                 455                 460

Ile Ala Arg Val Val Lys Glu Val Cys Glu Glu Tyr Gly Leu Pro Tyr
465                 470                 475                 480

Lys Asn Tyr Val Thr Phe Trp Asp Ala Val Cys Gly Met Val Gln His
                485                 490                 495

Leu Arg Leu Met Gly Ala Pro Pro Val Pro Thr Asn Gly Asp Lys Lys
            500                 505                 510

Ser

<210> SEQ ID NO 62
<211> LENGTH: 15617
<212> TYPE: DNA
<213> ORGANISM: Artificial Sequence
<220> FEATURE:
<223> OTHER INFORMATION: Plasmid pZKLY-G20444

<400> SEQUENCE: 62
aattctctct cttgagcttt tccataacaa gttcttctgc ctccaggaag tccatgggtg      60
gtttgatcat ggttttggtg tagtggtagt gcagtggtgg tatttgtgact ggggatgtag    120
ttgagaataa gtcatacaca agtcagcttt cttcgagcct catataagta taagtagttc     180
aacgtattag cactgtaccc agcatctccg tatcgagaaa cacaacaaca tgccccattg     240
gacagatcat gcggatacac aggttgtgca gtatcataca tactcgatca gacaggtcgt    300
ctgaccatca tacaagctga acaagcgctc catacttgca cgctctctat atacacagtt    360
aaattacata tccatagtct aacctctaac agttaatctt ctggtaagcc tcccagccag    420
ccttctggta tcgcttggcc tcctcaatag gatctcggtt ctggccgtac agacctcggc    480
cgacaattat gatatccgtt ccggtagaca tgacatcctc aacagttcgg tactgctgtc    540
cgagagcgtc tcccttgtcg tcaagaccca ccccggggt cagaataagc cagtcctcag      600
agtcgccctt aggtcggttc tgggcaatga agccaaccac aaactcgggg tcggatcggg    660
caagctcaat ggtctgcttg gagtactcgc cagtggccag agagcccttg caagacagct    720
cggccagcat gagcagacct ctggccagct tctcgttggg agaggggact aggaactcct    780
tgtactggga gttctcgtag tcagagacgt cctccttctt ctgttcagag acagtttcct    840
cggcaccagc tcgcaggcca gcaatgattc cggttccggg tacaccgtgg gcgttggtga    900
tatcggacca ctcggcgatt cggtgacacc ggtactggtg cttgacagtg ttgccaatat    960
ctgcgaactt tctgtcctcg aacaggaaga aaccgtgctt aagagcaagt tccttgaggg   1020
ggagcacagt gccggcgtag gtgaagtcgt caatgatgtc gatatgggtt ttgatcatgc   1080
acacataagg tccgacctta tcggcaagct caatgagctc cttggtggtg gtaacatcca   1140
gagaagcaca caggttggtt ttcttggctg ccacgagctt gagcactcga gcggcaaagg   1200
cggacttgtg gacgttagct cgagcttcgt aggagggcat tttggtggtg aagaggagac   1260
tgaaataaat ttagtctgca gaacttttta tcggaacctt atctgggca gtgaagtata    1320
tgttatggta atagttacga gttagttgaa cttatagata gactggacta tacggctatc   1380
ggtccaaatt agaaagaacg tcaatggctc tctgggcgtc gcctttgccg acaaaaatgt   1440
gatcatgatg aaagccagca atgacgttgc agctgatatt gttgtcggcc aaccgcgccg   1500
aaaacgcagc tgtcagaccc acagcctcca acgaagaatg tatcgtcaaa gtgatccaag   1560
```

```
cacactcata gttggagtcg tactccaaag gcggcaatga cgagtcagac agatactcgt    1620
cgaccttttc cttgggaacc accaccgtca gcccttctga ctcacgtatt gtagccaccg    1680
acacaggcaa cagtccgtgg atagcagaat atgtcttgtc ggtccatttc tcaccaactt    1740
taggcgtcaa gtgaatgttg cagaagaagt atgtgccttc attgagaatc ggtgttgctg    1800
atttcaataa agtcttgaga tcagtttggc cagtcatgtt gtgggggta attggattga     1860 gttatcgcct acagtctgta caggtatact cgctgcccac tttatacttt ttgattccgc    1920
tgcacttgaa gcaatgtcgt ttaccaaaag tgagaatgct ccacagaaca cacccccaggg  1980 tatggttgag caaaaaataa acactccgat acggggaatc gaaccccggt ctccacggtt    2040
ctcaagaagt attcttgatg agagcgtatc gatggttaat gctgctgtgt gctgtgtgtg    2100
tgtgttgttt ggcgctcatt gttgcgttat gcagcgtaca ccacaatatt ggaagcttat    2160
tagcctttct attttttcgt ttgcaaggct taacaacatt gctgtggaga gggatgggga    2220
tatggaggcc gctggaggga gtcggagagg cgttttggag cggcttggcc tggcgcccag    2280
ctcgcgaaac gcacctagga ccctttggca cgccgaaatg tgccactttt cagtctagta    2340
acgccttacc tacgtcattc catgcgtgca tgtttgcgcc ttttttccct tgcccttgat    2400
cgccacacag tacagtgcac tgtacagtgg aggttttggg ggggtcttag atgggagcta    2460
aaagcggcct agcggtacac tagtgggatt gtatggagtg gcatggagcc taggtggagc    2520
ctgacaggac gcacgaccgg ctagcccgtg acagacgatg ggtggctcct gttgtccacc    2580
gcgtacaaat gtttgggcca aagtcttgtc agccttgctt gcgaacctaa ttcccaattt    2640
tgtcacttcg caccccattt gatcgagccc taaccctgc ccatcaggca atccaattaa    2700
gctcgcattg tctgccttgt ttagtttggc tcctgcccgt ttcggcgtcc acttgcacaa    2760
acacaaacaa gcattatata taaggctcgt ctctccctcc caaccacact cactttttg     2820 cccgtcttcc cttgctaaca caaaagtcaa gaacacaaac aaccacccca accccccttac   2880 acacaagaca tatctacagc aatggccatg gccaaggtca aacccggtgg acctggcaag    2940
ccctcggaga tcgcttctct tccacctccc attcgacctg ttggcaaccc acctgcagcc    3000
tattacgacg ctctggccac ctccggtact ggacaggacc gaaagtttac catgcgagag    3060
gtcgctcgac acattgttcc caccgatggc tggttggcct gtcacgacgg tgtgtacgac    3120
atcaccgagt tcattggcaa gcatcccggt ggagatgtta tctctctcgg tctcggacga    3180
gactccacta ttctggtcga atcgtaccat cctgcaggac gacccgacaa ggttatggag    3240
aagtaccgaa tcggtacact tcaggatcac agaaccttct acgactggca ggcctccgct    3300
ttctacgccg agctcaagca gcgagtggtt cagactctca aggaggctgg acaacctcga    3360
cgtggtggcc tgtctgtcaa ggcagccctt gttatggctg cctttgctgc ctcgttctac    3420
ctcatggtga cacagggatc cttcttttgg gctgccgtct ggggtctggc aggctctcac    3480
attggactca gcatccagca cgacggcaat catggtgctt tctccaagtc tggacgactc    3540
aaccgtcttg ctggctgggg tatggacgtt atcggagcct cctcgactgc ctgggagtac    3600
caaacgtcat tggtcatca ccagtacacc aacctggtgt ccgatcccga gtttgctctt    3660
cccgagaacg atccagacgt tttcggaacc tatcccctca tgcggatgca tccggacact    3720
ccttggaaac cccaccatca gctgcaacac gtgtacgcct ttccgttgtt cgctctcatg    3780
accatcagca aggtcattat ctccgatttc acgttttgtc ttgccaagcg acgtggtccc    3840
atcgacttct ctgccagact cgttcccctc gagggtcaga tgctgttctg gggtgcaaag    3900
```

```
atcatgggct ttctcatgca gattgtgctt ccctgctacc tgcatggcat cgctcacgga    3960
ttggccctct tcattacagc tcatctggtt tctggcgagt accttgccgt ctgtttcatt    4020
atcaaccaca tttccgagtc gtgcgactac ctcaatccct cttccgttat cgctgcccga    4080
cggaccgaaa tgctcaagca ggccgagcag gaagccaagg cgaaacagaa gcaccccact    4140
ccacctccca acgactgggc tgcctcccaa gttctgtgtt gcgtcaactg gcgatctggt    4200
ggctactttt caaaccacct ttctggtgga ctcaaccacc agatcgagca tcacctgttt    4260
cccagcattt ctcacgccaa ctatcccacc attgctcctg ttgtcaaggg cgtgtgcgag    4320
gaatacggtc ttccctacaa gaactactct cagttttccg atgctctgta cggaatggtc    4380
gagcacttgc gagctatggg caccaaacct gcagacaacg acaagcttgc tcccactgca    4440
ggttccctgg aggatgtttg tcctgtgctc tctgctgccg ttgctgccca acccgacggc    4500
tccaccgacg gatctgctgc cggttgtcct gctgtcgcca ctctggctta agcggccgca    4560
ttgatgattg gaaacacaca catgggttat atctaggtga gagttagttg gacagttata    4620
tattaaatca gctatgccaa cggtaacttc attcatgtca acgaggaacc agtgactgca    4680
agtaatatag aatttgacca ccttgccatt ctccttgcact cctttactat atctcattta    4740
tttcttatat acaaatcact tcttcttccc agcatcgagc tcggaaacct catgagcaat    4800
aacatcgtgg atctcgtcaa tagagggctt tttggactcc ttgctgttgg ccacttgtc     4860
cttgctgttt aaacagagtg tgaaagactc actatggtcc gggcttatct cgaccaatag    4920
ccaaagtctg gagtttctga gagaaaaagg caagatacgt atgtaacaaa gcgacgcatg    4980
gtacaataat accggaggca tgtatcatag agagttagtg gttcgatgat ggcactggtg    5040
cctggtatga ctttatacgg ctgactacat atttgtcctc agacatacaa ttacagtcaa    5100
gcacttaccc ttggacatct gtaggtaccc cccggccaag acgatctcag cgtgtcgtat    5160
gtcggattgg cgtagctccc tcgctcgtca attggctccc atctactttc ttctgcttgg    5220
ctacacccag catgtctgct atggctcgtt ttcgtgcctt atctatcctc ccagtattac    5280
caactctaaa tgacatgatg tgattgggtc tacactttca tatcagagat aaggagtagc    5340
acagttgcat aaaaagccca actctaatca gcttcttcct ttcttgtaat tagtacaaag    5400
gtgattagcg aaatctggaa gcttagttgg ccctaaaaaa atcaaaaaaa gcaaaaaacg    5460
aaaaacgaaa aaccacagtt ttgagaacag ggaggtaacg aaggatcgta tatatatata    5520
tatatatata tacccacgga tcccgagacc ggcctttgat tcttccctac aaccaaccat    5580
tctcaccacc ctaattcaca accatggctg actctcccgt catcaacctc tccaccatgt    5640
ggaagcctct gtcgctcatg gccttggatc ttgctgttct gggacacgtc tggaagcagg    5700
cacaacagga gggctccatc tcggcttacg ccgactctgt gtggactccc ctcatcatgt    5760
ccggtctgta cctctccatg atcttcgtgg gatgtcgatg gatgaagaac cgagagccct    5820
tcgaaatcaa gacctacatg tttgcctaca acctgtacca gaccctcatg aacctttgca    5880
ttgtgctggg cttcctctac caggtccacg ctaccggtat gcgattctgg ggatctggcg    5940
tggaccgatc gcccaagggt ctgggaattg gcttttcat ctatgcccat taccacaaca    6000
agtacgtcga gtacttcgac acactcttca tggtgctgcg gaaaaagaac aaccagattt    6060
cctttcttca cgtctaccat cacgctctgc tcacctgggc ttggtttgcc gtggtctact    6120
tcgctcctgg aggtgacggc tggtttggag cctgctacaa ttcctccatt catgtcctga    6180
tgtactctta ctatctgctt gccacctctg gcatctcctg tccctgggaa aagatcctca    6240
cccagctgca aatggttcag ttctgctttt gcttcaccca ctcgatctac gtgtggattt    6300
```

```
gcggttccga aatctaccct cgacccttga ctgctctcca gtccttcgtg atggtcaaca    6360
tgctggttct ctttggcaac ttctacgtca agcagtattc tcagaagaat ggaaagcccg    6420
agaacggtgc cactcctgag aacggtgcca agcctcagcc ctgcgagaac ggtaccgtgg    6480
agaagcgaga aaacgacacc gccaatgttc gacccgctag acctgccggt cttccacccg    6540
caacttacta tgactctctc gccgtgtcgg gacagggcaa ggagcgactg ttcaccacag    6600
acgaggtcag acgacacatt cttcccaccg atggatggct cacctgtcac gaaggtgtgt    6660
acgacgtcac cgatttcctg gccaagcatc ctggaggtgg cgtcatcact ctcggacttg    6720
gtcgagactg caccattctg gtcgagtcct accatcccgc tggacgacca gacaaggtca    6780
tggagaagta ccgtatcggc acactccagg atcccaagac tttctacgct tggggagaat    6840
cggactttta ccctgagctc aaacgacggg ctcttgcacg actcaaggag ctggacagg     6900 cacgtcgagg tggactggga gtcaaggctc tcctggtgct tacctcttc tttgtctcct     6960 ggtacatgtg ggttgcccac aagtctttcc tgtgggctgc cgtctgggc tttgccggtt     7020 cgcatgtcgg actgagcatt caacacgatg caaccacgg tgctttctct cgatccaccc     7080
tggtcaacag actcgcagga tggggcatgg acttgatcgg tgcctcgtcc accgtgtggg    7140
agtaccagca tgtcattgga caccatcagt acacgaatct cgtttccgat acgctgttca    7200
gccttcccga gaacgaccca gatgtgtttt ccagctatcc tctcatgcga atgcatcccg    7260
acactgcttg gcagcctcat caccgatttc aacacctgtt cgcctttcct ctcttcgctc    7320
ttatgaccat ttccaaggtg ctcaccagcg actttgctgt ttgtctctcc atgaaaaagg    7380
gttctatcga ctgttcgtcc agactggttc cactcgaagg ccagctgttg ttctggggag    7440
ccaagctggc gaactttctc ttgcagattg tgctgccctg ctacctccac ggaactgcta    7500
tgggccttgc tctgttctct gttgcccacc ttgtgtctgg agagtacctg gccatctgtt    7560
tcatcattaa ccacatctcc gagtcttgcg aatttatgaa tacctccttt caaactgctg    7620
cccgacggac cgagatgctc caggcagctc atcaggcagc cgaggcgaaa aaggtcaagc    7680
ccactcctcc acccaacgat tgggctgtga cacaagtcca gtgctgtgtc aactggcgat    7740
ctggaggcgt gctggccaat cacctctccg gtggcctcaa ccatcagatc gagcaccatc    7800
tgtttcccag catctctcac gcgaactatc ccatcattgc tcgagttgtc aaggaagtgt    7860
gcgaggaata cggattgccc tacaagaact acgttacgtt ctgggatgcc gtgtgtggca    7920
tggttcagca tctgcgactc atgggtgctc ctcccgtgcc taccaacggc gacaaaaagt    7980
cctaagcggc cgcatgagaa gataaatata taaatacatt gagatattaa atgcgctaga    8040
ttagagagct tcatactgct cggagagaag ccaagacgag tactcaaagg ggattacacc    8100
atccatatcc acagacacaa gctggggaaa ggttctatat acactttccg gaataccgta    8160
gtttccgatg ttatcaatgg gggcagccag gatttcaggc acttcggtgt ctcggggtga    8220
aatggcgttc ttggcctcca tcaagtcgta ccatgtcttc atttgcctgt caaagtaaaa    8280
cagaagcaga tgaagaatga acttgaagtg aaggaattta aatgtaacga aactgaaatt    8340
tgaccagata ttgtgtccgc ggtggagctc cagcttttgt tccctttagt gagggttaat    8400
ttcgagcttg gcgtaatcat ggtcatagct gtttcctgtg tgaaattgtt atccgctcac    8460
aagcttccac acaacgtacg ttgattgagg tggagccaga tgggctattg tttcatatat    8520
agactggcag ccacctcttt ggcccagcat gtttgtatac ctggaaggga aaactaaaga    8580
agctggctag tttagtttga ttattatagt agatgtccta atcactagag attagaatgt    8640
```

```
cttggcgatg attagtcgtc gtccctgta tcatgtctag accaactgtg tcatgaagtt    8700
ggtgctggtg ttttacctgt gtactacaag taggtgtcct agatctagtg tacagagccg    8760
tttagaccca tgtggacttc accattaacg atggaaaatg ttcattatat gacagtatat    8820
tacaatggac ttgctccatt tcttccttgc atcacatgtt ctccacctcc atagttgatc    8880
aacacatcat agtagctaag gctgctgctc tcccactaca gtccaccaca agttaagtag    8940
caccgtcagt acagctaaaa gtacacgtct agtacgtttc ataactagtc aagtagcccc    9000
tattacagat atcagcacta tcacgcacga gttttctct gtgctatcta atcaacttgc     9060
caagtattcg gagaagatac actttcttgg catcaggtat acgagggagc ctatcagatg    9120
aaaaagggta tattggatcc attcatatcc acctacacgt tgtcataatc tcctcattca    9180
cgtgattcat ttcgtgacac tagtttctca ctttccccc cgcacctata gtcaacttgg     9240
cggacacgct acttgtagct gacgttgatt tatagaccca atcaaagcgg ttatcggtc     9300
aggtagcact tatcattcat cgttcatact acgatgagca atctcgggca tgtccggaaa    9360
agtgtcgggc gcgccagctg cattaatgaa tcggccaacg cgcggggaga ggcggtttgc    9420
gtattgggcg ctcttccgct tcctcgctca ctgactcgct gcgctcggtc gttcggctgc    9480
ggcgagcggt atcagctcac tcaaaggcgg taatacggtt atccacagaa tcaggggata    9540
acgcaggaaa gaacatgtga gcaaaaggcc agcaaaaggc caggaaccgt aaaaaggccg    9600
cgttgctggc gtttttccat aggctccgcc cccctgacga gcatcacaaa aatcgacgct    9660
caagtcagag gtggcgaaac ccgacaggac tataaagata ccaggcgttt cccctggaa     9720
gctccctcgt gcgctctcct gttccgaccc tgccgcttac cggatacctg tccgcctttc    9780
tcccttcggg aagcgtggcg ctttctcata gctcacgctg taggtatctc agttcggtgt    9840
aggtcgttcg ctccaagctg ggctgtgtgc acgaaccccc cgttcagccc gaccgctgcg    9900
ccttatccgg taactatcgt cttgagtcca acccggtaag acacgactta tcgccactgg    9960
cagcagccac tggtaacagg attagcagag cgaggtatgt aggcggtgct acagagttct   10020
tgaagtggtg gcctaactac ggctacacta gaagaacagt atttggtatc tgcgctctgc   10080
tgaagccagt taccttcgga aaaagagttg gtagctcttg atccggcaaa caaaccaccg   10140
ctggtagcgg tggttttttt gtttgcaagc agcagattac gcgcagaaaa aaaggatctc   10200
aagaagatcc tttgatcttt tctacggggt ctgacgctca gtggaacgaa aactcacgtt   10260
aagggatttt ggtcatgaga ttatcaaaaa ggatcttcac ctagatcctt ttaaattaaa   10320
aatgaagttt taaatcaatc taaagtatat atgagtaaac ttggtctgac agttaccaat   10380
gcttaatcag tgaggcacct atctcagcga tctgtctatt tcgttcatcc atagttgcct   10440
gactccccgt cgtgtagata actacgatac gggagggctt accatctggc cccagtgctg   10500
caatgatacc gcgagaccca cgctcaccgg ctccagattt atcagcaata aaccagccag   10560
ccggaagggc cgagcgcaga agtggtcctg caactttatc cgcctccatc cagtctatta   10620
attgttgccg ggaagctaga gtaagtagtt cgccagttaa tagtttgcgc aacgttgttg   10680
ccattgctac aggcatcgtg gtgtcacgct cgtcgtttgg tatggcttca ttcagctccg   10740
gttcccaacg atcaaggcga gttacatgat cccccatgtt gtgcaaaaaa gcggttagct   10800
ccttcggtcc tccgatcgtt gtcagaagta agttggccgc agtgttatca ctcatggtta   10860
tggcagcact gcataattct cttactgtca tgccatccgt aagatgcttt tctgtgactg   10920
gtgagtactc aaccaagtca ttctgagaat agtgtatgcg gcgaccgagt tgctcttgcc   10980
cggcgtcaat acgggataat accgcgccac atagcagaac tttaaaagtg ctcatcattg   11040
```

```
gaaaacgttc ttcggggcga aaactctcaa ggatcttacc gctgttgaga tccagttcga   11100
tgtaacccac tcgtgcaccc aactgatctt cagcatcttt tactttcacc agcgtttctg   11160
ggtgagcaaa acaggaagg caaaatgccg caaaaaggg aataagggcg acacggaaat    11220
gttgaatact catactcttc cttttcaat attattgaag catttatcag ggttattgtc    11280
tcatgagcgg atacatattt gaatgtattt agaaaaataa acaaataggg gttccgcgca   11340
catttccccg aaaagtgcca cctgatgcgg tgtgaaatac cgcacagatg cgtaaggaga   11400
aaataccgca tcaggaaatt gtaagcgtta atattttgtt aaaattcgcg ttaaatttt    11460 gttaaatcag ctcatttttt aaccaatagg ccgaaatcgg caaaatccct tataaatcaa   11520
aagaatagac cgagataggg ttgagtgttg ttccagtttg gaacaagagt ccactattaa   11580
agaacgtgga ctccaacgtc aaagggcgaa aaaccgtcta tcagggcgat ggcccactac   11640
gtgaaccatc accctaatca agttttttgg ggtcgaggtg ccgtaaagca ctaaatcgga   11700
accctaaagg gagcccccga tttagagctt gacggggaaa gccggcgaac gtggcgagaa   11760
aggaagggaa gaaagcgaaa ggagcgggcg ctagggcgct ggcaagtgta gcggtcacgc   11820
tgcgcgtaac caccacaccc gccgcgctta atgcgccgct acagggcgcg tccattcgcc   11880
attcaggctg cgcaactgtt gggaagggcg atcggtgcgg gcctcttcgc tattacgcca   11940
gctggcgaaa gggggatgtg ctgcaaggcg attaagttgg gtaacgccag ggttttccca   12000
gtcacgacgt tgtaaaacga cggccagtga attgtaatac gactcactat agggcgaatt   12060
gggcccgacg tcgcatgcat ccgacagca gcgactgggc accatgatca agcgaaacac   12120
cttcccccag ctgccctggc aaaccatcaa gaaccctact ttcatcaagt gcaagaacgg   12180
ttctactctt ctcacctccg gtgtctacgc tggtgccga aagcctaact acaccgctga   12240
tttcatcatg tgcctcacct gggctctcat gtgcggtgtt gcttctcccc tgccttactt   12300
ctacccggtc ttcttcttcc tggtgctcat ccaccgagct taccgagact ttgagcgact   12360
ggagcgaaag tacggtgagg actaccagga gttcaagcga caggtcccctt ggatcttcat   12420 cccttatgtt ttctaaacga taagcttagt gagcgaatgg tgaggttact taattgagtg   12480
gccagcctat gggattgtat aacagacagt caatatatta ctgaaaagac tgaacagcca   12540
gacggagtga ggttgtgagt gaatcgtaga gggcggctat tacagcaagt ctactctaca   12600
gtgtactaac acagcagaga acaaatacag gtgtgcattc ggctatctga gaattagttg   12660
gagagctcga gaccctcggc gataaactgc tcctcggttt tgtgtccata cttgtacgga   12720
ccattgtaat ggggcaagtc gttgagttct cgtcgtccga cgttcagagc acagaaacca   12780
atgtaatcaa tgtagcagag atggttctgc aaaagattga tttgtgcgag caggttaatt   12840
aaaaggcgtt gaaacagaat gagccagttt aaacagcaag acaaggtgg ccaacagcaa    12900 ggagtccaaa aagcccctcta ttgacgagat ccacgatgtt attgctcatg aggtttccga   12960
gctcgatgct gggaagaaga agtgatttgt atataagaaa taaatgagat atagtaaagg   13020
agtgcaagag aatggcaagg tggtcaaatt ctatattact tgcagtcact ggttcctcgt   13080
tgacatgaat gaagttaccg ttggcatagc tgatttaata tataactgtc caactaactc   13140
tcacctagat ataacccatg tgtgtgtttc caatcatcaa tgcggccgct taagcgacct   13200
ttttctcgtt tccgaggtac ttgagatgag acagcatctt gccataggcg gagaacaaag   13260
agggttcgga ctggtaagga acaccgtact cttcgcaagt cttctggaca acgtcctgga   13320
tgtgagcgta gttggtgtga caaatgctgg gaaacagatg gtgctcgatc tggtgggaga   13380
```

```
ggccaccgga gaagtgattc cagaaccacg atccaggaga ccagttgacg ctcgtttgac    13440
actgaacggc agcccagtcg ttgtagggaa catccttgac gttgcctcca ttggcagcct    13500
ttttggcctc ggcacgggtc tgctccattg gagttcgtcc agaaacggtt gtaggcttga    13560
actccacgtc cttggacaga ccgagagatt ctcccttttt gccaaaggac acaccctcga    13620
tgacgtgatt gacaatgaac atggttgcca gaagctctcc acaggcaaag tggccgatga    13680
gaaacagtcc aaggccacca aggattccgt ggaagtagca gggaacagcc agcatgtagc    13740
cgatggagag caccttcatc gaccaaaacc gaggacatt gagaatggaa ttgtatcggc    13800
acttggcgtc gatgtggtac agtcgctgag tggtagcgac ttcgatgtcc tgttggaaca    13860
ccttggcaag agtcatgaaa gcaaagagaa cgggtgcgta caggtgctga tatcggtggt    13920
accactcggc cttgtggtag gggtgcattc gcatgagagg aaacgaagag aagcatctg    13980 ggtcggactc ctgatccttg tcctccatag gacaatcgtc gccagcttcc tttcgcttct    14040
cttcgtccac gtccaggacg ttggtgtagg atggtgtcc gagcatatgc tgaatctccc    14100
atgtaaagcc agaagcaccg atcatgtcca gagtccagcc tgcaaccttg ttgagagcag    14160
ggctggtcga gaaggcaccg tggtttccat cgtgttgaat gcaagtgccg atgaaggcag    14220
caaagactcc catagacacg gaccacagcg aggcagccca gtaggtctcg ttgacggaca    14280
tcttgtagag gctgaaccag aatccagcca ggaggaatac tgccttgacc caaatctcgt    14340
agccacctct tcgaggcagg ttgagcttgt ccaatcgctc gaccactcga gctcgcaggg    14400
tcttgtaaaa gtcggaatcc cacgagtaga acgaggaggg aagttctccg tccttcatct    14460
tgccgacctg cagcttgtcg aggatcgagg tgggaacacc tcgaggatgg taagtctcga    14520
agagcacggt ggcatccttt cctgcggcaa gcagaatgat gtcgccacca ggatgccgtc    14580
gggcgaactc ggtaatgttg atgactctgc cgtggacggc agcccaggca tcctggggaa    14640
cgttgtgaga ccgcagctcg tctcgggaga tgagtcggtt cttgtcgaga gacttgtcgg    14700
tggcagcagt gtcggcagcc ttggtggact gagccatggt accagagctg ggttagtttg    14760
tgtagagagt gtgtgttgct agcgactttc ggattgtgtc attacacaaa acgcgtcgtc    14820
tcgacactga tcttgtcgtg gatactcacg gctcggaact ctgtgatgtg tagtttagat    14880
ttcgaatctg tggggaaaga aaggaaaaaa gagactggca accgattggg agagccactg    14940
tttatatata ccctagacaa gccccccgct tgtaagatgt tggtcaatgt aaaccagtat    15000
taaggttggc aagtcagga gaagcaaggt gtgggtaccg agcaatggaa atgtgcggaa    15060
ggcaaaaaaa tgaggccacg gcctattgtc ggggctatat ccaggggcg attgaagtac    15120 actaacatga catgtgtcca cagaccctca atctggcctg atgagccaaa tccatacgcg    15180
ctttcgcagc tctaaaggct ataacaagtc acaccaccct gctcgacctc agcgccctca    15240
ctttttgtta agacaaactg tacacgctgt tccagcgttt tctgcctgca cctggtggga    15300
catttggtgc aacctaaagt gctcggaacc tctgtggtgt ccagatcagc gcagcagttc    15360
cgaggtagtt ttgaggccct tagatgatgc aatggtgtca gtcgctggat cacgagtctt    15420
aatggcagta ttcgttctta tttgtgccat tgagccccgt tatcctcgta tcttctaccc    15480
cccatcccat cccttttgttg gtgcaaccct accatttat tgttgggtgc agcccaaccg    15540
acgtggagag cttggcttgg ccatataaaa aggcccccc ctagtggcaa tggcagaaag    15600
tcagctgtga gttgttg                                                    15617
```

<210> SEQ ID NO 63
<211> LENGTH: 2382

```
<212> TYPE: DNA
<213> ORGANISM: Euglena gracilis
<220> FEATURE:
<221> NAME/KEY: CDS
<222> LOCATION: (1)..(2382)
<223> OTHER INFORMATION: synthetic DHA synthase (codon-optimized for
      Yarrowia lipolytica)
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: U.S. Pat. Pub. No. 2008-0254191-A1
<311> PATENT FILING DATE: 2008-04-03
<312> PUBLICATION DATE: 2008-10-16
<313> RELEVANT RESIDUES IN SEQ ID NO: (1)..(2382)
<300> PUBLICATION INFORMATION:
<302> TITLE: MULTIZYMES AND THEIR USE IN MAKING POLYUNSATURATED FATTY
      ACIDS
<310> PATENT DOCUMENT NUMBER: WO 2008/124048
<311> PATENT FILING DATE: 2008-04-03
<312> PUBLICATION DATE: 2008-10-16
<313> RELEVANT RESIDUES IN SEQ ID NO: (1)..(2382)

<400> SEQUENCE: 63 atg gct gac tct ccc gtc atc aac ctc tcc acc atg tgg aag cct ctg      48
Met Ala Asp Ser Pro Val Ile Asn Leu Ser Thr Met Trp Lys Pro Leu
1               5                   10                  15 tcg ctc atg gcc ttg gat ctt gct gtt ctg gga cac gtc tgg aag cag      96
Ser Leu Met Ala Leu Asp Leu Ala Val Leu Gly His Val Trp Lys Gln
            20                  25                  30 gca caa cag gag ggc tcc atc tcg gct tac gcc gac tct gtg tgg act     144
Ala Gln Gln Glu Gly Ser Ile Ser Ala Tyr Ala Asp Ser Val Trp Thr
        35                  40                  45 ccc ctc atc atg tcc ggt ctg tac ctc tcc atg atc ttc gtg gga tgt     192
Pro Leu Ile Met Ser Gly Leu Tyr Leu Ser Met Ile Phe Val Gly Cys
    50                  55                  60 cga tgg atg aag aac cga gag ccc ttc gaa atc aag acc tac atg ttt     240
Arg Trp Met Lys Asn Arg Glu Pro Phe Glu Ile Lys Thr Tyr Met Phe
65                  70                  75                  80 gcc tac aac ctg tac cag acc ctc atg aac ctt tgc att gtg ctg ggc     288
Ala Tyr Asn Leu Tyr Gln Thr Leu Met Asn Leu Cys Ile Val Leu Gly
                85                  90                  95 ttc ctc tac cag gtc cac gct acc ggt atg cga ttc tgg gga tct ggc     336
Phe Leu Tyr Gln Val His Ala Thr Gly Met Arg Phe Trp Gly Ser Gly
            100                 105                 110 gtg gac cga tcg ccc aag ggt ctg gga att ggc ttt ttc atc tat gcc     384
Val Asp Arg Ser Pro Lys Gly Leu Gly Ile Gly Phe Phe Ile Tyr Ala
        115                 120                 125 cat tac cac aac aag tac gtc gag tac ttc gac aca ctc ttc atg gtg     432
His Tyr His Asn Lys Tyr Val Glu Tyr Phe Asp Thr Leu Phe Met Val
    130                 135                 140 ctg cgg aaa aag aac aac cag att tcc ttt ctt cac gtc tac cat cac     480
Leu Arg Lys Lys Asn Asn Gln Ile Ser Phe Leu His Val Tyr His His
145                 150                 155                 160 gct ctg ctc acc tgg gct tgg ttt gcc gtg gtc tac ttc gct cct gga     528
Ala Leu Leu Thr Trp Ala Trp Phe Ala Val Val Tyr Phe Ala Pro Gly
                165                 170                 175 ggt gac ggc tgg ttt gga gcc tgc tac aat tcc tcc att cat gtc ctg     576
Gly Asp Gly Trp Phe Gly Ala Cys Tyr Asn Ser Ser Ile His Val Leu
            180                 185                 190 atg tac tct tac tat ctg ctt gcc acc ttc ggc atc tcc tgt ccc tgg     624
Met Tyr Ser Tyr Tyr Leu Leu Ala Thr Phe Gly Ile Ser Cys Pro Trp
        195                 200                 205 aaa aag atc ctc acc cag ctg caa atg gtt cag ttc tgc ttt gcc ttc     672
Lys Lys Ile Leu Thr Gln Leu Gln Met Val Gln Phe Cys Phe Cys Phe
    210                 215                 220
```

```
acc cac tcg atc tac gtg tgg att tgc ggt tcc gaa atc tac cct cga      720
Thr His Ser Ile Tyr Val Trp Ile Cys Gly Ser Glu Ile Tyr Pro Arg
225                 230                 235                 240 ccc ttg act gct ctc cag tcc ttc gtg atg gtc aac atg ctg gtt ctc      768
Pro Leu Thr Ala Leu Gln Ser Phe Val Met Val Asn Met Leu Val Leu
                245                 250                 255 ttt ggc aac ttc tac gtc aag cag tat tct cag aag aat gga aag ccc      816
Phe Gly Asn Phe Tyr Val Lys Gln Tyr Ser Gln Lys Asn Gly Lys Pro
            260                 265                 270 gag aac ggt gcc act cct gag aac ggt gcc aag cct cag ccc tgc gag      864
Glu Asn Gly Ala Thr Pro Glu Asn Gly Ala Lys Pro Gln Pro Cys Glu
        275                 280                 285 aac ggt acc gtg gag aag cga gaa aac gac acc gcc aat gtt cga ccc      912
Asn Gly Thr Val Glu Lys Arg Glu Asn Asp Thr Ala Asn Val Arg Pro
290                 295                 300 gct aga cct gcc ggt ctt cca ccc gca act tac tat gac tct ctc gcc      960
Ala Arg Pro Ala Gly Leu Pro Pro Ala Thr Tyr Tyr Asp Ser Leu Ala
305                 310                 315                 320 gtg tcg gga cag ggc aag gag cga ctg ttc acc aca gac gag gtc aga     1008
Val Ser Gly Gln Gly Lys Glu Arg Leu Phe Thr Thr Asp Glu Val Arg
                325                 330                 335 cga cac att ctt ccc acc gat gga tgg ctc acc tgt cac gaa ggt gtg     1056
Arg His Ile Leu Pro Thr Asp Gly Trp Leu Thr Cys His Glu Gly Val
            340                 345                 350 tac gac gtc acc gat ttc ctg gcc aag cat cct gga ggt ggc gtc atc     1104
Tyr Asp Val Thr Asp Phe Leu Ala Lys His Pro Gly Gly Gly Val Ile
        355                 360                 365 act ctc gga ctt ggt cga gac tgc acc att ctg gtc gag tcc tac cat     1152
Thr Leu Gly Leu Gly Arg Asp Cys Thr Ile Leu Val Glu Ser Tyr His
370                 375                 380 ccc gct gga cga cca gac aag gtc atg gag aag tac cgt atc ggc aca     1200
Pro Ala Gly Arg Pro Asp Lys Val Met Glu Lys Tyr Arg Ile Gly Thr
385                 390                 395                 400 ctc cag gat ccc aag act ttc tac gct tgg gga gaa tcg gac ttt tac     1248
Leu Gln Asp Pro Lys Thr Phe Tyr Ala Trp Gly Glu Ser Asp Phe Tyr
                405                 410                 415 cct gag ctc aaa cga cgg gct ctt gca cga ctc aag gag gct gga cag     1296
Pro Glu Leu Lys Arg Arg Ala Leu Ala Arg Leu Lys Glu Ala Gly Gln
            420                 425                 430 gca cgt cga ggt gga ctg gga gtc aag gct ctc ctg gtg ctt acc ctc     1344
Ala Arg Arg Gly Gly Leu Gly Val Lys Ala Leu Leu Val Leu Thr Leu
        435                 440                 445 ttc ttt gtc tcc tgg tac atg tgg gtt gcc cac aag tct ttc ctg tgg     1392
Phe Phe Val Ser Trp Tyr Met Trp Val Ala His Lys Ser Phe Leu Trp
450                 455                 460 gct gcc gtc tgg ggc ttt gcc ggt tcg cat gtc gga ctg agc att caa     1440
Ala Ala Val Trp Gly Phe Ala Gly Ser His Val Gly Leu Ser Ile Gln
465                 470                 475                 480 cac gat ggc aac cac ggt gct ttc tct cga tcc acc ctg gtc aac aga     1488
His Asp Gly Asn His Gly Ala Phe Ser Arg Ser Thr Leu Val Asn Arg
                485                 490                 495 ctc gca gga tgg ggc atg gac ttg atc ggt gcc tcg tcc acc gtg tgg     1536
Leu Ala Gly Trp Gly Met Asp Leu Ile Gly Ala Ser Ser Thr Val Trp
            500                 505                 510 gag tac cag cat gtc att gga cac cat cag tac acg aat ctc gtt tcc     1584
Glu Tyr Gln His Val Ile Gly His His Gln Tyr Thr Asn Leu Val Ser
        515                 520                 525 gat acg ctg ttc agc ctt ccc gag aac gac cca gat gtg ttt tcc agc     1632
Asp Thr Leu Phe Ser Leu Pro Glu Asn Asp Pro Asp Val Phe Ser Ser
```

```
                    530                 535                 540
tat cct ctc atg cga atg cat ccc gac act gct tgg cag cct cat cac      1680
Tyr Pro Leu Met Arg Met His Pro Asp Thr Ala Trp Gln Pro His His
545                 550                 555                 560 cga ttt caa cac ctg ttc gcc ttt cct ctc ttc gct ctt atg acc att      1728
Arg Phe Gln His Leu Phe Ala Phe Pro Leu Phe Ala Leu Met Thr Ile
                565                 570                 575 tcc aag gtg ctc acc agc gac ttt gct gtt tgt ctc tcc atg aaa aag      1776
Ser Lys Val Leu Thr Ser Asp Phe Ala Val Cys Leu Ser Met Lys Lys
            580                 585                 590 ggt tct atc gac tgt tcg tcc aga ctg gtt cca ctc gaa ggc cag ctg      1824
Gly Ser Ile Asp Cys Ser Ser Arg Leu Val Pro Leu Glu Gly Gln Leu
        595                 600                 605 ttg ttc tgg gga gcc aag ctg gcg aac ttt ctc ttg cag att gtg ctg      1872
Leu Phe Trp Gly Ala Lys Leu Ala Asn Phe Leu Leu Gln Ile Val Leu
    610                 615                 620 ccc tgc tac ctc cac gga act gct atg ggc ctt gct ctg ttc tct gtt      1920
Pro Cys Tyr Leu His Gly Thr Ala Met Gly Leu Ala Leu Phe Ser Val
625                 630                 635                 640 gcc cac ctt gtg tct gga gag tac ctg gcc atc tgt ttc atc att aac      1968
Ala His Leu Val Ser Gly Glu Tyr Leu Ala Ile Cys Phe Ile Ile Asn
                645                 650                 655 cac atc tcc gag tct tgc gaa ttt atg aat acc tcc ttt caa act gct      2016
His Ile Ser Glu Ser Cys Glu Phe Met Asn Thr Ser Phe Gln Thr Ala
            660                 665                 670 gcc cga cgg acc gag atg ctc cag gca gct cat cag gca gcc gag gcg      2064
Ala Arg Arg Thr Glu Met Leu Gln Ala Ala His Gln Ala Ala Glu Ala
        675                 680                 685 aaa aag gtc aag ccc act cct cca ccc aac gat tgg gct gtg aca caa      2112
Lys Lys Val Lys Pro Thr Pro Pro Pro Asn Asp Trp Ala Val Thr Gln
    690                 695                 700 gtc cag tgc tgt gtc aac tgg cga tct gga ggc gtg ctg gcc aat cac      2160
Val Gln Cys Cys Val Asn Trp Arg Ser Gly Gly Val Leu Ala Asn His
705                 710                 715                 720 ctc tcc ggt ggc ctc aac cat cag atc gag cac cat ctg ttt ccc agc      2208
Leu Ser Gly Gly Leu Asn His Gln Ile Glu His His Leu Phe Pro Ser
                725                 730                 735 atc tct cac gcg aac tat ccc atc att gct cga gtt gtc aag gaa gtg      2256
Ile Ser His Ala Asn Tyr Pro Ile Ile Ala Arg Val Val Lys Glu Val
            740                 745                 750 tgc gag gaa tac gga ttg ccc tac aag aac tac gtt acg ttc tgg gat      2304
Cys Glu Glu Tyr Gly Leu Pro Tyr Lys Asn Tyr Val Thr Phe Trp Asp
        755                 760                 765 gcc gtg tgt ggc atg gtt cag cat ctg cga ctc atg ggt gct cct ccc      2352
Ala Val Cys Gly Met Val Gln His Leu Arg Leu Met Gly Ala Pro Pro
    770                 775                 780 gtg cct acc aac ggc gac aaa aag tcc taa                              2382
Val Pro Thr Asn Gly Asp Lys Lys Ser
785                 790

<210> SEQ ID NO 64
<211> LENGTH: 793
<212> TYPE: PRT
<213> ORGANISM: Euglena gracilis

<400> SEQUENCE: 64

Met Ala Asp Ser Pro Val Ile Asn Leu Ser Thr Met Trp Lys Pro Leu
1               5                   10                  15

Ser Leu Met Ala Leu Asp Leu Ala Val Leu Gly His Val Trp Lys Gln
            20                  25                  30
```

-continued

```
Ala Gln Gln Glu Gly Ser Ile Ser Ala Tyr Ala Asp Ser Val Trp Thr
            35                  40                  45
Pro Leu Ile Met Ser Gly Leu Tyr Leu Ser Met Ile Phe Val Gly Cys
 50                  55                  60
Arg Trp Met Lys Asn Arg Glu Pro Phe Glu Ile Lys Thr Tyr Met Phe
 65                  70                  75                  80
Ala Tyr Asn Leu Tyr Gln Thr Leu Met Asn Leu Cys Ile Val Leu Gly
                85                  90                  95
Phe Leu Tyr Gln Val His Ala Thr Gly Met Arg Phe Trp Gly Ser Gly
                100                 105                 110
Val Asp Arg Ser Pro Lys Gly Leu Gly Ile Gly Phe Phe Ile Tyr Ala
            115                 120                 125
His Tyr His Asn Lys Tyr Val Glu Tyr Phe Asp Thr Leu Phe Met Val
            130                 135                 140
Leu Arg Lys Lys Asn Asn Gln Ile Ser Phe Leu His Val Tyr His His
145                 150                 155                 160
Ala Leu Leu Thr Trp Ala Trp Phe Ala Val Val Tyr Phe Ala Pro Gly
                165                 170                 175
Gly Asp Gly Trp Phe Gly Ala Cys Tyr Asn Ser Ser Ile His Val Leu
            180                 185                 190
Met Tyr Ser Tyr Tyr Leu Leu Ala Thr Phe Gly Ile Ser Cys Pro Trp
            195                 200                 205
Lys Lys Ile Leu Thr Gln Leu Gln Met Val Gln Phe Cys Phe Cys Phe
            210                 215                 220
Thr His Ser Ile Tyr Val Trp Ile Cys Gly Ser Glu Ile Tyr Pro Arg
225                 230                 235                 240
Pro Leu Thr Ala Leu Gln Ser Phe Val Met Val Asn Met Leu Val Leu
                245                 250                 255
Phe Gly Asn Phe Tyr Val Lys Gln Tyr Ser Gln Lys Asn Gly Lys Pro
                260                 265                 270
Glu Asn Gly Ala Thr Pro Glu Asn Gly Ala Lys Pro Gln Pro Cys Glu
            275                 280                 285
Asn Gly Thr Val Glu Lys Arg Glu Asn Asp Thr Ala Asn Val Arg Pro
            290                 295                 300
Ala Arg Pro Ala Gly Leu Pro Ala Thr Tyr Tyr Asp Ser Leu Ala
305                 310                 315                 320
Val Ser Gly Gln Gly Lys Glu Arg Leu Phe Thr Thr Asp Glu Val Arg
                325                 330                 335
Arg His Ile Leu Pro Thr Asp Gly Trp Leu Thr Cys His Glu Gly Val
            340                 345                 350
Tyr Asp Val Thr Asp Phe Leu Ala Lys His Pro Gly Gly Gly Val Ile
            355                 360                 365
Thr Leu Gly Leu Gly Arg Asp Cys Thr Ile Leu Val Glu Ser Tyr His
            370                 375                 380
Pro Ala Gly Arg Pro Asp Lys Val Met Glu Lys Tyr Arg Ile Gly Thr
385                 390                 395                 400
Leu Gln Asp Pro Lys Thr Phe Tyr Ala Trp Gly Glu Ser Asp Phe Tyr
                405                 410                 415
Pro Glu Leu Lys Arg Arg Ala Leu Ala Arg Leu Lys Glu Ala Gly Gln
            420                 425                 430
Ala Arg Arg Gly Gly Leu Gly Val Lys Ala Leu Leu Val Leu Thr Leu
            435                 440                 445
```

```
Phe Phe Val Ser Trp Tyr Met Trp Val Ala His Lys Ser Phe Leu Trp
    450                 455                 460
Ala Ala Val Trp Gly Phe Ala Gly Ser His Val Gly Leu Ser Ile Gln
465                 470                 475                 480
His Asp Gly Asn His Gly Ala Phe Ser Arg Ser Thr Leu Val Asn Arg
                485                 490                 495
Leu Ala Gly Trp Gly Met Asp Leu Ile Gly Ala Ser Ser Thr Val Trp
            500                 505                 510
Glu Tyr Gln His Val Ile Gly His His Gln Tyr Thr Asn Leu Val Ser
        515                 520                 525
Asp Thr Leu Phe Ser Leu Pro Glu Asn Asp Pro Asp Val Phe Ser Ser
    530                 535                 540
Tyr Pro Leu Met Arg Met His Pro Asp Thr Ala Trp Gln Pro His His
545                 550                 555                 560
Arg Phe Gln His Leu Phe Ala Phe Pro Leu Phe Ala Leu Met Thr Ile
                565                 570                 575
Ser Lys Val Leu Thr Ser Asp Phe Ala Val Cys Leu Ser Met Lys Lys
            580                 585                 590
Gly Ser Ile Asp Cys Ser Ser Arg Leu Val Pro Leu Glu Gly Gln Leu
        595                 600                 605
Leu Phe Trp Gly Ala Lys Leu Ala Asn Phe Leu Leu Gln Ile Val Leu
    610                 615                 620
Pro Cys Tyr Leu His Gly Thr Ala Met Gly Leu Ala Leu Phe Ser Val
625                 630                 635                 640
Ala His Leu Val Ser Gly Glu Tyr Leu Ala Ile Cys Phe Ile Ile Asn
                645                 650                 655
His Ile Ser Glu Ser Cys Glu Phe Met Asn Thr Ser Phe Gln Thr Ala
            660                 665                 670
Ala Arg Arg Thr Glu Met Leu Gln Ala Ala His Gln Ala Ala Glu Ala
        675                 680                 685
Lys Lys Val Lys Pro Thr Pro Pro Asn Asp Trp Ala Val Thr Gln
    690                 695                 700
Val Gln Cys Cys Val Asn Trp Arg Ser Gly Val Leu Ala Asn His
705                 710                 715                 720
Leu Ser Gly Gly Leu Asn His Gln Ile Glu His His Leu Phe Pro Ser
                725                 730                 735
Ile Ser His Ala Asn Tyr Pro Ile Ile Ala Arg Val Val Lys Glu Val
            740                 745                 750
Cys Glu Glu Tyr Gly Leu Pro Tyr Lys Asn Tyr Val Thr Phe Trp Asp
        755                 760                 765
Ala Val Cys Gly Met Val Gln His Leu Arg Leu Met Gly Ala Pro Pro
    770                 775                 780
Val Pro Thr Asn Gly Asp Lys Lys Ser
785                 790

<210> SEQ ID NO 65
<211> LENGTH: 7
<212> TYPE: PRT
<213> ORGANISM: Artificial Sequence
<220> FEATURE:
<223> OTHER INFORMATION: 1-acyl-sn-glycerol-3-phosphate acyltransferase
      motif
<220> FEATURE:
<221> NAME/KEY: misc_feature
<222> LOCATION: (2)..(3)
<223> OTHER INFORMATION: Xaa can be any naturally occurring amino acid
<220> FEATURE:
```

```
<221> NAME/KEY: MISC_FEATURE
<222> LOCATION: (6)..(6)
<223> OTHER INFORMATION: Xaa = Asp [D] or Arg [R]
<300> PUBLICATION INFORMATION:
<301> AUTHORS: Tal M. Lewin, Ping Wang, and Rosalind A. Coleman
<302> TITLE: Analysis of Amino Acid Motifs Diagnostic for the
      sn-Glycerol-3-phosphate Acyltransferase Reaction
<303> JOURNAL: Biochemistry
<304> VOLUME: 38
<305> ISSUE: 18
<306> PAGES: 57645771
<307> DATE: 1999-04-15
<313> RELEVANT RESIDUES IN SEQ ID NO: (1)..(7)
<300> PUBLICATION INFORMATION:
<301> AUTHORS: Atsushi Yamashita, Hiroki Nakanishia, Hiroshi Suzukia,
      Ryo Kamataa, Ken Tanakaa, Keizo Wakua and Takayuki Sugiura
<302> TITLE: Topology of acyltransferase motifs and substrate
      specificity and accessibility in 1-acyl-sn-glycero-3-phosphate
      acyltransferase 1
<303> JOURNAL: Biochimica et Biophysica Acta
<304> VOLUME: 1771
<305> ISSUE: 9
<306> PAGES: 1202-1215
<307> DATE: 2007-07-17
<313> RELEVANT RESIDUES IN SEQ ID NO: (1)..(7)

<400> SEQUENCE: 65

Gly Xaa Xaa Phe Ile Xaa Arg
1               5

<210> SEQ ID NO 66
<211> LENGTH: 6
<212> TYPE: PRT
<213> ORGANISM: Artificial Sequence
<220> FEATURE:
<223> OTHER INFORMATION: 1-acyl-sn-glycerol-3-phosphate acyltransferase
      motif
<220> FEATURE:
<221> NAME/KEY: MISC_FEATURE
<222> LOCATION: (1)..(1)
<223> OTHER INFORMATION: Xaa = Val [V] or Ile [I]
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa = Ile [I] or Val [V] or Leu [L]
<220> FEATURE:
<221> NAME/KEY: MISC_FEATURE
<222> LOCATION: (4)..(4)
<223> OTHER INFORMATION: Xaa = Ile [I] or Val [V]
<220> FEATURE:
<221> NAME/KEY: MISC_FEATURE
<222> LOCATION: (6)..(6)
<223> OTHER INFORMATION: Xaa =  Val [V] or Ile [I]
<300> PUBLICATION INFORMATION:
<301> AUTHORS: Atsushi Yamashita, Hiroki Nakanishia, Hiroshi Suzukia,
      Ryo Kamataa, Ken Tanakaa, Keizo Waku and Takayuki Sugiura
<302> TITLE: Topology of acyltransferase motifs and substrate
      specificity and accessibility in 1-acyl-sn-glycero-3-phosphate
      acyltransferase 1
<303> JOURNAL: Biochimica et Biophysica Acta
<304> VOLUME: 1771
<305> ISSUE: 9
<306> PAGES: 1202-1215
<307> DATE: 2007-07-17
<313> RELEVANT RESIDUES IN SEQ ID NO: (1)..(6)

<400> SEQUENCE: 66

Xaa Xaa Xaa Xaa Pro Xaa
1               5

<210> SEQ ID NO 67
```

```
<211> LENGTH: 6
<212> TYPE: PRT
<213> ORGANISM: Artificial Sequence
<220> FEATURE:
<223> OTHER INFORMATION: 1-acyl-sn-glycerol-3-phosphate acyltransferase
      motif
<300> PUBLICATION INFORMATION:
<301> AUTHORS: Atsushi Yamashita, Hiroki Nakanishia, Hiroshi Suzukia,
      Ryo Kamataa, Ken Tanakaa, Keizo Wakua and Takayuki Sugiura
<302> TITLE: Topology of acyltransferase motifs and substrate
      specificity and accessibility in 1-acyl-sn-glycero-3-phosphate
      acyltransferase 1
<303> JOURNAL: Biochimica et Biophysica Acta
<304> VOLUME: 1771
<305> ISSUE: 9
<306> PAGES: 1202-1215
<307> DATE: 2007-07-17
<313> RELEVANT RESIDUES IN SEQ ID NO: (1)..(6)

<400> SEQUENCE: 67

Ile Val Pro Ile Val Met
1               5
```